US011566039B2

(12) United States Patent
Myers et al.

(10) Patent No.: US 11,566,039 B2
(45) Date of Patent: Jan. 31, 2023

(54) LINCOSAMIDE ANTIBIOTICS AND USES THEREOF

(71) Applicant: President and Fellows of Harvard College, Cambridge, MA (US)

(72) Inventors: Andrew G. Myers, Cambridge, MA (US); Matthew James Mitcheltree, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/637,477

(22) PCT Filed: Aug. 10, 2018

(86) PCT No.: PCT/US2018/046200
§ 371 (c)(1),
(2) Date: Feb. 7, 2020

(87) PCT Pub. No.: WO2019/032956
PCT Pub. Date: Feb. 14, 2019

(65) Prior Publication Data
US 2021/0087215 A1   Mar. 25, 2021

Related U.S. Application Data

(60) Provisional application No. 62/650,795, filed on Mar. 30, 2018, provisional application No. 62/585,271, filed on Nov. 13, 2017, provisional application No. 62/568,657, filed on Oct. 5, 2017, provisional application No. 62/557,893, filed on Sep. 13, 2017, provisional application No. 62/558,143, filed on Sep. 13, 2017, provisional application No. 62/543,808, filed on Aug. 10, 2017.

(51) Int. Cl.
*C07H 15/16*   (2006.01)

(52) U.S. Cl.
CPC .................................. *C07H 15/16* (2013.01)

(58) Field of Classification Search
None
See application file for complete search history.

(56) References Cited

U.S. PATENT DOCUMENTS

| | | | |
|---|---|---|---|
| 5,004,730 | A | 4/1991 | Philippe et al. |
| 7,199,105 | B2 * | 4/2007 | Lewis .................... C07H 13/10 514/24 |
| 7,199,106 | B2 * | 4/2007 | Lewis .................. C07D 405/12 514/24 |
| 7,361,743 | B2 | 4/2008 | Lewis et al. |
| 7,867,980 | B2 | 1/2011 | Umemura et al. |
| 7,879,808 | B2 | 2/2011 | Wakiyama et al. |
| 11,124,534 | B2 | 9/2021 | Meyers et al. |
| 2005/0043248 | A1 * | 2/2005 | Lewis ................... C07D 405/12 514/23 |
| 2009/0156512 | A1 | 6/2009 | Umemura et al. |
| 2010/0184746 | A1 | 7/2010 | Umemura et al. |
| 2010/0210570 | A1 | 8/2010 | Wakiyama et al. |
| 2012/0028222 | A1 | 2/2012 | Abdennour et al. |
| 2020/0339620 | A1 | 10/2020 | Meyers et al. |
| 2022/0073554 | A1 | 3/2022 | Meyers et al. |

FOREIGN PATENT DOCUMENTS

| | | | |
|---|---|---|---|
| WO | WO 2004/002992 A1 | 1/2004 | |
| WO | WO 2006/055070 A2 | 5/2006 | |
| WO | WO-2018161979 A1 * | 9/2018 | ............. C07H 15/18 |
| WO | WO 2019/032936 A1 | 2/2019 | |

OTHER PUBLICATIONS

Collin et al., Helvetica Chimica Acta—vol. 92, 2009, pp. 230-266. (Year: 2009).*
Invitation to Pay Additional Fees, dated Sep. 24, 2018, in connection with Application No. PCT/US2018/046200.
International Search Report and Written Opinion, dated Dec. 11, 2018, in connection with Application No. PCT/US2018/046200.
International Preliminary Report on Patentability, dated Feb. 20, 2020, in connection with Application No. PCT/US2018/046200.
International Search Report and Written Opinion, dated Sep. 26, 2018, in connection with Application No. PCT/US2018/046167.
International Preliminary Report on Patentability, dated Feb. 20, 2020, in connection with Application No. PCT/US2018/046167.
Invitation to Pay Additional Fees, dated Sep. 21, 2018, in connection with Application No. PCT/US2018/046178.
International Search Report and Written Opinion, dated Nov. 26, 2018, in connection with Application No. PCT/US2018/046178.
International Preliminary Report on Patentability, dated Feb. 20, 2020, in connection with Application No. PCT/US2018/046178.
Belanger et al., Stereocontrolled synthesis of triazacyclopenta[cd]pentalenes by intramolecular 1,3-dipolar cycloaddition reactions of azomethine imines. J Org Chem. Nov. 2002 1;67(22):7880-3.
U.S. Appl. No. 16/637,647, filed Feb. 7, 2020, Myers et al.
U.S. Appl. No. 16/637,644, filed Feb. 7, 2020, Myers et al.
PCT/US2018/046200, Sep. 24, 2018, Invitation to Pay Additional Fees.
PCT/US2018/046200, Dec. 11, 2018, International Search Report and Written Opinion.
PCT/US2018/046200, Feb. 20, 2020, International Preliminary Report on Patentability.
PCT/US2018/046167, Sep. 26, 2018, International Search Report and Written Opinion.

(Continued)

*Primary Examiner* — Traviss C McIntosh, III
(74) *Attorney, Agent, or Firm* — Wolf, Greenfield & Sacks, P.C.

(57) ABSTRACT

Provided are lincosamide compounds for the treatment of infectious diseases. The lincosamides described herein are modified at the C-7 position of the aminooctose (northern) region, thus distinguishing them from lincomycin and clindamycin. Also provided are methods for preparing the lincosamide compounds, pharmaceutical compositions comprising the lincosamide compounds, and methods of treating infectious diseases using the disclosed lincosamide compounds.

20 Claims, No Drawings

(56) References Cited

OTHER PUBLICATIONS

PCT/US2018/046167, Feb. 20, 2020, International Preliminary Report on Patentability.
PCT/US2018/046178, Sep. 21, 2018, Invitation to Pay Additional Fees.
PCT/US2018/046178, Nov. 26, 2018, International Search Report and Written Opinion.
PCT/US2018/046178, Feb. 20, 2020, International Preliminary Report on Patentability.
EP 18844834.4, Mar. 19, 2021, Extended European Search Report.
Extended European Search Report for Application No. 18844834.4, dated Mar. 19, 2021.
Kumura et al., Synthesis and antibacterial activity of novel lincomycin derivatives. I. Enhancement of antibacterial activities by introduction of substituted azetidines. J Antibiot (Tokyo). Jun. 2016;69(6):440-5. doi: 10.1038/ja.2015.134. Epub Jan. 13, 2016.
Umemura et al., Synthesis of novel lincomycin derivatives and their in vitro antibacterial activities. J Antibiot (Tokyo). Mar. 2013;66(3):195-8. doi: 10.1038/ja.2012.107. Epub Dec. 12, 2012.
Wakiyama et al., Synthesis and structure-activity relationships of novel lincomycin derivatives. Part 2. Synthesis of 7(S)-7-deoxy-7-(4-morpholinocarbonylphenylthio)lincomycin and its 3-dimensional analysis with rRNA. J Antibiot (Tokyo). Jun. 2016;69(6):428-39. doi: 10.1038/ja.2015.125. Epub Dec. 16, 2015.
Wakiyama et al., Synthesis and structure-activity relationships of novel lincomycin derivatives. Part 1. Newly generated antibacterial activities against Gram-positive bacteria with erm gene by C-7 modification. J Antibiot (Tokyo). May 2016;69(5):368-80. doi: 10.1038/ja.2015.119. Epub Dec. 16, 2015.
Wakiyama et al., Synthesis and structure-activity relationships of novel lincomycin derivatives part 3: discovery of the 4-(pyrimidin-5-yl)phenyl group in synthesis of 7(S)-thiolincomycin analogs. J Antibiot (Tokyo). Jan. 2017;70(1):52-64. doi: 10.1038/ja.2016.114. Epub Oct. 5, 2016.
International Search Report and Written Opinion, dated Oct. 1, 2021, in connection with Application No. PCT/US2021/033371.
Magerlein et al., Lincomycin. VI. 4'-Alkyl Analogs of Lincomycin. Relationship between Structure and Antibacterial Activity. J Med Chem. May 1, 1967; 10(3):355-9. doi: 10.1021/jm00315a015.
Mason et al., Practical Gram-Scale Synthesis of Iboxamycin, a Potent Antibiotic Candidate. J Am Chem Soc. Jul. 28, 2021;143(29):11019-11025. doi: 10.1021/jacs.1c03529. Epub Jul. 15, 2021.
Mason et al., Practical Synthesis of Iboxamycin, a Potent Antibiotic Candidate, in Amounts Suitable for Studies in Animal Infection Models. ChemRxiv. 2021:1-8.
Mitcheltree et al., A Practical, Component-Based Synthetic Route to Methylthiolin-cosamine Permitting Facile Northern-Half Diversification of Lin-cosamide Antibiotics. J Am Chem Soc. May 12, 2021;143(18):6829-6835. doi: 10.1021/jacs.1c03536. Epub Apr. 30, 2021.
Mitcheltree et al., A synthetic antibiotic class overcoming bacterial multidrug resistance. Nature. Nov. 18, 2021; 599: 507-12. And Supplemental Information.
Nadano et al., Rapid and slow generation of 1-trifluoromethylvinyllithium: syntheses and applications of CF3-containing allylic alcohols, allylic amines, and vinyl ketones. Asian J. Aug. 2, 2010;5(8):1875-83. doi: 10.1002/asia.201000139.
Silvestre, Design, Synthesis, and Study of Lincosamide Antibiotics Containing a Bicyclic Amino Acid Moiety. Doctoral dissertation, Harvard University, Graduate School of Arts & Sciences. 2019. 352 Pages.
Wakiyama et al., Synthesis and SARs of novel lincomycin derivatives Part 5: optimization of lincomycin analogs exhibiting potent antibacterial activities by chemical modification at the 6-and 7-positions. J Antibiot (Tokyo). Feb. 2018;71(2):298-317. doi: 10.1038/ja.2017.114. Epub Nov. 1, 2017.

* cited by examiner

LINCOSAMIDE ANTIBIOTICS AND USES THEREOF

RELATED APPLICATIONS

This application is a national stage filing under 35 U.S.C. § 371 of international PCT application, PCT/US2018/046200, filed Aug. 10, 2018, which claims priority under 35 U.S.C. § 119(e) to U.S. Provisional Applications, U.S. Ser. No. 62/543,808, filed Aug. 10, 2017; U.S. Ser. No. 62/557,893, filed Sep. 13, 2017; U.S. Ser. No. 62/558,143, filed Sep. 13, 2017; U.S. Ser. No. 62/568,657, filed Oct. 5, 2017; U.S. Ser. No. 62/585,271, filed Nov. 13, 2017; and U.S. Ser. No. 62/650,795, filed Mar. 30, 2018, each of which is incorporated herein by reference.

BACKGROUND

Emerging resistance to existing antibiotics is rapidly developing as a crisis of global proportions, especially for infections originating from drug-resistant Gram-negative bacteria. Pathogenic bacteria can transmit genes coding for antibiotic resistance both vertically (to their progeny) and horizontally (to neighboring bacteria of different lineages), and as a result antibiotic resistance can evolve quickly, particularly in nosocomial (hospital) settings. See, e.g., Wright, *Chem. Commun.* (2011) 47:4055-4061. More than 99,000 people die annually in the U.S. from healthcare-associated infections, more than all casualties from car accidents, HIV, and breast cancer combined, creating an estimated burden of up to $45 billion in U.S. healthcare costs. See, e.g., Klevens et al., *Public Health Rep* (2007) 122:160-166. The current crisis is exacerbated by decreased research in the development of new antibiotics by most major pharmaceutical companies. See, e.g., Projan, *Curr. Opin. Microbiol.* (2003) 6:427-430. The current rate of introduction of new antibiotics does not adequately address growing resistance, and with the ease of international travel and increasing population densities, the need for innovation in the field has never been higher.

The lincosamides are a class of antibiotics that prevent bacteria growth by interfering with the synthesis of proteins. They bind to the 23s portion of the 50S subunit of bacterial ribosomes and cause premature dissociation of the peptidyl-tRNA from the ribosome. Lincosamides do not interfere with protein synthesis in human cells (or those of other eukaryotes) because human ribosomes are structurally different from those of bacteria.

The first lincosamide to be discovered was lincomycin, but the use of lincomycin as an antibiotic has been largely superseded by clindamycin, which exhibits improved antibacterial activity. Clindamycin also exhibits some activity against parasitic protozoa and has been used to treat toxoplasmosis and malaria. Lincosamides are typically used to treat *Staphylococcus* and *Streptococcus* infections but have also proved to be useful in treating *Bacteroides fragilis* and other anaerobic infections. They are used in the treatment of toxic shock syndrome and thought to directly block the M protein production that leads to the severe inflammatory response.

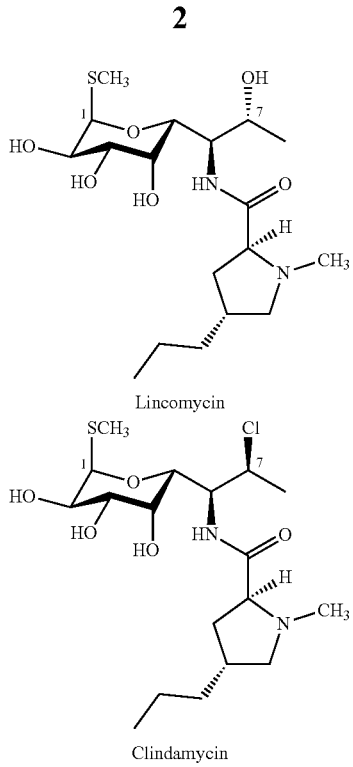

Lincomycin

Clindamycin

Target bacteria may alter the drug's binding site leading to resistance (similar to resistance found with macrolides and streptogramins). The resistance mechanism is methylation of the 23s binding site. If this occurs, then the bacteria are resistant to both macrolides and lincosamides. In rare instances, enzymatic inactivation of clindamycin has also been reported.

In addition, lincosamide antibiotics are associated with pseudomembranous colitis caused by *Clostridium difficile* (*C. difficile*). Pseudomembranous colitis is inflammation of the colon associated with an overgrowth of *C. difficile*. This overgrowth of *C. difficile* is most often related to recent lincosamide antibiotic use. For example, clindamycin, currently the only lincosamide in clinical use, carries a black-box warning for its tendency to promote *C. difficile*-associated diarrhea (CDAD).

Accordingly, the discovery and development of new antibiotics effective against drug-resistant bacteria, particularly lincosamides, represents a currently unmet medical need.

SUMMARY

A powerful synthetic platform for the discovery of new synthetic lincosamide antibiotics is disclosed herein. This platform enables the production of lincosamides bearing unprecedented modifications to both constituent halves of the lincosamides, namely the aminooctose (northern) and amino-acid (southern) portions. Lincosamides generated using this platform demonstrate potent activity against high-priority, clinically relevant pathogens including clindamycin- and azithromycin-resistant strains of *S. aureus*, *S. pneumoniae*, and *E. faecalis*-strains against which effective new antibiotics are in demand. Moreover, the disclosed lincosamides show potential promise as safer alternatives to clindamycin, owing to a diminished negative impact on commensal gut flora due to increased activity against *C. difficile*. The disclosed synthetic lincosamides also demonstrate activity against Gram-negative pathogens like *E. coli*.

In one aspect, the present disclosure provides compounds of Formula (I):

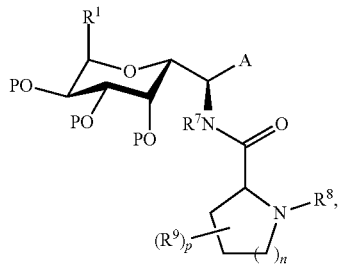

and pharmaceutically acceptable salts thereof, wherein:

P is independently hydrogen or a protecting group;

A is substituted or unsubstituted carbocyclyl, substituted or unsubstituted heterocyclyl,

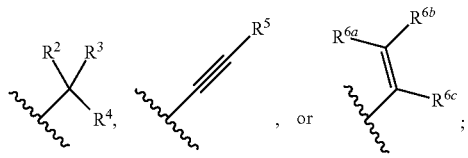

or A and $R^7$ are joined to form a substituted or unsubstituted heterocyclic ring;

$R^1$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, —$OR^A$, —$N(R^A)_2$, or —$SR^A$;

$R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —$OR^A$, —$N_3$, —$N(R^A)_2$, —$SR^A$, —CN, —SCN, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —$NO_2$, —$NR^A$C(=O)$R^A$, —$NR^A$C(=O)$OR^A$, —$NR^A$C(=O)N($R^A$)$_2$, —$NR^A$C(=$NR^A$)N($R^A$)$_2$, —OC(=O)$R^A$, —OC(=O)$OR^A$, —OC(=O)N($R^A$)$_2$, —$NR^A$S(O)$_2R^A$, —OS(O)$_2R^A$, or —S(O)$_2R^A$; $R^3$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^4$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^5$ is hydrogen, halogen, substituted or unsubstituted alkyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^{6a}$, $R^{6b}$, and $R^{6c}$ are each independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, or substituted or unsubstituted acyl;

$R^7$ is hydrogen or unsubstituted alkyl; or A and $R^7$ are joined to form a substituted or unsubstituted heterocyclic ring;

$R^8$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaliphatic, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —S(O)$_2R^A$, or a nitrogen protecting group;

each occurrence of $R^9$ is independently, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —$OR^A$, —$N(R^A)_2$, —$SR^A$, —CN, —SCN, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —$NO_2$, —$NR^A$C(=O)$R^A$, —$NR^A$C(=O)$OR^A$, —$NR^A$C(=O)N($R^A$)$_2$, —$NR^A$C(=$NR^A$)N($R^A$)$_2$, —OC(=O)$R^A$, —OC(=O)$OR^A$, —OC(=O)N($R^A$)$_2$, —$NR^A$S(O)$_2R^A$, —OS(O)$_2R^A$, or —S(O)$_2R^A$;

n is 1 or 2;

p is 1-3;

each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted carbocyclylalkyl, substituted or unsubstituted heterocyclyl, substituted or unsubstituted aryl, substituted or unsubstituted aralkyl, substituted or unsubstituted heteroaryl, substituted or unsubstituted hetaralkyl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring, or a substituted or unsubstituted heteroaryl ring;

provided that when $R^1$ is —$SR^A$ and $R^A$ is $C_{1-6}$ substituted or unsubstituted alkyl, A is not unsubstituted $C_{3-6}$ cycloalkyl,

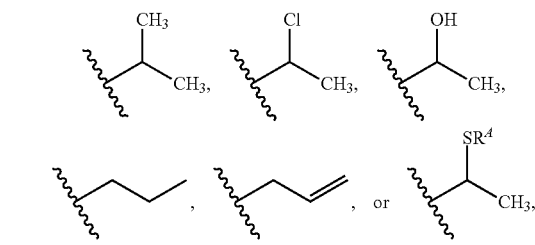

or CH₃, wherein $R^A$ is substituted or unsubstituted alkyl, substituted or unsubstituted alkenyl, substituted or unsubstituted heteroaryl, substituted or unsubstituted aryl, substituted or unsubstituted heterocyclyl, or substituted or unsubstituted acyl; and provided that when A is

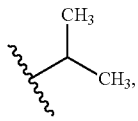

$R^1$ is not —$OR^A$, wherein $R^A$ is substituted or unsubstituted alkyl or substituted or unsubstituted alkyl.

In certain embodiments, the present disclosure provides compounds of Formulae (I-a), (I-b), (I-c), and (I-d):

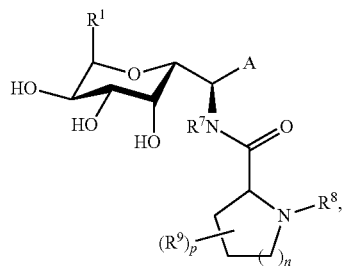

(I-a)

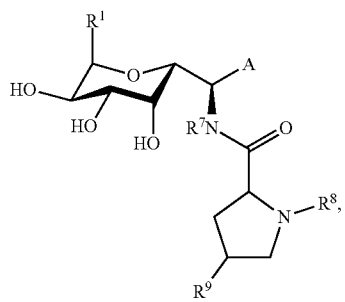

(I-b)

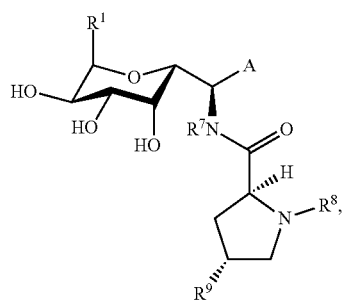

(I-c)

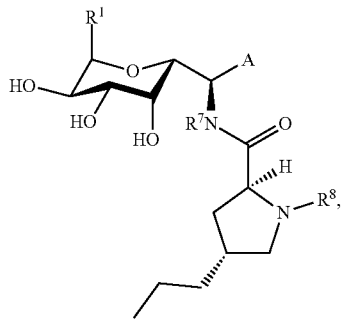

(I-d)

and pharmaceutically acceptable salts thereof.

In certain embodiments, the present disclosure provides compounds of Formulae (II), (II-a), (II-b), (II-c), (II-d), (II-e), (II-f), and (II-g):

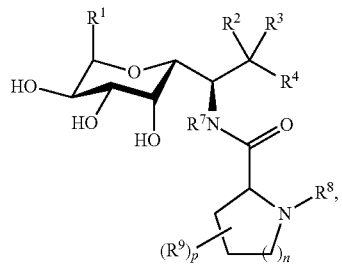

(II)

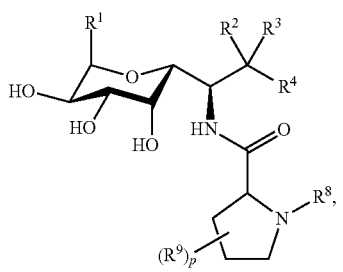

(II-a)

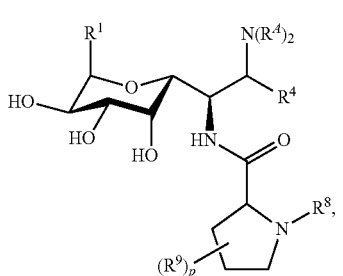

(II-b)

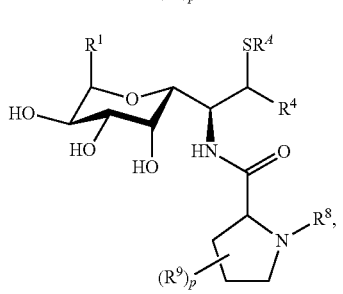

(II-c)

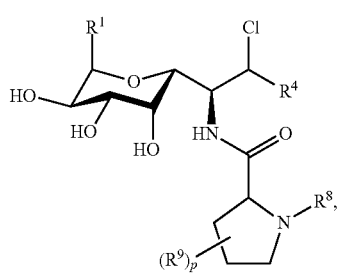

(II-d)

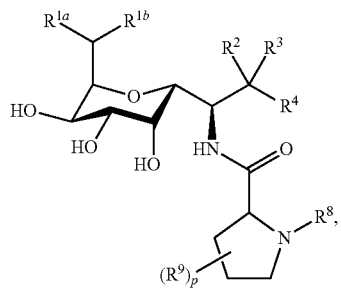

(II-e)

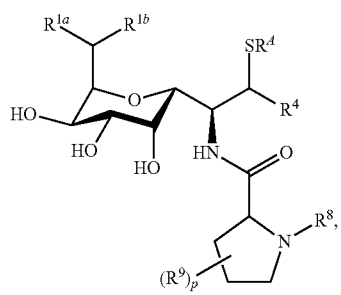

(II-f)

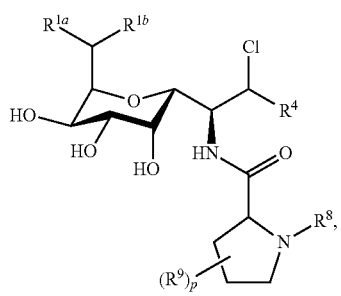

(II-g)

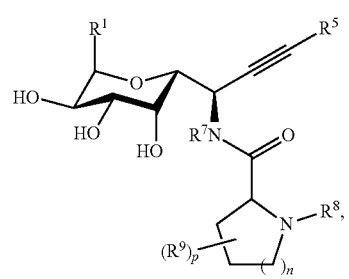

and pharmaceutically acceptable salts thereof.

In certain embodiments, the present disclosure provides compounds of Formulae (III) and (III-a):

(III)

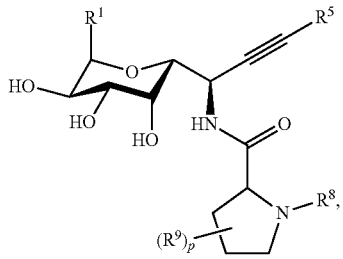

(III-a)

and pharmaceutically acceptable salts thereof.

In certain embodiments, the present disclosure provides compounds of Formulae (IV) and (IV-a):

(IV)

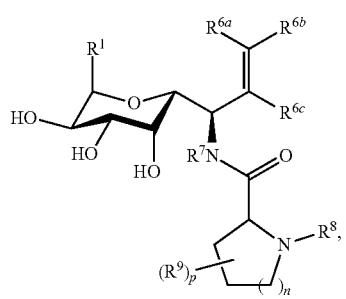

(IV-a)

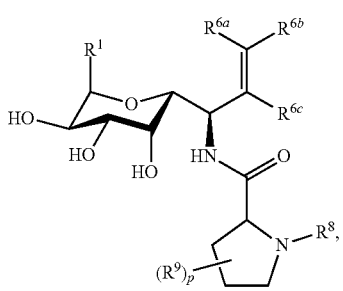

and pharmaceutically acceptable salts thereof.

The disclosed compounds have anti-microbial activity and may be used to treat and/or prevent infectious diseases. Pharmaceutical compositions of the compounds, kits comprising the compounds and/or compositions, and methods of treatment using the compounds and compositions thereof are provided herein. Infectious diseases which may be treated with the disclosed compounds include, but are not limited to, bacterial infections caused by *Staphylococcus, Streptococcus, Enterococcus, Acinetobacter, Clostridium, Bacteriodes, Klebsiella, Escherichia, Pseudomonas*, and *Haemophilus* species.

Methods of preparing the disclosed compounds are also provided herein. In certain embodiments, the disclosed compounds are prepared by an amide coupling of the aminooctose (northern) and amino-acid (southern) portions (e.g., Scheme 1).

The details of certain embodiments of the invention are set forth in the Detailed Description of Certain Embodiments, as described below. Other features, objects, and advantages of the invention will be apparent from the Definitions, Examples, and Claims.

DETAILED DESCRIPTION OF CERTAIN EMBODIMENTS

The compounds disclosed herein are lincosamide analogues. The disclosed compounds have increased structural diversity as compared to known lincosamides, such as lincomycin and clindamycin. In particular, the disclosed compounds have structures that are modified at the C-7 position of the aminooctose (northern) region. The disclosed lincosamides provide unexpected and potent activity against various microorganisms, including Gram negative bacteria. The disclosed lincosamides are non-hemolytic, non-toxic, and/or may possess improved activity profiles relative to clindamycin, such as increased activity against resistant strains of bacteria, including *Clostridium difficile*. Also disclosed are methods for the preparation of the disclosed compounds, uses of the compounds, pharmaceutical compositions comprising the disclosed compounds, and methods of using the compounds (e.g., treatment of an infectious disease, prevention of an infectious disease).

In one aspect, provided are compounds of Formula (I):

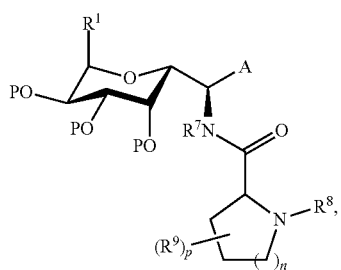

and pharmaceutically acceptable salts thereof, wherein:

P is independently hydrogen or a protecting group;

A is substituted or unsubstituted carbocyclyl, substituted or unsubstituted heterocyclyl,

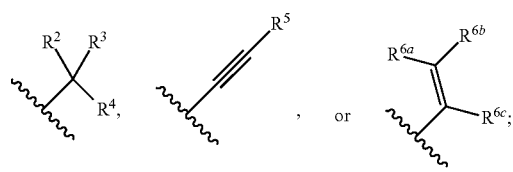

or A and $R^7$ are joined to form a substituted or unsubstituted heterocyclic ring;

$R^1$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, —$OR^A$, —$N(R^A)_2$, or —$SR^A$;

$R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —$OR^A$, —$N_3$, —$N(R^A)_2$, —$SR^A$, —CN, —SCN, —$C(=NR^A)R^A$, —$C(=NR^A)OR^A$, —$C(=NR^A)N(R^A)_2$, —$C(=O)R^A$, —$C(=O)OR^A$, —$C(=O)N(R^A)_2$, —$NO_2$, —$NR^AC(=O)R^A$, —$NR^AC(=O)OR^A$, —$NR^AC(=O)N(R^A)_2$, —$NR^AC(=NR^A)N(R^A)_2$, —$OC(=O)R^A$, —$OC(=O)OR^A$, —$OC(=O)N(R^A)_2$, —$NR^AS(O)_2R^A$, —$OS(O)_2R^A$, or —$S(O)_2R^A$;

$R^3$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^4$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^5$ is hydrogen, halogen, substituted or unsubstituted alkyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^{6a}$, $R^{6b}$, and $R^{6c}$ are each independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, or substituted or unsubstituted acyl;

$R^7$ is hydrogen or unsubstituted alkyl; or A and $R^7$ are joined to form a substituted or unsubstituted heterocyclic ring;

$R^8$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaliphatic, —$C(=NR^A)R^A$, —$C(=NR^A)OR^A$, —$C(=NR^A)N(R^A)_2$, —$C(=O)R^A$, —$C(=O)OR^A$, —$C(=O)N(R^A)_2$, —$S(O)_2R^A$, or a nitrogen protecting group;

each occurrence of $R^9$ is independently, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —$OR^A$, —$N(R^A)_2$, —$SR^A$, —CN, —SCN, —$C(=NR^A)R^A$, —$C(=NR^A)OR^A$, —$C(=NR^A)N(R^A)_2$, —$C(=O)R^A$, —$C(=O)OR^A$, —$C(=O)N(R^A)_2$, —$NO_2$, —$NR^AC(=O)R^A$, —$NR^AC(=O)OR^A$, —$NR^AC(=O)N(R^A)_2$, —$NR^AC(=NR^A)N(R^A)_2$, —$OC(=O)R^A$, —$OC(=O)OR^A$, —$OC(=O)N(R^A)_2$, —$NR^AS(O)_2R^A$, —$OS(O)_2R^A$, or —$S(O)_2R^A$;

n is 1 or 2;

p is 1-3;

each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted carbocyclylalkyl, substituted or unsubstituted heterocyclyl, substituted or unsubstituted aryl, substituted or unsubstituted aralkyl, substituted or unsubstituted heteroaryl, substituted or unsubstituted hetaralkyl, a nitrogen protecting group when attached to a nitrogen atom, an oxygen protecting group when attached to an oxygen atom, or a sulfur protecting group when attached to a sulfur atom, or two R$^A$ groups are joined to form a substituted or unsubstituted heterocyclic ring, or a substituted or unsubstituted heteroaryl ring;

provided that when R$^1$ is —SR$^A$ and R$^A$ is C$_{1-6}$ substituted or unsubstituted alkyl, A is not unsubstituted C$_{3-6}$ cycloalkyl,

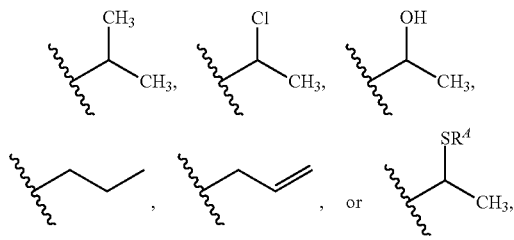

wherein R$^A$ is substituted or unsubstituted alkyl, substituted or unsubstituted alkenyl, substituted or unsubstituted heteroaryl, substituted or unsubstituted aryl, substituted or unsubstituted heterocyclyl, or substituted or unsubstituted acyl; and provided that when A is

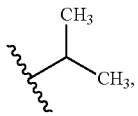

R$^1$ is not —OR$^A$, wherein R$^A$ is substituted or unsubstituted alkyl or substituted or unsubstituted alkyl.

In certain embodiments, provided are compounds of Formula (I):

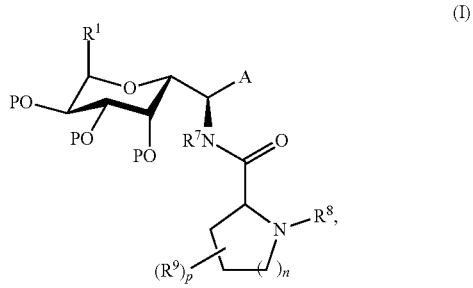

(I)

and pharmaceutically acceptable salts thereof, wherein:
P is independently hydrogen or a protecting group;
A is substituted or unsubstituted carbocyclyl, substituted or unsubstituted heterocyclyl,

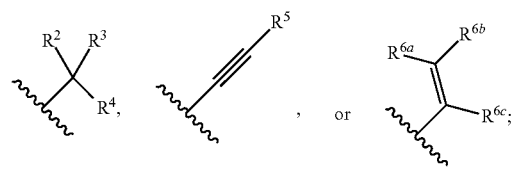

or A and R$^7$ are joined to form a substituted or unsubstituted heterocyclic ring;
R$^1$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, —OR$^A$, —N(R$^A$)$_2$, or —SR$^A$;

R$^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —OR$^A$, —N$_3$, —N(R$^A$)$_2$, —SR$^A$, —CN, —SCN, —C(=NR$^A$)R$^A$, —C(=NR$^A$)OR$^A$, —C(=NR$^A$)N(R$^A$)$_2$, —C(=O)R$^A$, —C(=O)OR$^A$, —C(=O)N(R$^A$)$_2$, —NO$_2$, —NR$^A$C(=O)R$^A$, —NR$^A$C(=O)OR$^A$, —NR$^A$C(=O)N(R$^A$)$_2$, —NR$^A$C(=NR$^A$)N(R$^A$)$_2$, —OC(=O)R$^A$, —OC(=O)OR$^A$, —OC(=O)N(R$^A$)$_2$, —NR$^A$S(O)$_2$R$^A$, —OS(O)$_2$R$^A$, or —S(O)$_2$R$^A$;

R$^3$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

R$^4$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

R$^5$ is hydrogen, halogen, substituted or unsubstituted alkyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

R$^{6a}$, R$^{6b}$, and R$^{6c}$ are each independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, or substituted or unsubstituted acyl;

R$^7$ is hydrogen or unsubstituted alkyl; or A and R$^7$ are joined to form a substituted or unsubstituted heterocyclic ring;

R$^8$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaliphatic, —C(=NR$^A$)R$^A$, —C(=NR$^A$)OR$^A$, —C(=NR$^A$)N(R$^A$)$_2$, —C(=O)R$^A$, —C(=O)OR$^A$, —C(=O)N(R$^A$)$_2$, —S(O)$_2$R$^A$, or a nitrogen protecting group;

each occurrence of R$^9$ is independently, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —OR$^A$, —N(R$^A$)$_2$, —SR$^A$, —CN, —SCN, —C(=NR$^A$)R$^A$, —C(=NR$^A$)OR$^A$, —C(=NR$^A$)N(R$^A$)$_2$, —C(=O)R$^A$, —C(=O)OR$^A$, —C(=O)N(R$^A$)$_2$, —NO$_2$, —NR$^A$C(=O)R$^A$, —NR$^A$C(=O)OR$^A$, —NR$^A$C(=O)N(R$^A$)$_2$, —NR$^A$C(=NR$^A$)N(R$^A$)$_2$, —OC(=O)R$^A$, —OC(=O)OR$^A$, —OC(=O)N(R$^A$)$_2$, —NR$^A$S(O)$_2$R$^A$, —OS(O)$_2$R$^A$, or —S(O)$_2$R$^A$;

n is 1 or 2;

p is 1-3;

each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted carbocyclylalkyl, substituted or unsubstituted heterocyclyl, substituted or unsubstituted aryl, substituted or unsubstituted aralkyl, substituted or unsubstituted heteroaryl, substituted or unsubstituted hetaralkyl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring, or a substituted or unsubstituted heteroaryl ring;

provided that when $R^1$ is —$SR^A$, A is not unsubstituted carbocyclyl,

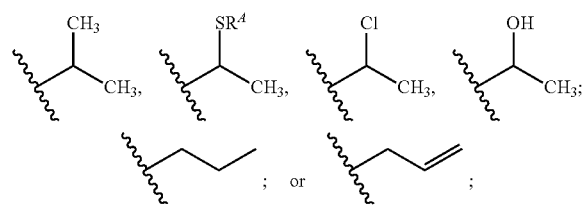

and provided that when A is

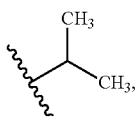

$R^1$ is not —$OR^A$, or substituted or unsubstituted alkyl.

In certain embodiments of the compound of Formula (I), each P is hydrogen.

Unless otherwise stated, any formulae described herein are also meant to include salts, solvates, hydrates, polymorphs, co-crystals, tautomers, stereoisomers, and isotopically labeled derivatives thereof. In certain embodiments, the provided compound is a salt of any of the formulae described herein. In certain embodiments, the provided compound is a pharmaceutically acceptable salt of any of the formulae described herein. In certain embodiments, the provided compound is a solvate of any of the formulae described herein. In certain embodiments, the provided compound is a hydrate of any of the formulae described herein. In certain embodiments, the provided compound is a polymorph of any of the formulae described herein. In certain embodiments, the provided compound is a co-crystal of any of the formulae described herein. In certain embodiments, the provided compound is a tautomer of any of the formulae described herein. In certain embodiments, the provided compound is a stereoisomer of any of the formulae described herein. In certain embodiments, the provided compound is of an isotopically labeled form of any of the formulae described herein. For example, compounds having the present structures except for the replacement of hydrogen by deuterium or tritium, replacement of 19F with 18F, or the replacement of a $^{12}C$ by a $^{13}C$ or $^{14}C$ are within the scope of the disclosure. In certain embodiments, the provided compound is a deuterated form of any of the formulae or compounds described herein.

Group A

As generally defined herein, A is substituted or unsubstituted carbocyclyl, substituted or unsubstituted heterocyclyl,

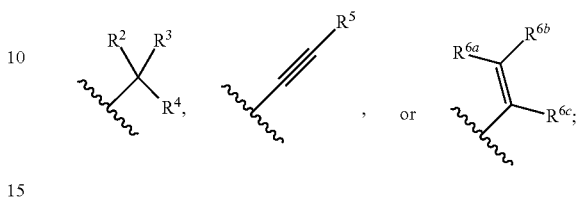

or A and $R^7$ are joined to form a substituted or unsubstituted heterocyclic ring;

$R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —$OR^A$, —$N_3$, —$N(R^A)_2$, —$SR^A$, —CN, —SCN, —$C(=NR^A)R^A$, —$C(=NR^A)OR^A$, —$C(=NR^A)N(R^A)_2$, —$C(=O)R^A$, —$C(=O)OR^A$, —$C(=O)N(R^A)_2$, —$NO_2$, —$NR^AC(=O)R^A$, —$NR^AC(=O)OR^A$, —$NR^AC(=O)N(R^A)_2$, —$NR^AC(=NR^A)N(R^A)_2$, —$OC(=O)R^A$, —$OC(=O)OR^A$, —$OC(=O)N(R^A)_2$, —$NR^AS(O)_2R^A$, —$OS(O)_2R^A$, or —$S(O)_2R^A$;

$R^3$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^4$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

$R^5$ is hydrogen, halogen, substituted or unsubstituted alkyl, substituted or unsubstituted carbocyclyl, substituted or unsubstituted heterocyclyl, substituted or unsubstituted aryl, substituted or unsubstituted heteroaryl, or substituted or unsubstituted heteroaliphatic; and $R^{6a}$, $R^{6b}$, and $R^{6c}$ are each independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, or substituted or unsubstituted acyl.

In certain embodiments, A is

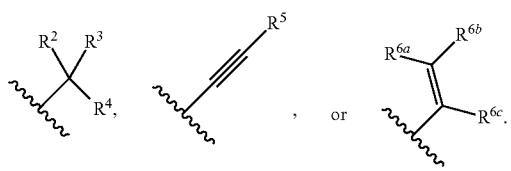

In certain embodiments, A is

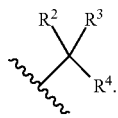

In certain embodiments, $R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, substituted or unsubstituted heteroalkyl, —$OR^A$, —$N_3$, —$N(R^A)_2$, —$SR^A$, —$NR^AC(=O)R^A$, or —$OC(=O)N(R^A)_2$.

In certain embodiments, $R^2$ is halogen, substituted or unsubstituted alkyl, substituted or unsubstituted alkenyl, substituted or unsubstituted heteroaryl, —$OR^A$, —$N_3$, —$N(R^A)_2$, —$SR^A$, —$NR^AC(=O)R^A$, or —$OC(=O)N(R^A)_2$. In certain embodiments, $R^2$ is substituted or unsubstituted heteroaryl. In certain embodiments, $R^2$ is substituted or unsubstituted 5-membered heteroaryl. In certain embodiments, $R^2$ is substituted or unsubstituted pyrrolyl, imidazolyl, pyrazolyl, or triazolyl.

In certain embodiments, $R^2$ is halogen, substituted or unsubstituted alkyl, —$OR^A$, —$N_3$, —$N(R^A)_2$, or —$SR^A$. In certain embodiments, $R^2$ is halogen or —$SR^A$. In certain embodiments, $R^2$ is —Cl or —$SCH_3$. In certain embodiments, $R^2$ is —Cl. In certain embodiments, $R^2$ is —$SCH_3$.

In certain embodiments, $R^3$ is hydrogen, halogen, substituted or unsubstituted alkyl, or substituted or unsubstituted alkenyl. In certain embodiments, $R^3$ is hydrogen or substituted or unsubstituted alkyl. In certain embodiments, $R^3$ is hydrogen. In certain embodiments, $R^3$ is substituted or unsubstituted $C_{1-6}$ alkyl. In certain embodiments, $R^3$ is unsubstituted $C_{1-6}$ alkyl. In certain embodiments, $R^3$ is unsubstituted $C_{1-3}$ alkyl. In certain embodiments, $R^3$ is unsubstituted $C_{1-2}$ alkyl. In certain embodiments, $R^3$ is ethyl. In certain embodiments, $R^3$ is methyl.

In certain embodiments, $R^4$ is hydrogen, halogen, substituted or unsubstituted alkyl, substituted or unsubstituted alkenyl. In certain embodiments, $R^4$ is hydrogen or substituted or unsubstituted alkyl. In certain embodiments, $R^4$ is hydrogen. In certain embodiments, $R^4$ is substituted or unsubstituted $C_{1-6}$ alkyl. In certain embodiments, $R^4$ is unsubstituted $C_{1-6}$ alkyl. In certain embodiments, $R^4$ is unsubstituted $C_{1-3}$ alkyl. In certain embodiments, $R^4$ is unsubstituted $C_{1-2}$ alkyl. In certain embodiments, $R^4$ is ethyl. In certain embodiments, $R^4$ is methyl.

In certain embodiments, $R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, substituted or unsubstituted heteroalkyl, —$OR^A$, —$N_3$, —$N(R^A)_2$, —$SR^A$, —$NR^AC(=O)R^A$, or —$OC(=O)N(R^A)_2$; $R^3$ is hydrogen, halogen, substituted or unsubstituted alkyl, or substituted or unsubstituted alkenyl; and $R^4$ is hydrogen, halogen, substituted or unsubstituted alkyl, substituted or unsubstituted alkenyl.

In certain embodiments, $R^2$ is halogen, substituted or unsubstituted alkyl, substituted or unsubstituted alkenyl, substituted or unsubstituted heteroaryl, —$OR^A$, —$N_3$, —$N(R^A)_2$, —$SR^A$, —$NR^AC(=O)R^A$, or —$OC(=O)N(R^A)_2$; $R^3$ is hydrogen, halogen, substituted or unsubstituted alkyl, or substituted or unsubstituted alkenyl; and $R^4$ is hydrogen, halogen, substituted or unsubstituted alkyl, substituted or unsubstituted alkenyl.

In certain embodiments, $R^2$ is halogen, substituted or unsubstituted alkyl, —$OR^A$, —$N_3$, —$N(R^A)_2$, or —$SR^A$; $R^3$ is hydrogen, halogen, substituted or unsubstituted alkyl, or substituted or unsubstituted alkenyl; and $R^4$ is hydrogen, halogen, substituted or unsubstituted alkyl, substituted or unsubstituted alkenyl.

In certain embodiments, $R^2$ is halogen, substituted or unsubstituted alkyl, —$OR^A$, —$N_3$, —$N(R^A)_2$, or —$SR^A$; $R^3$ is hydrogen or substituted or unsubstituted alkyl; and $R^4$ is hydrogen or substituted or unsubstituted alkyl.

In certain embodiments, $R^2$ is is halogen or —$SR^A$; $R^3$ is hydrogen or substituted or unsubstituted alkyl; and $R^4$ is hydrogen or substituted or unsubstituted alkyl. In certain embodiments, $R^2$ is is halogen or —$SR^A$; $R^3$ is substituted or unsubstituted alkyl; and $R^4$ is hydrogen. In certain embodiments, $R^2$ is is —Cl or —$SCH_3$; $R^3$ is substituted or unsubstituted alkyl; and $R^4$ is hydrogen.

In certain embodiments, $R^2$ is halogen; $R^3$ is halogen; and $R^4$ is hydrogen or halogen. In certain embodiments, $R^2$ is halogen; $R^3$ is halogen; and $R^4$ is halogen. In certain embodiments, $R^2$ is —F; $R^3$ is —F; and $R^4$ is —F. In certain embodiments, $R^2$ is —F; $R^3$ is —F; and $R^4$ is hydrogen. In certain embodiments, $R^2$ is —F; $R^3$ is hydrogen; and $R^4$ is hydrogen.

In certain embodiments, A is —$CF_3$, —$CHF_2$, or $CH_2F$. In certain embodiments, A is —$CF_3$. In certain embodiments, A is —$CHF_2$. In certain embodiments, A is $CH_2F$.

In certain embodiments, when $R^4$ is methyl and $R^3$ is hydrogen, $R^2$ is not methyl, chlorine, or hydroxyl.

In certain embodiments, A is

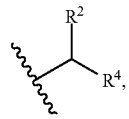

wherein $R^4$ is hydrogen, halogen, $C_{1-4}$ alkyl, or $C_{1-4}$haloalkyl. In certain embodiments, A is

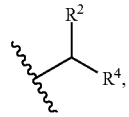

wherein $R^4$ is hydrogen, fluorine, chlorine, or $C_{1-4}$ alkyl.

In certain embodiments, A is

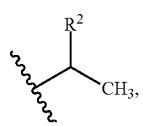

wherein $R^2$ is halogen, —$OR^A$, or —$SR^A$.

In certain embodiments, A is

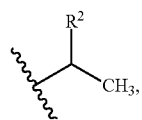

wherein $R^2$ is halogen, —$OR^A$, or —$SR^A$; and $R^A$ is substituted or unsubstituted aryl, substituted or unsubstituted heteroaryl, substituted or unsubstituted alkyl, or hydrogen.

In certain embodiments, A is

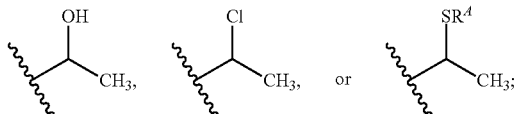

and $R^A$ is substituted or unsubstituted aryl, or substituted or unsubstituted alkyl.

In certain embodiments, A is

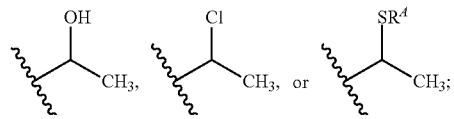

and $R^A$ is substituted or unsubstituted aryl.

In certain embodiments, A is

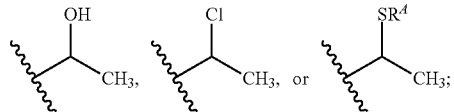

and $R^A$ is substituted aryl.

In certain embodiments, A is

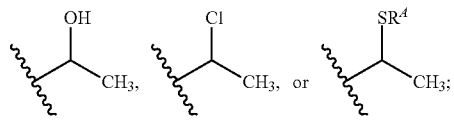

and $R^A$ is substituted phenyl.

In certain embodiments, A is of the formula:

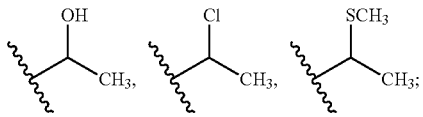

-continued

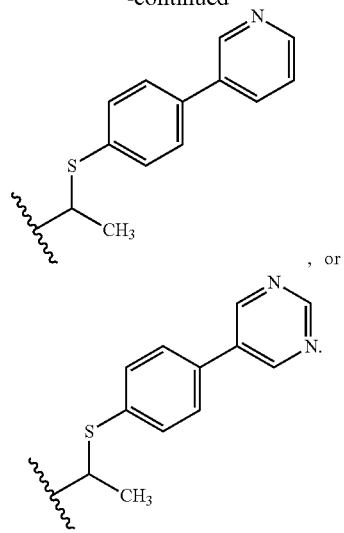

, or

In certain embodiments, A is

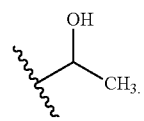

In certain embodiments, A is

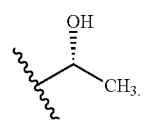

In certain embodiments, A is

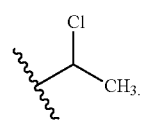

In certain embodiments, A is

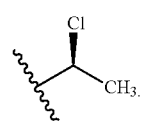 [SMILES: *[C@H](C)Cl]

In certain embodiments, A is

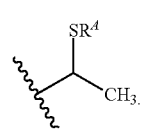

In certain embodiments, A is

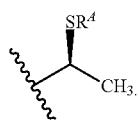

In certain embodiments, A is

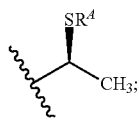

and $R^A$ is substituted or unsubstituted aryl, or substituted or unsubstituted alkyl.

In certain embodiments, A is of the formula:

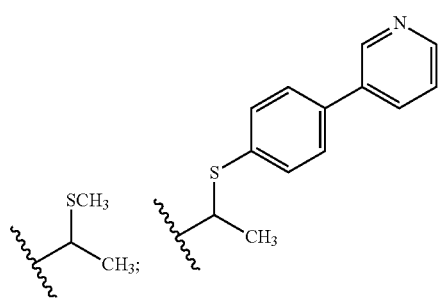

, or

In certain embodiments, A is of the formula:

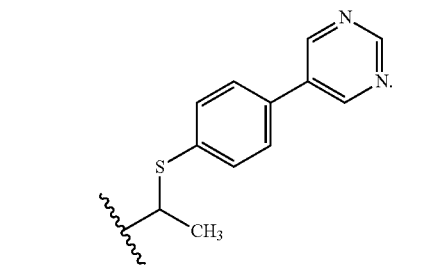

, or

In certain embodiments, A is of the formula:

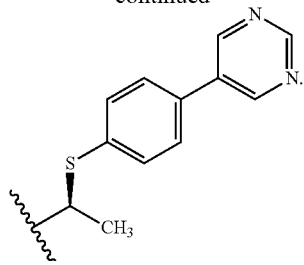

In certain embodiments, A is of the formula:

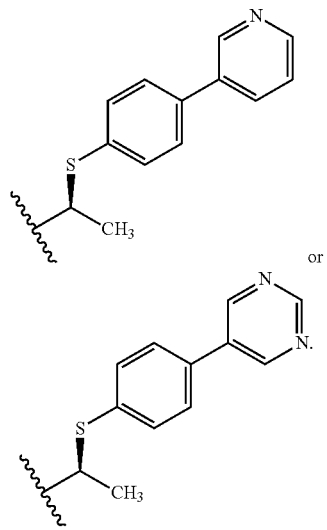

or

In certain embodiments, A is of the formula:

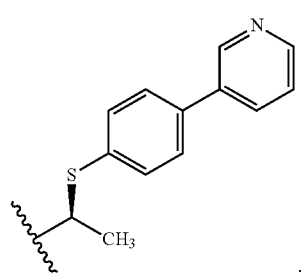 [SMILES: *[C@H](C)Sc1ccc(-c2cccnc2)cc1]

.

In certain embodiments, A is of the formula:

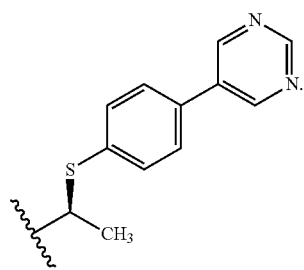 [SMILES: *[C@H](C)Sc1ccc(-c2cncnc2)cc1]

In certain embodiments, A is
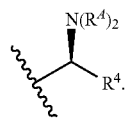
In certain embodiments, A is
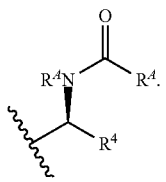
In certain embodiments, A is
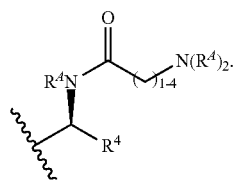
In certain embodiments, A is of the formula:
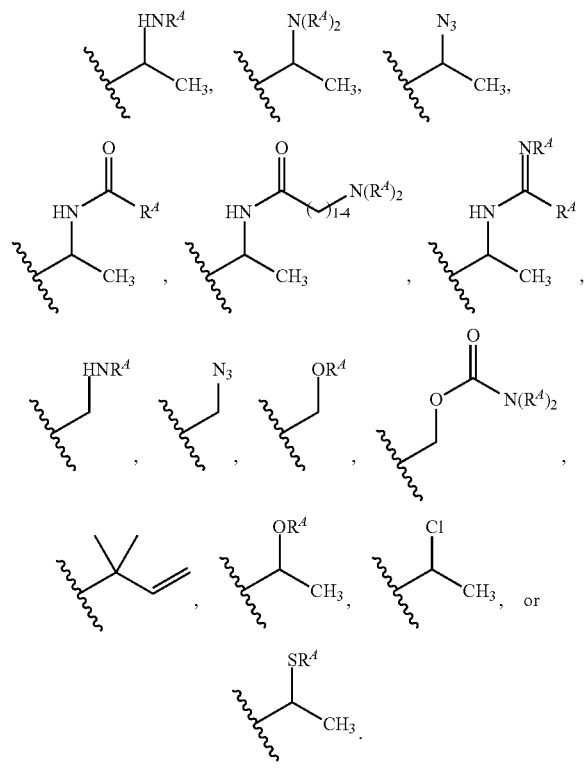
In certain embodiments, A is of the formula:
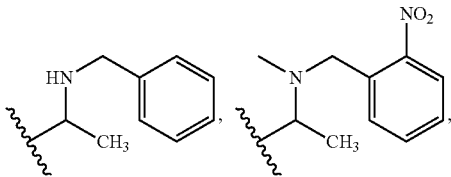
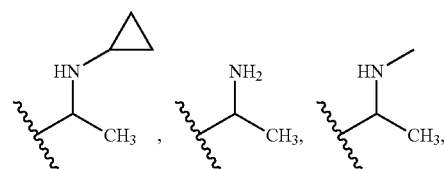
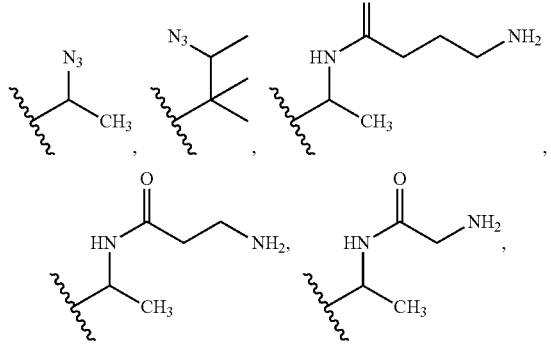
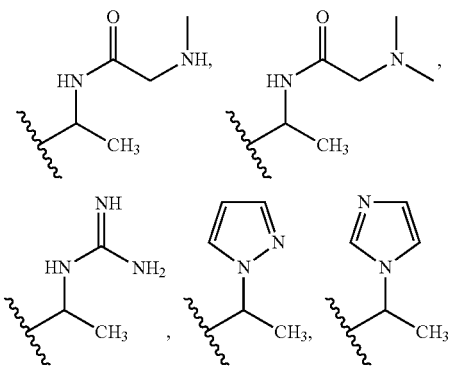
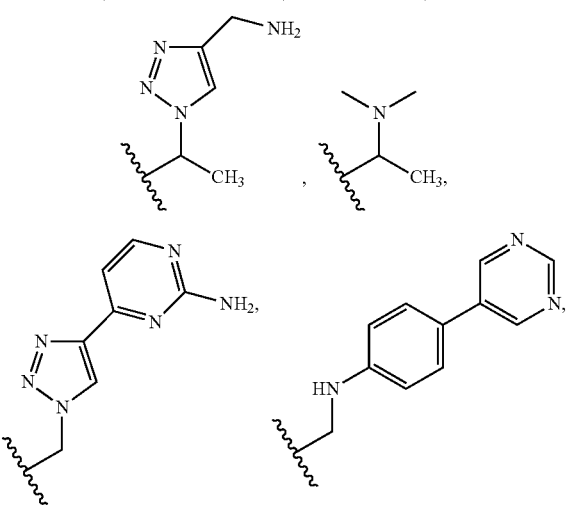

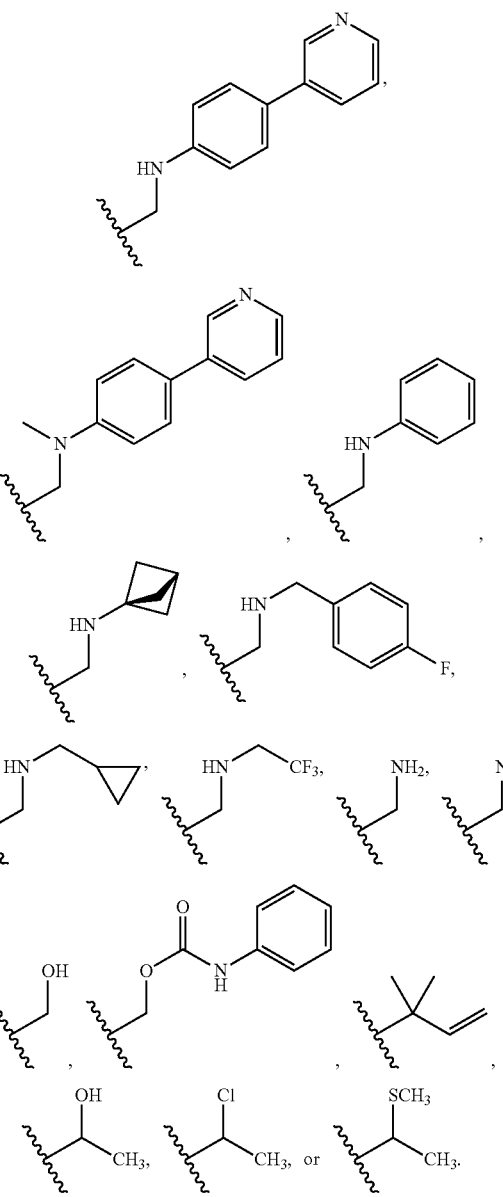
In certain embodiments, A is of the formula:
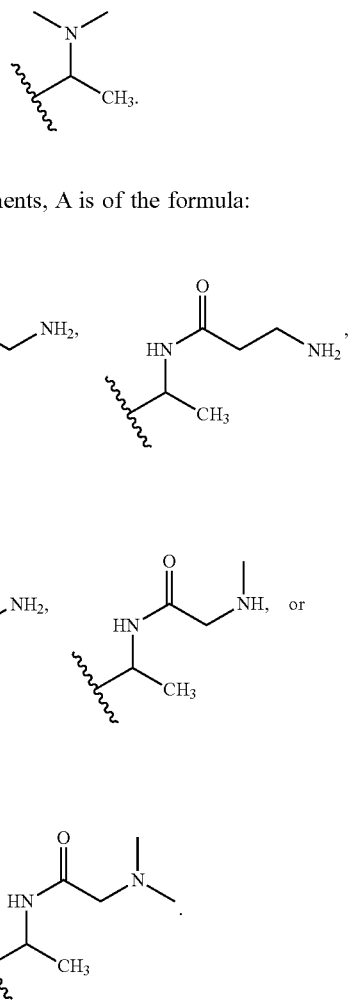
In certain embodiments, A is of the formula:
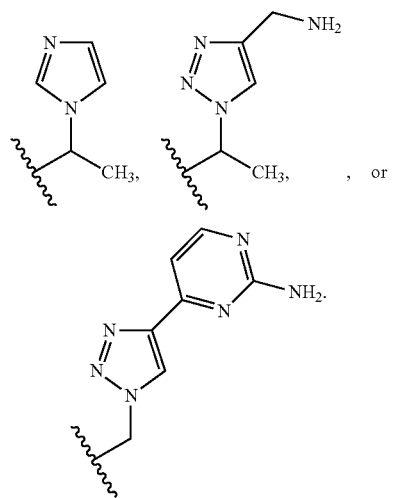

In certain embodiments, A is of the formula:

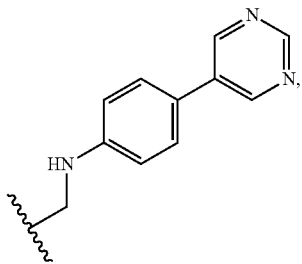

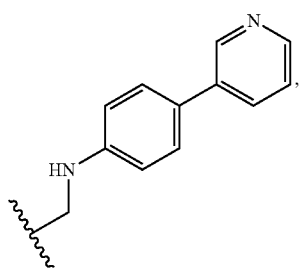

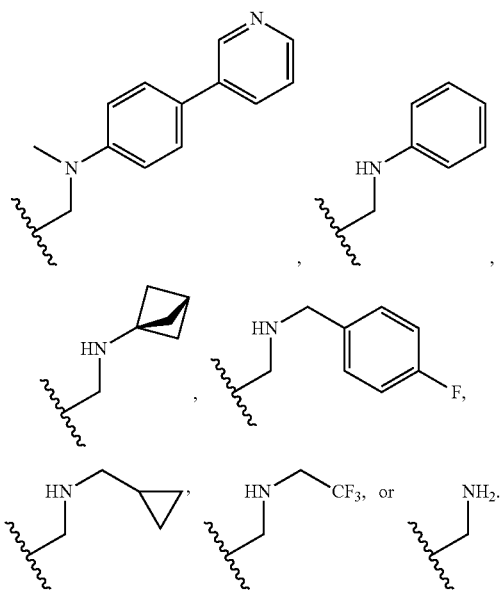

In certain embodiments, A is of the formula:

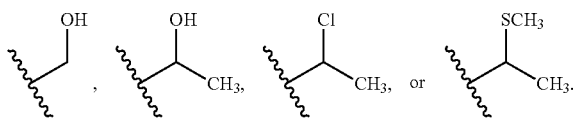

In certain embodiments, A is of the formula:

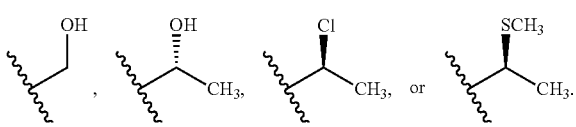

In certain embodiments, A is

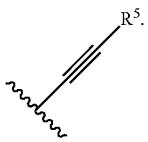

In certain embodiments, $R^5$ is hydrogen, halogen, substituted or unsubstituted alkyl, substituted or unsubstituted aryl, or substituted or unsubstituted heteroaryl. In certain embodiments, $R^5$ is substituted or unsubstituted aryl, or substituted or unsubstituted heteroaryl. In certain embodiments, $R^5$ is substituted or unsubstituted aryl. In certain embodiments, $R^5$ is substituted or unsubstituted phenyl. In certain embodiments, $R^5$ is substituted or unsubstituted heteroaryl. In certain embodiments, $R^5$ is substituted or unsubstituted pyrazolyl, imidazolyl, triazolyl, tetrazolyl, pyrrolyl, oxazolyl, isoxazolyl, thienyl, furanyl, pyridyl, pyrimidinyl, pyrazinyl, pyridazinyl, or triazolinyl. In certain embodiments, $R^5$ is hydrogen.

In certain embodiments, A is

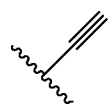

In certain embodiments, A is

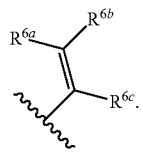

In certain embodiments, $R^{6a}$, $R^{6b}$, and $R^{6c}$ are each independently hydrogen, halogen, substituted or unsubstituted alkyl, substituted or unsubstituted aryl, substituted or unsubstituted heteroaryl, or substituted or unsubstituted acyl. In certain embodiments, $R^{6a}$, $R^{6b}$, and $R^{6c}$ are each hydrogen.

In certain embodiments, A is

In certain embodiments, A is substituted or unsubstituted carbocyclyl, or substituted or unsubstituted heterocyclyl. In certain embodiments, A is substituted or unsubstituted carbocyclyl. In certain embodiments, A is substituted or unsubstituted cycloalkyl or cycloalkenyl. In certain embodiments, A is substituted or unsubstituted $C_{3-6}$ cycloalkyl or $C_{3-6}$ cycloalkenyl. In certain embodiments, A is substituted or unsubstituted $C_{3-6}$ cycloalkyl. In certain embodiments, A is substituted or unsubstituted $C_{3-6}$ cycloalkenyl. In certain embodiments, A is substituted or unsubstituted heterocyclyl. In certain embodiments, A is substituted or unsubstituted 4-7 membered heterocyclyl. In certain embodiments, A is substituted or unsubstituted 5-6 membered heterocyclyl. In certain embodiments, A is substituted or unsubstituted dihydropyrrolyl or tetrahydropyridyl.

In certain embodiments, A is of the formula:

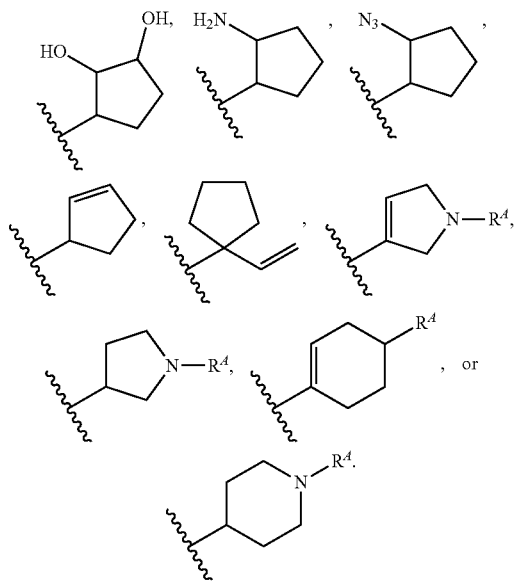

Group R¹

As generally defined herein, R¹ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, substituted or unsubstituted heteroaliphatic, —OR$^A$, —N(R$^A$)$_2$, or —SR$^A$.

In certain embodiments, R¹ is substituted or unsubstituted alkyl, substituted or unsubstituted alkenyl, substituted or unsubstituted carbocyclyl, substituted or unsubstituted heterocyclyl, substituted or unsubstituted heteroaryl, substituted or unsubstituted heteroaralkyl, substituted or unsubstituted heteroalkyl, —OR$^A$, —N(R$^A$)$_2$, or —SR$^A$.

In certain embodiments, R¹ is substituted or unsubstituted alkyl, substituted or unsubstituted carbocyclyl, substituted or unsubstituted heteroaralkyl, or —SR$^A$.

In certain embodiments, R¹ is substituted or unsubstituted alkyl, substituted or unsubstituted carbocyclyl, or —SR$^A$.

In certain embodiments, R¹ is

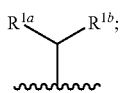

wherein R$^{1a}$ and R$^{1b}$ are each independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —OR$^A$, —N$_3$, —N(R$^A$)$_2$, —SR$^A$, —CN, —SCN, —C(=NR$^A$)R$^A$, —C(=NR$^A$)OR$^A$, —C(=NR$^A$)N(R$^A$)$_2$, —C(=O)R$^A$, —C(=O)OR$^A$, —C(=O)N(R$^A$)$_2$, —NO$_2$, —NR$^A$C(=O)R$^A$, —NR$^A$C(=O)OR$^A$, —NR$^A$C(=O)N(R$^A$)$_2$, —NR$^A$C(=NR$^A$)N(R$^A$)$_2$, —OC(=O)R$^A$, —OC(=O)OR$^A$, —OC(=O)N(R$^A$)$_2$, —NR$^A$S(O)$_2$R$^A$, —OS(O)$_2$R$^A$, or —S(O)$_2$R$^A$, or R$^{1a}$ and R$^{1b}$ are joined to form a substituted or unsubstituted heterocyclic ring, or a substituted or unsubstituted carbocyclic ring.

In certain embodiments, R$^{1a}$ and R$^{1b}$ are each independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —OR$^A$, —OS(O)$_2$R$^A$, —N$_3$, or —N(R$^A$)$_2$, or R$^{1a}$ and R$^{1b}$ are joined to form a substituted or unsubstituted carbocyclic ring.

In certain embodiments, R$^{1a}$ and R$^{1b}$ are each independently hydrogen, halogen, substituted or unsubstituted alkyl, substituted or unsubstituted heteroaryl, or —N(R$^A$)$_2$; or R$^{1a}$ and R$^{1b}$ are joined to form a substituted or unsubstituted carbocyclic ring.

In certain embodiments, R$^{1a}$ and R$^{1b}$ together with the carbon to which they are attached form an optionally substituted cycloalkyl or optionally substituted heterocyclyl ring.

In certain embodiments, R$^{1a}$ and R$^{1b}$ together with the carbon to which they are attached form an optionally substituted cycloalkyl ring. In certain embodiments, R$^{1a}$ and R$^{1b}$ together with the carbon to which they are attached form an optionally substituted C$_{3-6}$ cycloalkyl ring. In certain embodiments, R$^{1a}$ and R$^{1b}$ together with the carbon to which they are attached form an optionally substituted C$_{3-5}$ cycloalkyl ring. In certain embodiments, R$^{1a}$ and R$^{1b}$ together with the carbon to which they are attached form an optionally substituted C$_{3-4}$ cycloalkyl ring. In certain embodiments, R$^{1a}$ and R$^{1b}$ together with the carbon to which they are attached form an optionally substituted cyclopentyl ring. In certain embodiments, R$^{1a}$ and R$^{1b}$ together with the carbon to which they are attached form an optionally substituted cyclobutyl ring. In certain embodiments, R$^{1a}$ and R$^{1b}$ together with the carbon to which they are attached form an optionally substituted cyclopropyl ring. In certain embodiments, R$^{1a}$ and R$^{1b}$ together with the carbon to which they are attached form an unsubstituted cyclopropyl ring.

In certain embodiments, R$^{1a}$ and R$^{1b}$ together with the carbon to which they are attached form an optionally substituted heterocyclyl ring. In certain embodiments, R$^{1a}$ and R$^{1b}$ together with the carbon to which they are attached form an optionally substituted 3-7 membered heterocyclyl ring. In certain embodiments, R$^{1a}$ and R$^{1b}$ together with the carbon to which they are attached form an optionally substituted 4-7 membered heterocyclyl ring. In certain embodiments, R$^{1a}$ and R$^{1b}$ together with the carbon to which they are attached form an optionally substituted 4-6 membered heterocyclyl ring. In certain embodiments, R$^{1a}$ and R$^{1b}$ together with the carbon to which they are attached form an optionally substituted 4-6 membered heterocyclyl ring with at least one nitrogen atom in the ring. In certain embodiments, R$^{1a}$ and R$^{1b}$ together with the carbon to which they are attached form an optionally substituted azetidine, pyrrolidine, or piperidine. In certain embodiments, R$^{1a}$ and R$^{1b}$ together with the carbon to which they are attached form a substituted azetidine, pyrrolidine, or piperidine.

In certain embodiments, R¹ is of the formula:

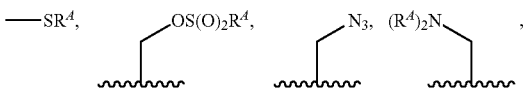

-continued

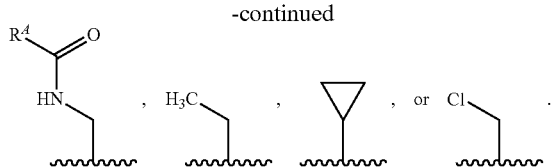

In certain embodiments, $R^1$ is of the formula:

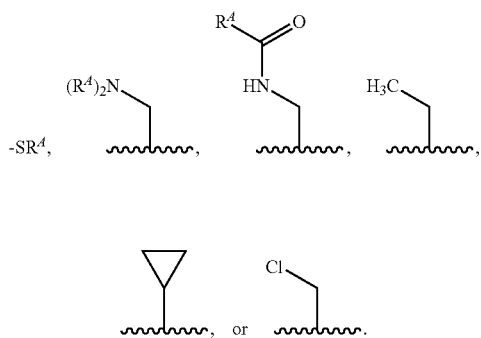

In certain embodiments, $R^1$ is of the formula:

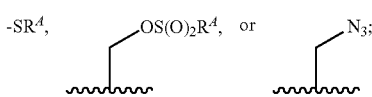

and $R^A$ is substituted or unsubstituted aryl or substituted or unsubstituted alkyl.

In certain embodiments, $R^1$ is —$SR^A$. In certain embodiments, $R^1$ is —$SR^A$; and $R^A$ is a substituted or unsubstituted alkyl. In certain embodiments, $R^1$ is —$SR^A$; and $R^A$ is an unsubstituted alkyl. In certain embodiments, $R^1$ is —$SR^A$; and $R^A$ is an unsubstituted $C_{1-4}$ alkyl. In certain embodiments, $R^1$ is —$SCH_3$.

Group $R^7$

As generally defined herein, $R^7$ is hydrogen or unsubstituted alkyl; or A and $R^7$ are joined to form a substituted or unsubstituted heterocyclic ring.

In certain embodiments, $R^7$ is hydrogen or unsubstituted alkyl. In certain embodiments, $R^7$ is unsubstituted alkyl. In certain embodiments, $R^7$ is unsubstituted $C_{1-6}$ alkyl. In certain embodiments, $R^7$ is unsubstituted $C_{1-4}$ alkyl. In certain embodiments, $R^7$ is unsubstituted $C_{1-3}$ alkyl. In certain embodiments, $R^7$ is unsubstituted $C_{1-2}$ alkyl. In certain embodiments, $R^7$ is ethyl. In certain embodiments, $R^7$ is methyl. In certain embodiments, $R^7$ is hydrogen.

In certain embodiments, A and $R^7$ are joined to form a substituted or unsubstituted heterocyclic ring. In certain embodiments, A and $R^7$ are joined to form a substituted or unsubstituted pyrrolidine, piperidine, piperazine, azepine, or azepane. In certain embodiments, A and $R^7$ are joined to form a substituted or unsubstituted pyrrolidine.

In certain embodiments, A and $R^7$ are joined to form

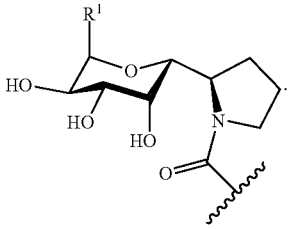

Group $R^8$

As generally defined herein, $R^8$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaliphatic, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —S(O)$_2$$R^A$, or a nitrogen protecting group.

In certain embodiments, $R^8$ is hydrogen, substituted or unsubstituted alkyl, or —C(=O)$R^A$. In certain embodiments, $R^8$ is hydrogen or substituted or unsubstituted alkyl. In certain embodiments, $R^8$ is hydrogen or unsubstituted alkyl. In certain embodiments, $R^8$ is hydrogen or unsubstituted $C_{1-6}$ alkyl. In certain embodiments, $R^8$ is hydrogen or unsubstituted $C_{1-4}$ alkyl. In certain embodiments, $R^8$ is hydrogen or unsubstituted $C_{1-3}$ alkyl. In certain embodiments, $R^8$ is hydrogen or unsubstituted $C_{1-2}$ alkyl. In certain embodiments, $R^8$ is hydrogen or ethyl. In certain embodiments, $R^8$ is hydrogen or methyl. In certain embodiments, $R^8$ is hydrogen.

In certain embodiments, $R^8$ is unsubstituted $C_{1-6}$ alkyl. In certain embodiments, $R^8$ is unsubstituted $C_{1-4}$ alkyl. In certain embodiments, $R^8$ is unsubstituted $C_{1-3}$ alkyl. In certain embodiments, $R^8$ is unsubstituted $C_{1-2}$ alkyl. In certain embodiments, $R^8$ is ethyl. In certain embodiments, $R^8$ is methyl.

Group $R^9$

As generally defined herein, each occurrence of $R^9$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —$OR^A$, —N($R^A$)$_2$, —$SR^A$, —CN, —SCN, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —NO$_2$, —$NR^A$C(=O)$R^A$, —$NR^A$C(=O)$OR^A$, —$NR^A$C(=O)N($R^A$)$_2$, —$NR^A$C(=$NR^A$)N($R^A$)$_2$, —OC(=O)$R^A$, —OC(=O)$OR^A$, —OC(=O)N($R^A$)$_2$, —$NR^A$S(O)$_2$$R^A$, —OS(O)$_2$$R^A$, or —S(O)$_2$$R^A$.

In certain embodiments, $R^9$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroalkyl.

In certain embodiments, $R^9$ is substituted or unsubstituted alkyl. In certain embodiments, $R^9$ is substituted or unsubstituted $C_{1-6}$ alkyl. In certain embodiments, $R^9$ is substituted or unsubstituted $C_{1-4}$ alkyl. In certain embodiments, $R^9$ is substituted or unsubstituted $C_{1-3}$ alkyl. In certain embodiments, $R^9$ is substituted or unsubstituted $C_{1-2}$ alkyl. In certain embodiments, $R^9$ is substituted or unsubstituted n-propyl. In certain embodiments, $R^9$ is substituted or unsubstituted ethyl. In certain embodiments, $R^8$ is substituted or unsubstituted methyl.

In certain embodiments, $R^9$ is unsubstituted alkyl. In certain embodiments, $R^9$ is unsubstituted $C_{1-6}$ alkyl. In certain embodiments, $R^9$ is unsubstituted $C_{1-4}$ alkyl. In certain embodiments, $R^9$ is unsubstituted $C_{1-3}$ alkyl. In certain embodiments, $R^9$ is unsubstituted $C_{1-2}$ alkyl. In certain embodiments, $R^9$ is unsubstituted n-propyl. In certain embodiments, $R^9$ is unsubstituted ethyl. In certain embodiments, $R^8$ is unsubstituted methyl.

In certain embodiments, $R^9$ is n-propyl.

Embodiments of Formula (I)

In certain embodiments, n is 1. In certain embodiments, n is 2. In certain embodiments, p is 1. In certain embodiments, p is 2, In certain embodiments, p is 3. In certain embodiments, n is 1 or 2; and p is 1. In certain embodiments, n is 1; and p is 1.

In certain embodiments, the compound of Formula (I) is a compound of Formula (I-a):

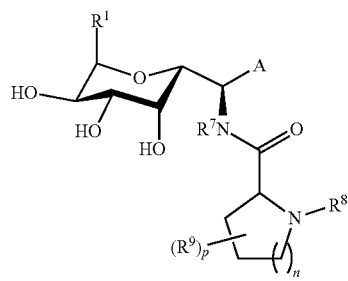

(I-a)

or a pharmaceutically acceptable salt thereof, wherein A, $R^1$, $R^7$, $R^8$, $R^9$, n, and p are as defined herein.

In certain embodiments of the compound of Formula (I-a), $R^1$ is —$SR^A$; $R^7$ is hydrogen; $R^8$ is hydrogen or methyl; and $R^9$ is substituted or unsubstituted $C_{1-6}$ alkyl. In certain embodiments of the compound of Formula (I-a), $R^1$ is —$SCH_3$; $R^7$ is hydrogen; $R^8$ is hydrogen or methyl; and $R^9$ is substituted or unsubstituted $C_{1-6}$ alkyl. In certain embodiments of the compound of Formula (I-a), $R^1$ is —$SCH_3$; $R^7$ is hydrogen; $R^8$ is hydrogen; and $R^9$ is substituted or unsubstituted $C_{1-6}$ alkyl. In certain embodiments of the compound of Formula (I-a), $R^1$ is —$SCH_3$; $R^7$ is hydrogen; $R^8$ is methyl; and $R^9$ is substituted or unsubstituted $C_{1-6}$ alkyl.

In certain embodiments, the compound of Formula (I) is a compound of Formula (I-b):

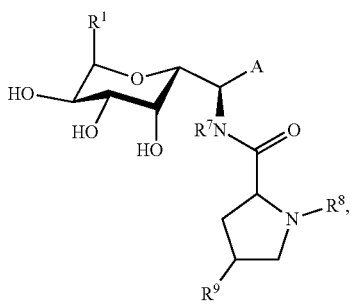

(I-b)

or a pharmaceutically acceptable salt thereof, wherein A, $R^1$, $R^7$, $R^8$, and $R^9$ are as defined herein.

In certain embodiments of the compound of Formula (I-b), $R^1$ is —$SR^A$; $R^7$ is hydrogen; $R^8$ is hydrogen or methyl; and $R^9$ is substituted or unsubstituted $C_{1-6}$ alkyl. In certain embodiments of the compound of Formula (I-b), $R^1$ is —$SCH_3$; $R^7$ is hydrogen; $R^8$ is hydrogen or methyl; and $R^9$ is substituted or unsubstituted $C_{1-6}$ alkyl. In certain embodiments of the compound of Formula (I-b), $R^1$ is —$SCH_3$; $R^7$ is hydrogen; $R^8$ is hydrogen; and $R^9$ is substituted or unsubstituted $C_{1-6}$ alkyl. In certain embodiments of the compound of Formula (I-b), $R^1$ is —$SCH_3$; $R^7$ is hydrogen; $R^8$ is methyl; and $R^9$ is substituted or unsubstituted $C_{1-6}$ alkyl.

In certain embodiments, the compound of Formula (I) is a compound of Formula (I-c):

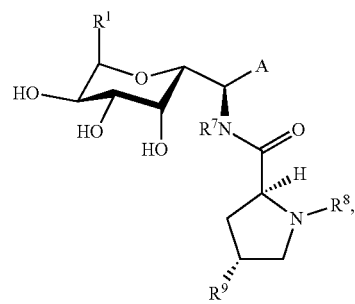

(I-c)

or a pharmaceutically acceptable salt thereof, wherein A, $R^1$, $R^7$, $R^8$, and $R^9$ are as defined herein.

In certain embodiments of the compound of Formula (I-c), $R^1$ is —$SR^A$; $R^7$ is hydrogen; $R^8$ is hydrogen or methyl; and $R^9$ is substituted or unsubstituted $C_{1-6}$ alkyl. In certain embodiments of the compound of Formula (I-c), $R^1$ is —$SCH_3$; $R^7$ is hydrogen; $R^8$ is hydrogen or methyl; and $R^9$ is substituted or unsubstituted $C_{1-6}$ alkyl. In certain embodiments of the compound of Formula (I-c), $R^1$ is —$SCH_3$; $R^7$ is hydrogen; $R^8$ is hydrogen; and $R^9$ is substituted or unsubstituted $C_{1-6}$ alkyl. In certain embodiments of the compound of Formula (I-c), $R^1$ is —$SCH_3$; $R^7$ is hydrogen; $R^8$ is methyl; and $R^9$ is substituted or unsubstituted $C_{1-6}$ alkyl.

In certain embodiments, the compound of Formula (I) is a compound of Formula (I-d):

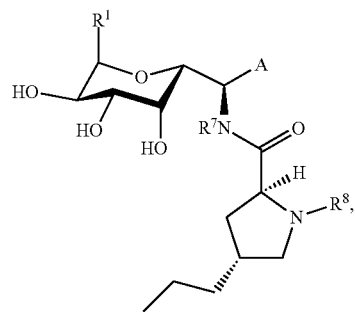

(I-d)

or a pharmaceutically acceptable salt thereof, wherein A, $R^1$, $R^7$, and $R^8$ are as defined herein.

In certain embodiments of the compound of Formula (I-d), $R^1$ is —$SR^A$; $R^7$ is hydrogen; and $R^8$ is hydrogen or methyl. In certain embodiments of the compound of Formula (I-d), $R^1$ is —$SCH_3$; $R^7$ is hydrogen; and $R^8$ is hydrogen or methyl. In certain embodiments of the compound of Formula (I-d), $R^1$ is —$SCH_3$; $R^7$ is hydrogen; and $R^8$ is hydrogen. In certain embodiments of the compound of Formula (I-d), $R^1$ is —$SCH_3$; $R^7$ is hydrogen; and $R^8$ is methyl.

In certain embodiments, the compound of Formula (I) is a compound of Formula (II):

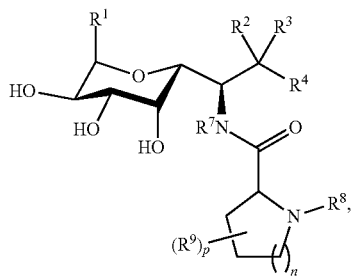

(II)

or a pharmaceutically acceptable salt thereof, wherein $R^1$, $R^2$, $R^3$, $R^4$, $R^7$, $R^8$, $R^9$, p, and n are as defined herein.

In certain embodiments of the compound of Formula (II), $R^1$ is —$SR^A$; $R^7$ is hydrogen; $R^8$ is hydrogen or methyl; and $R^9$ is substituted or unsubstituted $C_{1-6}$ alkyl. In certain embodiments of the compound of Formula (II), $R^1$ is —$SCH_3$; $R^7$ is hydrogen; $R^8$ is hydrogen or methyl; and $R^9$ is substituted or unsubstituted $C_{1-6}$ alkyl. In certain embodiments of the compound of Formula (II), $R^1$ is —$SCH_3$; $R^7$ is hydrogen; $R^8$ is hydrogen; and $R^9$ is substituted or unsubstituted $C_{1-6}$ alkyl. In certain embodiments of the compound of Formula (II), $R^1$ is —$SCH_3$; $R^7$ is hydrogen; $R^8$ is methyl; and $R^9$ is substituted or unsubstituted $C_{1-6}$ alkyl.

In certain embodiments, the compound of Formula (I) is a compound of Formula (II-a):

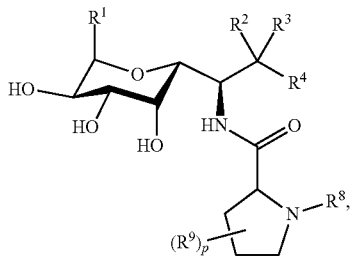

(II-a)

or a pharmaceutically acceptable salt thereof, wherein $R^1$, $R^2$, $R^3$, $R^4$, $R^8$, $R^9$, and p are as defined herein.

In certain embodiments of the compound of Formula (II-a), $R^1$ is —$SR^A$; $R^8$ is hydrogen or methyl; and $R^9$ is substituted or unsubstituted $C_{1-6}$ alkyl. In certain embodiments of the compound of Formula (II-a), $R^1$ is —$SCH_3$; $R^8$ is hydrogen or methyl; and $R^9$ is substituted or unsubstituted $C_{1-6}$ alkyl. In certain embodiments of the compound of Formula (II-a), $R^1$ is —$SCH_3$; $R^8$ is hydrogen; and $R^9$ is substituted or unsubstituted $C_{1-6}$ alkyl. In certain embodiments of the compound of Formula (II-a), $R^1$ is —$SCH_3$; $R^8$ is methyl; and $R^9$ is substituted or unsubstituted $C_{1-6}$ alkyl.

In certain embodiments, the compound of Formula (I) is a compound of Formula (II-b):

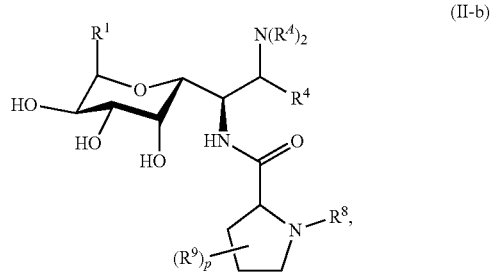

(II-b)

or a pharmaceutically acceptable salt thereof, wherein $R^1$, $R^4$, $R^A$, $R^8$, $R^9$, and p are as defined herein.

In certain embodiments of the compound of Formula (I-b), $R^1$ is —$SR^A$; $R^8$ is hydrogen or methyl; and $R^9$ is substituted or unsubstituted $C_{1-6}$ alkyl. In certain embodiments of the compound of Formula (II-b), $R^1$ is —$SCH_3$; $R^8$ is hydrogen or methyl; and $R^9$ is substituted or unsubstituted $C_{1-6}$ alkyl. In certain embodiments of the compound of Formula (II-b), $R^1$ is —$SCH_3$; $R^8$ is hydrogen; and $R^9$ is substituted or unsubstituted $C_{1-6}$ alkyl. In certain embodiments of the compound of Formula (II-b), $R^1$ is —$SCH_3$; $R^8$ is methyl; and $R^9$ is substituted or unsubstituted $C_{1-6}$ alkyl.

In certain embodiments, the compound of Formula (I) is a compound of Formula (II-c):

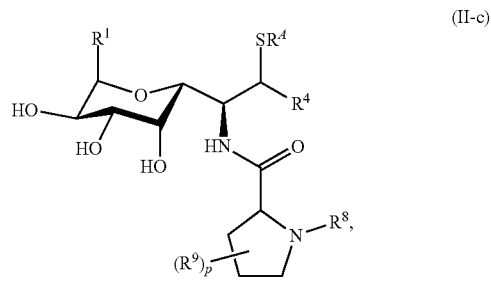

(II-c)

or a pharmaceutically acceptable salt thereof, wherein $R^1$, $R^4$, $R^A$, $R^8$, $R^9$, and p are as defined herein.

In certain embodiments of the compound of Formula (II-c), $R^1$ is —$SR^A$; $R^8$ is hydrogen or methyl; and $R^9$ is substituted or unsubstituted $C_{1-6}$ alkyl. In certain embodiments of the compound of Formula (II-c), $R^1$ is —$SCH_3$; $R^8$ is hydrogen or methyl; and $R^9$ is substituted or unsubstituted $C_{1-6}$ alkyl. In certain embodiments of the compound of Formula (II-c), $R^1$ is —$SCH_3$; $R^8$ is hydrogen; and $R^9$ is substituted or unsubstituted $C_{1-6}$ alkyl. In certain embodiments of the compound of Formula (II-c), $R^1$ is —$SCH_3$; $R^8$ is methyl; and $R^9$ is substituted or unsubstituted $C_{1-6}$ alkyl.

In certain embodiments, the compound of Formula (I) is a compound of Formula (II-d):

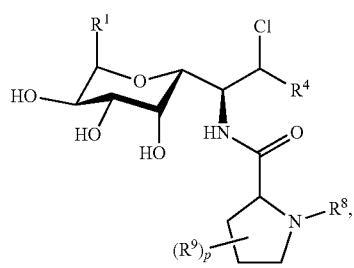

(II-d)

or a pharmaceutically acceptable salt thereof, wherein $R^1$, $R^4$, $R^8$, $R^9$, and p are as defined herein.

In certain embodiments of the compound of Formula (II-d), $R^1$ is —$SR^4$; $R^8$ is hydrogen or methyl; and $R^9$ is substituted or unsubstituted $C_{1-6}$ alkyl. In certain embodiments of the compound of Formula (II-d), $R^1$ is —$SCH_3$; $R^8$ is hydrogen or methyl; and $R^9$ is substituted or unsubstituted $C_{1-6}$ alkyl. In certain embodiments of the compound of Formula (II-d), $R^1$ is —$SCH_3$; $R^8$ is hydrogen; and $R^9$ is substituted or unsubstituted $C_{1-6}$ alkyl. In certain embodiments of the compound of Formula (II-d), $R^1$ is —$SCH_3$; $R^8$ is methyl; and $R^9$ is substituted or unsubstituted $C_{1-6}$ alkyl.

In certain embodiments, the compound of Formula (I) is a compound of Formula (II-e):

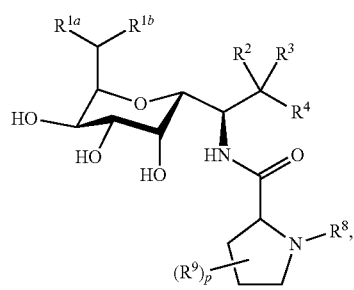

(II-e)

or a pharmaceutically acceptable salt thereof, wherein $R^{1a}$, $R^{1b}$, $R^2$, $R^3$, $R^4$, $R^8$, $R^9$, and p are as defined herein.

In certain embodiments, of the compound of Formula (II-e), $R^8$ is hydrogen or methyl; and $R^9$ is substituted or unsubstituted $C_{1-6}$ alkyl. In certain embodiments of the compound of Formula (II-e), $R^8$ is hydrogen; and $R^9$ is substituted or unsubstituted $C_{1-6}$ alkyl. In certain embodiments of the compound of Formula (II-e), $R^8$ is methyl; and $R^9$ is substituted or unsubstituted $C_{1-6}$ alkyl.

In certain embodiments, the compound of Formula (I) is a compound of Formula (II-f):

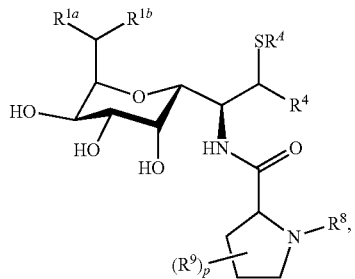

(II-f)

or a pharmaceutically acceptable salt thereof, wherein $R^{1a}$, $R^{1b}$, $R^4$, $R^4$, $R^8$, $R^9$, and p are as defined herein.

In certain embodiments, of the compound of Formula (II-f), $R^8$ is hydrogen or methyl; and $R^9$ is substituted or unsubstituted $C_{1-6}$ alkyl. In certain embodiments of the compound of Formula (II-f), $R^8$ is hydrogen; and $R^9$ is substituted or unsubstituted $C_{1-6}$ alkyl. In certain embodiments of the compound of Formula (II-f), $R^8$ is methyl; and $R^9$ is substituted or unsubstituted $C_{1-6}$ alkyl.

In certain embodiments, the compound of Formula (I) is a compound of Formula (II-g):

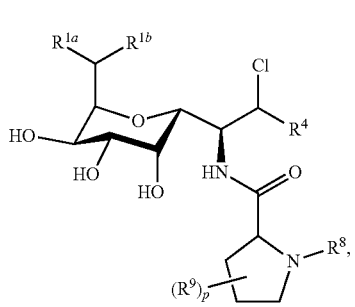

(II-g)

or a pharmaceutically acceptable salt thereof, wherein $R^{1a}$, $R^{1b}$, $R^4$, $R^8$, $R^9$, and p are as defined herein.

In certain embodiments of the compound of Formula (II-g), $R^8$ is hydrogen or methyl; and $R^9$ is substituted or unsubstituted $C_{1-6}$ alkyl. In certain embodiments of the compound of Formula (II-g), $R^8$ is hydrogen; and $R^9$ is substituted or unsubstituted $C_{1-6}$ alkyl. In certain embodiments of the compound of Formula (II-g), $R^8$ is methyl; and $R^9$ is substituted or unsubstituted $C_{1-6}$ alkyl.

In certain embodiments, the compound of Formula (I) is a compound of Formula (III):

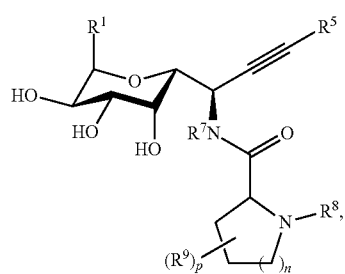

(III)

or a pharmaceutically acceptable salt thereof, wherein $R^1$, $R^5$, $R^7$, $R^8$, $R^9$, n, and p are as defined herein.

In certain embodiments of the compound of Formula (III), $R^1$ is —$SR^A$; $R^7$ is hydrogen; $R^8$ is hydrogen or methyl; and $R^9$ is substituted or unsubstituted $C_{1-6}$ alkyl. In certain embodiments of the compound of Formula (III), $R^1$ is —$SCH_3$; $R^7$ is hydrogen; $R^8$ is hydrogen or methyl; and $R^9$ is substituted or unsubstituted $C_{1-6}$ alkyl. In certain embodiments of the compound of Formula (III), $R^1$ is —$SCH_3$; $R^7$ is hydrogen; $R^8$ is hydrogen; and $R^9$ is substituted or unsubstituted $C_{1-6}$ alkyl. In certain embodiments of the compound of Formula (III), $R^1$ is —$SCH_3$; $R^7$ is hydrogen; $R^8$ is methyl; and $R^9$ is substituted or unsubstituted $C_{1-6}$ alkyl.

In certain embodiments, the compound of Formula (I) is a compound of Formula (III-a):

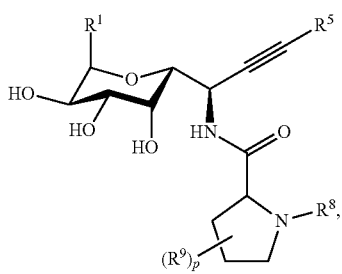

(III-a)

or a pharmaceutically acceptable salt thereof, wherein $R^1$, $R^5$, $R^8$, $R^9$, n, and p are as defined herein.

In certain embodiments of the compound of Formula (III-a), $R^1$ is —$SR^A$; $R^8$ is hydrogen or methyl; and $R^9$ is substituted or unsubstituted $C_{1-6}$ alkyl. In certain embodiments of the compound of Formula (III-a), $R^1$ is —$SCH_3$; $R^8$ is hydrogen or methyl; and $R^9$ is substituted or unsubstituted $C_{1-6}$ alkyl. In certain embodiments of the compound of Formula (III-a), $R^1$ is —$SCH_3$; $R^8$ is hydrogen; and $R^9$ is substituted or unsubstituted $C_{1-6}$ alkyl. In certain embodiments, of the compound of Formula (III-a), $R^1$ is —$SCH_3$; $R^8$ is methyl; and $R^9$ is substituted or unsubstituted $C_{1-6}$ alkyl.

In certain embodiments, the compound of Formula (I) is a compound of Formula (IV):

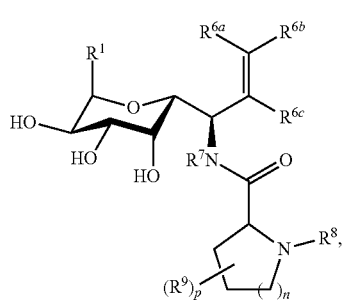

(IV)

or a pharmaceutically acceptable salt thereof, wherein $R^1$, $R^{6a}$, $R^{6b}$, $R^{6c}$, $R^7$, $R^8$, $R^9$, n, and p are as defined herein.

In certain embodiments, of the compound of Formula (IV), $R^1$ is —$SR^A$; $R^7$ is hydrogen; $R^8$ is hydrogen or methyl; and $R^9$ is substituted or unsubstituted $C_{1-6}$ alkyl. In certain embodiments, of the compound of Formula (IV), $R^1$ is —$SCH_3$; $R^8$ is hydrogen or methyl; and $R^9$ is substituted or unsubstituted $C_{1-6}$ alkyl. In certain embodiments, of the compound of Formula (IV), $R^1$ is —$SCH_3$; $R^7$ is hydrogen; $R^8$ is hydrogen; and $R^9$ is substituted or unsubstituted $C_{1-6}$ alkyl. In certain embodiments, of the compound of Formula (IV), $R^1$ is —$SCH_3$; $R^7$ is hydrogen; $R^8$ is methyl; and $R^9$ is substituted or unsubstituted $C_{1-6}$ alkyl.

In certain embodiments, the compound of Formula (I) is a compound of Formula (IV-a):

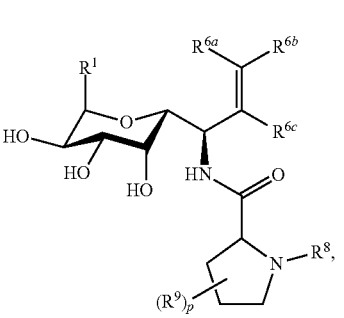

(IV-a)

or a pharmaceutically acceptable salt thereof, wherein $R^1$, $R^{6a}$, $R^{6b}$, $R^{6c}$, $R^8$, $R^9$, and p are as defined herein.

In certain embodiments, of the compound of Formula (IV-a), $R^1$ is —$SR^A$; $R^8$ is hydrogen or methyl; and $R^9$ is substituted or unsubstituted $C_{1-6}$ alkyl. In certain embodiments, of the compound of Formula (IV-a), $R^1$ is —$SCH_3$; $R^8$ is hydrogen or methyl; and $R^9$ is substituted or unsubstituted $C_{1-6}$ alkyl. In certain embodiments, of the compound of Formula (IV-a), $R^1$ is —$SCH_3$; $R^8$ is hydrogen; and $R^9$ is substituted or unsubstituted $C_{1-6}$ alkyl. In certain embodiments, of the compound of Formula (IV-a), $R^1$ is —$SCH_3$; $R^8$ is methyl; and $R^9$ is substituted or unsubstituted $C_{1-6}$ alkyl.

Exemplary Compounds
Exemplary compounds of Formula (I) include, but are not limited to, the compounds listed in Table 1.
TABLE 1
Exemplary compounds of Formula (I)
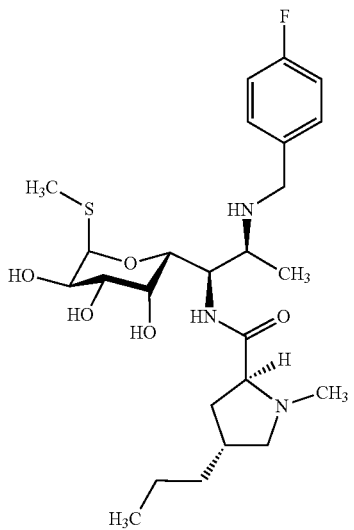
FSA-215025d
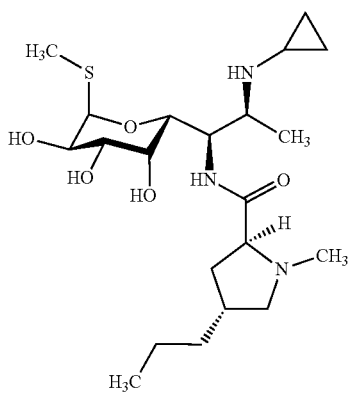
FSA-215028c
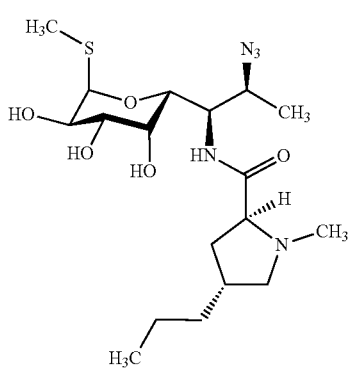
FSA-215038
TABLE 1-continued
Exemplary compounds of Formula (I)
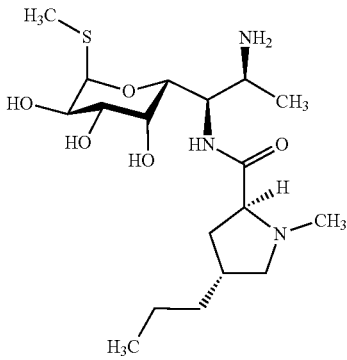
FSA-215049
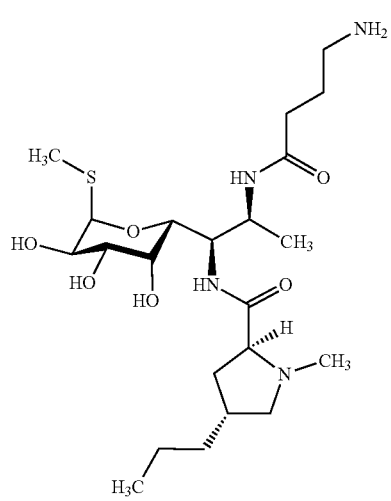
FSA-215052
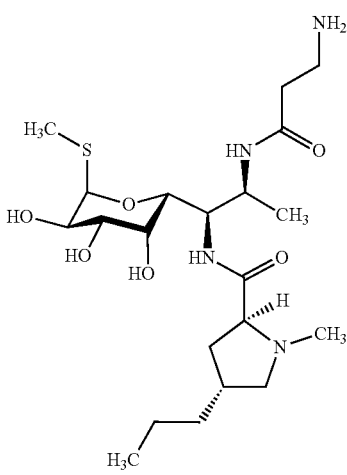
FSA-215054

TABLE 1-continued

Exemplary compounds of Formula (I)

FSA-215059

FSA-215064

FSA-215070

FSA-215071

FSA-215072

FSA-215078a

FSA-215078b

TABLE 1-continued
Exemplary compounds of Formula (I)
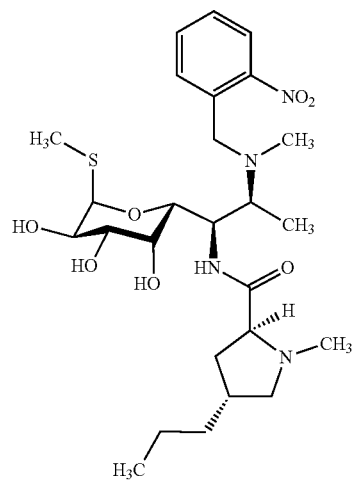
FSA-215081
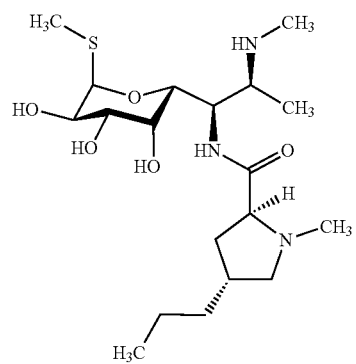
FSA-215082
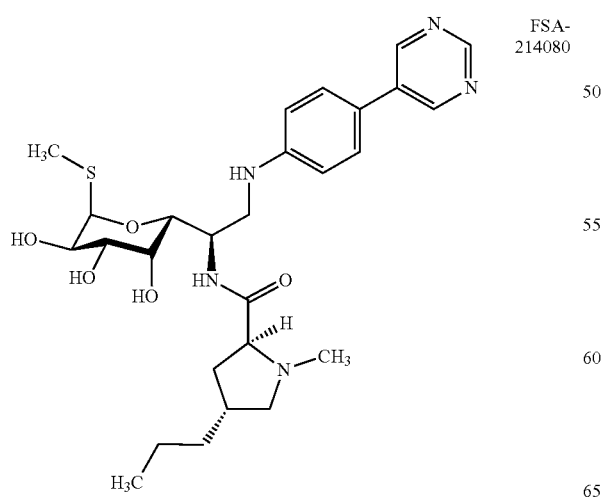
FSA-214080
TABLE 1-continued
Exemplary compounds of Formula (I)
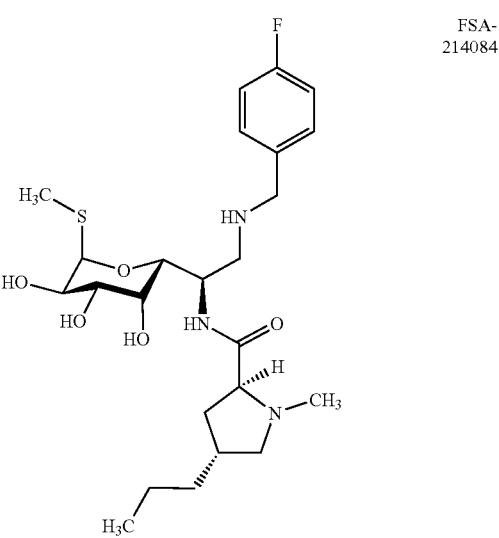
FSA-214084
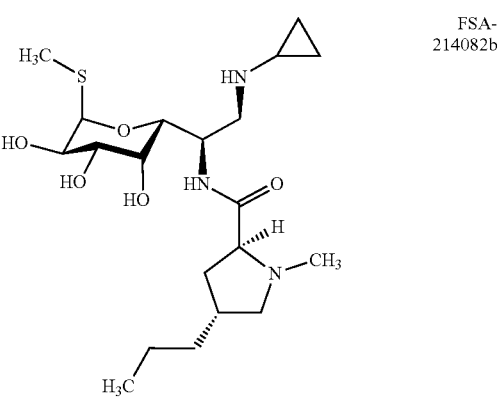
FSA-214082b
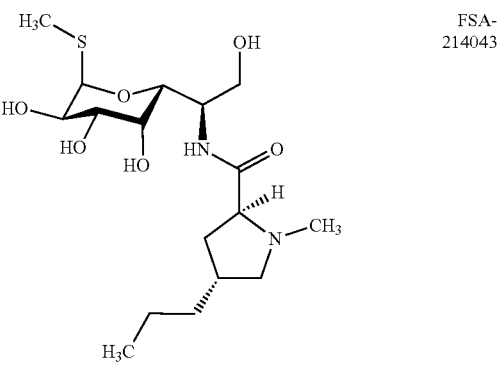
FSA-214043

TABLE 1-continued
Exemplary compounds of Formula (I)
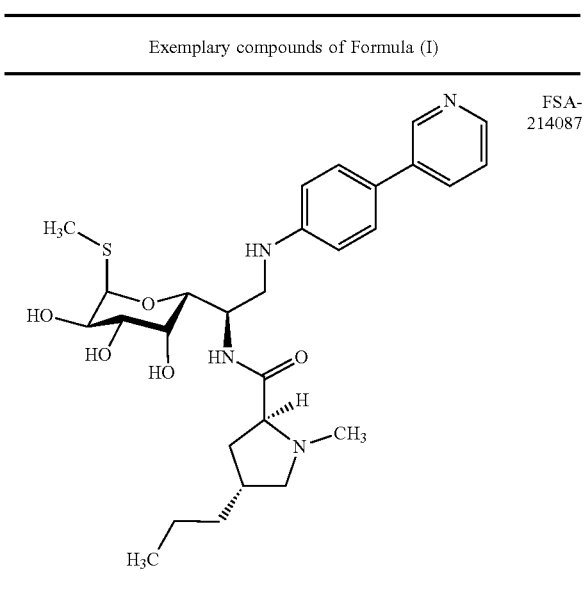
FSA-214087
FSA-214088
FSA-214099
TABLE 1-continued
Exemplary compounds of Formula (I)
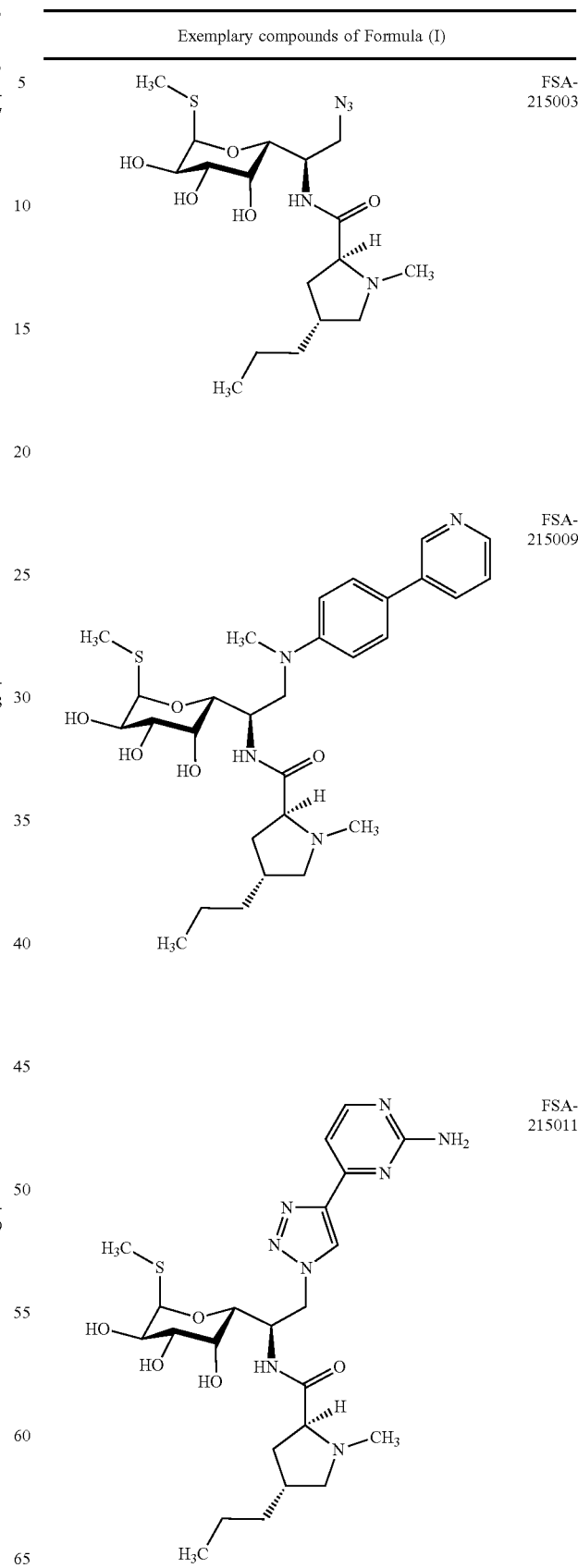
FSA-215003
FSA-215009
FSA-215011

TABLE 1-continued
Exemplary compounds of Formula (I)
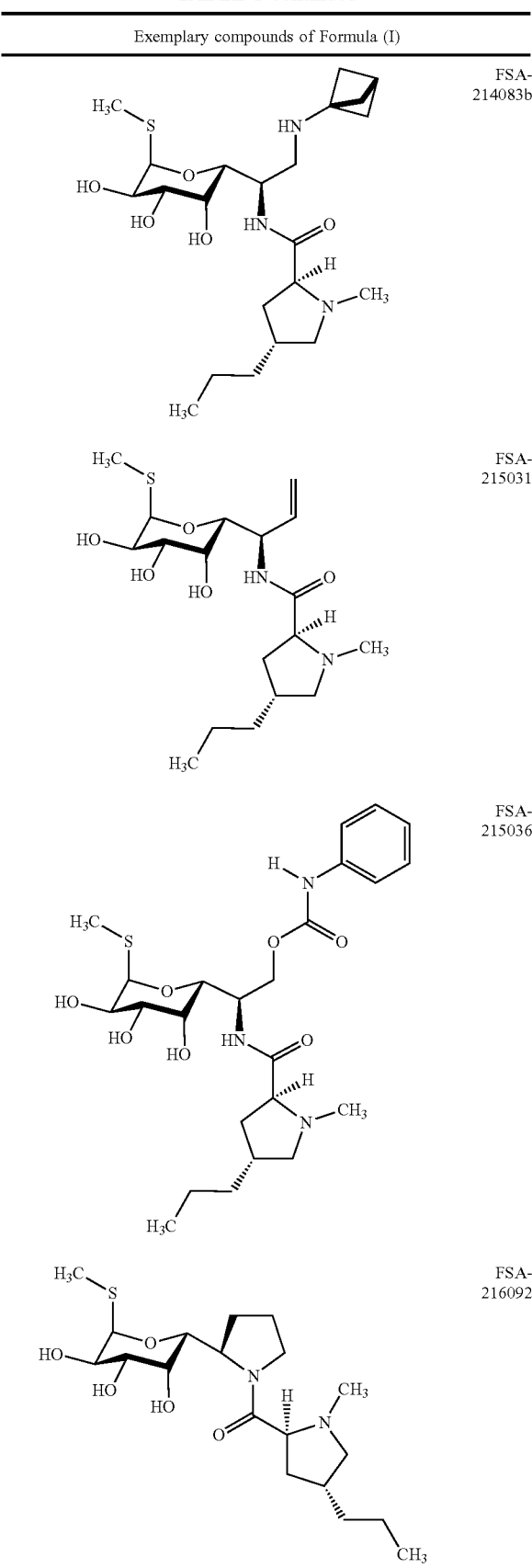
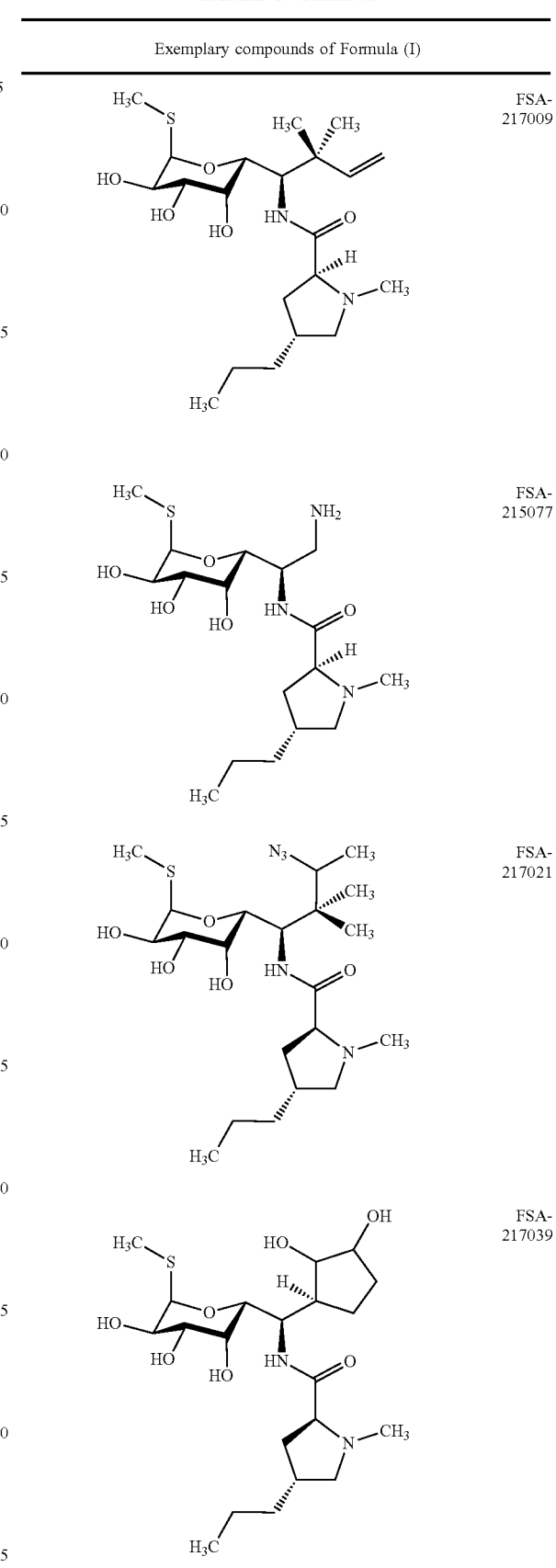

TABLE 1-continued

Exemplary compounds of Formula (I)

[Chemical structure: FSA-217045]

[Chemical structure: FSA-217003]

or

[Chemical structure: FSA-217031]

TABLE 2

Exemplary compounds of Formula (I)

[Chemical structures]

Exemplary compounds of Formula (I) also include, but are not limited to, the compounds listed in Table 2, wherein $R^4$ is as defined herein.

TABLE 2-continued

Exemplary compounds of Formula (I)

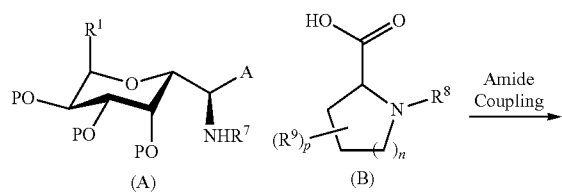

or

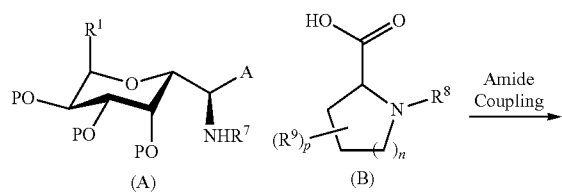

Preparation of Compounds of Formula (I)

In certain embodiments, compounds of the present disclosure are prepared by coupling a compound of Formula (A) and a compound of Formula (B) as depicted in Scheme 1 below.

Exemplary methods that may be used in the preparation of a compound of the present disclosure are described below and are not to be construed as limiting. The compounds disclosed herein may be prepared by other methods as would be appreciated by those of skill in the art, and the procedures described herein may be modified or combined in whole or in part with other known methods.

Scheme 1.

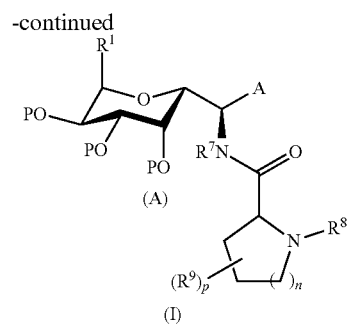

(A) → (B) Amide Coupling →

-continued

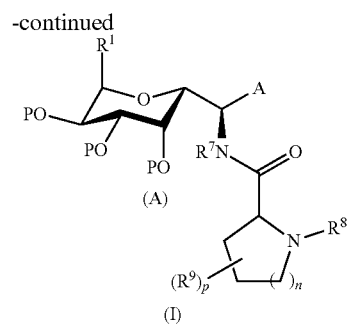

(I)

For all intermediates, A, $R^1$, $R^7$, $R^8$, $R^9$, n, and p are as defined herein for a compound of Formula (I), unless otherwise stated.

In certain embodiments, the amide bond formation is promoted by an amide coupling reagent (e.g., 1-[bis(dimethylamino)methylene]-1H-1,2,3-triazolo[4,5-b]pyridinium 3-oxide hexafluorophosphate (HATU), 1-ethyl-3-(3-dimethylaminopropyl)carbodiimide (EDC), hydroxybenzotriazole (HOBt), and the like, or a combination thereof). In certain embodiments, the amide coupling reagent (e.g., HATU, EDC, HOBt) is reacted with the compound of Formula (B). In certain embodiments, the amide coupling reagent (e.g., HATU, EDC, HOBt) is reacted with the compound of Formula (B) prior to amide coupling with the compound of Formula (A). In certain embodiments, the amide coupling reagent is HATU.

In certain embodiments, the method comprises adding up to 1.0, 1.1, 1.2, 1.3, 1.4, 1.5, 1.6, 1.7, 1.8. 1.9, or 2.0 equivalents of the amide coupling reagent. In certain embodiments, the method comprises performing the coupling reaction at room temperature, ambient temperature, or elevated temperature. In certain embodiments, the method comprises performing the coupling reaction at 20-60° C., 20-50° C., 20-40° C., 20-30° C., 20-25° C., or 25-30° C.

In certain embodiments, an additional reagent may be added to the amide bond forming reaction. In certain embodiments, the additional reagent may facilitate amide coupling by protecting the free hydroxyls of the compound of Formula (A). In certain embodiments, the additional reagent is a silylating reagent. In certain embodiments, the silylating reagent reacts with the free hydroxyl groups of the compound of Formula (A) to form silyl protecting groups in situ during the reaction. In certain embodiments, the additional reagent is added to the compound of Formula (A) before the amide coupling. In certain embodiments, the additional reagent is N,O-bis(trimethylsilyl)trifluoroacetamide. In certain embodiments, the method comprises adding up to 1.0, 1.1, 1.2, 1.3, 1.4, 1.5, 1.6, 1.7, 1.8. 1.9, 2.0, 2.1, 2.2, 2.3, 2.4, 2.5, 2.6, 2.7, 2.8. 2.9, 3.0, or more equivalents of the silylating reagent.

Pharmaceutical Compositions and Administration

The present disclosure provides pharmaceutical compositions comprising a compound as described herein, or a pharmaceutically acceptable salt thereof, and a pharmaceutically acceptable excipient.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sci-*

*ences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the compound of the present disclosure. The amount of the compound is generally equal to the dosage of the compound which would be administered to a subject and/or a convenient fraction of such a dosage such as, for example, one-half or one-third of such a dosage.

Relative amounts of the compound, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) compound.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the compounds, the liquid dosage forms may comprise inert diluents commonly used in the art such as, for example, water or other solvents, solubilizing agents, and emulsifiers, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium.

Solid dosage forms for oral administration include capsules, tablets, pills, powders, and granules. In such solid dosage forms, the compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Dosage forms for topical and/or transdermal administration of a compound of this disclosure may include ointments, pastes, creams, lotions, gels, powders, solutions, sprays, inhalants and/or patches. Generally, the compound is admixed under sterile conditions with a pharmaceutically acceptable carrier and/or any needed preservatives and/or buffers as can be required.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily amount of the compound will be decided by the attending physician within the scope of sound medical judgment. The specific therapeutically effective dose level for any particular subject will depend upon a variety of factors including the disease, disorder, or condition being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In general, the most appropriate route of administration will depend upon a variety of factors including the nature of the agent, the therapeutic regimen, and/or the condition of the subject. Oral administration is the preferred mode of administration. However, in certain embodiments, the subject may not be in a condition to tolerate oral administration, and thus intravenous, intramuscular, and/or rectal administration are also preferred alternative modes of administration.

An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein.

It will be also appreciated that a compound or composition, as described herein, can be administered in combination with one or more additional therapeutically active agents. The compound or composition can be administered concurrently with, prior to, or subsequent to, one or more additional therapeutically active agents. In general, each agent will be administered at a dose and/or on a time schedule determined for that agent. It will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In certain embodiments, the levels utilized in combination will be lower than those utilized individually.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, the additional therapeutically active agent is an antibiotic. Exemplary antibiotics include, but are not limited to, penicillins (e.g., penicillin, amoxicillin), cephalosporins (e.g., cephalexin), compounds (e.g., erythromycin, clarithormycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, and quinupristin/dalfoprisin (Syndercid™)

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In certain embodiments, provided kits may optionally further include a second container comprising a pharmaceutical excipient for dilution or suspension of an inventive pharmaceutical composition or compound. In certain embodiments, the inventive pharmaceutical composition or compound provided in the container and the second container are combined to form one unit dosage form. In certain embodiments, the kits may contain a full course of the inventive pharmaceutical composition or compound. In certain embodiments, the full course may be 5, 6, 7, 8, 9, 10, 11, 12, 13, or 14 days worth of the inventive pharmaceutical composition or compound.

Methods of Treatment and Uses

The present disclosure contemplates using compounds of the present invention for the treatment of infectious diseases, for example, fungal, bacterial, viral, and/or parasitic infections. Lincosamides are generally known to exhibit antibacterial activity.

Thus, as generally described herein, provided is a method of treating an infectious disease comprising administering an effective amount of a compound of the present disclosure, or a pharmaceutically acceptable salt thereof, to a subject in need thereof. Such a method can be conducted in vivo (i.e., by administration to a subject). Treating, as used herein, encompasses therapeutic treatment and prophylactic treatment.

In certain embodiments, the effective amount is a therapeutically effective amount. For example, in certain embodiments, the method slows the progress of an infectious disease in the subject. In certain embodiments, the method improves the condition of the subject suffering from an infectious disease. In certain embodiments, the subject has a suspected or confirmed infectious disease.

In certain embodiments, the effective amount is a prophylactically effective amount. For example, in certain embodiments, the method prevents or reduces the likelihood of an infectious disease, e.g., in certain embodiments, the method comprises administering a compound of the present invention to a subject in need thereof in an amount sufficient to prevent or reduce the likelihood of an infectious disease. In certain embodiments, the subject is at risk of an infectious disease (e.g., has been exposed to another subject who has a suspected or confirmed infectious disease or has been exposed or thought to be exposed to a pathogen).

In one aspect, provided is a method of killing a microorganism (e.g., fungus, bacterium, virus, parasite) comprising contacting the microorganism with an effective amount of a compound of the present disclosure. The compound may contact the microorganism in vivo (e.g., in a subject in need thereof) or in vitro.

In another aspect, provided is a method of inhibiting the growth of a microorganism (e.g., fungus, bacterium, virus, parasite) comprising contacting the microorganism with an effective amount of a compound of the present disclosure.

The compound may contact the microorganism in vivo (e.g., in a subject in need thereof) or in vitro.

In another aspect, provided is an in vitro method of inhibiting pathogenic growth comprising contacting a pathogen (e.g., a bacteria, virus, fungus, or parasite) with an effective amount of a compound of the present disclosure. In another aspect, provided is a method of inhibiting protein synthesis (e.g., by interfering with the synthesis of proteins by binding to the 23s portion of the 50S subunit of the bacterial ribosome and causing premature dissociation of the peptidyl-tRNA from the ribosome) with an effective amount of a compound of the present disclosure. In certain embodiments, inhibiting protein synthesis comprises inhibiting the ribosome of bacteria with an effective amount of a compound of the present disclosure. Protein synthesis may be inhibited in vivo or in vitro.

As used herein, the terms "infectious disease" and "microbial infection" are used interchangeably, and refer to an infection with a pathogen, such as a fungus, bacteria, virus, or a parasite. In certain embodiments, the infectious disease is caused by a fungus, bacteria, or a parasite. In certain embodiments, the infectious disease is caused by a pathogen resistant to other treatments. In certain embodiments, the infectious disease is caused by a pathogen that is multi-drug tolerant or resistant, e.g., the infectious disease is caused by a pathogen that neither grows nor dies in the presence of or as a result of other treatments.

In certain embodiments, the infectious disease is a bacterial infection. For example, in certain embodiments, provided is a method of treating a bacterial infection comprising administering an effective amount of a compound of the present invention, or a pharmaceutically acceptable salt thereof, to a subject in need thereof.

In certain embodiments, the compound has a mean inhibitory concentration (MIC), with respect to a particular bacteria, of less than 50 µg/mL, less than 25 µg/mL, less than 20 µg/mL, less than 10 µg/mL, less than 5 µg/mL, or less than 1 µg/mL.

In certain embodiments, the bacteria is susceptible (e.g., responds to) or resistant to a known commercial antibiotic, such as azithromycin, lincomycin, clindamycin, telithromycin, erythromycin, spiramycin, and the like. In certain embodiments, the bacteria is resistant to a known antibiotic. For example, in certain embodiments, the bacteria is lincomycin- or clindamycin-resistant.

In certain embodiments, the bacterial infection is resistant to other antibiotic (e.g., compound) therapy. For example, in certain embodiments, the pathogen is vancomycin resistant (VR). In certain embodiments, the pathogen is methicillin-resistant (MR), e.g., in certain embodiments, the bacterial infection is an methicillin-resistant *S. aureus* infection (a MRSA infection). In certain embodiments, the pathogen is quinolone resistant (QR). In certain embodiments, the pathogen is fluoroquinolone resistant (FR).

Exemplary bacterial infections include, but are not limited to, infections with a Gram positive bacteria (e.g., of the phylum Actinobacteria, phylum Firmicutes, or phylum Tenericutes); Gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacterial infection is an infection caused by a Gram positive bacterium.

In certain embodiments, the Gram positive bacterium is a bacterium of the phylum Firmicutes.

In certain embodiments, the bacteria is a member of the phylum Firmicutes and the genus *Enterococcus*, i.e., the bacterial infection is an *Enterococcus* infection. Exemplary Enterococci bacteria include, but are not limited to, *E. avium, E. durans, E. faecalis, E. faecium, E. gallinarum, E. solitarius, E. casseliflavus,* and *E. raffinosus*.

In certain embodiments, the bacteria is a member of the phylum Firmicutes and the genus *Staphylococcus*, i.e., the bacterial infection is a *Staphylococcus* infection. Exemplary Staphylococci bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri,* and *S. xylosus*. In certain embodiments, the *Staphylococcus* infection is an *S. aureus* infection.

In certain embodiments, the *S. aureus* has an efflux (e.g., mef, msr) genotype. Bacteria of the efflux genotypes actively pump drug out of the cell via efflux pumps.

In certain embodiments, the *S. aureus* has a methylase (e.g., erm) genotype. In certain embodiments, erm is the bacterial gene class coding for erythromycin ribosomal methylase, which methylates a single adenine in 23S rRNA, itself a component of 50S rRNA.

In certain embodiments, the bacteria is a member of the phylum Firmicutes and the genus *Bacillus*, i.e., the bacterial infection is a *Bacillus* infection. Exemplary *Bacillus* bacteria include, but are not limited to, *B. alcalophilus, B. alvei, B. aminovorans, B. amyloliquefaciens, B. aneurinolyticus, B. anthracis, B. aquaemaris, B. atrophaeus, B. boroniphilus, B. brevis, B. caldolyticus, B. centrosporus, B. cereus, B. circulans, B. coagulans, B. firmus, B. flavothermus, B. fusiformis, B. globigii, B. infernus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis,* and *B. weihenstephanensis*. In certain embodiments, the *Bacillus* infection is a *B. subtilis* infection. In certain embodiments, the *B. subtilis* has an efflux (e.g., mef, msr) genotype. In certain embodiments, the *B. subtilis* has a methylase (e.g., erm) genotype.

In certain embodiments, the bacteria is a member of the phylum Firmicutes and the genus *Streptococcus*, i.e., the bacterial infection is a *Streptococcus* infection. Exemplary *Streptococcus* bacteria include, but are not limited to, *S. agalactiae, S. anginosus, S. bovis, S. canis, S. constellatus, S. dysgalactiae, S. equinus, S. iniae, S. intermedius, S. mitis, S. mutans, S. oralis, S. parasanguinis, S. peroris, S. pneumoniae, S. pyogenes, S. ratti, S. salivarius, S. thermophilus, S. sanguinis, S. sobrinus, S. suis, S. uberis, S. vestibularis, S. viridans,* and *S. zooepidemicus*. In certain embodiments, the

*Streptococcus* infection is an *S. pyogenes* infection. In certain embodiments, the *Streptococcus* infection is an *S. pneumoniae* infection. In certain embodiments, the *S. pneumoniae* has an efflux (e.g., mef, msr) genotype. In certain embodiments, the *S. pneumoniae* has a methylase (e.g., erm) genotype.

In certain embodiments, the bacteria is a member of the phylum Firmicutes and the genus *Clostridium*, i.e., the bacterial infection is a *Clostridium* infection. Exemplary Clostridia bacteria include, but are not limited to, *C. botulinum, C. difficile, C. perfringens, C. tetani*, and *C. sordellii*.

In certain embodiments, the compounds of the disclosure are a safer alternative to clindamycin due to reduced incidence of pseudomembranous colitis after administration. In certain embodiments, the compounds of the disclosure have increased activity against *Clostridium difficile* (*C. difficile*) in comparison to clindamycin. In certain embodiments, the compounds have a mean inhibitory concentration (MIC), with respect to *C. difficile*, of less than 50 μg/mL, less than 25 μg/mL, less than 20 μg/mL, less than 10 μg/mL, less than 5 μg/mL, or less than 1 μg/mL.

In certain embodiments, the bacterial infection is an infection caused by a Gram negative bacteria.

In certain embodiments, the Gram negative bacteria is a bacteria of the phylum Proteobacteria and the genus *Escherichia*. i.e., the bacterial infection is an *Escherichia* infection. Exemplary *Escherichia* bacteria include, but are not limited to, *E. albertii, E. blattae, E. coli, E. fergusonii, E. hermannii*, and *E. vulneris*. In certain embodiments, the *Escherichia* infection is an *E. coli* infection.

In certain embodiments, the Gram negative bacteria is a bacteria of the phylum Proteobacteria and the genus *Haemophilus*. i.e., the bacterial infection is an *Haemophilus* infection. Exemplary *Haemophilus* bacteria include, but are not limited to, *H. aegyptius, H. aphrophilus, H. avium, H. ducreyi, H. felis, H. haemolyticus, H. influenzae, H. parainfluenzae, H. paracuniculus, H. parahaemolyticus, H. pittmaniae, H. segnis*, and *H. somnus*. In certain embodiments, the *Haemophilus* infection is an *H. influenzae* infection.

In certain embodiments, the Gram negative bacteria is a bacteria of the phylum Proteobacteria and the genus *Acinetobacter*. i.e., the bacterial infection is an *Acinetobacter* infection. Exemplary *Acinetobacter* bacteria include, but are not limited to, *A. baumanii, A. haemolyticus*, and *A. lwoffii*. In certain embodiments, the *Acinetobacter* infection is an *A. baumanii* infection.

In certain embodiments, the Gram negative bacteria is a bacteria of the phylum Proteobacteria and the genus *Klebsiella*. i.e., the bacterial infection is a *Klebsiella* infection. Exemplary *Klebsiella* bacteria include, but are not limited to, *K. granulomatis, K. oxytoca, K. michiganensis, K. pneumoniae, K. quasipneumoniae*, and *K. variicola*. In certain embodiments, the *Klebsiella* infection is a *K. pneumoniae* infection.

In certain embodiments, the Gram negative bacteria is a bacteria of the phylum Proteobacteria and the genus *Pseudomonas*. i.e., the bacterial infection is a *Pseudomonas* infection. Exemplary *Pseudomonas* bacteria include, but are not limited to, *P. aeruginosa, P. oryzihabitans, P. plecoglissicida, P. syringae, P. putida*, and *P. fluoroscens*. In certain embodiments, the *Pseudomonas* infection is a *P. aeruginosa* infection.

In certain embodiments, the Gram negative bacteria is a bacteria of the phylum Bacteroidetes and the genus *Bacteroides*. i.e., the bacterial infection is a *Bacteroides* infection. Exemplary *Bacteroides* bacteria include, but are not limited to, *B. fragilis, B. distasonis, B. ovatus, B. thetaiotaomicron*, and *B. vulgatus*. In certain embodiments, the *Bacteroides* infection is a *B. fragilis* infection.

In certain embodiments, the bacteria is an atypical bacteria, i.e., are neither Gram positive nor Gram negative.

In certain embodiments, the infectious disease is an infection with a parasitic infection. Thus, in certain embodiments, provided is a method of treating a parasitic infection comprising administering an effective amount of a compound of the present invention, or a pharmaceutically acceptable salt thereof, to a subject in need thereof.

In certain embodiments, the compound has an $IC_{50}$ (uM) with respect to a particular parasite, of less than 50 uM, less than 25 uM, less than 20 uM, less than 10 uM, less than 5 uM, or less than 1 uM.

Exemplary parasites include, but are not limited to, *Trypanosoma* spp. (e.g., *Trypanosoma cruzi, Trypansosoma brucei*), *Leishmania* spp., *Giardia* spp., *Trichomonas* spp., *Entamoeba* spp., *Naegleria* spp., *Acanthamoeba* spp., *Schistosoma* spp., *Plasmodium* spp. (e.g., *P. flaciparum*), *Crytosporidium* spp., *Isospora* spp., *Balantidium* spp., *Pneumocystis* spp., *Babesia, Loa Loa, Ascaris lumbricoides, Dirofilaria immitis*, and *Toxoplasma* ssp. (e.g. *T. gondii*).

As generally described herein, the present disclosure further provides a method of treating an inflammatory condition comprising administering an effective amount of a compound of the present disclosure, or a pharmaceutically acceptable salt thereof, to a subject in need thereof. Such a method can be conducted in vivo (i.e., by administration to a subject) or in vitro (e.g., upon contact with a tissue or cell culture). Treating, as used herein, encompasses therapeutic treatment and prophylactic treatment.

In certain embodiments, the effective amount is a therapeutically effective amount. For example, in certain embodiments, the method slows the progress of an inflammatory condition in the subject. In certain embodiments, the method improves the condition of the subject suffering from an inflammatory condition. In certain embodiments, the subject has a suspected or confirmed inflammatory condition.

In certain embodiments, the effective amount is a prophylatically effective amount. For example, in certain embodiments, the method prevents or reduces the likelihood of an inflammatory condition, e.g., in certain embodiments, the method comprises administering a compound of the present invention to a subject in need thereof in an amount sufficient to prevent or reduce the likelihood of an inflammatory condition. In certain embodiments, the subject is at risk of developing an inflammatory condition.

The term "inflammatory condition" refers to those diseases, disorders, or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent). Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

In certain embodiments, the inflammatory condition is an acute inflammatory condition (e.g., for example, inflammation resulting from an infection). In certain embodiments, the inflammatory condition is a chronic inflammatory condition. In certain embodiments, the inflammatory condition is inflammation associated with cancer.

As generally described herein, the present disclosure further provides a method of treating a central nervous system disorder comprising administering an effective amount of a compound of the present disclosure, or a pharmaceutically acceptable salt thereof, to a subject in need thereof. Such a method can be conducted in vivo (i.e., by administration to a subject) or in vitro (e.g., upon contact with a tissue or cell culture). Treating, as used herein, encompasses therapeutic treatment and prophylactic treatment.

In certain embodiments, the effective amount is a therapeutically effective amount. For example, in certain embodiments, the method slows the progress of a central nervous system disorder in the subject. In certain embodiments, the method improves the condition of the subject suffering from a central nervous system disorder. In certain embodiments, the subject has a suspected or confirmed central nervous system disorder.

In certain embodiments, the effective amount is a prophylatically effective amount. For example, in certain embodiments, the method prevents or reduces the likelihood of a central nervous system disorder, e.g., in certain embodiments, the method comprises administering a compound of the present disclosure to a subject in need thereof in an amount sufficient to prevent or reduce the likelihood of a central nervous system disorder. In certain embodiments, the subject is at risk of developing a central nervous system disorder.

In certain embodiments, compounds of the present disclosure may treat a central nervous system disorder by modulating the serotonin 5-HT$_{2C}$ receptor. In certain embodiments, the compounds of the present disclosure are allosteric modulators of the serotonin 5-HT$_{2C}$ receptor, e.g., see Zhou et al. *ACS Chemical Neuroscience* 2012, 3, 538-545, and Dinh et al. *Molecular Pharmacology* 2003, 64, 78-84.

In certain embodiments, the central nervous system disorder is addiction, anxiety, depression, obesity, eating disorders, Parkinson's disease, or schizophrenia.

Definitions

Chemical Terms

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ∼∼∼ is a single bond where the stereochemistry of the moieties immediately attached thereto is not specified, --- is absent or a single bond, and === or ≡≡≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In certain embodiments, an alkyl group has 1 to 9 carbon atoms ("$C_{1-9}$ alkyl"). In certain embodiments, an alkyl group has 1 to 8 carbon atoms ("$C_{1-8}$ alkyl"). In certain embodiments, an alkyl group has 1 to 7 carbon atoms ("$C_{1-7}$ alkyl"). In certain embodiments, an alkyl group has 1 to 6 carbon atoms ("$C_{1-6}$ alkyl"). In certain embodiments, an alkyl group has 1 to 5 carbon atoms ("$C_{1-5}$ alkyl"). In certain embodiments, an alkyl group has 1 to 4 carbon atoms ("$C_{1-4}$ alkyl"). In certain embodiments, an alkyl group has 1 to 3 carbon atoms ("$C_{1-3}$ alkyl"). In certain embodiments, an alkyl group has 1 to 2 carbon atoms ("$C_{1-2}$ alkyl"). In certain embodiments, an alkyl group has 1 carbon atom ("$C_1$ alkyl"). In certain embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In certain embodiments, the haloalkyl moiety has 1 to 8 carbon atoms ("$C_{1-8}$ haloalkyl"). In certain embodiments, the haloalkyl moiety has 1 to 6 carbon atoms ("$C_{1-6}$ haloalkyl"). In certain embodiments, the haloalkyl moiety has 1 to 4 carbon atoms ("$C_{1-4}$ haloalkyl"). In certain embodiments, the haloalkyl moiety has 1 to 3 carbon atoms ("$C_{1-3}$ haloalkyl"). In certain embodiments, the haloalkyl moiety has 1 to 2 carbon atoms ("$C_{1-2}$ haloalkyl"). Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In certain embodiments, a heteroalkyl group is a saturated group having 1 to 9 carbon atoms and 1 or more heteroatoms within the parent chain ("hetero$C_{1-9}$ alkyl"). In certain embodiments, a heteroalkyl group is a saturated group having 1 to 8 carbon atoms and 1 or more heteroatoms within the parent chain ("hetero$C_{1-8}$ alkyl"). In certain embodiments, a heteroalkyl group is a saturated group having 1 to 7 carbon atoms and 1 or more heteroatoms within the parent chain ("hetero$C_{1-7}$ alkyl"). In certain embodiments, a heteroalkyl group is a saturated group having 1 to 6 carbon atoms and 1 or more heteroatoms within the parent chain ("hetero$C_{1-6}$ alkyl"). In certain embodiments, a heteroalkyl group is a saturated group having 1 to 5 carbon atoms and 1 or 2 heteroatoms within the parent chain ("hetero$C_{1-5}$ alkyl"). In certain embodiments, a heteroalkyl group is a saturated group having 1 to 4 carbon atoms and 1 or 2 heteroatoms within the parent chain ("hetero$C_{1-4}$ alkyl"). In certain embodiments, a heteroalkyl group is a saturated group having 1 to 3 carbon atoms and 1 heteroatom within the parent chain ("hetero$C_{1-3}$ alkyl"). In certain embodiments, a heteroalkyl group is a saturated group having 1 to 2 carbon atoms and 1 heteroatom within the parent chain ("hetero$C_{1-2}$ alkyl"). In certain embodiments, a heteroalkyl group is a saturated group having 1 carbon atom and 1 heteroatom ("hetero$C_1$ alkyl"). In certain embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-0}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In certain embodiments, an alkenyl group has 2 to 9 carbon atoms ("$C_{2-9}$ alkenyl"). In certain embodiments, an alkenyl group has 2 to 8 carbon atoms ("$C_{2-8}$ alkenyl"). In certain embodiments, an alkenyl group has 2 to 7 carbon atoms ("$C_{2-7}$ alkenyl"). In certain embodiments, an alkenyl group has 2 to 6 carbon atoms ("$C_{2-6}$ alkenyl"). In certain embodiments, an alkenyl group has 2 to 5 carbon atoms ("$C_{2-5}$ alkenyl"). In certain embodiments, an alkenyl group has 2 to 4 carbon atoms ("$C_{2-4}$ alkenyl"). In certain embodiments, an alkenyl group has 2 to 3 carbon atoms ("$C_{2-3}$ alkenyl"). In certain embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

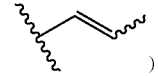

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In certain embodiments, a heteroalkenyl group has 2 to 9 carbon atoms at least one double bond, and 1 or more heteroatoms within the parent chain ("hetero$C_{2-9}$ alkenyl"). In certain embodiments, a heteroalkenyl group has 2 to 8 carbon atoms, at least one double bond, and 1 or more heteroatoms within the parent chain ("hetero$C_{2-8}$ alkenyl"). In certain embodiments, a heteroalkenyl group has 2 to 7 carbon atoms, at least one double bond, and 1 or more heteroatoms within the parent chain ("hetero$C_{2-7}$ alkenyl"). In certain embodiments, a heteroalkenyl group has 2 to 6 carbon atoms, at least one double bond, and 1 or more heteroatoms within the parent chain ("hetero$C_{2-6}$ alkenyl"). In certain embodiments, a heteroalkenyl group has 2 to 5 carbon atoms, at least one double bond, and 1 or 2 heteroatoms within the parent chain ("hetero$C_{2-5}$ alkenyl"). In certain embodiments, a heteroalkenyl group has 2 to 4 carbon atoms, at least one double bond, and 1 or 2 heteroatoms within the parent chain ("hetero$C_{2-4}$ alkenyl"). In certain embodiments, a heteroalkenyl group has 2 to 3 carbon atoms, at least one double bond, and 1 heteroatom within the parent chain ("hetero$C_{2-3}$ alkenyl"). In certain embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In certain embodiments, an alkynyl group has 2 to 9 carbon atoms ("C$_{2-9}$ alkynyl"). In certain embodiments, an alkynyl group has 2 to 8 carbon atoms ("C$_{2-8}$ alkynyl"). In certain embodiments, an alkynyl group has 2 to 7 carbon atoms ("C$_{2-7}$ alkynyl"). In certain embodiments, an alkynyl group has 2 to 6 carbon atoms ("C$_{2-6}$ alkynyl"). In certain embodiments, an alkynyl group has 2 to 5 carbon atoms ("C$_{2-5}$ alkynyl"). In certain embodiments, an alkynyl group has 2 to 4 carbon atoms ("C$_{2-4}$ alkynyl"). In certain embodiments, an alkynyl group has 2 to 3 carbon atoms ("C$_{2-3}$ alkynyl"). In certain embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In certain embodiments, a heteroalkynyl group has 2 to 9 carbon atoms, at least one triple bond, and 1 or more heteroatoms within the parent chain ("heteroC$_{2-9}$ alkynyl"). In certain embodiments, a heteroalkynyl group has 2 to 8 carbon atoms, at least one triple bond, and 1 or more heteroatoms within the parent chain ("heteroC$_{2-8}$ alkynyl"). In certain embodiments, a heteroalkynyl group has 2 to 7 carbon atoms, at least one triple bond, and 1 or more heteroatoms within the parent chain ("heteroC$_2$-7 alkynyl"). In certain embodiments, a heteroalkynyl group has 2 to 6 carbon atoms, at least one triple bond, and 1 or more heteroatoms within the parent chain ("heteroC$_{2-6}$ alkynyl"). In certain embodiments, a heteroalkynyl group has 2 to 5 carbon atoms, at least one triple bond, and 1 or 2 heteroatoms within the parent chain ("heteroC$_{2-5}$ alkynyl"). In certain embodiments, a heteroalkynyl group has 2 to 4 carbon atoms, at least one triple bond, and 1 or 2 heteroatoms within the parent chain ("heteroC$_{2-4}$ alkynyl"). In certain embodiments, a heteroalkynyl group has 2 to 3 carbon atoms, at least one triple bond, and 1 heteroatom within the parent chain ("heteroC$_{2-3}$ alkynyl"). In certain embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In certain embodiments, a carbocyclyl group has 3 to 10 ring carbon atoms ("C$_{3-10}$ carbocyclyl"). In certain embodiments, a carbocyclyl group has 3 to 8 ring carbon atoms ("C$_{3-8}$ carbocyclyl"). In certain embodiments, a carbocyclyl group has 3 to 7 ring carbon atoms ("C$_{3-7}$ carbocyclyl"). In certain embodiments, a carbocyclyl group has 3 to 6 ring carbon atoms ("C$_{3-6}$ carbocyclyl"). In certain embodiments, a carbocyclyl group has 4 to 6 ring carbon atoms ("C$_{4-6}$ carbocyclyl"). In certain embodiments, a carbocyclyl group has 5 to 6 ring carbon atoms ("C$_{5-6}$ carbocyclyl"). In certain embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In certain embodiments, "carbocyclyl" is a monocyclic, saturated carbocyclyl group having from 3 to 14 ring carbon atoms ("C$_{3-14}$ cycloalkyl"). In certain embodiments, a cycloalkyl group has 3 to 10 ring carbon atoms ("C$_{3-10}$ cycloalkyl"). In certain embodiments, a cycloalkyl group has 3 to 8 ring carbon atoms ("C$_{3-8}$ cycloalkyl"). In certain embodiments, a cycloalkyl group has 3 to 6 ring carbon atoms ("C$_{3-6}$ cycloalkyl"). In certain embodiments, a cycloalkyl group has 4 to 6 ring carbon atoms ("C$_{4-6}$ cycloalkyl"). In certain embodiments, a cycloalkyl group has 5 to 6 ring carbon atoms ("$C_{5-6}$ cycloalkyl"). In certain embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

"Carbocyclylalkyl" is a subset of "alkyl" and refers to an alkyl group substituted by a carbocyclyl group, wherein the point of attachment is on the alkyl moiety.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In certain embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In certain embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In certain embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In certain embodiments, the 5-6 membered heterocyclyl has 1-3 ring heteroatoms selected from nitrogen, oxygen, and sulfur. In certain embodiments, the 5-6 membered heterocyclyl has 1-2 ring heteroatoms selected from nitrogen, oxygen, and sulfur. In certain embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofur3nyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

"Heterocyclylalkyl" is a subset of "alkyl" and refers to an alkyl group substituted by an heterocyclyl group, wherein the point of attachment is on the alkyl moiety.

The term "aryl" refers to a radical of a monocyclic or polycyclic (e.g., bicyclic or tricyclic) 4n+2 aromatic ring system (e.g., having 6, 10, or 14 T electrons shared in a cyclic array) having 6-14 ring carbon atoms and zero heteroatoms provided in the aromatic ring system ("$C_{6-14}$ aryl"). In certain embodiments, an aryl group has 6 ring carbon atoms ("$C_6$ aryl"; e.g., phenyl). In certain embodiments, an aryl group has 10 ring carbon atoms ("$C_{10}$ aryl"; e.g., naphthyl such as 1-naphthyl and 2-naphthyl). In certain embodiments, an aryl group has 14 ring carbon atoms ("$C_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In certain embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In certain embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In certain embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In certain embodiments, the 5-6 membered heteroaryl has 1-3 ring heteroatoms selected from nitrogen, oxygen, and sulfur. In certain embodiments, the 5-6 membered heteroaryl has 1-2 ring heteroatoms selected from nitrogen, oxygen, and sulfur. In certain embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that result in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$. —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$SO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OS$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$. —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$. —NH(C$_{1-6}$ alkyl)$_2$$^+$X$^-$.—NH$_2$(C$_{1-6}$ alkyl)$^+$X$^-$.—NH$_3$$^+$X$^-$.—N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$ and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein Rx is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "silyl" refers to the group —Si(R$^{aa}$)$_3$, wherein R$^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^c$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$$R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{aa})OR^{aa}$, $-C(=NR^{bb})N(R^{bb})_2$, $-S(=O)R^{aa}$, $-SO_2R^{aa}$, $-Si(R^{aa})_3$, $-P(R^{aa})_2$, $-P(R^{aa})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxide, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{aa})_2$, $-P(R^{aa})_3$, $-P(=O)_2R^{aa}$, $-P(=O)(R^{aa})_2$, $-P(=O)(OR)_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March *Advanced Organic Chemistry* 6th ed. (501-502). Exemplary leaving groups include, but are not limited to, halo (e.g., chloro, bromo, iodo), $-OR^{aa}$ (when the O atom is attached to a carbonyl group, wherein $R^{aa}$ is as defined herein), $-O(C=O)R^{LG}$, or $-O(SO)_2R^{LG}$ (e.g., tosyl, mesyl, besyl), wherein $R^{LG}$ is optionally substituted alkyl, optionally substituted aryl, or optionally substituted heteroaryl. In certain embodiments, the leaving group is a halogen. In certain embodiments, the leaving group is I.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., 24) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an a anomer, the —OH substituent on the anomeric carbon rests on the opposite side (trans) of the ring from the —CH$_2$OH side branch. The alternative form, in which the —CH$_2$OH substituent and the anomeric hydroxyl are on the same side (cis) of the plane of the ring, is called a anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, or rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

These and other exemplary substituents are described in more detail in the Detailed Description, Examples, and claims. The invention is not intended to be limited in any manner by the above exemplary listing of substituents.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R-x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5$H_2O$)), and polyhydrates (x is a number greater than 1, e.g., dihydrates (R.2$H_2O$) and hexahydrates (R.6$H_2O$)).

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-8}$ alkyl, $C_{2-8}$ alkenyl, $C_{2-8}$ alkynyl, aryl, $C_{7-12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal "Disease," "disorder," and "condition" are used interchangeably herein.

The term "administer," "administering," or "administration" refers to implanting, absorbing, ingesting, injecting, inhaling, or otherwise introducing a compound described herein, or a composition thereof, in or on a subject.

As used herein, and unless otherwise specified, the terms "treat," "treating" and "treatment" contemplate an action that occurs while a subject is suffering from the specified infectious disease or inflammatory condition, which reduces the severity of the infectious disease or inflammatory condition, or retards or slows the progression of the infectious disease or inflammatory condition ("therapeutic treatment"), and also contemplates an action that occurs before a subject begins to suffer from the specified infectious disease or inflammatory condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of an infectious disease or inflammatory condition, or to delay or minimize one or more symptoms associated with the infectious disease or inflammatory condition. A therapeutically effective amount of a compound means an amount of therapeutic agent, alone or in combination with other therapies, which provides a therapeutic benefit in the treatment of the infectious disease or inflammatory condition. The term "therapeutically effective amount" can encompass an amount that improves overall therapy, reduces or avoids symptoms or causes of infectious disease or inflammatory condition, or enhances the therapeutic efficacy of another therapeutic agent.

As used herein, and unless otherwise specified, a "prophylactically effective amount" of a compound is an amount sufficient to prevent an infectious disease or inflammatory condition, or one or more symptoms associated with the infectious disease or inflammatory condition, or prevent its recurrence. A prophylactically effective amount of a compound means an amount of a therapeutic agent, alone or in combination with other agents, which provides a prophylactic benefit in the prevention of the infectious disease or inflammatory condition. The term "prophylactically effective amount" can encompass an amount that improves overall prophylaxis or enhances the prophylactic efficacy of another prophylactic agent.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Synthesis of Lincosamide Analogues

General Experimental Procedures: All reactions were performed in oven- or flame-dried round-bottomed or modified Schlenk flasks fitted with rubber septa under a positive pressure of argon (dried by passage through a column of Drierite calcium sulfate desiccant), unless otherwise noted. Air- and moisture-sensitive liquids and solutions were transferred via syringe or stainless steel cannula. When necessary (so noted), solutions were deoxygenated by three cycles of freezing (liquid nitrogen), evacuation, and thawing under static vacuum. Organic solutions were concentrated by rotary evaporation (house vacuum, 60 Torr) at 23-30° C. Flash-column chromatography was performed as described by Still et al., (Still, W. C.; Kahn, M.; Mitra, A., *J. Org. Chem.* 1978, 43 (14), 2923-2925), employing silica gel (60-Å pore size, 230-400 mesh, Agela Technologies, Chicago, Ill.; or RediSep silica cartridges, Teledyne Isco, Lincoln, Nebr.). Analytical thin-layer chromatography (TLC) was performed using glass plates pre-coated with silica gel (0.25 mm, 60-Å pore size, 230-400 mesh, Merck KGA) impregnated with a fluorescent indicator (254 nm). In special cases (so noted), analytical TLC was performed with aminopropyl-modified silica gel ($NH_2$ silica gel, 60-Å pore size, Wako Chemicals USA) impregnated with a fluorescent indicator (254 nm). TLC plates were visualized by exposure to ultraviolet light (UV) and/or exposure to iodine vapor ($I_2$), basic aqueous potassium permanganate solution ($KMnO_4$), acidic ethanolic para-anisaldehyde solution (PAA), acidic aqueous ceric ammonium molybdate solution (CAM), or ethanolic solution of phosphomolybdic acid (PMA) followed by brief heating on a hot plate as needed (~200° C., ≤15 s). In some cases, reaction monitoring was carried out by analytical liquid chromatography-mass spectrometry (LCMS), or by flow-injection analysis-high-resolution mass spectrometry (FIA-HRMS).

Materials: Commercial reagents and solvents were used as received, unless mentioned otherwise. Dichloromethane, diethyl ether, tetrahydrofuran, 1,4-dioxane, N,N-dimethylformamide, toluene, and benzene were purified by passage through $Al_2O_3$ under argon, according to the method of Pangborn et al. (Pangborn, A. B.; Giardello, M. A.; Grubbs, R. H.; Rosen, R. K.; Timmers, F. *J. Organometallics* 1996, 15 (5), 1518-1520) Ethynyltriisopropylsilane, triethylphosphonoacetate, 1,8-diazabicyclo[5.4.0]undec-7-ene, (−)-diethyl-D-tartrate, tert-butyldiphenylchlorosilane, imidazole, trimethyl phosphite, sodium triacetoxyborohydride, trifluoroacetic acid, 1-[2-(trimethylsilyl)ethoxycarbonyloxy]pyrrolidin-2,5-dione (Teoc-OSu), Oxone monopersulfate compound, and HATU were purchased from Oakwood Products, Inc. (Estill, S.C., USA). Tungsten hexacarbonyl (99%, <0.3% molybdenum) was purchased from Strem Chemicals, Inc. (Newburyport, Mass., USA). N-Boc-p-alanine N-hydroxysuccinimide ester was purchased from Santa Cruz Biotechnology (Dallas, Tex., USA). 1-Chloro-3-methyl-2-butene (prenyl chloride) and ethynyltrimethylsilane were purchased from Alfa Aesar (Haverhill, Mass., USA). 4-Pyrimidin-5-ylaniline was purchased from Enamine Ltd. (Monmouth Jet., N.J., USA). 4-Pyridin-3-ylaniline was purchased from Maybridge Chemical Company (Altrincham, UK). 4-Ethynylpyrimidin-2-amine was prepared according to literature procedures (Tibiletti, F.; Simonetti, M.; Nicholas, K. M.; Palmisano, G.; Parravicini, M.; Imbesi, F.; Tollari, S.; Penoni, A. *Tetrahedron* 2010, 66 (6), 1280-

1288.). All other chemicals and reagents were purchased from Sigma-Aldrich Corporation (Natick, Mass., USA).

Instrumentation: Proton nuclear magnetic resonance ($^1$H NMR) spectra and carbon nuclear magnetic resonance ($^{13}$C NMR) spectra were recorded on Varian Mercury 400 (400 MHz/100 MHz), Varian Inova 500 (500 MHz/125 MHz), or Varian Inova 600 (600 MHz/150 MHz) NMR spectrometers at 23° C. Proton chemical shifts are expressed in parts per million (ppm, δ scale) and are referenced to residual protium in the NMR solvent (CHC$_3$, δ 7.26; CHD$_3$OD, δ 3.31; C$_6$H$_5$D, δ 7.16). Carbon chemical shifts are expressed as parts per million (ppm, δ scale) and are referenced to the carbon resonance of the NMR solvent (CDCl$_3$, δ 77.2; CD$_3$OD, δ 49.0; C$_6$D$_6$, δ 128.1). Data are reported as follows: Chemical shift, multiplicity (s=singlet, d=doublet, t=triplet, q=quartet, qn=quintet, dd=doublet of doublets, td=triplet of doublets, ABq=AB quartet, m=multiplet, br=broad, app=apparent), integration, and coupling constant (J) in Hertz (Hz). Infrared transmittance (IR) spectra were obtained using a Bruker ALPHA FTIR spectrophotometer referenced to a polystyrene standard. Data are represented as follows: Frequency of absorption (cm$^{-1}$), and intensity (s=strong, m=medium, br=broad). Melting points were determined using a Thomas Scientific capillary melting point apparatus. High-resolution mass spectrometry (including FIA-HRMS reaction monitoring) was performed at the Harvard University Mass Spectrometry Facility using a Bruker micrOTOF-QII mass spectrometer. X-ray crystallographic analysis was performed at the Harvard University X-Ray Crystallographic Laboratory by Dr. Shao-Liang Zheng. Ultra high-performance liquid chromatography-mass spectrometry (LCMS) was performed using an Agilent Technologies 1260-series analytical HPLC system in tandem with an Agilent Technologies 6120 Quadrupole mass spectrometer; a Zorbax Eclipse Plus reverse-phase C$_{18}$ column (2.1×50 mm, 1.8 μm pore size, 600 bar rating; Agilent Technologies, Santa Clara, Calif.) was employed as stationary phase. LCMS samples were eluted at a flow rate of 650 μL/min, beginning with 5% acetonitrile-water containing 0.1% formic acid, grading linearly to 100% acetonitrile containing 0.1% formic acid over 3 minutes, followed by 100% acetonitrile containing 0.1% formic acid for 2 minutes (5 minute total run time).

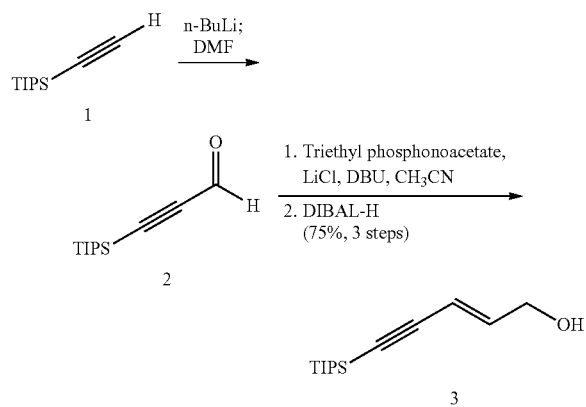

To a solution of ethynyltriisopropylsilane (1, 20.0 g, 110 mmol, 1 equiv) in diethyl ether (100 mL) was added n-butyllithium solution (2.12 M in hexane, 51.7 mL, 110 mmol, 1.00 equiv) slowly by cannula at 0° C. over approximately 15 min. The resulting solution was stirred at 0° C. for an additional 40 min. This lithium acetylide solution was then transferred via cannula over a period of 5-10 min to a 500-mL round-bottomed flask containing a mixture of N,N-dimethylformamide (25.5 mL, 329 mmol, 3.00 equiv) and diethyl ether (100 mL) chilled to −78° C. A white suspension formed. The reaction mixture was stirred at −78° C. for 1 h before warming to 0° C., at which temperature the mixture became homogeneous. After 1 h of stirring at 0° C., the mixture was transferred to an ice-cold aqueous sulfuric acid solution (5% v/v, 250 mL). The resulting biphasic mixture was stirred at 0° C. for 1 h, and then the layers were separated. The aqueous phase was extracted with diethyl ether (3×150 mL), and the combined organic extracts were washed with saturated aqueous sodium chloride solution (150 mL). The washed organic solution was dried over sodium sulfate, the dried solution was filtered, and the filtrate was concentrated to give 3-(triisopropylsilyl)propiolaldehyde (2) as a colorless oil that was used in the next step without further purification. The $^1$H NMR data matched literature values.

An oven-dried 2-L round-bottomed flask was charged with lithium chloride (5.60 g, 132 mmol, 1.20 equiv), and the apparatus was flame-dried. Once cooled, the flask was charged with a magnetic stir bar and acetonitrile (1.3 L), and the resulting suspension was stirred at 23° C. for 10 min (lithium chloride does not fully dissolve). 3-(Triisopropylsilyl)propriolaldehyde (2, theoretically 110 mmol, 1 equiv) and triethyl phosphonoacetate (22.5 mL, 112 mmol, 1.02 equiv) were then added sequentially. 1,8-Diazabicyclo[5.4.0]undec-7-ene (DBU, 16.6 mL, 110 mmol, 1.00 equiv) was added dropwise over 5 min, causing the mixture to warm to approximately 40° C. with concomitant transformation of the originally colorless reaction solution to an opaque, off-white suspension. Progress was monitored by TLC (20% dichloromethane-hexanes, UV+PAA); after 10 min, the reaction was judged to be complete. The mixture was concentrated by rotary evaporation to a volume of approximately 300 mL, and the concentrated mixture was transferred to a separatory funnel containing saturated aqueous ammonium chloride solution (400 mL) and diethyl ether (300 mL). The mixture was shaken, and the layers were separated. The aqueous phase was extracted with diethyl ether (3×300 mL); the combined organic layers were then washed sequentially with water (250 mL) and saturated aqueous sodium chloride solution (250 mL). The washed organic solution was dried over sodium sulfate, the dried solution was filtered, and the filtrate was concentrated to give ethyl (E)-5-(triisopropylsilyl)pent-2-en-4-ynoate as a colorless oil that was used in the next step without further purification. The $^1$H NMR data matched literature values.

To a rapidly stirred solution of crude ethyl (E)-5-(triisopropylsilyl)pent-2-en-4-ynoate (theoretically 110 mmol, 1 equiv) in diethyl ether (220 mL) was added diisobutyl aluminum hydride (1.0 M solution in hexane, 243 mL, 2.2 equiv) by cannula at −78° C. The mixture was stirred at −78° C. for 1 h, then at 0° C. for 1.5 h. The reaction mixture was then transferred by wide-bore cannula to a 2-L round-bottomed flask containing a rapidly stirred aqueous Rochelle salt solution (potassium sodium tartrate, 0.80 M, 410 mL, 328 mmol, 3.0 equiv) pre-chilled to 0° C. A cloudy slurry formed immediately upon aqueous quenching of the reaction mixture; after approximately 3 min of stirring at 0° C., this suspension thickened to form a gel. Gas evolution was then observed, followed by gradual collapse of the gel to form a cloudy, light yellow emulsion. The mixture was stirred at 23° C. overnight under an atmosphere of nitrogen gas, during which time the emulsion separated into a biphasic mixture. The layers were separated at the end of this period, and the aqueous phase was extracted with diethyl ether (3×200 mL). The combined organic layers were then washed with saturated aqueous sodium chloride solution (200 mL), and the washed organic product solution was dried over sodium sulfate. The dried solution was filtered, and the filtrate was concentrated to give a light yellow oil. This residue was purified by flash-column chromatography (500 g silica gel, eluting with 5% ethyl acetate-hexanes initially, grading to 10% ethyl acetate-hexanes) to afford allylic alcohol 3 as a colorless oil (19.7 g, 75%, 3 steps). The $^1$H NMR data matched literature values.

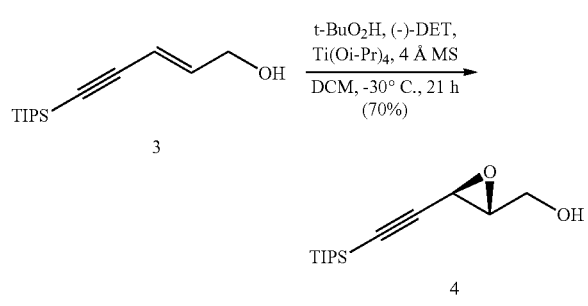

A 1-L, 2-necked round-bottomed flask was oven-dried. Once cooled, the flask was charged with a magnetic stir bar and powdered 4-Å molecular sieves (20.0 g, Sigma-Aldrich, activated by heating overnight in a vacuum drying oven [200° C., ~70 Torr]). A thermocouple probe was fitted to one neck of the flask, while the other neck was sealed with a rubber septum. Dichloromethane (229 mL) was added, and the resulting slurry was cooled to −30° C. in a CryoCool bath. (−)-Diethyl-D-tartrate (7.21 mL, 41.9 mmol, 0.500 equiv) was added. Titanium(IV) isopropoxide (9.83 mL, 33.6 mmol, 0.400 equiv) was then added dropwise over 2 min, causing the internal temperature to rise to −26° C. briefly. The resulting mixture was stirred at −30° C. for 20 min, after which time a solution of allylic alcohol 3 (20.0 g, 84.0 mmol, 1 equiv) in dichloromethane (295 mL) was added slowly by cannula over 10 min. The mixture was incubated at −30° C. for 30 min. tert-Butylhydroperoxide solution (TBHP, 5.5 M solution in decane, 30.5 mL, 170 mmol, 2.0 equiv) was finally added at a rate of 2.0 mL/min with a syringe pump, such that the internal temperature of the mixture did not rise above −28° C. Stirring was maintained at −30° C. following the addition of TBHP, and progress was monitored by TLC (10% ethyl acetate-dichloromethane, UV+PAA). After 21 h, the reaction was judged to be complete. A solution comprising iron(II) sulfate heptahydrate (27 g, 97 mmol, 1.2 equiv), DL-tartaric acid (62 g, 0.41 mol, 4.9 equiv), and water (517 mL) was added to the reaction mixture, and the resulting biphasic mixture was stirred at 0° C. for 10 min at a moderate stir rate (350 rpm) The mixture was then transferred to a separatory funnel where the layers were separated. The aqueous phase was extracted with diethyl ether (3×300 mL), and the combined organic layers were washed with saturated aqueous sodium chloride solution (2×200 mL). The washed organic solution was dried over sodium sulfate, the dried solution was filtered, and the filtrate was concentrated to give a slightly cloudy colorless oil. This residue was purified by flash-column chromatography (800 g silica gel, eluting with 5% ethyl acetate-hexanes initially, grading to 15% ethyl acetate-hexanes) to give epoxyalcohol 4 as a colorless, viscous oil (14.9 g, 70%). The $^1$H NMR data matched reported values.

The enantiomeric excess was determined by conversion to the corresponding Mosher esters. In this procedure, a solution of epoxyalcohol 4 (10 mg, 39 μmol, 1 equiv) in 4:1 dichloromethane-pyridine (200 μL) was treated with (R)-3,3,3-trifluoro-2-methoxy-2-phenylpropanoyl chloride (8.8 μL, 47 μmol, 1.2 equiv) at 23° C. The mixture was stirred at 23° C. for 30 min, at which point TLC analysis (50% ethyl acetate-hexanes, UV+KMnO$_4$) indicated complete consumption of starting material. The reaction mixture was concentrated, and the crude residue was subjected to $^1$H NMR analysis (600 MHz, CDCl$_3$). Integration of the major methylene resonance at δ 4.60 (dd, J=12.3, 3.2 Hz, 1H) relative to its minor diastereomeric counterpart at δ 4.66 (dd, J=12.5, 3.0 Hz, 1H, derived from undesired (2S,3S)-product enantiomer) demonstrated an enantiomeric ratio of 94:6 (88% ee). Use of the enantiomeric (S)-Mosher acyl chloride reagent gave the same result.

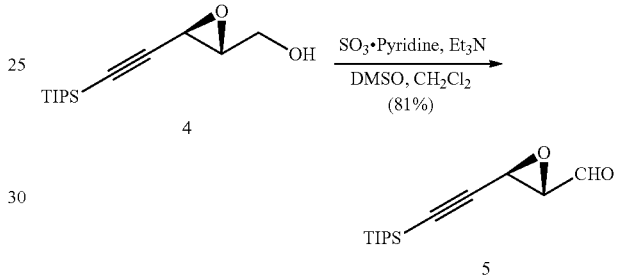

A solution of epoxyalcohol 4 (14.9 g, 58.6 mmol, 1 equiv) in dichloromethane (468 mL) and anhydrous dimethyl sulfoxide (117 mL) was treated with triethylamine (65.3 mL, 468 mmol, 8.00 equiv). Sulfur trioxide-pyridine complex (37.3 g, 234 mmol, 4.00 equiv) was then added in three portions over 15 min at 23° C. The resulting salmon-pink solution was stirred at 23° C., and after 2 h, TLC analysis (30% ethyl acetate-hexanes, PAA) indicated complete consumption of starting material. The reaction mixture was transferred to a separatory funnel containing 1.2 L of 0.5 M copper(II) sulfate solution. The layers were shaken, then separated, and the aqueous phase was extracted with dichloromethane (3×300 mL). The combined organic layers were then washed with saturated aqueous sodium chloride solution (200 mL), and the washed organic product solution was dried over sodium sulfate. The dried solution was filtered, and the filtrate was concentrated to give a brown oil. This residue was purified by flash-column chromatography (600 g silica gel, eluting with 5% ethyl acetate-hexanes initially, grading to 10% ethyl acetate-hexanes) to afford 5 as a colorless oil (12.0 g, 81%). $^1$H NMR (500 MHz, CDCl$_3$): δ 9.02 (d, J=6.1 Hz, 1H), 3.69 (d, J=1.8 Hz, 1H), 3.54 (dd, J=6.1, 1.8 Hz, 1H), 1.07 (s, 21H).

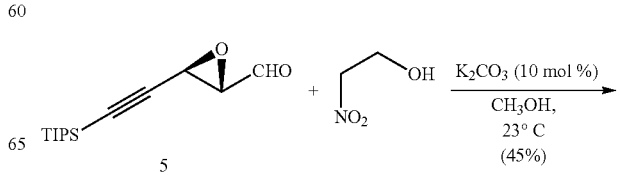

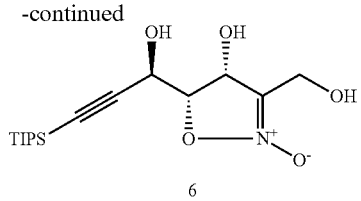

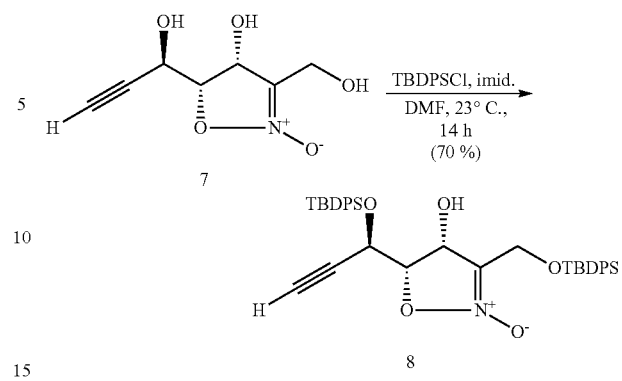

In a 100-mL round-bottomed flask, epoxyaldehyde 5 (4.93 g, 19.5 mmol, 1 equiv) was dissolved in methanol (39.1 mL). To this solution were added nitroethanol (2.80 mL, 39.1 mmol, 2.0 equiv) and potassium carbonate (270 mg, 1.95 mmol, 0.100 equiv). After stirring for 2 h at 23° C., TLC analysis (60% ethyl acetate-hexanes, CAM) showed complete consumption of epoxyaldehyde starting material, as well as the disappearance of intermediate, linear, mid-polar nitroaldol adducts ($R_f$'s 0.63-0.77, 60% ethyl acetate-hexanes, CAM). The mixture was concentrated in vacuo, and crude $^1$H-NMR analysis of the residue revealed a 62:38 diastereomeric ratio favoring the desired C5 epimer. This crude mixture was subjected to flash-column chromatographic separation (700 g silica gel, eluting with 50% ethyl acetate-hexanes initially, grading to 80% ethyl acetate-hexanes) to afford isoxazoline N-oxide 6 as a brilliant white powder (3.00 g, 45%). Melting point: 55-57° C. $^1$H NMR (500 MHz, CDCl$_3$) δ 5.51 (app t, J=6.9 Hz, 1H), 4.89 (dd, J=6.6, 5.0 Hz, 1H), 4.67 (dd, J=7.4, 5.0 Hz, 1H), 4.56-4.53 (m, 2H), 3.42 (d, J=6.6 Hz, 1H), 2.97 (d, J=6.7 Hz, 1H), 2.42 (t, J=6.3 Hz, 1H), 1.09-1.08 (m, 21H).

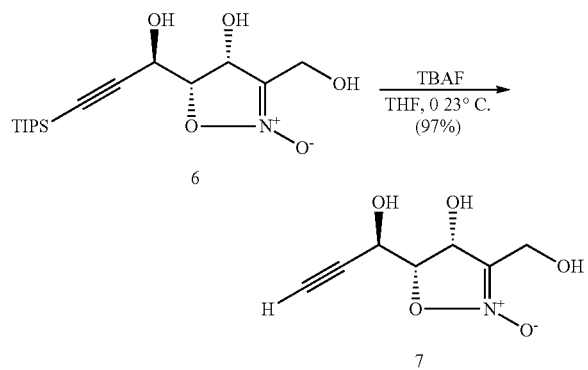

To a solution of isoxazoline N-oxide 6 (4.70 g, 13.7 mmol, 1 equiv) in tetrahydrofuran (137 mL) was added tetrabutylammonium fluoride solution (1.0 M in tetrahydrofuran, 32.8 mL, 32.8 mmol, 2.40 equiv) dropwise at 0° C. The resulting colorless solution was immediately warmed to 23° C., and after 2 h of stirring at that temperature, TLC analysis (5% methanol-ethyl acetate, CAM) indicated complete consumption of starting material. The mixture was loaded directly onto a column of silica gel (500 g) pre-equilibrated with ethyl acetate. The product was eluted with 5% methanol-ethyl acetate, and product-containing fractions were pooled. The pooled fractions were concentrated to give the alkyne 7 as a buff white solid (221 mg, 97%). $^1$H NMR (500 MHz, CD$_3$OD) δ 5.25 (d, J=6.3 Hz, 1H), 4.73 (dd, J=8.1, 2.2 Hz, 1H), 4.45 (dd, J=6.3, 8.1 Hz, 1H), 4.43 (d, J=14.6 Hz, 1H), 4.33 (d, J=14.1 Hz, 1H), 2.91 (d, J=2.2 Hz, 1H).

To a solution of triol 7 (2.35 g, 12.6 mmol, 1 equiv) and imidazole (4.27 g, 62.8 mmol, 8.00 equiv) in N,N-dimethylformamide (62.8 mL) was added tert-butyl(chloro)diphenylsilane (7.26 mL, 28.3 mmol, 4.00 equiv) dropwise at 0° C. The mixture was then warmed to 23° C. Silylation of the primary alcohol was fast (generally complete within 5 min), while silylation of the propargylic alcohol was substantially slower—after 14 h of stirring at 23° C., TLC analysis (60% ethyl acetate-hexanes, UV+KMnO$_4$) showed complete consumption of the mono-silylated intermediate ($R_f$=0.61). Excess chlorosilane reagent was quenched with the addition of saturated aqueous ammonium chloride (100 mL), and the resulting mixture was stirred rapidly at 23° C. for 10 min. The mixture was then extracted with 20% ethyl acetate-hexanes (4×100 mL); the organic extracts were then combined, washed with saturated aqueous sodium chloride solution (100 mL), dried over sodium sulfate, filtered, and concentrated to give a light golden-amber oil. This residue was purified by flash-column chromatography (500 g silica gel, eluting with hexanes initially, grading to 20% ethyl acetate-hexanes) to provide the bis-silyl ether 8 as a white, foaming, amorphous solid (5.87 g, 70%). $^1$H NMR (500 MHz, CDCl$_3$) δ 7.80-7.78 (m, 2H), 7.76-7.71 (m, 6H), 7.51-7.46 (m, 4H), 7.45-7.40 (m, 8H), 5.34 (app t, J=7.7 Hz, 1H), 4.81 (dd, J=5.1, 2.3 Hz, 1H), 4.64 (d, J=13.7 Hz, 1H), 4.57 (d, J=13.8 Hz, 1H), 4.46 (dd, J=7.2, 5.1 Hz, 1H), 3.38 (d, J=8.1 Hz, 1H), 2.47 (d, J=2.3 Hz, 1H), 1.12 (s, 18H).

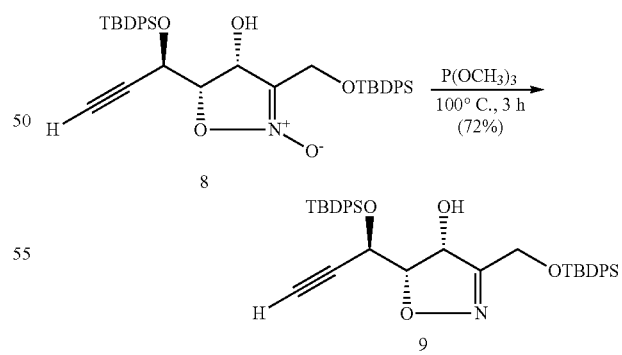

In a 100-mL round-bottomed flask, isoxazoline N-oxide 8 (2.50 g, 3.77 mmol, 1 equiv) was dried by azeotropic removal of benzene. The dried starting material was then dissolved in trimethyl phosphite (15.1 mL), the flask was fitted with an oven-dried reflux condenser, and the reaction solution was heated to 100° C. in a pre-heated oil bath. After 3 h, TLC analysis (20% ethyl acetate-hexanes, PAA) showed complete consumption of starting material. The mixture was cooled to 0° C. and diluted in diethyl ether (200 mL); the organic product solution was then washed sequentially with 0.1 M aqueous HCl solution (2×40 mL) and saturated aqueous sodium chloride solution (50 mL). The washed organic solution was dried over sodium sulfate, filtered, and concentrated to give a light yellow foaming solid. This residue was purified by flash-column chromatography (220 g silica gel, eluting with hexanes initially, grading to 20% ethyl acetate-hexanes) to provide isoxazoline 9 as a white, foaming, amorphous solid (1.76 g, 72%). $^1$H NMR (600 MHz, CDCl$_3$) δ 7.78-7.76 (m, 2H), 7.74-7.71 (m, 4H), 7.70-7.68 (m, 2H), 7.48-7.44 (m, 4H), 7.42-7.39 (m, 8H), 5.43 (app t, J=8.8 Hz, 1H), 4.85 (dd, J=4.0, 2.4 Hz, 1H), 4.60 (d, J=13.1 Hz, 1H), 4.56 (d, J=12.9 Hz, 1H), 4.39 (dd, J=8.5, 3.9 Hz, 1H), 3.90 (d, J=9.0 Hz, 1H), 2.48 (d, J=2.3 Hz, 1H), 1.08 (s, 9H), 1.06 (s, 9H).

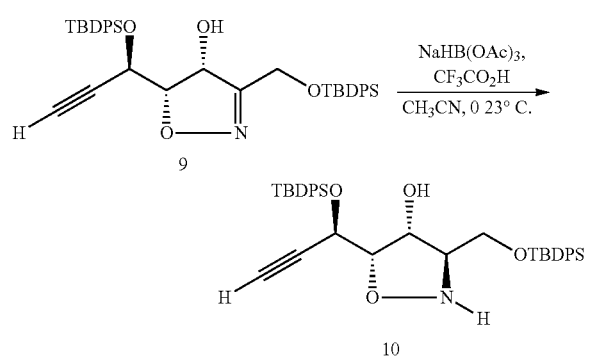

To a rapidly stirred, ice-cold suspension of isoxazoline 9 (2.00 g, 3.09 mmol, 1 equiv) and sodium triacetoxyborohydride (3.27 mg, 15.4 mmol, 5.00 equiv) in acetonitrile (25.7 mL) was added trifluoroacetic acid (23.8 mL, 309 mmol, 100 equiv) dropwise over 2 min. The mixture was then warmed to 23° C., and over the course of 1.5 h, the originally opaque white suspension gradually clarified, giving a light yellow, homogeneous solution. After 3.5, TLC analysis (20% ethyl acetate-hexanes, PAA) showed full consumption of isoxazoline starting material. The reaction mixture was transferred by cannula to a rapidly stirred, ice-cold biphasic mixture of aqueous sodium hydroxide solution (2.0 M, 155 mL, 309 mmol) and dichloromethane (155 mL). Additional 2.0 M aqueous sodium hydroxide solution was added as necessary to achieve pH≥8.0, and rapid stirring was maintained for 10 min. The layers were then separated, and the aqueous layer was extracted with dichloromethane (3×75 mL). The combined organic extracts were dried over sodium sulfate, filtered, and concentrated to give isoxazolidine 10 as a foaming, dull-white solid that was used in the next step without further purification. For characterization purposes, a small quantity (ca. 25 mg) of crude residue was purified by HPLC on a Waters SunFire Prep C18 column (5 μm, 250×19 mm; eluting with 0.1% formic acid-25% acetonitrile-water initially, grading to 0.1% formic acid-95% acetonitrile-water over 20 min, then holding at 0.1% formic acid-95% acetonitrile-water for 20 min with a flow rate of 15 mL/min; monitored by UV absorbance at 254 nm; R$_f$=31.9 min) to give analytically pure sample with the following spectroscopic properties: $^1$H NMR (500 MHz, CDCl$_3$) δ 7.80-7.72 (m, 4H), 7.67-7.61 (m, 4H), 7.50-7.36 (m, 12H), 4.90 (dd, J=5.3, 2.9 Hz, 1H), 4.77 (dd, J=4.8, 2.2 Hz, 1H), 3.94-3.88 (m, 2H), 3.71 (dd, J=11.0, 5.6 Hz, 1H), 3.43 (dt, J=6.4, 3.6 Hz, 1H), 2.44 (d, J=2.2 Hz, 1H), 1.11 (s, 9H), 1.08 (s, 9H).

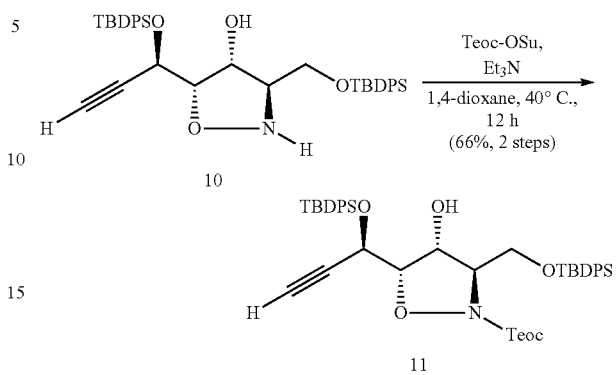

A solution of isoxazolidine 10 (theoretically 3.09 mmol, 1 equiv) and N-[2-(trimethylsilyl)ethoxycarbonyloxy]succinimide (Teoc-OSu, 1.20 mg, 4.64 mmol, 1.50 equiv) in 1,4-dioxane (7.73 mL) was treated with triethylamine (2.15 mL, 15.5 mmol, 5.00 equiv) at 23° C., and the resulting solution was warmed to 40° C. After 12 h of stirring at this temperature, LCMS analysis showed full consumption of starting material, and the reaction mixture was diluted with ethyl acetate (200 mL). The resulting product solution was washed sequentially with saturated aqueous ammonium chloride solution (2×40 mL) and saturated sodium chloride solution (40 mL). The washed solution was then dried over sodium sulfate, filtered, and concentrated to provide a foaming, gummy oil. This crude residue was purified by flash-column chromatography (120 g silica gel, eluting with hexanes initially, grading to 15% ethyl acetate-hexanes) to furnish alkynol 11 as a crispy white amorphous solid (1.61 g, 66%, 2 steps). $^1$H NMR (500 MHz, CDCl$_3$) δ 7.83-7.80 (m, 4H), 7.71-7.67 (m, 4H), 7.51-7.38 (m, 8H), 4.96 (app t, J=3.8 Hz, 1H), 4.87 (dd, J=5.6, 2.3 Hz, 1H), 4.34 (dd, J=6.6, 4.1 Hz, 1H), 4.27 (dd, J=5.6, 3.6 Hz), 4.26-4.14 (m, 2H), 3.90 (dd, J=10.8, 4.1 Hz, 1H), 3.73 (dd, J=10.8, 6.6 Hz, 1H), 3.61 (d, J=3.8 Hz, 1H), 2.42 (d, J=2.2 Hz, 1H), 1.14 (s, 9H), 1.10 (s, 9H), 1.02-0.98 (m, 1H), 0.93-0.89 (m, 1H), 0.06 (s, 9H).

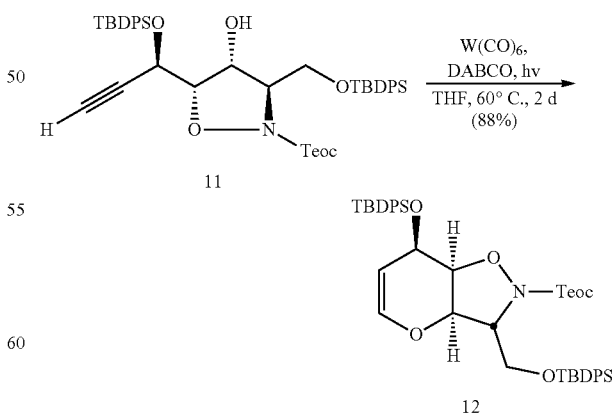

In a 100-mL borosilicate glass microwave reaction vial, alkynol 11 (1.60 g, 2.02 mmol, 1 equiv) was dried by azeotropic removal of benzene. To the dried starting material was added tungsten hexacarbonyl (177 mg, 0.504 mmol, 0.250 equiv) and 1,4-diazabicyclo[2.2.2]octane (452 mg, 4.03 mmol, 2.00 equiv). CAUTION: Tungsten hexacarbonyl is a volatile source of metal and of carbon monoxide. Manipulations of this reagent should be conducted within a well-ventilated fume hood. The vial was flushed with dry argon gas, and then anhydrous, degassed tetrahydrofuran (20.2 mL) was added at 23° C. The resulting colorless solution attained a vibrant fluorescent yellow color within 3 minutes. The vial was sealed, and was transferred to a pre-heated oil bath (60° C.) positioned inside a photochemistry safety cabinet. The reaction mixture was heated with constant UV irradiation from an adjacent 200-Watt mercury-vapor bulb filtered through a water-cooled Pyrex glass jacket (CAUTION: Exposure to high-intensity UV light can cause irreversible vision loss—never open the safety cabinet when the UV lamp is on). Progress was monitored by TLC (20% ethyl acetate-hexanes, UV+KMnO$_4$). After 2 d, full consumption of alkynol substrate was achieved, and the crude product mixture was concentrated to dryness in vacuo. The goldenrod, oily residue was purified by flash-column chromatography (120 g silica gel, eluting with hexanes initially, grading to 15% ethyl acetate-hexanes) to provide glycal 12 as a viscous, colorless oil (1.40 g, 88%). $^1$H NMR (500 MHz, C$_6$D$_6$) δ 7.93-7.91 (m, 2H), 7.88-7.85 (m, 2H), 7.70-7.65 (m, 4H), 7.28-7.18 (m, 12H), 5.98 (dd, J=6.5, 2.2 Hz, 1H), 4.69 (app dt, J=6.5, 1.9 Hz, 1H), 4.64 (dd, J=7.0, 4.1 Hz, 1H), 4.61 (app dt, J=4.4, 2.1 Hz), 4.32-4.26 (m, 2H), 4.24-4.17 (m, 2H), 3.85 (dd, J=10.9, 4.1 Hz, 1H), 3.69 (dd, J=10.8, 7.0 Hz, 1H), 1.22 (s, 9H), 1.10 (s, 9H), 0.91 (t, J=8.3 Hz, 2H), −0.07 (s, 9H).

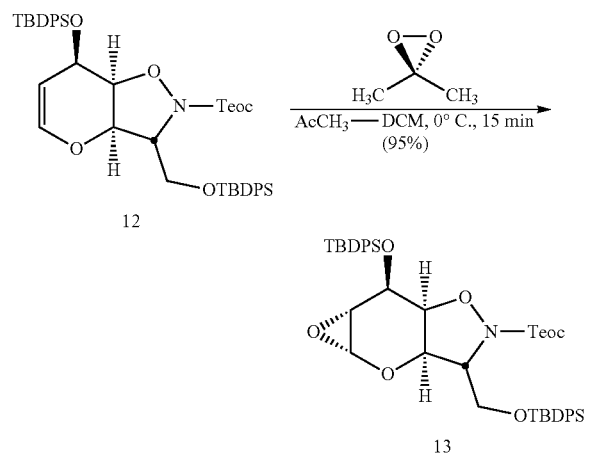

A solution of glycal 12 (920 mg, 1.16 mmol, 1 equiv) in dichloromethane (11.6 µL) was cooled to 0° C., whereupon dimethyldioxirane solution (0.0775 M in acetone, 17.9 mL, 1.39 µmol, 1.20 equiv) was added dropwise over 3 min. The reaction mixture was stirred at 0° C. for 15 min, at which point TLC analysis (NH$_2$ silica gel, 20% ethyl acetate-hexanes, UV+PAA) indicated full consumption of starting material. The mixture was then concentrated under a stream of dry argon, and the residue was dried by azeotropic removal of benzene to afford glycal epoxide 13 as a colorless oil that was suitable for use without further purification (quantitative yield, ≥95% purity by NMR). H NMR (500 MHz, C$_6$D$_6$) δ 7.89-7.86 (m, 2H), 7.80-7.76 (m, 2H), 7.65-7.59 (m, 4H), 7.22-7.13 (m, 12H), 4.65 (app dt, J=2.3, 1.1 Hz, 1H), 4.61 (dd, J=7.1, 4.3 Hz, 1H), 4.31 (d, J=5.1 Hz, 1H), 4.28-4.17 (m, 2H), 4.12 (d, J=2.0, 1H), 3.88 (d, J=4.9 Hz, 1H), 3.74 (dd, J=10.9, 4.3 Hz, 1H), 3.53 (dd, J=10.8, 7.2 Hz, 1H), 2.94 (app t, J=1.1 Hz, 1H), 1.19 (s, 9H), 1.04 (s, 9H), 0.88 (t, J=8.3 Hz, 2H), −0.11 (s, 9H).

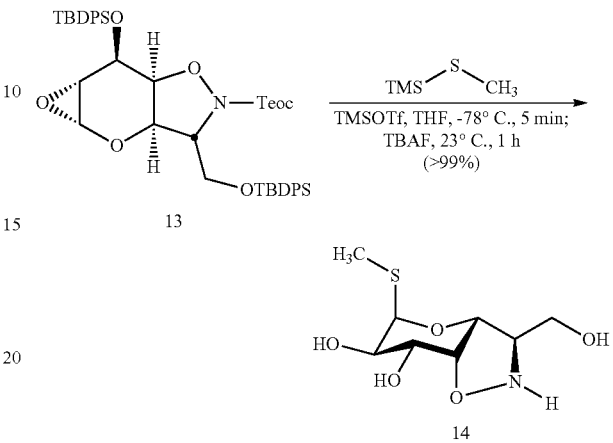

In a 25-mL round-bottomed flask fitted with a magnetic stir bar, glycal epoxide 13 (321 mg, 396 mmol, 1 equiv) was dried by azeotropic removal of benzene. Once dried, the starting material was dissolved in tetrahydrofuran (3.96 mL), and the resulting solution was chilled to −78° C. Once cooled, (methylthio)trimethylsilane (169 µL, 1.19 mmol, 3.00 equiv) was added; next, trimethylsilyl trifluoromethanesulfonate (14.3 µL, 79.0 µmol, 0.200 equiv) was added dropwise. After 5 min, TLC analysis (NH$_2$ silica gel, 2% methanol-20% ethyl acetate-hexanes, UV+CAM) showed complete conversion of starting material to a slightly more polar product. At this point the reaction was quenched with the addition of tetra-n-butylammonium fluoride solution (1.0 M in tetrahydrofuran, 2.8 mL, 2.8 mmol, 7.0 equiv), and the mixture was warmed to 23° C. After 1 h of stirring at 23° C., LCMS analysis showed that global desilylation was complete. The mixture was loaded directly onto a column of silica gel (20 g) that had been pre-equilibrated with ethyl acetate; the column was eluted first with ethyl acetate (300 mL), then with 5% methanol-ethyl acetate (300 mL), and finally with 10% methanol-ethyl acetate (600 mL). Fractions containing product were identified by TLC (10% methanol-ethyl acetate, PAA), and these fractions were pooled and concentrated to afford isoxazolidine triol 14 (103 mg, 110%) that was sufficiently pure for use in the subsequent N—O bond cleavage reaction.

For characterization purposes, a small quantity (ca. 20 mg) of this product was subjected to preparative HPLC (with a flow rate of 15 mL/min, eluting with 0.1% trifluoroacetic acid-1% acetonitrile-water for 2 min, then grading to 0.1% trifluoroacetic acid-20% acetonitrile-water over 18 min; monitored by UV absorbance at 210 nm; product R$_f$=8.75 min) to give the trifluoroacetic acid salt of 14.CF$_3$CO$_2$H in pure form. H NMR (hydrotrifluoroacetate salt, 500 MHz, CD$_3$OD) δ 5.27 (d, J=5.0 Hz, 1H), 4.98 (d, J=2.0 Hz, 1H), 4.71 (dd, J=3.8, 2.1 Hz, 1H), 4.12 (dd, J=10.1, 5.1 Hz, 1H), 4.10 (app t, J=5.5 Hz, 1H), 3.99 (dd, J=10.0, 3.8 Hz, 1H), 3.87 (dd, J=12.0, 4.8 Hz, 1H), 3.83 (dd, J=12.0, 6.0 Hz, 1H), 2.14 (s, 3H). $^{19}$F NMR (hydrotrifluoroacetate salt, 471 MHz, CD$_3$OD) δ −77.3 (s, 3F).

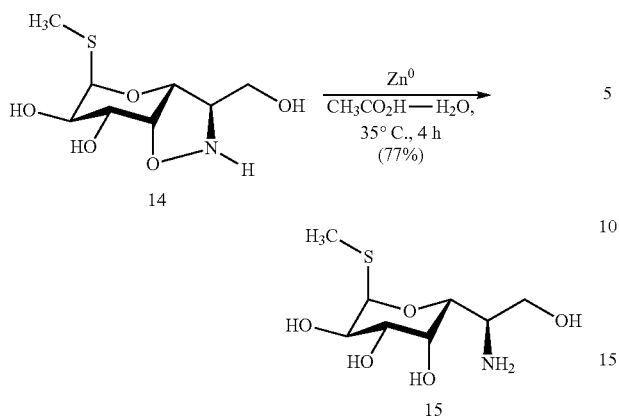

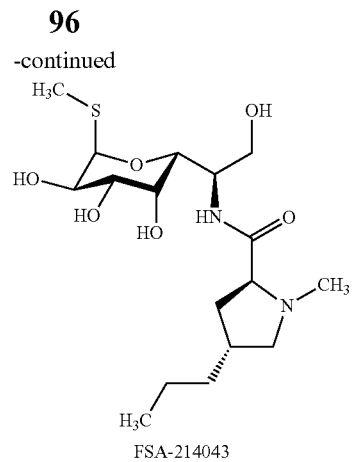

To a solution of isoxazolidine triol 14 (234 mg, 986 μmol, 1 equiv) in 50% v/v acetic acid-water (9.86 mL) was added activated zinc powder (258 mg, 3.94 mmol, 4.00 equiv). The mixture was heated to 35° C. with stirring, and after 4 h, LCMS showed complete conversion of starting material to aminotetraol product. The mixture was cooled before it was filtered through a Celite pad. The filter cake was washed with methanol (3×5 mL), and the combined filtrates were concentrated to dryness. Residual acetic acid was removed by repeated concentration from 50% v/v methanol-toluene. Once dried, the crude residue, containing the hydroacetate salt of the desired product as well as zinc acetate as a major impurity, was dissolved in methanol (20 mL) and was treated with Amberlyst A26 resin (hydroxide form, 4.00 g). After stirring the mixture at 23° C. for 1 h, the ion-exchange beads were removed by filtration, and the filtrate was concentrated to give a white solid. This crude residue was finally purified by flash-column chromatography (25 silica gel, eluting with 1% ammonium hydroxide-10% methanol-dichloromethane initially, grading to 10% ammonium hydroxide-40% methanol-dichloromethane) to provide methylthio-8-norlincosamine (15) as a white solid (182 mg, 77%). $^1$H NMR (400 MHz, D$_2$O) δ 5.17 (d, J=5.7 Hz, 1H), 3.95-3.92 (m, 2H), 3.84 (d, J=9.2 Hz, 1H), 3.63 (dd, J=11.0, 2.5 Hz, 1H), 3.54 (dd, J=10.2, 2.9 Hz, 1H), 3.38 (dd, J=11.2, 6.1 Hz, 1H), 2.91 (ddd, J=9.0, 6.1, 3.2 Hz, 1H), 1.92 (s, 3H).

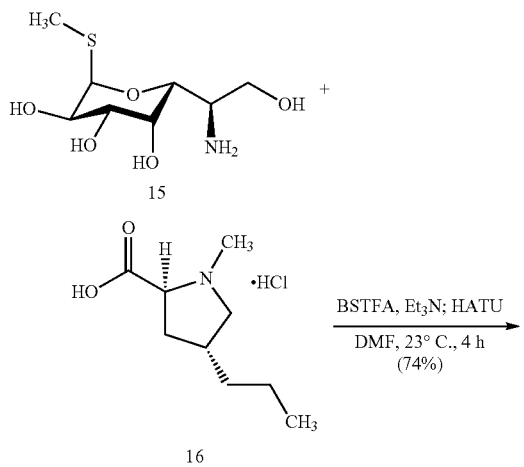

In a 2-5 mL glass microwave vial fitted with a magnetic stir bar, methylthio-8-norlincosamine (15, 100 mg, 418 μmol, 1 equiv) was dissolved in N,N-dimethylformamide (2.09 mL). Triethylamine (262 μL, 1.88 mmol, 4.50 equiv) and N,O-bis(trimethylsilyl)trifluoroacetamide (224 μL, 836 μmol, 2.00 equiv) were added next, and the solution was stirred at 23° C. for 1 h to ensure complete O-silylation. After this period, trans-4-n-propyl-L-hygric acid hydrochloride (16) (104 mg, 501 μmol, 1.20 equiv) and HATU (222 mg, 585 μmol, 1.40 equiv) were added, causing the reaction mixture to attain a canary yellow hue. Following 4 h of stirring at 23° C., LCMS analysis showed complete conversion of aminotetraol starting material and its (oligo)silylated congeners to amide products. The reaction mixture was consequently diluted with ethyl acetate (25 mL) and the diluted solution was washed with saturated aqueous sodium bicarbonate solution (10 mL). The aqueous layer was extracted with ethyl acetate (3×10 mL), and the combined organic layers were then washed with saturated aqueous sodium chloride solution (15 mL). The washed organic solution was dried over sodium sulfate, filtered, and concentrated; and the residue thus obtained was re-dissolved in 50% v/v methanol-acetic acid. This colorless solution was stirred at 40° C. for 24 h to ensure complete desilylation before it was concentrated to dryness in vacuo. Residual acetic acid was removed by repeated concentration of the mixture from 50% v/v methanol-toluene. Once thoroughly dried, the crude residue was treated with methanol (10 mL) and Amberlyst A26 resin (hydroxide form, 2.00 g). The resulting mixture was stirred at 23° C. for 1 h before the ion-exchange beads were removed by filtration and the filtrate was concentrated. This light amber-colored oily residue was purified by flash-column chromatography (18 g silica gel, eluting with 0.5% ammonium hydroxide-5% methanol-dichloromethane initially; grading to 1% ammonium hydroxide-10% methanol-dichloromethane) to furnish 8-norlincomycin (FSA-214043) as a light yellow, foaming solid (121 mg, 74%). $^1$H NMR (500 MHz, CD$_3$OD) δ 5.29 (d, J=5.6 Hz, 1H), 4.17 (d, J=8.9 Hz, 1H), 4.12-4.08 (m, 2H), 3.78 (app dt, J=6.6, 5.1 Hz, 2H), 3.72 (dd, J=10.7, 4.2 Hz, 1H), 3.63 (dd, J=10.1, 3.4 Hz, 1H), 3.21 (dd, J=8.7, 6.0 Hz, 1H), 2.95 (dd, J=10.6, 4.8 Hz, 1H), 2.37 (s, 3H), 2.19-2.15 (m, 1H), 2.08 (s, 3H), 2.05 (dd, J=10.1, 8.8 Hz, 1H), 1.99 (ddd, J=13.0, 8.2, 4.8 Hz, 1H), 1.84 (app dt, J=12.9, 10.3 Hz, 1H), 1.36-1.31 (m, 4H), 0.92 (t, J=6.5 Hz, 3H). HRMS (ESI+, m/z): [M+H]$^+$ calcd for C$_{17}$H$_{32}$N$_2$O$_6$S, 393.2054; found 393.2050.

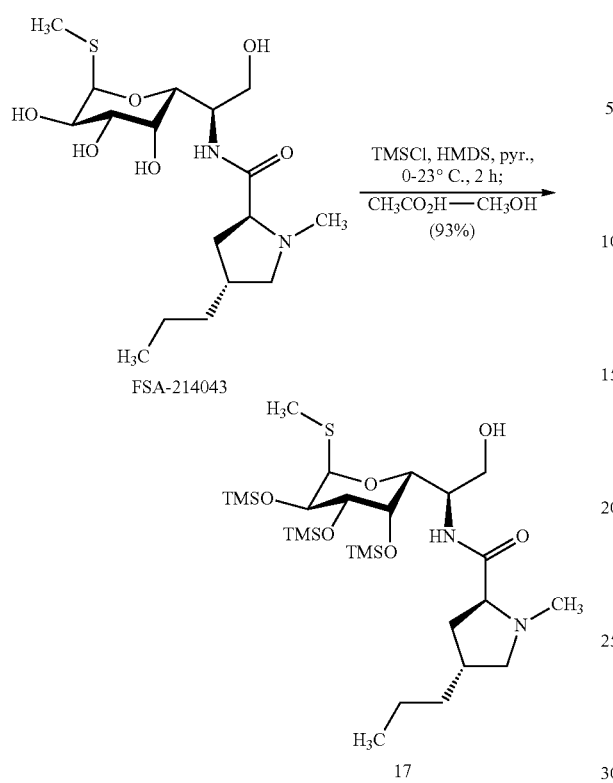

FSA-214043

17

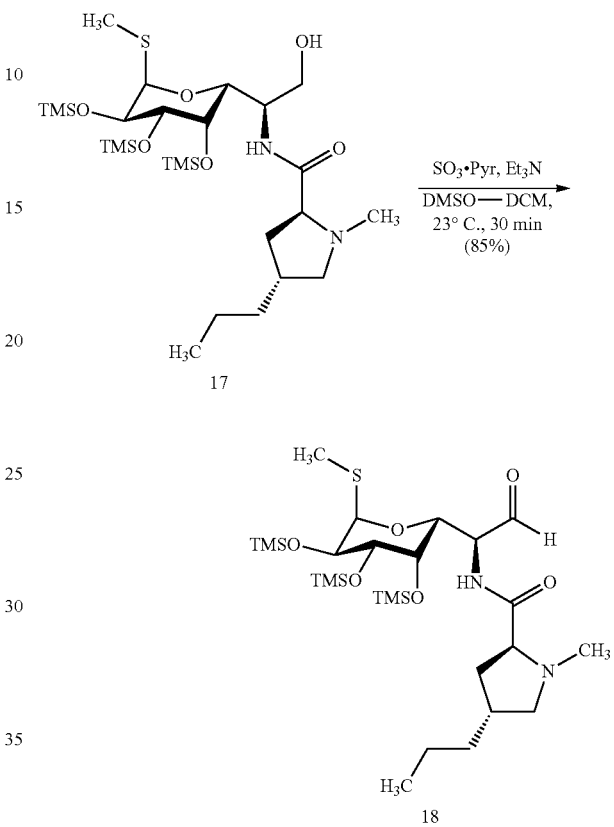

17

18

In a 2-5 mL glass microwave vial, an ice-cold solution of 8-norlincomycin (FSA-214043, 90.0 mg, 229 μmol, 1 equiv) in pyridine (382 μL) was treated sequentially with hexamethyldisilazane (121 μL, 578 μmol, 2.52 equiv) and chlorotrimethylsilane (168 μL, 1.31 mmol, 5.72 equiv). Following the addition of these reagents, the mixture was warmed to 23° C., and stirring was maintained for 2 h. The mixture was then concentrated to dryness in vacuo, and the residue was partitioned between hexanes (10 mL) and water (10 mL). The layers were separated, and the aqueous phase was extracted with additional hexanes (3×5 mL). The combined organic extracts were then dried over sodium sulfate, the dried solution was filtered, and the filtrate was concentrated to afford crude, persilylated 8-norlincomycin as a brilliant white solid. This material was then suspended in methanol (887 μL), and 80% v/v acetic acid-water (133 μL) was added to the suspension, causing the mixture to become a homogeneous, colorless solution. Desilylation was monitored by TLC (40% ethyl acetate-hexanes, CAM; persilylated intermediate $R_f$=0.64; alcohol product $R_f$=0.16), and after 40 min of stirring at 23° C., the reaction was judged to be complete. The reaction mixture was transferred to a separatory funnel containing hexanes (10 mL) and saturated aqueous sodium bicarbonate solution (10 mL). The mixture was shaken vigorously, and the layers were separated. The aqueous layer was extracted with fresh hexanes (3×5 mL), and the combined organic extracts were washed with saturated aqueous sodium chloride solution (10 mL). The washed organic solution was then dried over sodium sulfate, filtered, and concentrated to provide 2,3,4-tris-O-trimethylsilyl-8-norlincomycin (17) as a white, foaming, amorphous solid (115 mg, 93%). $^1$H NMR (600 MHz, CDCl$_3$) δ 7.73 (d, J=8.8 Hz, 1H), 5.22 (d, J=5.6 Hz, 1H), 4.17-4.11 (m, 3H), 3.92 (br d, J=11.0 Hz, 1H), 3.81 (d, J=2.6 Hz, 1H), 3.70 (br d, J=10.8 Hz, 1H), 3.66 (dd, J=9.4, 2.6 Hz, 1H), 3.16-3.12 (m, 1H), 2.94 (dd, J=10.8, 4.2 Hz, 1H), 2.57 (br, 1H), 2.34 (s, 3H), 2.07 (s, 3H), 2.04-2.02 (m, 2H), 1.97-1.93 (m, 1H), 1.85-1.80 (m, 1H), 1.30-1.24 (m, 4H), 0.87 (t, J=6.7 Hz, 3H), 0.17 (s, 9H), 0.12 (s, 9H), 0.11 (s, 9H). HRMS (ESI+, m/z): [M+H]$^+$ calcd for $C_{26}H_{56}N_2O_6SSi_3$, 609.3240; found 609.3259.

To a solution of 2,3,4-tris-O-trimethylsilyl-8-norlincomysin (17, 50 mg, 82 μmol, 1 equiv) in dichloromethane (660 μL) and dimethyl sulfoxide (160 μL) were added triethylamine (92 μL, 660 μmol, 8.0 equiv) and sulfur trioxide-pyridine complex (52 mg, 330 μmol, 4.0 equiv) at 23° C. After 15 min, TLC analysis (10% methanol-dichloromethane, PAA) showed that reaction progress had stalled, and additional portions of triethylamine (92 μL, 660 μmol, 8.0 equiv) and sulfur trioxide-pyridine complex (52 mg, 330 μmol, 4.0 equiv) were added. After an additional 15 min of stirring at 23° C., TLC analysis showed the reaction was complete. The mixture was diluted with dichloromethane (10 mL), and the diluted solution was transferred to a separatory funnel containing saturated aqueous sodium bicarbonate solution (10 mL). The layers were shaken vigorously, then separated, and the aqueous phase was extracted with fresh portions of dichloromethane (3×5 mL). The combined organic extracts were then washed with saturated aqueous sodium chloride solution (10 mL) before being dried over sodium sulfate, filtered, and concentrated to provide crude aldehyde 18 as a dull white solid. This material was unstable toward column chromatography, and thus an analytically pure sample could not be obtained; instead, purity of ≥85% was assumed based on crude $^1$H NMR analysis (CDCl$_3$), and this material was used directly in subsequent transformations whereafter 2-step yields were determined.

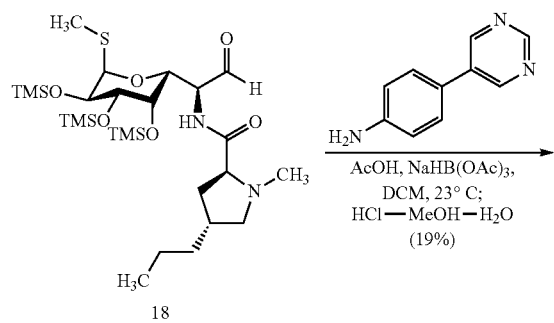
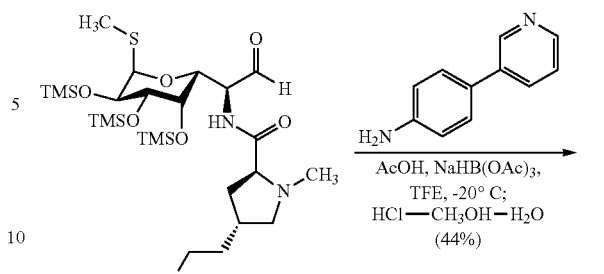

FSA-214080

FSA-214087

To a solution of aldehyde 18 (theoretically 9.7 mg, 16 mmol, 1 equiv) in dichloromethane (400 mL) were added 4-(pyrimidin-5-yl)aniline (6.9 mg, 40 µmol, 2.5 equiv) and acetic acid (9.2 µL, 160 µmol, 10 equiv) at 23° C. After 15 min of stirring, the mixture was then treated with sodium triacetoxyborohydride (6.8 mg, 32 µmol, 2.0 equiv), and 2 h later, LCMS analysis showed complete consumption of aldehyde starting material and imine intermediate. The reaction mixture was concentrated under a stream of nitrogen, and the residue was re-suspended in 50% v/v methanol-1N aqueous hydrogen chloride solution (1.0 mL). The resulting canary yellow suspension was stirred at 23° C. for 5 min, whereupon LCMS analysis showed global desilylation was complete. The mixture was filtered through a 0.2-µm PTFE filter, and the filtrate was concentrated. The crude residue was subjected to purification by preparative HPLC on a Waters SunFire Prep C18 column (5 µm, 250×19 mm; eluting with 0.1% formic acid-5% acetonitrile-water, grading to 0.1% formic acid-40% acetonitrile-water over 40 min, with a flow rate of 15 mL/min; monitored by UV absorbance at 280 nm; $R_t$=15.8 min) to provide (pyrimidyl)aniline analog FSA-214080.$HCO_2H$ as a white solid (1.9 mg, 19%, 2 steps). $^1H$ (600 MHz, $CD_3OD$) δ 8.98 (s, 1H), 8.96 (s, 2H), 8.44 (br s, 1H), 7.51 (d, J=8.7 Hz, 2H), 6.83 (d, J=8.7 Hz, 2H), 5.31 (d, J=5.6 Hz, 1H), 4.44 (app q, J=6.5 Hz, 1H), 4.32 (dd, J=6.4, 1.3 Hz, 1H), 4.12 (dd, J=10.2, 5.6 Hz, 1H), 3.94 (dd, J=3.4, 1.3 Hz, 1H), 3.64 (dd, J=10.1, 3.4 Hz, 1H), 3.49 (dd, J=13.7, 5.2 Hz, 1H), 3.40 (dd, J=13.6, 7.5 Hz, 1H), 3.25 (app t, J=7.7 Hz, 1H), 3.22-3.17 (m, 1H), 2.45 (s, 3H), 2.23-2.18 (m, 1H), 2.12 (s, 3H), 2.01-1.96 (m, 1H), 1.94-1.89 (m, 1H), 1.84-1.78 (m, 1H), 1.29-1.16 (m, 4H), 0.80 (t, J=7.1 Hz, 3H). HRMS (ESI+, m/z): $[M+H]^+$ calcd for $C_{27}H_{39}N_5O_5S$, 546.2745; found 546.2753.

A 4-mL glass vial fitted with a PTFE-lined screw cap was charged with a magnetic stir bar, aldehyde 18 (theoretically 10 mg, 16 µmol, 1 equiv), 2,2,2-trifluoroethanol (330 µL), and powdered, activated 4A molecular sieves (10 mg). The suspension was chilled to −20° C. in an acetone bath, whereupon acetic acid (5.7 µL, 99 µmol, 6.0 equiv) was added. 4-(Pyridin-3-yl)aniline (8.4 mg, 49 µmol, 3.0 equiv) was added next, causing the mixture to turn tennis-ball yellow; and the mixture was stirred at −20° C. for 15 min before the mixture was treated with sodium triacetoxyborohydride (10 mg, 49 µmol, 3.0 equiv). After 30 min, LCMS analysis showed complete consumption of aldehyde starting material and imine intermediate. The mixture was warmed to 23° C., and was concentrated to dryness before being re-suspended in 50% v/v methanol-1N aqueous hydrogen chloride solution. After 5 min of stirring at 23° C., LCMS analysis showed that global desilylation was complete, and the yellow mixture was filtered through a 0.2-µm PTFE filter. The filtrate was concentrated, and the crude residue was purified by preparative HPLC on a Waters SunFire Prep C18 column (5 µm, 250×19 mm; eluting with 0.1% trifluoroacetic acid-water, grading to 0.1% trifluoroacetic acid-50% acetonitrile-water over 40 min, with a flow rate of 15 mL/min; monitored by UV absorbance at 280 nm; $R_t$=22.2 min) to provide (pyridyl)aniline analog FSA-214087.$CF_3CO_2H$ as a white solid (5.6 mg, 44%, 2 steps). $^1H$ (500 MHz, $CD_3OD$) δ 9.03 (d, J=2.1 Hz, 1H), 8.77 (ddd, J=8.4, 2.3, 1.3 Hz, 1H), 8.62 (dd, J=5.6, 1.1 Hz, 1H), 8.03 (dd, J=8.3, 5.6 Hz, 1H), 7.63 (d, J=8.7 Hz, 2H), 6.82 (d, J=8.7 Hz, 2H), 5.35 (d, J=5.6 Hz, 1H), 4.50 (app td, J=9.1, 3.9 Hz, 1H), 4.25 (d, J=8.9 Hz, 1H), 4.16-4.11 (m, 2H), 3.91 (dd, J=3.3, 1.1 Hz, 1H), 3.72-3.66 (m, 2H), 3.62 (dd, J=10.1, 3.3 Hz, 1H), 3.37 (dd, J=14.1, 9.3 Hz, 1H), 2.91 (s, 3H), 2.83

(app t, J=11.0 Hz, 1H), 2.23-2.16 (m, 1H), 2.09 (s, 3H), 2.09-2.00 (m, 2H), 1.43-1.30 (m, 2H), 1.27-1.19 (m, 2H), 0.84 (t, J=7.2 Hz, 3H). HRMS (ESI+, m/z): [M+2H]$^{2+}$ calcd for $C_{28}H_{40}N_4O_5S$, 273.1432; found 273.1432.

J=8.6, 5.9 Hz, 1H), 4.26 (dd, J=9.1, 1.5 Hz, 1H), 4.14 (dd, J=10.1, 5.6 Hz, 1H), 3.99 (dd, J=10.3, 6.1 Hz, 1H), 3.90 (dd, J=3.4, 1.3 Hz, 1H), 3.76-7.74 (m, 2H), 3.63-3.59 (m, 2H), 3.05 (s, 3H), 2.85 (s, 3H), 2.72 (app t, J=11.1 Hz, 1H), 2.14 (s, 3H), 1.96-1.90 (m, 1H), 1.76 (dt, J=13.4, 9.8 Hz, 1H), 1.49 (ddd, J=13.9, 8.5, 6.1 Hz, 1H), 1.24 (ddd, J=15.7, 8.2, 5.9 Hz, 1H), 1.16-1.10 (m, 1H), 1.08-1.01 (m, 2H), 0.68 (t, J=7.3 Hz, 3H). HRMS (ESI+, m/z): [M+2H]$^{2+}$ calcd for $C_{29}H_{42}N_4O_5S$, 280.1511; found 280.1514.

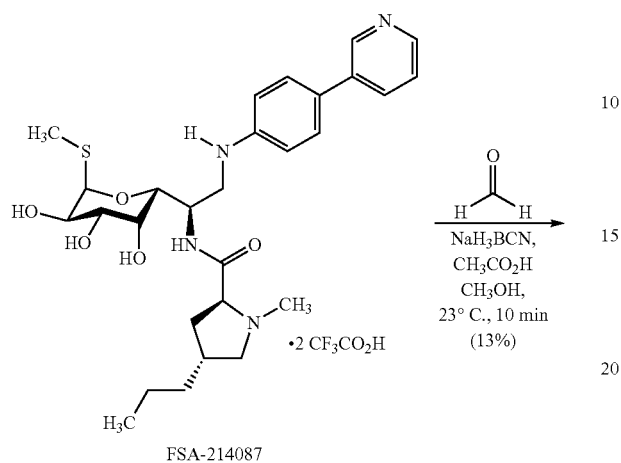

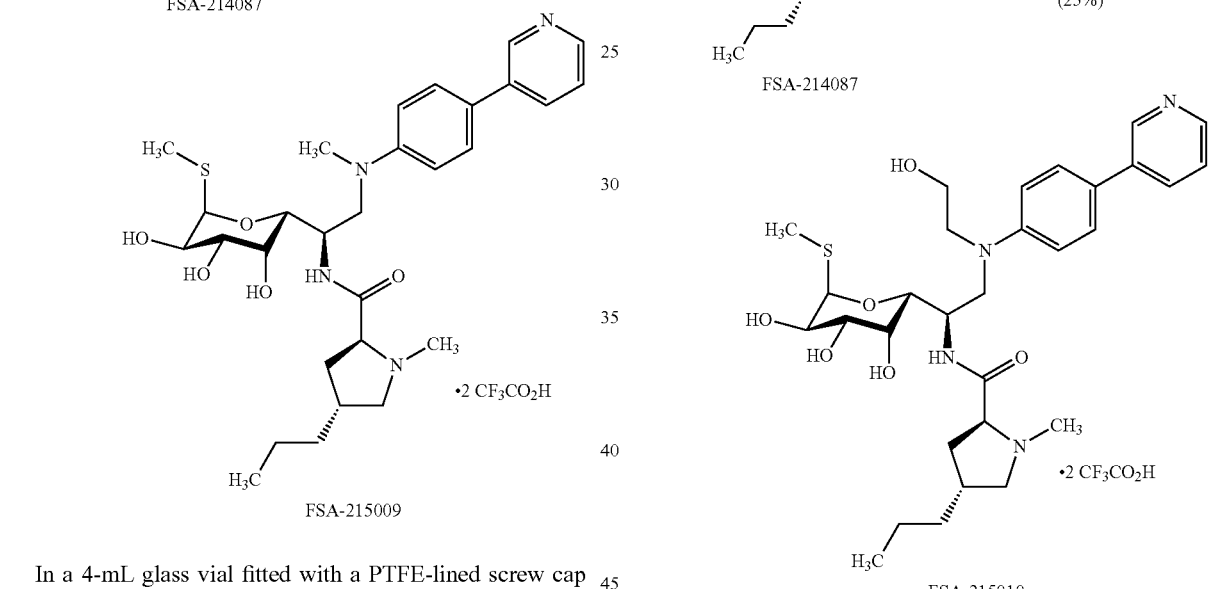

In a 4-mL glass vial fitted with a PTFE-lined screw cap and a magnetic stir bar, aniline FSA-214087 (22 mg, 41 μmol, 1 equiv) was dissolved in methanol (820 μL) to which a spatula tipful of bromocresol green pH indicator had been added. The pH of the solution was adjusted to reach pH 4-5 (indicated by a forest green color) by addition of acetic acid. Formalin (92 μL, 1.2 mmol, 30 equiv) and sodium cyanoborohydride (13 mg, 210 μmol, 5.0 equiv) were then added, and the mixture was stirred at 23° C. for 10 min, whereupon LCMS analysis showed that the reaction was complete. The mixture was passed through a 0.2-μm PTFE filter, the filtrate was concentrated, and the crude residue was purified by preparative HPLC-MS on a Waters SunFire Prep C18 column (5 μm, 250×19 mm; eluting with 0.1% trifluoroacetic acid-water, grading to 0.1% trifluoroacetic acid-35% acetonitrile-water over 40 min, with a flow rate of 15 mL/min; monitored by UV absorbance at 280 nm and ESI+ selected ion monitoring [m/z=280]; $R_t$=29.2 min) to provide (pyridyl)aniline analog FSA-215009.2CF$_3$CO$_2$H as a white solid (4.1 mg, 13%)$^1$H (600 MHz, CD$_3$OD) δ 9.06 (d, J=2.2 Hz, 1H), 8.77 (ddd, J=8.3, 2.3, 1.3 Hz, 1H), 8.62 (d, J=5.4 Hz, 1H), 8.02 (dd, J=8.3, 5.6, 1H), 7.71 (d, J=9.1 Hz, 2H), 6.94 (d, J=9.0 Hz, 2H), 5.35 (d, J=5.7 Hz, 1H), 4.72 (app td, In a 4-mL glass vial fitted with a PTFE-lined screw cap and a magnetic stir bar, aniline FSA-214087 (22 mg, 41 μmol, 1 equiv) was dissolved in methanol (820 μL) to which a spatula tipful of bromocresol green pH indicator had been added. The pH of the solution was adjusted to reach pH 4-5 (indicated by a forest green color) by addition of acetic acid. Glycolaldehyde dimer (74 mg, 0.62 mmol, 15 equiv) and sodium cyanoborohydride (13 mg, 0.21 mmol, 5.0 equiv) were then added, and the mixture was stirred at 23° C. for 20 h, whereupon LCMS analysis indicated that the reaction was complete. The mixture was passed through a 0.2-μm PTFE filter, the filtrate was concentrated, and the crude residue was purified by preparative HPLC on a Waters SunFire Prep C18 column (5 μm, 250×19 mm; eluting with 0.1% trifluoroacetic acid-water, grading to 0.1% trifluoroacetic acid-35% acetonitrile-water over 40 min, with a flow rate of 15 mL/min; monitored by UV absorbance at 280 nm; $R_t$=26.0 min) to provide ethanolamine analog FSA-215010.2CF$_3$CO$_2$H as a white solid (8.3 mg, 25%). $^1$H (600 MHz, CD$_3$OD) δ 9.08 (d, J=2.1 Hz, 1H), 8.81 (ddd, J=8.4, 2.3, 1.3 Hz, 1H), 8.64 (app dt, J=5.6, 1.1 Hz, 1H), 8.05 (ddd, J=8.4, 5.6, 0.7 Hz, 1H), 7.71 (d, J=9.0, 2H), 6.99 (d, J=9.1 Hz, 2H), 5.36 (d, J=5.7 Hz, 1H), 4.71 (ddd, J=10.9, 8.9, 3.5 Hz, 1H), 4.26 (d, J=9.2 Hz, 1H), 4.14 (dd, J=10.1, 5.6 Hz, 1H), 4.04 (dd, J=10.1, 6.2 Hz, 1H), 3.90 (d, J=3.2 Hz, 2H), 3.79-3.72 (m, 3H), 3.65-3.60 (m, 3H), 3.59-3.55 (m, 1H), 2.86 (s, 3H), 2.75 (app t, J=11.1 Hz, 1H), 2.14 (s, 3H), 2.02-1.96 (m, 1H), 1.84 (dt, J=13.4, 9.6 Hz, 1H), 1.58 (ddd, J=13.0, 8.6, 6.3 Hz, 1H), 1.32-1.26 (m, 1H), 1.20-1.14 (m, 1H), 1.12-1.07 (m, 2H), 0.72 (t, J=7.3 Hz, 3H). HRMS (ESI+, m/z): [M+2H]$^{2+}$ calcd for $C_{30}H_{44}N_4O_6$, 295.1564; found 295.1561.

In a 4-mL glass vial fitted with a PTFE-lined screw cap and a magnetic stir bar, aldehyde 18 (theoretically 10 mg, 16 μmol, 1 equiv), dichloromethane (410 μL), acetic acid (9.4 μL, 0.17 mmol, 10 equiv) and cyclopropylamine (2.9 μL, 41 μmol, 2.5 equiv) were combined. This mixture was stirred for 15 min at 23° C. before sodium triacetoxyborohydride (7.0 mg, 33 μmol, 2.0 equiv) was added. After 1 h, LCMS analysis showed that the reaction was complete. The mixture was concentrated to dryness, and the residue was re-suspended in 50% v/v methanol-1N aqueous hydrogen chloride solution (1.0 mL). After 15 min, LCMS showed that global desilylation was complete, and the mixture was passed through a 0.2-μm PTFE filter. The filtrate was concentrated, and the crude residue was purified by preparative HPLC on a Waters SunFire Prep C18 column (5 μm, 250×19 mm; eluting with 0.1% trifluoroacetic acid-water, grading to 0.1% trifluoroacetic acid-40% acetonitrile-water over 40 min, with a flow rate of 15 mL/min; monitored by UV absorbance at 210 nm; FSA-214082a R$_t$=22.4 min, FSA-214082b R$_t$=23.7 min) to provide cyclopropylamine analogs FSA-214082a.2CF$_3$CO$_2$H (2.3 mg, 26%, 2 steps) and FSA-214082b.2CF$_3$CO$_2$H (2.1 mg, 23%, 2 steps) as white solids.

FSA-214082a: $^1$H NMR (600 MHz, CD$_3$OD) δ 5.30 (d, J=5.5 Hz, 1H), 4.69 (ddd, J=9.8, 5.7, 3.7 Hz, 1H), 4.24-4.18 (m, 2H), 4.10 (dd, J=10.1, 5.5 Hz, 1H), 3.93 (dd, J=3.4, 1.4 Hz, 1H), 3.76 (dd, J=10.8, 6.3 Hz, 1H), 3.61 (dd, J=10.0, 3.3 Hz, 1H), 3.50 (dd, J=13.0, 3.7 Hz, 1H), 3.36 (dd, J=13.0, 10.4 Hz, 1H), 2.98-2.94 (m, 4H), 2.91-2.83 (m, 2H), 2.37-2.29 (m, 2H), 2.26-2.19 (m, 1H), 2.11 (s, 3H), 1.51-1.44 (m, 2H), 1.40-1.33 (m, 2H), 0.97-0.90 (m, 8H). HRMS (ESI+, m/z): [M+H]$^+$ calcd for $C_{20}H_{37}N_3O_5S$, 432.2527; found 432.2516.

FSA-214082b: $^1$H NMR (600 MHz, CD$_3$OD) δ 5.34 (d, J=5.6 Hz, 1H), 4.52 (app td, J=7.7, 4.9 Hz, 1H), 4.31 (dd, J=7.3, 1.3 Hz, 1H), 4.19 (dd, J=10.3, 6.5 Hz, 1H), 4.10 (dd, J=10.1, 5.6 Hz, 1H), 3.89 (dd, J=3.4, 1.3 Hz, 1H), 3.76 (dd, J=11.0, 6.7 Hz, 1H), 3.60-3.59 (m, 1H), 3.59-3.58 (m, 1H), 3.40 (dd, J=13.0, 8.0 Hz, 1H), 2.94 (s 3H), 2.90 (app t, J=10.9 Hz, 1H), 2.82 (app tt, J=7.3, 4.4 Hz, 1H), 2.40-2.31 (m, 2H), 2.25-2.19 (m, 1H), 2.12 (s, 3H), 1.51-1.46 (m, 2H), 1.40-1.35 (m, 2H), 0.96 (t, J=7.3 Hz, 3H), 0.93-0.92 (m, 4H). HRMS (ESI+, m/z): [M+H]$^+$ calcd for $C_{20}H_{37}N_3O_5S$, 432.2527; found 432.2519.

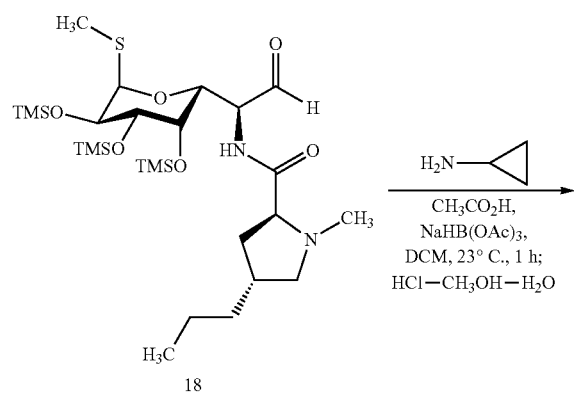

18

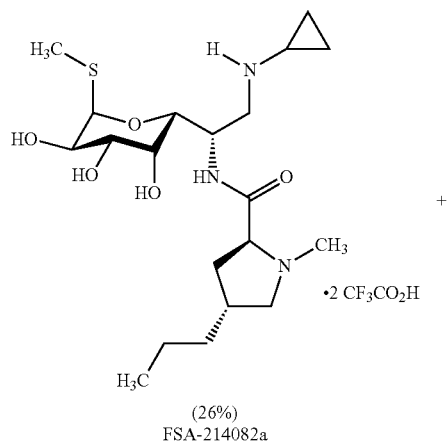

(26%)
FSA-214082a

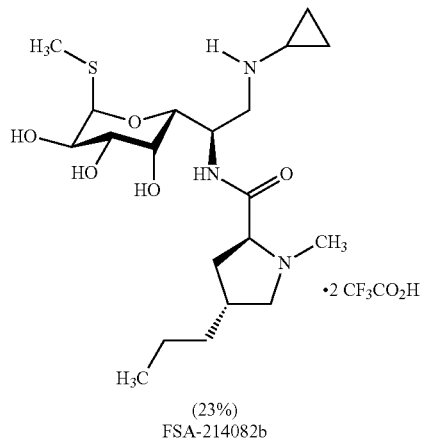

(23%)
FSA-214082b

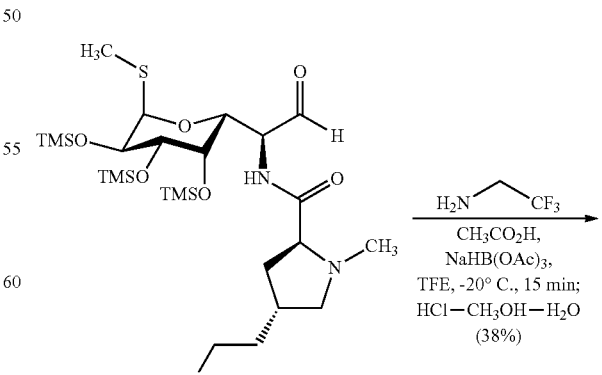

18

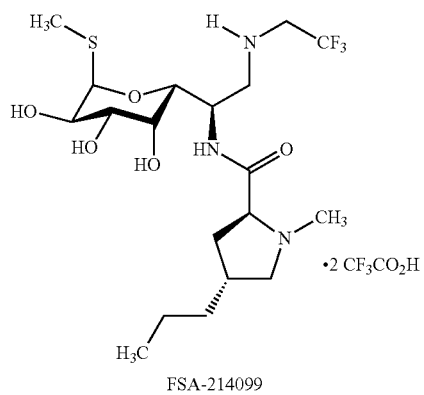

FSA-214099

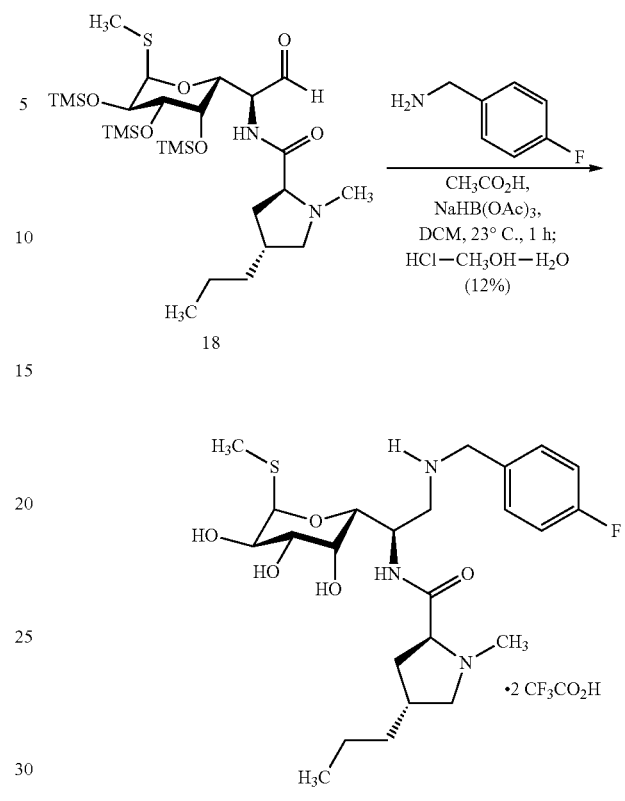

FSA-214084

A 4-mL glass vial fitted with a PTFE-lined screw cap was charged with a magnetic stir bar, aldehyde 18 (theoretically 20 mg, 33 µmol, 1 equiv), 2,2,2-trifluoroethanol (660 µL), and powdered, activated 4A molecular sieves (20 mg). The suspension was chilled to −20° C. in an acetone bath, whereupon acetic acid (11 µL, 0.20 µmol, 6.0 equiv) was added. 2,2,2-Trifluoroethan-1-amine (7.8 µL, 99 µmol, 3.0 equiv) was added next, and the mixture was stirred at −20° C. for 15 min before the mixture was treated with sodium triacetoxyborohydride (21 mg, 99 µmol, 3.0 equiv). After 1 h, LCMS analysis showed complete consumption of aldehyde starting material and imine intermediate. The mixture was concentrated to dryness, and the residue was re-suspended in 50% v/v methanol-1N aqueous hydrogen chloride solution (1.0 mL). After 15 min of stirring at 23° C., LCMS analysis demonstrated that global desilylation was complete, and the mixture was filtered through a 0.2-µm PTFE filter. The filtrate was concentrated, and the crude residue was purified by preparative HPLC-MS on a Waters SunFire Prep C18 column (5 µm, 250×19 mm; eluting with 0.1% trifluoroacetic acid-water, grading to 0.1% trifluoroacetic acid-40% acetonitrile-water over 40 min, with a flow rate of 15 mL/min; monitored by UV absorbance at 210 nm and ESI+ selected ion monitoring [m/z=474]; $R_f$=20.7 min) to provide trifluoroethylamine analog FSA-214099.2CF$_3$CO$_2$H as a white solid (8.8 mg, 38%, 2 steps). $^1$H NMR (500 MHz, CD$_3$OD) δ 5.31 (d, J=5.6 Hz, 1H), 4.42 (td, J=8.0, 4.5 Hz, 1H), 4.23 (dd, J=7.8, 1.2 Hz, 1H), 4.19 (dd, J=10.2, 6.0 Hz, 1H), 4.10 (dd, J=10.1, 5.6 Hz, 1H), 3.89 (dd, J=3.4, 1.2 Hz, 1H), 3.76 (dd, J=11.0, 6.6 Hz, 1H), 3.74-3.64 (m, 2H), 3.58 (dd, J=10.1, 3.3 Hz, 1H), 3.39 (dd, J=12.7, 4.5 Hz, 1H), 3.15 (dd, J=12.7, 8.2 Hz, 1H), 2.89 (app t, J=10.7 Hz, 1H), 2.40-2.30 (m, 2H), 2.26-2.19 (m, 1H), 1.51-1.45 (m, 2H), 1.41-1.32 (m, 2H), 0.95 (t, J=7.3 Hz, 3H). $^{19}$F NMR (471 MHz, CD$_3$OD) δ −71.30 (s, 3F), −77.18 (s, 6F). HRMS (ESI+, m/z): [M+H]$^+$ calcd for C$_{19}$H$_{34}$F$_3$N$_3$O$_5$S, 474.2244; found 474.2252.

In a 4-mL glass vial fitted with a PTFE-lined screw cap and a magnetic stir bar, aldehyde 18 (theoretically 10 mg, 16 µmol, 1 equiv), dichloromethane (410 µL), acetic acid (9.4 µL, 0.17 mmol, 10 equiv) and 4-fluorobenzylamine (4.7 µL, 41 µmol, 2.5 equiv) were combined. This mixture was stirred for 15 min at 23° C. before sodium triacetoxyborohydride (7.0 mg, 33 µmol, 2.0 equiv) was added. After 1 h, LCMS analysis showed that the reaction was complete. The mixture was concentrated to dryness, and the residue was re-suspended in 50% v/v methanol-1N aqueous hydrogen chloride solution (1.0 mL). After 15 min, LCMS showed that global desilylation was complete, and the mixture was passed through a 0.2-µm PTFE filter. The filtrate was concentrated, and the crude residue was purified by preparative HPLC on a Waters SunFire Prep C18 column (5 µm, 250×19 mm; eluting with 0.1% formic acid-water, grading to 0.1% formic acid-40% acetonitrile-water over 40 min, with a flow rate of 15 mL/min; monitored by UV absorbance at 210 nm; $R_f$=13.5 min) to provide 4-fluorobenzylamine analog FSA-214084 as a white solid (1.0 mg, 12%, 2 steps). $^1$H NMR (500 MHz, CD$_3$OD) δ 7.58 (dd, J=8.6, 5.3 Hz, 2H), 7.20 (app t, J=8.7 Hz, 2H), 5.28 (d, J=5.6 Hz, 1H), 4.44 (app td, J=8.3, 4.8 Hz, 1H), 4.34-4.30 (m, 3H), 4.28-4.24 (m, 1H), 4.08 (dd, J=10.1, 5.6 Hz, 1H), 3.87 (d, J=2.9 Hz, 1H), 3.76 (dd, J=11.0, 6.6 Hz, 1H), 3.57 (dd, J=10.1, 3.2 Hz, 1H), 3.43 (dd, J=13.1, 4.8 Hz, 1H), 2.96 (s, 3H), 2.91 (app t, J=10.8 Hz, 1H), 2.41-2.35 (m, 1H), 2.33-2.29 (m, 2H), 2.01 (s, 3H), 1.52-1.48 (m, 2H), 1.41-1.35 (m, 2H), 0.96 (t, J=7.3 Hz, 3H). $^{19}$F NMR (471 MHz, CD$_3$OD) δ −113.45 (s, 1F). HRMS (ESI+, m/z): [M+H]$^+$ calcd for C$_{24}$H$_{38}$FN$_3$O$_5$S, 500.2589; found 500.2577.

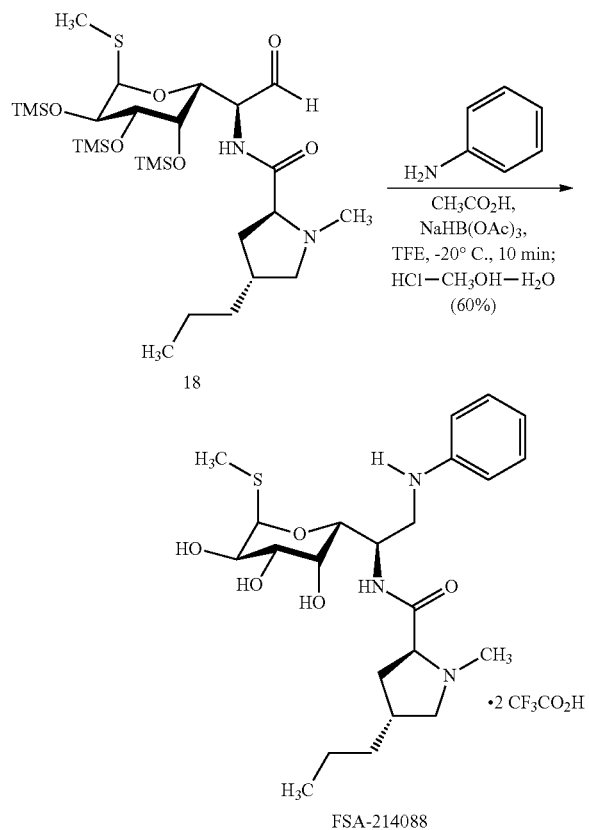

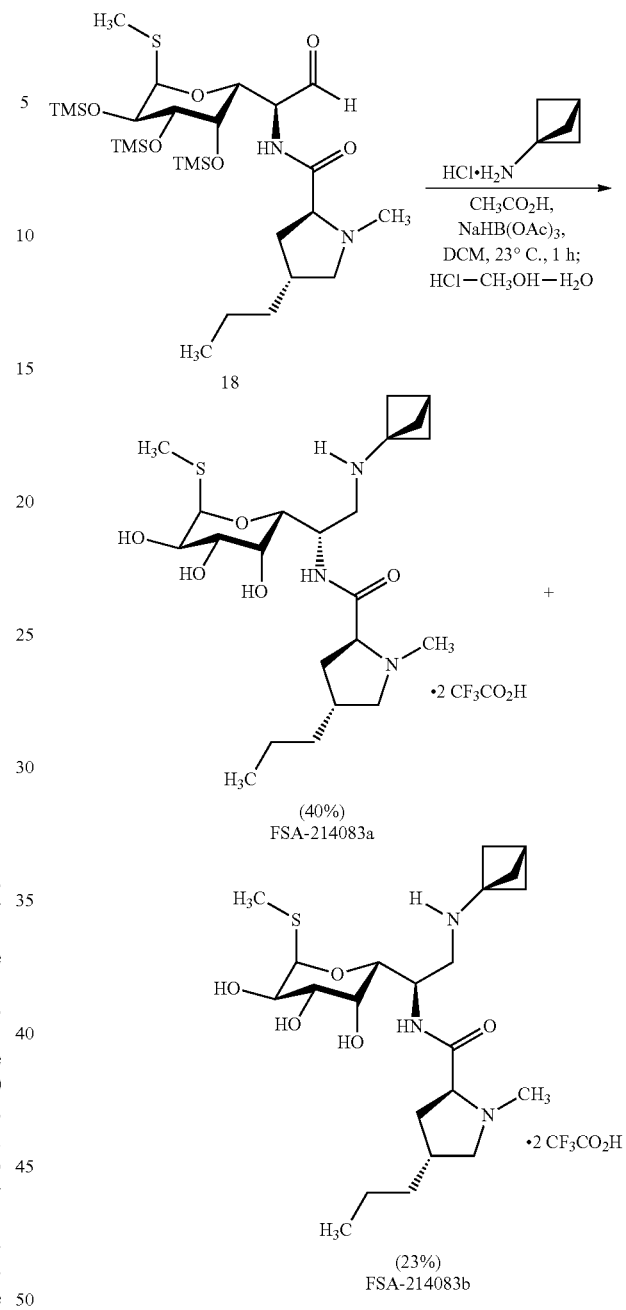

A 4-mL glass vial fitted with a PTFE-lined screw cap was charged with a magnetic stir bar, aldehyde 18 (theoretically 10 mg, 16 µmol, 1 equiv), 2,2,2-trifluoroethanol (330 µL), and powdered, activated 4A molecular sieves (10 mg). The suspension was chilled to −20° C. in an acetone bath, whereupon acetic acid (5.7 µL, 0.10 µmol, 6.0 equiv) was added. Aniline (4.5 µL, 49 µmol, 3.0 equiv) was added next, and the mixture was stirred at −20° C. for 15 min before the mixture was treated with sodium triacetoxyborohydride (10 mg, 49 µmol, 3.0 equiv). After 10 min, LCMS analysis showed complete consumption of aldehyde starting material and imine intermediate. The mixture was concentrated to dryness, and the residue was re-suspended in 50% v/v methanol-1N aqueous hydrogen chloride solution (1.0 mL). After 15 min of stirring at 23° C., LCMS analysis demonstrated that global desilylation was complete, and the mixture was filtered through a 0.2-µm PTFE filter. The filtrate was concentrated, and the crude residue was purified by preparative HPLC-MS on a Waters SunFire Prep C18 column (5 µm, 250×19 mm; eluting with 0.1% trifluoroacetic acid-water, grading to 0.1% trifluoroacetic acid-50% acetonitrile-water over 40 min, with a flow rate of 15 mL/min; monitored by UV absorbance at 254 nm; $R_t$=28.3 min) to provide aniline analog FSA-214088·2CF$_3$CO$_2$H as a white solid (5.7 mg, 60%, 2 steps). $^1$H NMR (600 MHz, CD$_3$OD) δ 7.17-7.14 (m, 2H), 6.79-6.71 (m, 3H), 5.33 (d, J=5.7 Hz, 1H), 4.47 (app td, J=8.8, 4.2 Hz, 1H), 4.23 (d, J=8.6 Hz, 1H), 4.14-4.09 (m, 2H), 3.89 (d, J=2.6 Hz, 1H), 3.71 (dd, J=10.8, 6.9 Hz, 1H), 3.64-3.59 (m, 2H), 3.35 (dd, J=13.7, 8.9 Hz, 1H), 2.90 (s, 3H), 2.82 (app t, J=11.1 Hz, 1H), 2.23-2.18 (m, 1H), 2.09 (s, 3H), 2.05-1.97 (m, 2H), 1.43-1.35 (m, 2H), 1.33-1.28 (m, 2H), 0.93 (t, J=7.3 Hz, 3H). HRMS (ESI+, m/z): [M+H]$^+$ calcd for C$_{23}$H$_{37}$N$_3$O$_5$S, 468.2527; found 468.2538.

In a 4-mL glass vial fitted with a PTFE-lined screw cap and a magnetic stir bar, aldehyde 18 (theoretically 10 mg, 16 µmol, 1 equiv), dichloromethane (410 µL), acetic acid (9.4 µL, 0.17 mmol, 10 equiv) and bicyclo[1.1.1]pentan-1-amine hydrochloride (4.9 mg, 41 µmol, 2.5 equiv) were combined. This mixture was stirred for 15 min at 23° C. before sodium triacetoxyborohydride (7.0 mg, 33 µmol, 2.0 equiv) was added. After 1 h, LCMS analysis showed that the reaction was complete. The mixture was concentrated to dryness, and the residue was re-suspended in 50% v/v methanol-1N aqueous hydrogen chloride solution (1.0 mL). After 15 min, LCMS showed that global desilylation was complete, and the mixture was passed through a 0.2-µm PTFE filter. The filtrate was concentrated, and the crude residue was purified by preparative HPLC on a Waters SunFire Prep C18 column (5 µm, 250×19 mm; eluting with 0.1% trifluoroacetic acid-water, grading to 0.1% trifluoroacetic acid-40% acetonitrile-water over 40 min, with a flow rate of 15 mL/min; monitored by UV absorbance at 210 nm; FSA-214083a $R_t$=27.1 min; FSA-214083b $R_t$=29.4 min) to provide propellamine analogs FSA-214083a.2CF$_3$CO$_2$H (3.8 mg, 40%, 2 steps) and FSA-214083b.2CF$_3$CO$_2$H (2.2 mg, 23%, 2 steps) as white solids.

FSA-214083a: $^1$H NMR (600 MHz, CD$_3$OD) δ 5.29 (d, J=5.5 Hz, 1H), 4.63 (ddd, J=10.2, 6.1, 3.8 Hz, 1H), 4.22 (dd, J=10.3, 5.0 Hz, 1H), 4.20 (dd, J=6.1, 1.5 Hz, 1H), 3.93 (dd, J=3.4, 1.5 Hz, 1H), 3.76 (ddd, J=7.5, 5.8, 3.2 Hz, 1H), 3.61 (dd, J=10.0, 3.3 Hz, 1H), 3.35 (dd, J=12.9, 3.8 Hz, 1H), 3.20 (dd, J=12.8, 10.4 Hz, 1H), 2.95 (s, 3H), 2.89 (app t, J=10.6 Hz, 1H), 2.73 (s, 1H), 2.34-2.29 (m, 2H), 2.23-2.21 (m, 1H), 2.14 (s, 6H), 2.10 (s, 3H), 1.49-1.44 (m, 2H), 1.38-1.33 (m, 2H), 0.95 (t, J=7.3 Hz, 3H). HRMS (ESI+, m/z): [M+H]$^+$ calcd for C$_{22}$H$_{39}$N$_3$O$_5$S, 458.2683; found 458.2676.

FSA-214083b: $^1$H NMR (600 MHz, CD$_3$OD) δ 5.34 (d, J=5.6 Hz, 1H), 4.46 (app td, J=7.5, 5.2 Hz, 1H), 4.30 (dd, J=7.0, 1.3 Hz, 1H), 4.18 (dd, J=10.3, 6.5 Hz, 1H), 4.10 (dd, J=10.1, 5.6 Hz, 1H), 3.89 (dd, J=3.3, 1.3 Hz, 1H), 3.76 (dd, J=10.9, 6.7 Hz, 1H), 3.59 (dd, J=10.1, 3.2 Hz, 1H), 3.44 (dd, J=12.9, 5.2 Hz, 1H), 3.21 (dd, J=12.9, 7.8 Hz, 1H), 2.94 (s, 3H), 2.90 (app t, J=10.8 Hz, 1H), 2.74 (s, 1H), 2.39-2.31 (m, 2H), 2.24-2.22 (m, 1H), 2.14 (s, 6H), 2.11 (s, 3H), 1.51-1.46 (m, 2H), 1.40-1.35 (m, 2H), 0.96 (t, J=7.3 Hz, 3H). HRMS (ESI+, m/z): [M+H]$^+$ calcd for C$_{22}$H$_{39}$N$_3$O$_5$S, 458.2683; found 458.2676.

An oven-dried 4-mL glass vial was charged with a magnetic stir bar, methyltriphenylphosphonium bromide (16 mg, 46 µmol, 1.4 equiv), and tetrahydrofuran (330 µL). The vial was sealed with a silicone septum-lined screw cap, and the mixture was chilled to 0° C. before potassium tert-butoxide solution (1.0 M in tetrahydrofuran, 40 µL, 40 µmol, 1.2 equiv) was added. Upon treatment with alkoxide base, the heterogeneous mixture immediately attained a vibrant, highlighter-yellow color. This mixture was stirred at 0° C. for 30 min before a solution of aldehyde 18 (theoretically 20 mg, 33 µmol, 1 equiv) in tetrahydrofuran (330 µL) was added by cannula, causing the yellow color to disappear. After 5 min of stirring at 0° C., TLC analysis (7% methanol-dichloromethane, PAA) revealed that no starting material remained, and excess Wittig reagent was quenched with the addition of acetone (150 µL). The product mixture was diluted with hexanes (15 mL), dried over sodium sulfate, filtered, and concentrated to give a white film that was re-dissolved in 50% v/v methanol-1N aqueous hydrogen chloride solution (1.5 mL). This mixture was stirred at 23° C. for 1 h, at which point LCMS analysis indicated that global desilylation was complete. The mixture was passed through a 0.2-µm PTFE filter, the filtrate was concentrated, and the crude residue was purified by preparative HPLC-MS on a Waters SunFire Prep C18 column (5 µm, 250×19 mm; eluting with 0.1% formic acid-water, grading to 0.1% formic acid-35% acetonitrile-water over 40 min, with a flow rate of 15 mL/min; monitored by UV absorbance at 210 nm and ESI+ selected ion monitoring [m/z=389]; $R_t$=18.9 min) to provide vinyl analog FSA-215031.HCO$_2$H as a white solid (1.5 mg, 11%, 2 steps). $^1$H NMR (600 MHz, CD$_3$OD) δ 8.37 (s, 1H), 6.01 (ddd, J=17.3, 10.5, 5.5 Hz, 1H), 5.28 (d, J=5.6 Hz, 1H), 5.23 (app dt, J=17.3, 1.5 Hz, 1H), 5.21 (app dt, J=10.4, 1.4 Hz, 1H), 4.71 (app ddt, J=8.5, 5.5, 1.6 Hz, 1H), 4.11 (dd, J=10.1, 5.7 Hz, 1H), 4.09 (dd, J=8.2, 0.8 Hz, 1H), 3.88 (dd, J=3.5, 1.3 Hz, 1H), 3.59 (dd, J=10.1, 3.3 Hz, 1H), 3.44-3.41 (m, 1H), 2.59 (s, 3H), 2.38 (app t, J=10.0 Hz, 1H), 2.30-2.23 (m, 1H), 2.08 (ddd, J=13.5, 8.3, 5.4 Hz, 1H), 2.04 (s, 3H), 2.01-1.95 (m, 1H), 1.42-1.32 (m, 4H), 0.94 (t, J=7.1 Hz, 3H). HRMS (ESI+, m/z): [M+H]$^+$ calcd for C$_{18}$H$_{32}$N$_2$O$_5$S, 389.2105; found 389.2111.

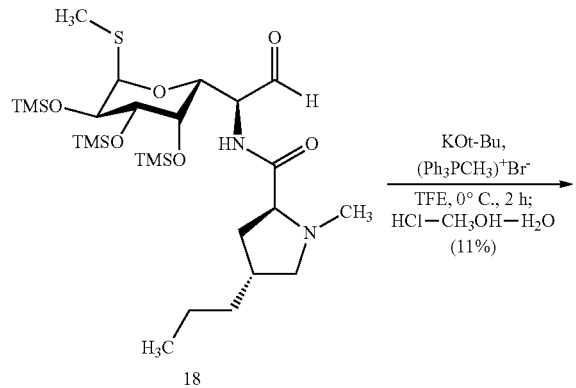

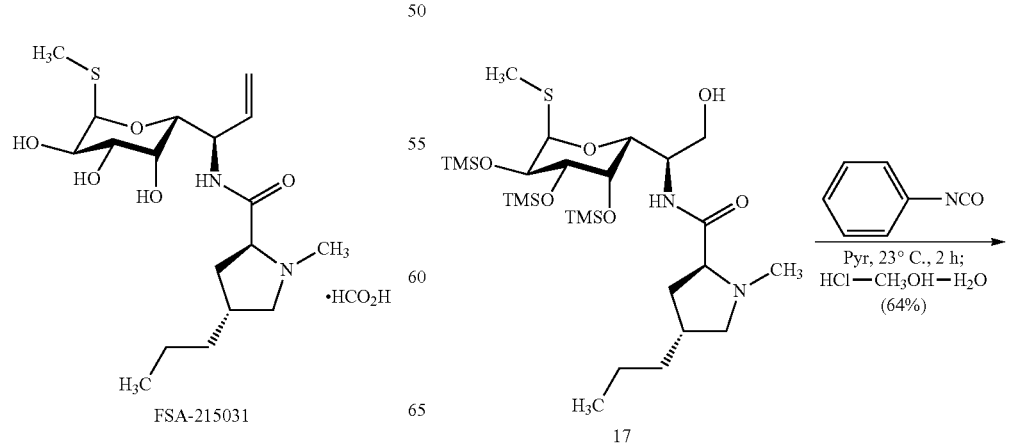

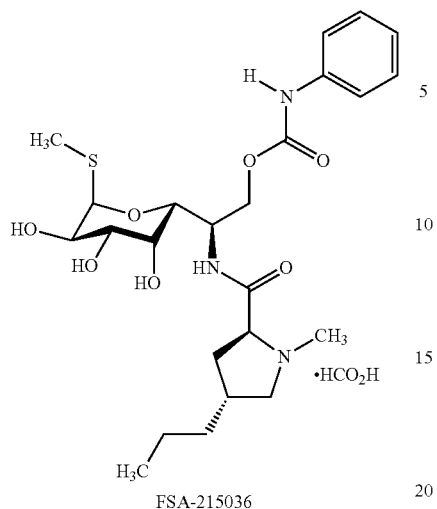

FSA-215036

A 1-mL glass vial was charged with a magnetic stir bar, 2,3,4-tris-O-trimethylsilyl-8-norlincomycin (17, 10 mg, 16 μmol, 1 equiv), pyridine (82 μL), and phenyl isocyanate (3.6 μL, 33 μmol, 2.0 equiv). The vial was sealed with a PTFE-lined screw cap, and the reaction mixture was stirred at 23° C. for 2 h, at which point TLC analysis (8% methanol-dichloromethane, PAA) showed that all the starting material had been consumed. Excess phenyl isocyanate was quenched with the addition of methanol (1 drop), and the mixture was then concentrated to dryness. The residue was then re-dissolved in 50% v/v methanol-1N aqueous hydrogen chloride solution (500 μL), after 30 min, LCMS analysis showed that global desilylation was complete. The product solution was passed through a 0.2-μm PTFE filter, the filtrate was concentrated, and the crude residue was purified by preparative HPLC on a on a Waters SunFire Prep C18 column (5 μm, 250×19 mm; eluting with 0.1% formic acid-5% acetonitrile-water, grading to 0.1% formic acid-50% acetonitrile-water over 40 min, with a flow rate of 15 mL/min; monitored by UV absorbance at 254 nm; $R_f$=21.8 min) to provide phenyl carbamate analog FSA-215036.HCO$_2$H as a white solid (5.8 mg, 64%). $^1$H NMR (600 MHz, CD$_3$OD) δ 8.38 (s, 1H), 7.43 (d, J=8.0 Hz, 2H), 7.28-7.25 (m, 2H), 7.02 (tt, J=7.4, 1.0 Hz, 1H), 5.31 (d, J=5.6 Hz, 1H), 4.48 (app dt, J=9.6, 5.1 Hz, 1H), 4.41-4.38 (m, 2H), 4.25 (dd, J=9.2, 1.2 Hz, 1H), 4.12 (dd, J=10.1, 5.6 Hz, 1H), 3.85 (dd, J=3.4, 1.2 Hz, 1H), 3.61 (dd, J=10.1, 3.3 Hz, 1H), 3.52-3.50 (m, 1H), 3.44 (dd, J=9.9, 6.5 Hz, 1H), 2.60 (s, 3H), 2.41 (app t, J=10.3 Hz, 1H), 2.21-2.15 (m, 1H), 2.11-2.09 (m, 1H), 2.08 (s, 3H), 1.95 (app dt, J=13.0, 9.9 Hz, 1H), 1.34-1.21 (m, 4H), 0.87 (t, J=7.2 Hz, 3H). HRMS (ESI+, m/z): [M+H]$^+$ calcd for C$_{24}$H$_{37}$N$_3$O$_7$S, 512.2425; found 512.2444.

Taking no special precautions to exclude air or moisture, a 300-mL round-bottomed flask was charged with a magnetic stir bar, (4-(tert-butylthio)phenyl)boronic acid (20, 4.79 g, 22.8 mmol, 1.20 equiv), potassium phosphate heptahydrate (12.9 g, 38.0 mmol, 2.00 equiv), palladium(II) acetate (43.0 mg, 0.190 mmol, 0.0100 equiv), and ethylene glycol (146 mL). 3-Bromopyridine (19, 1.83 mL, 19.0 mmol, 1 equiv) was added last, stirring was initiated, and the reaction mixture was heated to 80° C. (open to the atmosphere) in a pre-heated oil bath. Within 30 min, the suspension had clarified, forming an amber-brown homogeneous solution; and after 1 h, the mixture became a light tan, turbid suspension. After 2 h of stirring at 80° C., TLC analysis (60% ethyl acetate-hexanes, UV) showed that no starting material remained. The mixture was cooled to 23° C., and was then poured into a separatory funnel containing saturated aqueous sodium chloride solution (250 mL). The aqueous suspension was extracted with diethyl ether (4×50 mL), and the combined organic extracts were washed with a fresh portion of saturated aqueous sodium chloride solution (50 mL). The washed organic product solution was then dried over sodium sulfate, filtered, and concentrated to give a milky, light yellow oil that was purified by flash-column chromatography (120 g silica gel, eluting with 10% ethyl acetate-hexanes initially, grading to 40% ethyl acetate-hexanes) to furnish 3-(4-(tert-butylthio)phenyl)pyridine (21) as a brilliant white, fluffy powder (3.04 g, 66%). $^1$H NMR (600 MHz, CDCl$_3$) δ 8.86 (d, J=1.7 Hz, 1H), 8.61 (dd, J=4.7, 1.6 Hz, 1H), 7.88 (ddd, J=7.9, 2.4, 1.6 Hz, 1H), 7.64 (d, J=8.3 Hz, 2H), 7.55 (d, J=8.2 Hz, 2H), 7.38 (ddd, J=7.8, 4.8, 0.9 Hz, 1H), 1.33 (s, 9H). HRMS (ESI+, m/z): [M+H]$^+$ calc'd for C$_{15}$H$_{17}$NS, 244.1154; found 244.1167.

In a 500-mL round-bottomed flask containing a magnetic stir bar, tert-butanesulfide 21 (3.00 g, 12.3 mmol, 1 equiv) and concentrated hydrochloric acid (38% w/w in water, 123 mL) were combined. The headspace was flushed with argon, and the mixture was heated to 90° C. with constant stirring; the starting material gradually dissolved upon warming.

After 5 h, LCMS analysis showed that no starting material remained, and the reaction mixture was cooled to 0° C. The chilled solution was basified with the careful addition of aqueous 6N sodium hydroxide solution, until pH=8 was achieved. The aqueous mixture was then extracted with diethyl ether (4×75 mL), the combined extracts were dried over sodium sulfate, the dried solution was filtered, and the filtrate was concentrated to give a colorless oil. This crude residue was finally purified by flash-column chromatography (80 g silica gel, eluting with 20% ethyl acetate-hexanes initially, grading to 60% ethyl acetate-hexanes) to provide arenethiol 22 as a light yellow solid (1.92 g, 83%). $^1$H NMR (600 MHz, CDCl$_3$) δ 8.79 (d, J=2.4 Hz, 1H), 8.56 (dd, J=4.8, 1.6 Hz, 1H), 7.79 (dt, J=7.9, 2.0 Hz, 1H), 7.42 (d, J=8.3 Hz, 2H), 7.34 (d, J=8.3 Hz, 2H), 7.32 (dd, J=7.9, 4.9 Hz, 1H), 3.55 (s, 1H). HRMS (ESI+, m/z): [M+H]$^+$ calc'd for C$_{11}$H$_9$NS, 188.0528; found 188.0526.

re-dissolved in 50% v/v methanol-1N aqueous hydrogen chloride solution (800 μL). After 30 min of stirring at 23° C., LCMS analysis showed that global desilylation was complete, and the mixture was passed through a 0.2-μm PTFE filter. The filtrate was concentrated, and the crude residue was subjected to preparative HPLC on a on a Waters SunFire Prep C18 column (5 μm, 250×19 mm; eluting with 0.1% trifluoroacetic acid-water, grading to 0.1% trifluoroacetic acid-40% acetonitrile-water over 40 min, with a flow rate of 15 mL/min; monitored by UV absorbance at 254 nm; R$_t$=27.8 min) to provide arenesulfide analog FSA-215002.2CF$_3$CO$_2$H as a white solid (4.8 mg, 19%). $^1$H NMR (600 MHz, CD$_3$OD) δ 9.09 (s, 1H), 8.75 (d, J=4.9 Hz, 1H), 8.70 (d, J=8.2 Hz, 1H), 8.00 (dd, J=8.2, 5.4 Hz, 1H), 7.75 (d, J=8.5 Hz, 2H), 7.54 (d, J=8.5 Hz, 2H), 5.33 (d, J=5.6 Hz, 1H), 4.50 (app td, J=9.0, 3.4 Hz, 1H), 4.24 (dd, J=8.8, 1.3 Hz, 1H), 4.16 (dd, J=9.8, 6.3 Hz, 1H), 4.11 (dd, J=10.1, 5.6 Hz, 1H), 3.90 (dd, J=3.4, 1.2 Hz, 1H), 3.74 (dd, J=11.1, 6.8 Hz, 1H), 3.70 (dd, J=14.0, 3.5 Hz, 1H), 3.60 (dd, J=10.1, 3.3 Hz, 1H), 3.14 (dd, J=14.0, 9.2 Hz, 1H), 2.92 (s, 3H), 2.86 (app t, J=11.1 Hz, 1H), 2.34-2.26 (m, 1H), 2.22-2.15 (m, 2H), 2.11 (s, 3H), 1.46-1.39 (m, 2H), 1.33-1.28 (m, 2H), 0.90 (t, J=7.3 Hz, 3H). HRMS (ESI+, m/z): [M+2H]$^{2+}$ calc'd for C$_{28}$H$_{39}$N$_3$O$_5$S$_2$, 281.6238; found 281.6238.

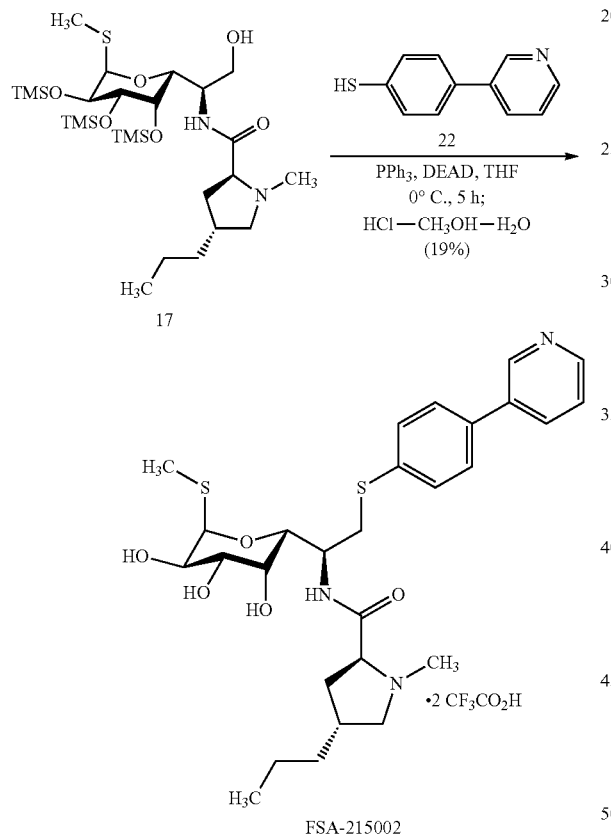

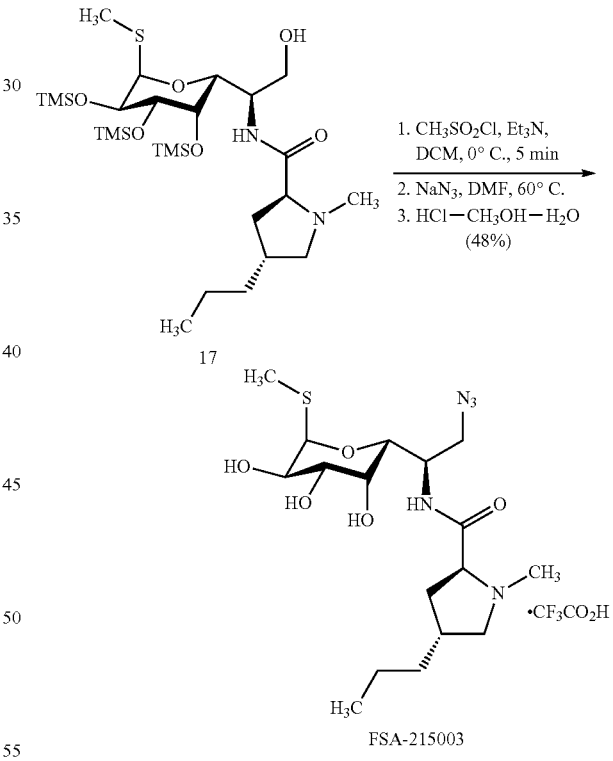

In a 1-mL glass vial, 2,3,4-tris-O-trimethylsilyl-8-norlincomycin (17, 20 mg, 33 μmol, 1 equiv) and triphenylphosphine (17 mg, 66 μmol, 2.0 equiv) were dissolved in tetrahydrofuran (660 μL), and the resulting solution was chilled to 0° C. With constant stirring, diethyl azodicarboxylate solution (40% w/w in toluene, 30 μL, 66 μmol, 2.0 equiv) was added dropwise, and the mixture was stirred at 0° C. for 5 min, during which time the original orange color of the azodicarboxylate reagent faded to afford a colorless reaction mixture. 4-(Pyridin-3-yl)benzenethiol (22, 15 mg, 82 μmol, 2.5 equiv) was added next, resulting in a flash of yellow-orange color that then disappeared. Progress was monitored by LCMS, and after 5 h, the reaction was judged to be complete The mixture was concentrated to dryness under a stream of nitrogen, and the residue was then In a 1-mL glass vial fitted with a magnetic stir bar and a PTFE-lined screw cap, 2,3,4-tris-O-trimethylsilyl-8-norlincomycin (17, 20 mg, 33 μmol, 1 equiv) was dissolved in chloroform (160 μL). Triethylamine (11 μL, 82 μmol, 2.5 equiv) was added, the vial was sealed, and the solution was chilled to 0° C. Methanesulfonyl chloride (5.1 μL, 66 μmol, 2.0 equiv) was then added, the vial re-sealed, and the mixture stirred at 0° C. for 5 min, whereupon TLC analysis (10% methanol-dichloromethane, PAA) revealed that all of the starting material had been consumed. The reaction mixture was diluted with dichloromethane (1 mL), and the diluted mixture was transferred to a separatory funnel containing hexanes (10 mL) and saturated aqueous sodium bicarbonate solution (10 mL). The biphasic mixture was shaken vigorously for 1 min before the layers were separated; the aqueous layer was extracted with fresh hexanes (2×5 mL), and the combined organic extracts were washed with saturated aqueous sodium chloride solution (5 mL). The washed organic solution was dried over sodium sulfate, filtered, and concentrated to give crude methanesulfonate ester intermediate as a white solid. This material was transferred to a 4-mL glass vial and was dried by azeotropic removal of benzene before sodium azide (21 mg, 330 μmol, 10 equiv) and N,N-dimethylformamide (330 μL) were added. The vial was sealed with a PTFE-lined screw cap, and the reaction mixture was heated to 60° C. in a pre-heated oil bath. After 18 h, LCMS analysis showed that all the intermediate sulfonate ester had been consumed, and the product mixture was transferred to a separatory funnel containing 50% v/v saturated aqueous sodium bicarbonate solution-saturated aqueous sodium chloride solution (10 mL). This mixture was then extracted with ethyl acetate (4×5 mL), the combined organic extracts were dried over sodium sulfate, the dried product solution was filtered, and the filtrate was concentrated. The residue thus obtained was then re-dissolved in 50% v/v methanol-1N aqueous hydrogen chloride solution; after 30 min of stirring this mixture, LCMS analysis showed that global desilylation was complete, and the mixture was passed through a 0.2-μm PTFE filter. The filtrate was concentrated, and the crude residue was subjected to preparative HPLC on a Waters SunFire Prep C18 column (5 μm, 250×19 mm; eluting with 0.1% trifluoroacetic acid-water, grading to 0.1% trifluoroacetic acid-40% acetonitrile-water over 40 min, with a flow rate of 15 mL/min; monitored by UV absorbance at 210 nm; $R_f$=28.6 min) to provide azide analog FSA-215003.$CF_3CO_2H$ as a white solid (8.4 mg, 48%). $^1$H NMR (600 MHz, $CD_3OD$) δ 5.29 (d, J=5.7 Hz, 1H), 4.42 (ddd, J=9.3, 5.8, 3.3 Hz, 1H), 4.22 (dd, J=9.5, 1.3 Hz, 1H), 4.18 (dd, J=9.7, 6.6 Hz, 1H), 4.09 (dd, J=10.2, 5.6 Hz, 1H), 3.85 (dd, J=3.4, 1.3 Hz, 1H), 3.77 (dd, J=11.1, 6.8 Hz, 1H), 3.69 (dd, J=12.7, 3.4 Hz, 1H), 3.59 (dd, J=10.2, 3.3 Hz, 1H), 3.53 (dd, J=12.7, 5.9 Hz, 1H), 2.94 (s, 3H), 2.89 (app t, J=11.0 Hz, 1H), 2.39-2.32 (m, 1H), 2.29-2.24 (m, 2H), 2.10 (s, 3H), 1.52-1.45 (m, 2H), 1.39-1.34 (m, 2H), 0.95 (t, J=7.3 Hz, 3H). HRMS (ESI+, m/z): [M+H]$^+$ calc'd for $C_{17}H_{31}N_5O_5S$, 418.2119; found 418.2132.

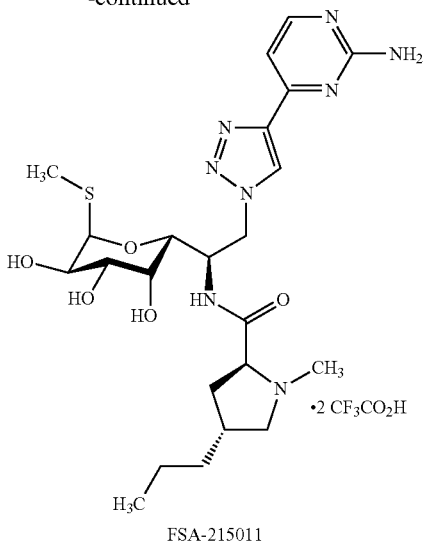

FSA-215011

To a stirred suspension containing azide FSA-215003.$CF_3CO_2H$ (6.3 mg, 12 μmol, 1 equiv), 4-ethylnylpyrimidin-2-amine (4.2 mg, 35 μmol, 3.0 equiv), freshly prepared aqueous sodium ascorbate solution (0.10 M, 24 μL, 2.4 μmol, 0.20 equiv), and 0.10 M sodium phosphate buffer (120 μL), aqueous cupric sulfate solution (0.10 M, 5.9 μL, 0.59 μmol, 0.050 equiv) was added by micropipette at 23° C. The originally white suspension immediately attained a vibrant sunset orange color. After 40 min of stirring, LCMS analysis indicated that no starting material remained. The crude reaction mixture was directly subjected to preparative HPLC on a Waters SunFire Prep C18 column (5 μm, 250×19 mm; eluting with 0.1% trifluoroacetic acid-water, grading to 0.1% trifluoroacetic acid-50% acetonitrile-water over 40 min, with a flow rate of 15 mL/min; monitored by UV absorbance at 254 nm; $R_f$=19.0 min) to provide triazole analog FSA-215011.2$CF_3CO_2H$ as a white solid (4.4 mg, 49%). $^1$H NMR (600 MHz, $CD_3OD$) δ 8.78 (s, 1H), 8.34 (d, J=6.3 Hz, 1H), 7.52 (d, J=6.3 Hz, 1H), 5.38 (d, J=5.6 Hz, 1H), 5.03 (dd, J=14.0, 3.5 Hz, 1H), 4.79 (app td, J=10.0, 3.4 Hz, 1H), 4.63 (dd, J=14.0, 10.2 Hz, 1H), 4.31 (dd, J=9.1, 1.5 Hz, 1H), 4.15 (dd, J=10.2, 5.6 Hz, 1H), 4.07 (dd, J=9.7, 5.0 Hz, 1H), 3.91 (dd, J=3.3, 1.3 Hz, 1H), 3.64 (dd, J=10.7, 5.9 Hz, 1H), 3.61 (dd, J=10.1, 3.3 Hz, 1H), 2.86 (s, 3H), 2.78 (app t, J=10.5 Hz, 1H), 2.18 (s, 3H), 2.13-2.06 (m, 3H), 1.44-1.40 (m, 2H), 1.34-1.28 (m, 2H), 0.94 (t, J=7.3 Hz, 3H). HRMS (ESI+, m/z): [M+2H]$^{2+}$ calc'd for $C_{23}H_{36}N_8O_5S$, 269.1337; found 269.1328.

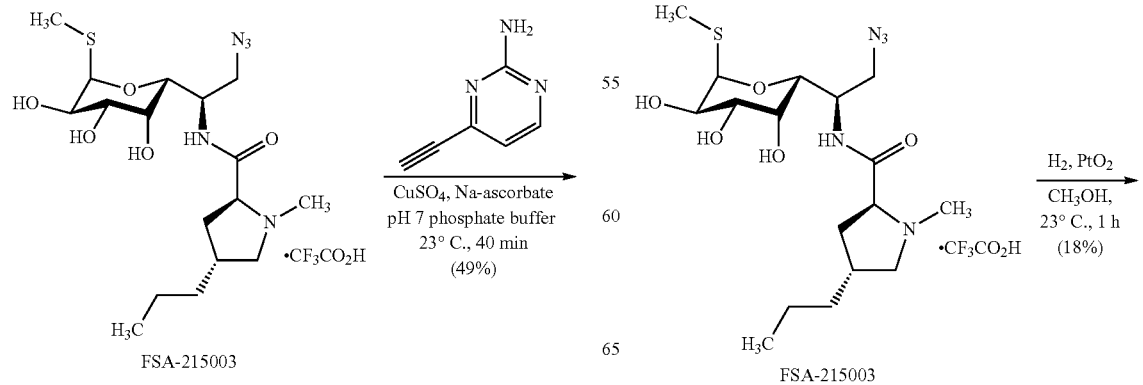

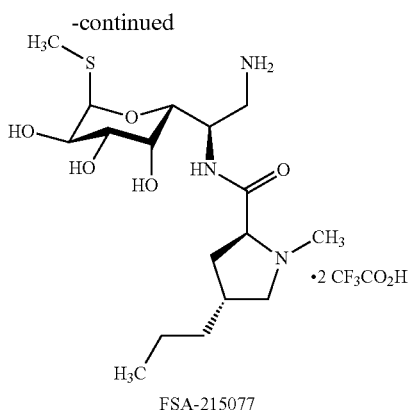

FSA-215077

A solution of azide FSA-215003 (14 mg, 33 µmol, 1 equiv) in methanol (330 µL) was treated sequentially with acetic acid (19 µL, 330 µmol, 10 equiv) and platinum(IV) oxide (7.5 mg, 33 µmol, 1.0 equiv). The headspace was flushed with hydrogen gas, and the dark gray heterogeneous mixture was stirred at 23° C. under 1 atm of hydrogen for 1 h, whereupon LCMS analysis indicated that no starting material remained. The reaction mixture was diluted with methanol (500 µL), and activated charcoal was added in order to adsorb the platinum-black particles; the mixture was stirred 5 min to ensure complete adsorption. The black suspension was then filtered through a Celite pad, and the filter cake was rinsed with fresh methanol (2×1 mL). The filtrate was concentrated, and the residue thus obtained was purified by preparative HPLC-MS on a Waters SunFire Prep C18 column (5 µm, 250×19 mm; eluting with 0.1% trifluoroacetic acid-water, grading to 0.1% trifluoroacetic acid-30% acetonitrile-water over 40 min, with a flow rate of 15 mL/min; monitored by UV absorbance at 210 nm and ESI+ selected ion monitoring [m/z=392]; $R_t$=16.9 min) to provide diamine analog FSA-215077.2CF$_3$CO$_2$H as a white solid (3.7 mg, 18%). $^1$H NMR (500 MHz, CD$_3$OD) δ 5.33 (d, J=5.6 Hz, 1H), 4.42 (app td, J=8.0, 5.0 Hz, 1H), 4.31 (d, J=7.9 Hz, 1H), 4.21 (dd, J=10.3, 6.2 Hz, 1H), 4.10 (dd, J=10.1, 5.6 Hz, 1H), 3.88 (3.2, 1.3 Hz, 1H), 3.76 (dd, J=11.0, 6.7 Hz, 1H), 3.59 (dd, J=10.1, 3.3 Hz, 1H), 3.41 (dd, J=13.1, 5.0 Hz, 1H), 3.17 (dd, J=13.1, 8.2 Hz, 1H), 2.95 (s, 3H), 2.90 (app t, J=10.8 Hz, 1H), 2.40-2.31 (m, 2H), 2.26-2.20 (m, 1H), 2.10 (s, 3H), 1.51-1.46 (m, 2H), 1.40-1.34 (m, 2H), 0.96 (t, J=7.2 Hz, 3H). HRMS (ESI+, m/z): [M+H]$^+$ calc'd for C$_{17}$H$_{33}$N$_3$O$_5$S, 392.2214; found 392.2224.

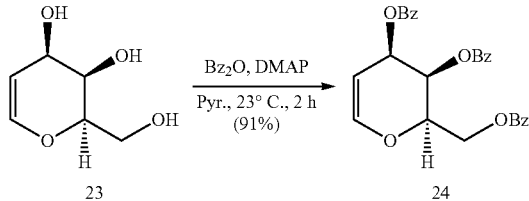

In a 500-mL round-bottomed flask, D-galactal (23, 4.40 g, 30.1 mmol, 1 equiv) was dissolved in pyridine (44.0 mL). To this solution was added benzoic anhydride (52.8 g, 233 mmol, 7.75 equiv), followed by 4-dimethylaminopyridine (368 mg, 3.01 mmol, 0.10 equiv). Upon addition of benzoic anhydride, the solution became cold (ca. 5° C.). The mixture was stirred at ambient temperature, and after 2 h, TLC analysis (20% ethyl acetate-hexanes, UV+KMnO$_4$) showed the reaction was complete. Excess benzoic anhydride was quenched with the dropwise addition of N,N-dimethylethylenediamine (18.1 mL, 166 mmol, 5.50 equiv), and the mixture was stirred at 23° C. for 10 min to ensure complete reaction. The mixture was then diluted with ethyl acetate (500 mL), and the diluted mixture was washed repeatedly with 1N aqueous hydrogen chloride solution (150 mL each), until the aqueous washes were acidic (pH≤0). The organic solution was then washed with water (150 mL), saturated aqueous sodium chloride solution (150 mL), and saturated aqueous sodium chloride solution (150 mL). The washed organic product solution was then dried over sodium sulfate, the dried solution was filtered, and the filtrate was concentrated to provide tri-O-benzoyl-D-galactal (24) as a foaming white solid (12.6 g, 91%) suitable for use in the subsequent epoxidation reaction without further purification. The corresponding $^1$H NMR, $^3$C NMR, and HRMS spectral data were identical to those reported in the literature for tri-O-benzoyl-D-galactal.

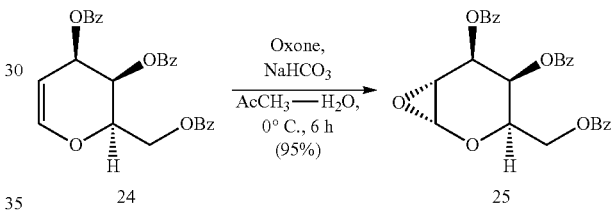

To a solution of glycal 24 (12.6 g, 27.5 mmol, 1 equiv) in dichloromethane (139 mL) was added acetone (30.3 mL, 412 mmol, 15.0 equiv) and saturated aqueous sodium bicarbonate solution (278 mL). The resulting biphasic mixture was chilled to 0° C. before a solution of Oxone monopersulfate compound (50.7 g) in water (194 mL) was added dropwise. Rapid stirring (>700 rpm) was maintained at 0° C. throughout the course of the reaction to ensure vigorous mixing of the two phases. After 6 h, TLC analysis (30% ethyl acetate-hexanes, UV+PAA) showed complete consumption of the starting material, and the mixture was transferred to a separatory funnel, where the layers were separated. The aqueous phase was extracted with dichloromethane (2×100 mL), and the combined organic phases were then washed sequentially with saturated aqueous sodium bicarbonate solution (200 mL) and water (200 mL). The washed organic solution was dried over sodium sulfate, the dried solution was filtered, and the filtrate was concentrated to afford epoxide 25 as a white, foaming solid (12.4 g, 95%). This material was used without further purification. $^1$H NMR (500 MHz, C$_6$D$_6$) δ 8.10-8.08 (m, 2H), 8.07-8.05 (m, 2H), 7.97-7.95 (m, 2H), 7.14-7.08 (m, 2H), 7.06-6.99 (m, 5H), 6.93 (app t, J=7.8 Hz, 2H), 5.69 (d, J=4.1 Hz, 1H), 5.43 (d, J=0.9 Hz, 1H), 4.85 (d, J=2.2 Hz, 1H), 4.56 (dd, J=11.4, 6.8 Hz, 1H), 4.28 (dd, J=11.5, 5.8 Hz, 1H), 4.03 (app t, J=6.3 Hz, 1H), 2.74 (dd, J=2.3, 1.5 Hz, 1H). HRMS (ESI+, m/z): [M+H]$^+$ calc'd for C$_{27}$H$_{22}$O$_8$, 475.1387; found 475.1408.

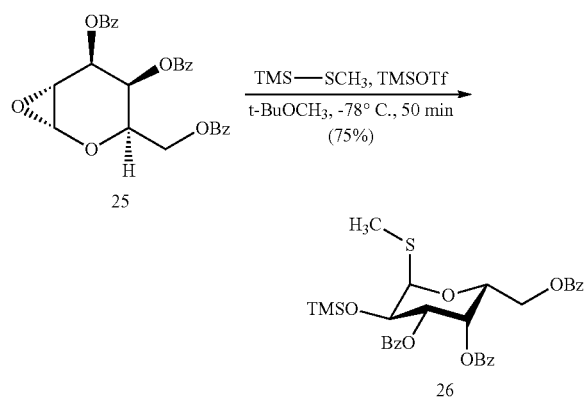

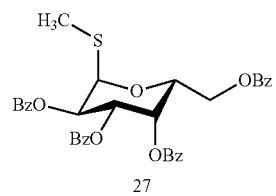

A 200-mL round-bottomed flask fitted with a stir bar and charged with 3.00 g of powdered, activated 4A molecular sieves was flame-dried. Once cooled, the flask was then charged with epoxide 25 (3.00 g, 6.32 mmol, 1 equiv) and anhydrous tert-butyl methyl ether (63.2 mL). The resulting suspension was chilled to −78° C., whereupon (methylthio)trimethylsilane (2.69 mL, 19.0 mmol, 3.00 equiv) was added. Trimethylsilyl trifluoromethanesulfonate (1.14 mL, 6.32 mmol, 1.00 equiv) was added dropwise next, and stirring was continued at −78° C. After 50 min, TLC analysis (NH$_2$ silica gel, 30% ethyl acetate-hexanes, UV+CAM) showed disappearance of both starting material and of a polar spot believed to arise by quenching of unreacted oxocarbenium intermediate during TLC spotting. A 5% v/v triethylamine-dichloromethane solution (88.2 mL, 31.6 mmol triethylamine, 5.00 equiv) was added before the reaction mixture was warmed to 23° C. Celite (3.00 g) was added to the warmed mixture (to facilitate filtration), and the mixture was filtered through a pad of Celite. The filtrate was washed with saturated aqueous sodium bicarbonate solution (100 mL), and the aqueous layer was extracted with dichloromethane (2×50 mL). The combined organic layers were washed with water (100 mL), dried over sodium sulfate, and filtered to obtain a white foaming solid residue. This crude product was purified by flash-column chromatography (120 g silica gel; eluting with hexanes initially, grading to 25% ethyl acetate-hexanes) to furnish α-methylthioglycoside 26 as a foaming white solid (2.82, 75%). $^1$H NMR (600 MHz, CDCl$_3$) δ 8.07 (dd, J=8.4, 1.5 Hz, 2H), 8.02 (dd, J=8.4, 1.4 Hz, 2H), 7.84 (dd, J=8.4, 1.4 Hz, 2H), 7.61 (td, J=7.4, 1.3 Hz, 1H), 7.53 (td, J=7.4, 1.4 Hz, 1H), 7.49-7.45 (m, 3H), 7.40 (app t, J=7.8 Hz, 2H), 7.29 (app t, J=7.9 Hz, 2H), 5.97 (dd, J=3.6, 1.3 Hz, 1H), 5.59 (dd, J=9.9, 3.5 Hz, 1H), 5.49 (d, J=5.6 Hz, 1H), 4.92 (ddd, J=7.1, 5.2, 1.3 Hz, 1H), 4.66 (dd, J=9.9, 5.5 Hz, 1H), 4.63 (dd, J=11.5, 7.5 Hz, 1H), 4.41 (dd, J=11.5, 5.2 Hz, 1H), 2.10 (s, 3H), 0.08 (s, 9H). HRMS (ESI+, m/z): [M+H]$^-$ calc'd for C$_{31}$H$_{34}$O$_8$SSi, 595.1816; found 595.1820.

To a stirred solution of trimethylsilyl ether 26 (6.15 g, 10.3 mmol, 1 equiv) in methanol (103 mL) were added 2 drops of 1N aqueous hydrogen chloride solution at 23° C. Within 10 minutes, TLC analysis (60% ethyl acetate-hexanes, UV) demonstrated complete consumption of starting material, with concomitant formation of desilylated intermediate (R$_f$=0.56, 40% ethyl acetate-hexanes, UV+PAA). The stir bar was removed from the flask, and the reaction mixture was concentrated in vacuo; in order to remove residual methanol, the residue was then re-dissolved in toluene (100 mL) and this solution was re-concentrated. To this dried residue were then added pyridine (25.8 mL), benzoic anhydride (2.80 g, 12.4 mmol, 1.20 equiv), and 4-(dimethylamino)pyridine (126 mg, 1.03 mmol, 0.100 equiv) sequentially. After 1 h of stirring at 23° C., TLC analysis (40% ethyl acetate-hexanes, UV+PAA) showed complete consumption of the intermediate alcohol, and excess benzoic anhydride was quenched with the dropwise addition of N,N-dimethylethylenediamine (563 µL, 5.15 mmol, 0.500 equiv). Following this quench, the mixture was incubated at 23° C. for 10 min before toluene (100 mL) was added and the mixture concentrated in vacuo (to remove excess pyridine). The residue was dissolved in ethyl acetate (250 mL), and the organic solution was washed sequentially with 1N aqueous hydrogen chloride solution (3×100 mL), water (100 mL), saturated aqueous sodium bicarbonate solution (100 mL), and saturated aqueous sodium chloride solution (100 mL). The washed organic solution was then dried over sodium sulfate, filtered, and concentrated to provide a white foaming solid. This residue was purified by flash-column chromatography (330 g silica gel; eluting with hexanes initially, grading to 30% ethyl acetate-hexanes) to furnish tetra-O-benzoyl galactoside 27 as a brilliant white, foaming solid (5.48 g, 85%). $^1$H NMR (600 MHz, CDCl$_3$) δ 8.12 (dd, J=8.4, 1.3 Hz, 2H), 8.04 (dd, J=8.4, 1.3 Hz, 2H), 8.00 (dd, J=8.4, 1.3 Hz, 2H), 7.81 (dd, J=8.4, 1.3 Hz, 2H), 7.63 (ddt, J=8.8, 7.1, 1.3 Hz, 1H), 7.56 (ddt, J=8.8, 7.1, 1.3 Hz, 1H), 7.53-7.49 (m, 3H), 7.45-7.41 (m, 3H), 7.39 (ddt, J=7.4, 6.2, 1.1 Hz, 2H), 7.27-7.24 (m, 2H), 6.07 (app q, J=1.4 Hz, 1H), 5.95-5.92 (m, 3H), 5.01 (ddd, J=6.9, 5.4, 1.3 Hz, 1H), 4.65 (dd, J=11.6, 7.4 Hz, 1H), 4.48 (dd, J=11.6, 5.4 Hz, 1H), 2.13 (s, 3H). HRMS (ESI+, m/z): [M+H]$^+$ calc'd for C$_{35}$H$_{30}$O$_9$S, 627.1683; found 627.1688.

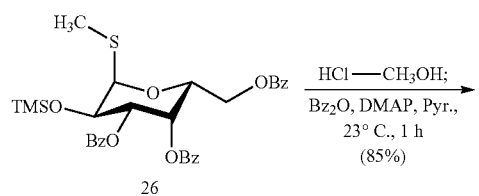

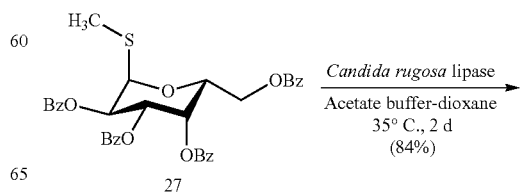

-continued

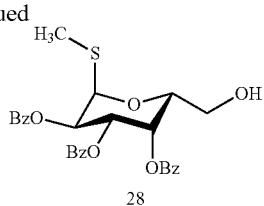
28

Sodium acetate buffer was prepared by dissolving acetic acid (5.71 mL, 0.1 mmol) in water (450 mL) to which a small quantity of aqueous bromocresol green solution had been added as pH indicator. Aqueous sodium hydroxide (1N) solution was then added until pH 4.5-5.0 was achieved (indicated by aquamarine color, and corroborated by testing with a pH strip).

In a 1-L round-bottomed flask fitted with a large magnetic stir bar, tetra-O-benzoyl galactoside 27 (5.48 g, 8.74 mmol, 1 equiv) was dissolved in 1,4-dioxane (131 mL). To this solution was added freshly prepared acetate buffer (306 mL), followed by *Candida rugosa* lipase (11.0 g, type VII, ≥700 unit/mg, Aldrich). After the headspace of the vessel was flushed with argon, rapid stirring (900 rpm) was initiated, and the heterogeneous mixture was heated to 35° C. in a pre-heated oil bath. After 2 d, TLC analysis (40% ethyl acetate-hexanes, UV+PAA) showed complete consumption of starting material. The mixture was filtered through a Celite pad, and the filter cake was rinsed with ethyl acetate (500 mL). The filtrate was separated, and the organic phase was washed with saturated aqueous sodium bicarbonate solution (100 ml), water (100 mL), and saturated aqueous sodium chloride solution (100 mL). The washed solution was then dried over sodium sulfate, filtered, and concentrated to give a foaming syrup. This crude residue was purified by flash-column chromatography (220 g silica gel; eluting with 10% ethyl acetate-hexanes initially, grading to 40% ethyl acetate-hexanes) to afford alcohol 28 as a white, foaming solid (3.82 g, 84%). $^1$H NMR (500 MHz, CDCl$_3$) δ 8.11 (d, J=8.3 Hz, 2H), 7.99 (d, J=8.3 Hz, 2H), 7.81 (d, J=8.3 Hz, 2H), 7.64 (t, J=7.5 Hz, 1H), 7.55-7.49 (m, 3H), 7.45-7.38 (m, 3H), 5.94-5.86 (m, 4H), 4.69 (app t, J=6.7 Hz, 1H), 3.78 (app dt, J=13.0, 6.8 Hz, 1H), 3.68 (app dt, J=12.4, 6.6 Hz, 1H), 2.40 (t, J=6.9 Hz, 1H), 2.13 (s, 3H). HRMS (ESI+, m/z): [M+H]$^+$ calc'd for C$_{28}$H$_{26}$O$_8$S, 523.1421; found 523.1421.

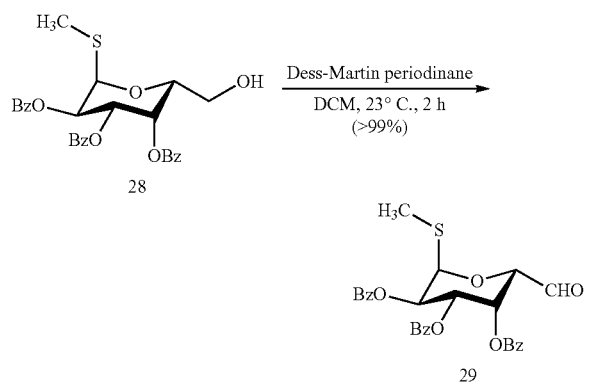

To a solution of alcohol 28 (3.80 g, 7.27 mmol, 1 equiv) in dichloromethane (48.5 mL) was added Dess-Martin periodinane (4.63 g, 10.9 mmol, 1.50 equiv) at 23° C. After 2 h, TLC analysis (60% ethyl acetate-hexanes, UV+PAA) showed complete consumption of starting material. Consequently, and with constant stirring throughout, the mixture was diluted with diethyl ether (200 mL); the diluted mixture was then treated with saturated aqueous sodium bicarbonate solution (75 mL), followed by aqueous sodium thiosulfate solution (50 wt %, 75 mL). The mixture was stirred at 23° C. for 1 h, at which time both the organic and aqueous phases had become clear. These layers were separated, and the aqueous phase was extracted with diethyl ether (3×30 mL). The combined organic extracts were washed with fresh saturated aqueous sodium bicarbonate solution (75 mL), then with saturated aqueous sodium chloride solution (75 mL). The washed organic solution was dried over sodium sulfate, filtered, and concentrated to provide aldehyde 29 as a white solid (4.00 g, 106%). This material was sufficiently pure for use in subsequent sulfinimine condensations without further purification.

For characterization purposes, a small portion of crude product (~30 mg) was purified by flash-column chromatography (4 g silica gel, eluting with hexanes initially, grading to 80% ethyl acetate-hexanes) to furnish an analytically pure sample. $^1$H NMR (400 MHz, CDCl$_3$) δ 9.67 (d, J=0.6 Hz, 1H), 8.01-7.97 (m, 4H), 7.81-7.79 (m, 2H), 7.62-7.58 (m, 1H), 7.56-7.51 (m, 1H), 7.48-7.44 (m, 3H), 7.40 (t, J=7.9 Hz, 2H), 7.27 (t, J=7.9 Hz, 2H), 6.30 (dd, J=3.0, 1.7 Hz, 1H), 6.02 (d, J=5.0 Hz, 1H), 5.90-5.82 (m, 2H), 5.11 (d, J=1.6 Hz, 1H), 2.17 (s, 3H). HRMS (ESI+, m/z): [M+H]$^+$ calc'd for C$_{28}$H$_{24}$O$_8$S, 521.1265; found 521.1288.

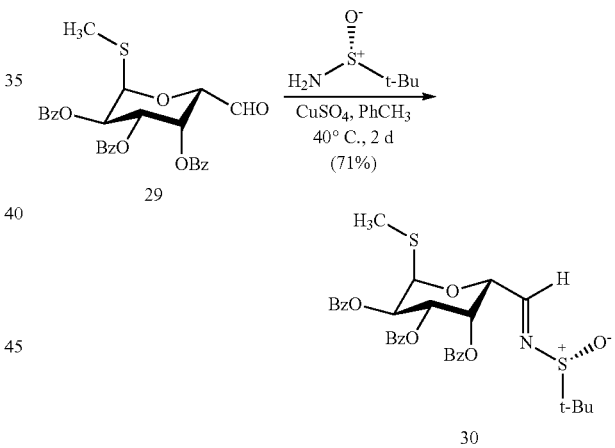

In a flame-dried 10-20 mL glass microwave vial fitted with a magnetic stir bar, aldehyde 29 (1.00 g, 1.92 mmol, 1 equiv), (R)-(+)-2-methyl-2-propanesulfinamide (466 mg, 3.84 mmol, 2.00 equiv), and anhydrous cupric sulfate (460 mg, 2.88 mmol, 1.50 equiv) were combined. To this mixture was added toluene (6.40 mL); the vial was then sealed, and the mixture was heated to 40° C. in a pre-heated oil bath. After stirring for 2 d, TLC analysis (60% ethyl acetate-hexanes, UV+PAA) showed complete consumption of aldehyde starting material, as well as disappearance of a polar spot (R$_f$=0.28, UV-active, staining brown with PAA) believed to represent hemiaminal intermediate. The mixture was filtered through a pad of Celite to remove insoluble salts, and the filter cake was rinsed with dichloromethane (3×15 mL). The filtrate was concentrated to provide a lime green-colored oily residue, which was purified by flash-column chromatography (30 g silica gel; eluting with 10% ethyl acetate-hexanes initially, grading to 50% ethyl acetate-hexanes) to provide (R$_S$)-sulfinimine 30 as a white solid (845 mg, 71%). $^1$H NMR (600 MHz, CDCl$_3$) δ 8.06 (d, J=2.2 Hz, 1H), 7.98 (dd, J=8.3, 1.3 Hz, 2H), 7.97 (dd, J=8.4, 1.3 Hz, 2H), 7.79 (dd, J=8.4, 1.3 Hz, 2H), 7.59 (tt, J=7.8, 1.3 Hz, 1H), 7.52 (tt, J=7.8, 1.3 Hz, 1H), 7.46-7.42 (m, 3H), 7.40-7.37 (m, 2H), 7.26-7.24 (m, 2H), 6.32 (dd, J=3.2, 1.5 Hz, 1H), 6.01 (d, J=5.4 Hz, 1H), 5.89 (dd, J=10.6, 5.4 Hz, 1H), 5.85 (dd, J=10.6, 3.2 Hz, 1H), 5.49 (app t, J=1.9 Hz, 1H), 2.15 (s, 3H), 0.98 (s, 9H). HRMS (ESI+, m/z): [M+H]$^+$ calc'd for C$_{32}$H$_{33}$NO$_8$S$_2$, 624.1720; 624.1743.

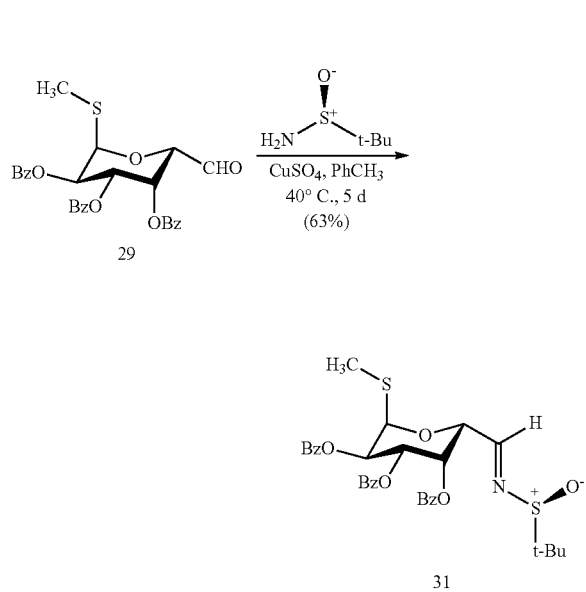

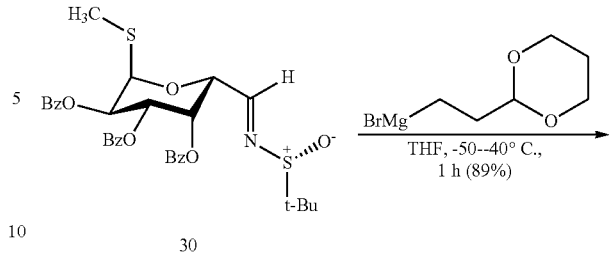

In a flame-dried 10-20 mL glass microwave vial fitted with a magnetic stir bar, aldehyde 29 (750 mg, 1.44 mmol, 1 equiv), (S)-(−)-2-methyl-2-propanesulfinamide (349 mg, 2.88 mmol, 2.00 equiv), and anhydrous cupric sulfate (345 mg, 2.16 mmol, 1.50 equiv) were combined. To this mixture was added toluene (4.80 mL); the vial was then sealed, and the mixture was heated to 40° C. in a pre-heated oil bath. After stirring for 5 d, TLC analysis showed complete consumption of aldehyde starting material, as well as disappearance of a polar spot (R$_f$~0.25, UV-active, staining brown with PAA) believed to represent hemiaminal intermediate. The mixture was filtered through a pad of Celite to remove insoluble salts, and the filter cake was rinsed with dichloromethane (3×10 mL). The filtrate was concentrated to provide a yellow moss-green oil that was subjected to flash column chromatography (40 mg silica gel; eluting with 10% ethyl acetate-hexanes initially, grading to 50% ethyl acetate-hexanes) to give (S$_S$)-sulfinimine 31 as a white solid (563 mg, 63%). $^1$H NMR (500 MHz, CDCl$_3$) δ 8.05 (d, J=2.2 Hz, 1H), 8.00-7.97 (m, 4H), 7.82-7.79 (m, 2H), 7.59 (tt, J=7.1, 1.3 Hz, 1H), 7.52 (tt, J=7.1, 1.3 Hz, 1H), 7.47-7.42 (m, 3H), 7.40-7.37 (m, 2H), 7.27-7.24 (m, 2H), 6.29 (dd, J=2.8, 1.5 Hz, 1H), 6.00 (d, J=4.5 Hz, 1H), 5.91-5.86 (m, 2H), 5.43 (app t, J=1.9 Hz, 1H), 2.16 (s, 3H), 1.13 (s, 9H). HRMS (ESI+, m/z): [M+H]$^+$ calc'd for C$_{32}$H$_{33}$NO$_8$S$_2$, 624.1720; found 624.1731.

In a 2-5 mL microwave vial, sulfinimine 30 (100 mg, 160 mmol, 1 equiv) was dried by azeotropic removal of benzene. The dried starting material was then dissolved in tetrahydrofuran (802 μL), and the resulting solution was chilled to −50° C. in an acetone bath. With constant stirring throughout, a solution of (1,3-dioxan-2-ylethyl)magnesium bromide (0.5 M, 481 μL, 240 μmol, 1.50 equiv) was added dropwise, and the temperature of the cooling bath was allowed to warm to −40° C. gradually over approximately 15 min. After 1 h of stirring at that temperature, TLC analysis (60% ethyl acetate-hexanes, UV) showed full consumption of starting material. Excess Grignard reagent was quenched with the addition of saturated aqueous ammonium chloride solution (1 mL), and the mixture was warmed to 23° C. The warmed mixture then diluted with additional saturated aqueous ammonium chloride solution (5 mL), and the diluted mixture was extracted with ethyl acetate (3×6 mL). The combined organic extracts were washed with saturated aqueous sodium chloride solution (5 mL), and the washed organic solution was dried over sodium sulfate. The dried solution was filtered, and the filtrate was concentrated to provide crude sulfinamide as a colorless film that produced a foaming white solid upon re-concentration from hexanes. This crude residue was purified by flash-column chromatography (12 g silica gel; eluting with 50% ethyl acetate-hexanes initially; grading to 90% ethyl acetate-hexanes) to afford pure sulfinamide 32 as a white solid (105 mg, 89%). $^1$H NMR (500 MHz, CDCl$_3$) δ 8.09 (dd, J=8.3, 1.3 Hz, 2H), 7.97 (dd, J=8.4, 1.3 Hz, 2H), 7.76 (dd, J=8.4, 1.3 Hz, 2H), 7.62 (tt, J=7.1, 1.3 Hz, 1H), 7.53-7.47 (m, 3H), 7.42 (tt, J=7.7, 1.3, 1H), 7.39-7.36 (m, 2H), 7.24-7.21 (m, 2H), 6.08 (dd, J=3.3, 1.1 Hz, 1H), 5.90 (d, J=5.6 Hz, 1H), 5.83 (dd, J=10.6, 5.6 Hz, 1H), 5.77 (dd, J=10.6, 3.2 Hz, 1H), 4.75 (d, J=7.5 Hz, 1H), 4.49 (t, J=4.4 Hz, 1H), 3.98-3.93 (m, 2H), 3.92 (d, J=5.6 Hz, 1H), 3.68-3.57 (m, 3H), 2.15 (s, 3H), 2.09-2.03 (m, 1H), 1.94-1.86 (m, 1H) 1.85-1.74 (m, 3H), 1.23-1.20 (m, 1H), 1.18 (s, 9H). HRMS (ESI+, m/z): [M+H]$^+$ calc'd for C$_{38}$H$_{45}$NO$_{10}$S$_2$, 740.2558; found 740.2556.

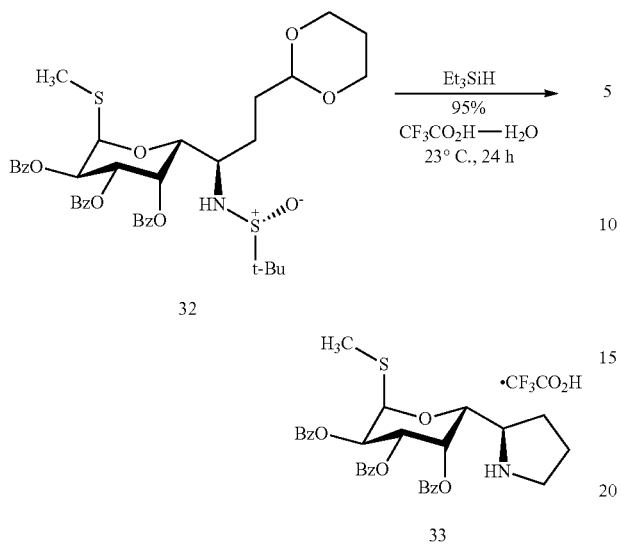

In a 4-mL glass scintillation vial in open air, sulfinamide 32 (39 mg, 53 μmol, 1 equiv) was dissolved in 95% v/v trifluoroacetic acid-water. The vial was sealed with a PTFE-lined screw-cap, and the resulting solution was stirred at 23° C. for 30 min in order for desulfinylative cyclization to occur. The vessel was then opened, triethylsilane (84 μL, 530 μmol, 10 equiv) was then added, the vial was re-sealed, and the mixture was stirred for 22 h at 23° C. Finally, the reaction mixture was concentrated to dryness in vacuo to provide crude amine 33.CF$_3$CO$_2$H (>95%, $^1$H NMR), which was used without purification in the subsequent hydrazinolysis step.

For characterization purposes, a small quantity (ca. 10 mg) of crude residue was purified by HPLC-MS on a Waters SunFire Prep C18 column (5 μm, 250×19 mm; eluting with 0.1% trifluoroacetic acid-10% acetonitrile-water initially, grading to 0.1% trifluoroacetic acid-acetonitrile over 30 min, with a flow rate of 15 mL/min; monitored by UV absorbance at 254 nm and ESI+ selected ion monitoring [m/z=562]; R$_f$=20.0 min) to afford 33.CF$_3$CO$_2$H as a white solid. $^1$H NMR (500 MHz, CDCl$_3$) δ 9.73 (br, 1H), 9.42 (br, 1H), 7.99 (dd, J=4.3, 1.2 Hz, 2H), 7.97 (dd, J=4.4, 1.3 Hz, 2H), 7.73 (dd, J=8.4, 1.3 Hz, 2H), 7.60 (tt, J=7.5, 1.3 Hz, 1H), 7.52 (tt, J=7.1, 1.3 Hz, 1H), 7.47-7.37 (m, 5H), 7.24-7.20 (m, 2H), 6.03 (d, J=3.0 Hz, 1H), 5.86 (d, J=5.6 Hz, 1H), 5.82 (dd, J=10.6, 5.6 Hz, 1H), 5.74 (dd, J=10.6, 3.2 Hz, 1H), 4.99 (d, J=8.2 Hz, 1H), 3.88 (br, 1H), 3.40 (br, 1H), 2.28-2.21 (m, 1H), 2.15 (s, 3H), 2.10-2.03 (m, 2H), 1.98-1.90 (m, 2H). $^{19}$F NMR (471 Hz, CDCl$_3$) δ -75.8 (s, 3F). HRMS (ESI+, m/z): [M+H]$^+$ calc'd for C$_{31}$H$_{31}$NO$_7$S, 562.1894; found 562.1891.

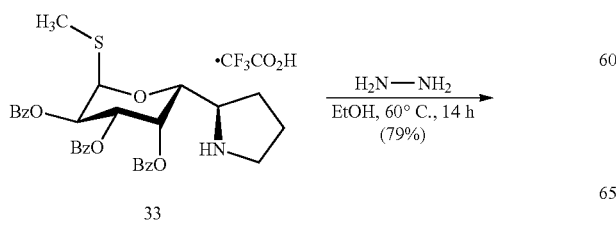

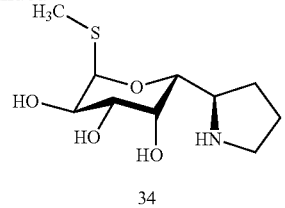

In an 8-mL glass scintillation vial, triester 33.CF$_3$CO$_2$H (theoretically 53 μmol, crude product of reductive cyclization) was dissolved in ethanol (960 μL). Hydrazine (anhydrous, 96 μL) was added, the reaction vial was capped with a PTFE-lined screw-cap, and the mixture was heated to 60° C. with stirring in a pre-heated oil bath. After 15 h, LCMS analysis showed the reaction was complete, and the reaction mixture was consequently diluted with toluene. The diluted mixture was concentrated under a stream of argon, and residual hydrazine was removed by repeated concentration from 50% v/v toluene-methanol. The white solid residue thus obtained was purified by flash-column chromatography (4.0 g silica gel; eluting with 2% ammonium hydroxide-5% methanol-dichloromethane initially, grading to 5% ammonium hydroxide-10% methanol-dichloromethane) to provide aminotriol 34 (10.5 mg, 79%, 2 steps) as a white solid. $^1$H NMR (500 MHz, CD$_3$OD) δ 5.27 (d, J=5.6 Hz, 1H), 4.10 (dd, J=10.1, 5.6 Hz, 1H), 4.01 (dd, J=3.3, 1.0 Hz, 1H), 3.95 (dd, J=7.5, 0.9 Hz, 1H), 3.59 (dd, J=10.1, 3.3 Hz, 1H), 3.44 (app q, J=7.7 Hz, 1H), 3.02-2.91 (m, 2H), 2.07 (s, 3H), 2.07-2.01 (m, 1H), 1.90-1.77 (m, 2H), 1.62 (app dq, J=12.7, 8.4 Hz, 1H). HRMS (ESI+, m/z): [M+H]$^+$ calc'd for C$_{10}$H$_{19}$NO$_4$S, 250.1108; found 250.1118.

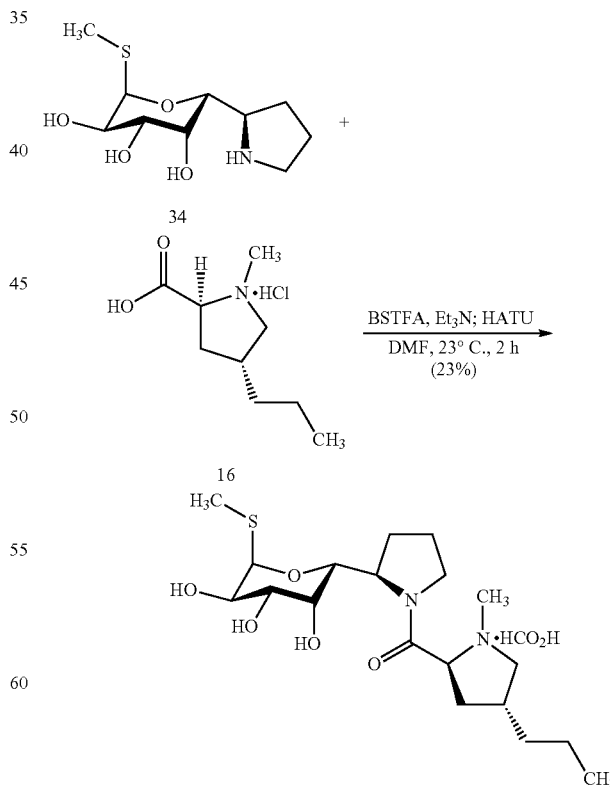

FSA-216092

In a flame-dried, 0.5-2 mL conical microwave vial, aminotriol 34 (10.0 mg, 40.0 µmol, 1.00 equiv) was dissolved in anhydrous N,N-dimethylformamide (201 µL). The resulting solution was chilled to 0° C., whereupon triethylamine (25.2 µL, 180 µmol, 4.50 equiv) and N,O-bis(trimethylsilyl)trifluoroacetamide (16.1 µL, 60.0 µmol, 1.50 equiv) were added. The mixture was allowed to warm to 23° C. with stirring over the course of 1 h, at which point trans-4-n-propyl-L-hygric acid hydrochloride (16, 10.8 mg, 52.0 µmmol, 1.30 equiv) was added, followed by HATU (22.9 mg, 60.0 µmol, 1.50 equiv). The dull sand-brown cloudy mixture adopted a vibrant canary-yellow color upon addition of HATU. The mixture was stirred at 23° C. for 2 h, at which point LCMS analysis indicated full consumption of aminotriol and its (oligo)trimethylsilylated congeners. The mixture was diluted with ethyl acetate (15 mL), and the diluted solution was washed sequentially with saturated aqueous sodium bicarbonate solution (7 mL), water (7 mL), and saturated aqueous sodium chloride solution (7 mL). The washed organic solution was then dried over sodium sulfate, the dried solution was filtered, and the filtrate was concentrated. The colorless residue was then re-dissolved in 4 mL of 50% v/v methanol-1N aqueous hydrochloric acid, and the resulting solution was incubated at 23° C. for 30 min to effect global desilylation. The mixture was then passed through a 0.2-µm PTFE syringe filter, the filtrate was concentrated, and the residue was purified by preparative HPLC-MS on a Waters SunFire Prep C18 column (5 µm, 250×19 mm; eluting with 0.1% formic acid-5% acetonitrile-water, grading to 0.1% formic acid-30% acetonitrile-water over 40 min, with a flow rate of 15 mL/min; monitored by UV absorbance at 210 nm and ESI+ selected ion monitoring [m/z=403]; $R_t$=19.0 min; mixed fractions containing product contaminated with tetramethylurea [ESI+m/z=117] were discarded) to afford pyrrolidinamide analog FSA-216092.HCO$_2$H (4.2 mg, 23%) as a white solid. $^1$H NMR (500 MHz, CD$_3$OD) δ 8.28 (br s, 1H), 5.29 (d, J=5.5 Hz, 1H), 4.43 (dd, J=10.3, 6.7 Hz, 1H), 4.35 (app t, J=7.5 Hz, 1H), 4.11-4.08 (m, 2H), 3.78 (d, J=3.2 Hz, 1H), 3.75 (dd, J=10.6, 6.6 Hz, 1H), 3.63 (ddd, J=10.9, 8.8, 2.9 Hz, 1H), 3.58 (ddd, J=10.2, 3.5, 1.4 Hz, 1H), 3.44 (app q, J=8.5 Hz, 1H), 2.89 (s, 3H), 2.87 (app t, J=11.2 Hz, 1H), 2.44-2.37 (m, 1H), 2.35-2.27 (m, 2H), 2.24-2.17 (m, 1H), 2.10-1.92 (m, 3H), 2.06 (s, 3H), 1.52-1.48 (m, 2H), 1.44-1.32 (m, 2H), 0.96 (t, J=7.2 Hz, 3H). HRMS (ESI+, m/z): [M+H]$^+$ calc'd for C$_{19}$H$_{34}$N$_2$O$_5$S, 403.2261; found 403.2280.

Ina 100-mL round-bottomed flask, lithium chloride (892 mg, 21.0 mmol) was flame-dried. Once the apparatus had cooled, activated zinc powder (2.50 g, 38.2 mmol) was added, followed by tetrahydrofuran (19.1 mL). The mixture was stirred at 23° C. for 10 min to ensure complete saturation of the solution with lithium chloride; then 1,2-dibromoethane (33 µL, 382 µmol) and trimethylsilyl chloride (122 µL, 956 µmol) were added. The resulting mixture was stirred at 23° C. for 10 min before a solution of prenyl chloride (2.16 mL, 19.1 mmol) in tetrahydrofuran (19.1 mL) was added dropwise via cannula over a period of approximately 5 min. Zinc insertion was monitored by aliquot NMR: After 2.5 h, a small aliquot of the reaction mixture (~100 µL) was diluted with chloroform-d (~300 µL), and this mixture was filtered through a cotton plug to remove insoluble zinc solids. $^1$H-NMR analysis of this mixture revealed complete consumption of prenyl chloride, signaling completion of the reaction. Stirring was discontinued, and the suspension was allowed to settle for 1 h. The supernatant was then transferred via cannula to an oven-dried Shlenck bomb flask for storage. Titration of this reagent solution against iodine indicated a reagent concentration of 0.40 M (theoretical titer=0.50 M, 80% yield).

An oven-dried 25-mL round-bottomed flask was charged with a stir bar and freshly titrated prenylzinc chloride-lithium chloride reagent solution (2.4 mL, 0.40 M in tetrahydrofuran, 960 µmol, 3.0 equiv). This mixture was then chilled to −78° C. before a solution of sulfinimine 30 (200 mg, 320 µmol, 1 equiv) in tetrahydrofuran (1.0 mL) was added by cannula. After 3 h of stirring at −78° C., the mixture was warmed to −60° C. The mixture was stirred at −60° C. for 24 h, whereupon TLC analysis (60% ethyl acetate-hexanes, UV+PAA) demonstrated complete consumption of starting material. The mixture was diluted with ethyl acetate (10 mL), and excess prenylzinc reagent was quenched with the addition of saturated aqueous ammonium chloride solution (20 mL). The resulting biphasic mixture, once warmed to 23° C., was separated; and the aqueous layer was extracted with ethyl acetate (3×20 mL). The combined organic extracts were then dried over sodium sulfate, filtered, and concentrated to provide a solid white residue. This crude product was purified by flash-column chromatography (24 g silica gel; eluting with 10% ethyl acetate-hexanes initially, grading to 50% ethyl acetate-hexanes) to provide sulfinamide 35 as a white foaming solid (190 mg, 85%). $^1$H NMR (600 MHz, CDCl$_3$) δ 8.11 (dd, J=8.3, 1.3 Hz, 2H), 7.94 (dd, J=8.3, 1.4 Hz, 2H), 7.71 (dd, J=8.4, 1.3 Hz, 2H), 7.63-7.60 (m, 1H), 7.50-7.46 (m, 3H), 7.39 (tt, J=7.5, 1.3 Hz, 1H), 7.35-7.33 (m, 2H), 7.21-7.18 (m, 2H), 6.17 (d, J=2.9 Hz, 1H), 5.96 (d, J=5.9 Hz, 1H), 5.92 (dd, J=17.4, 10.7 Hz, 1H), 5.84 (dd, J=10.7, 5.8 Hz, 1H), 5.64 (dd, J=10.7, 3.2 Hz, 1H), 5.13 (dd, J=12.5, 1.0 Hz, 1H), 5.11 (dd, J=5.8, 1.0 Hz, 1H), 4.84 (d, J=5.1 Hz, 1H), 3.99 (d, J=6.6 Hz, 1H), 3.45 (dd, J=6.6, 5.0 Hz, 1H), 2.18 (s, 3H), 1.18 (s, 3H), 1.10 (s, 3H), 1.08 (s, 9H). HRMS (ESI+, m/z): [M+H]$^+$ calc'd for C37H$_{43}$NO$_8$S$_2$, 694.2503; found 694.2530.

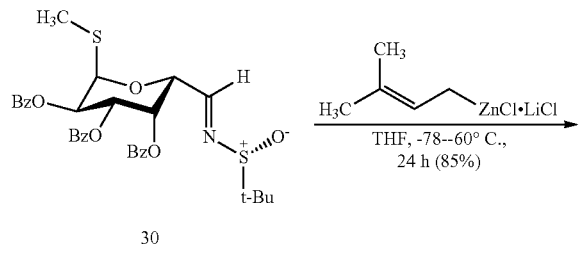

30

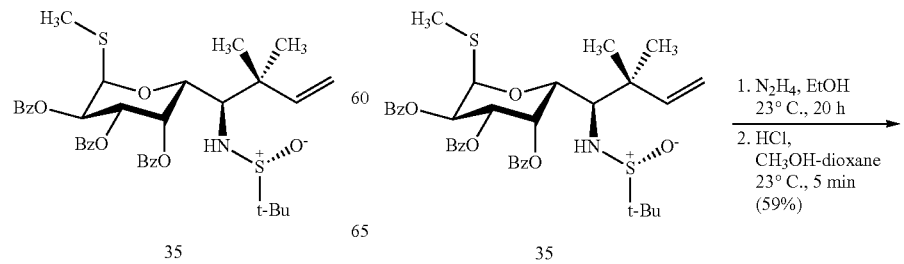

35

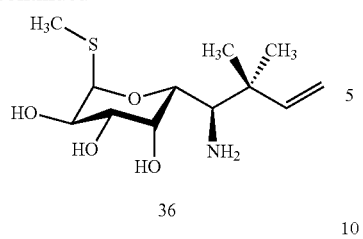

36

In a 2-5 mL glass microwave vial, sulfinamide 35 (123 mg, 177 mmol, 1 equiv) was dissolved in ethanol (1.61 mL). Anhydrous hydrazine (161 μL) was then added, and the mixture was stirred at 23° C. After 20 h, FIA-HRMS analysis of the reaction mixture showed debenzoylation was complete; the mixture was diluted with toluene (2 mL), and volatiles were then removed in vacuo to give a white solid. This residue was re-dissolved in anhydrous methanol (443 μL) before hydrogen chloride solution (4.0 M in 1,4-dioxane, 443 μL) was added at 23° C. (upon acidification, the colorless methanolic solution became an opaque white suspension). After 5 min, removal of the tert-butanesulfinyl group was confirmed by LCMS analysis. The reaction mixture was diluted with toluene (1.5 mL), and the mixture was concentrated in vacuo. The resulting residue was then re-dissolved in methanol (10 mL), the resulting solution was treated with Amberlyst A26 resin (hydroxide form, 1.50 g), and the mixture was stirred at 23° C. for 1 h prior to filtration to remove the ion-exchange beads. The filtrate was concentrated to provide crude aminotriol product in free-base form, contaminated with benzoylhydrazine by-product. This mixture was separated by flash-column chromatography (10 g silica gel; eluting with 0.2% ammonium hydroxide-2% methanol-dichloromethane initially; grading to 1% ammonium hydroxide-10% methanol-dichloromethane) to provide pure aminotriol 36 as a white solid (28.7 mg, 59%). $^1$H NMR (500 MHz, CD$_3$OD) δ 5.96 (dd, J=17.4, 10.9 Hz, 1H), 5.22 (d, J=5.6 Hz, 1H), 5.08 (dd, J=9.1, 1.4 Hz, 1H), 5.05 (app q, J=1.4 Hz, 1H), 4.11-4.08 (m, 2H), 4.05 (dd, J=3.3, 1.3 Hz, 1H), 3.48 (dd, J=10.2, 3.2 Hz, 1H), 2.90 (d, J=6.0 Hz, 1H), 2.14 (s, 3H), 1.13 (s, 3H), 1.12 (s, 3H). HRMS (ESI+, m/z): [M+H]$^+$ calc'd for C$_{12}$H$_{23}$NO$_4$S, 278.1421; found 278.1434.

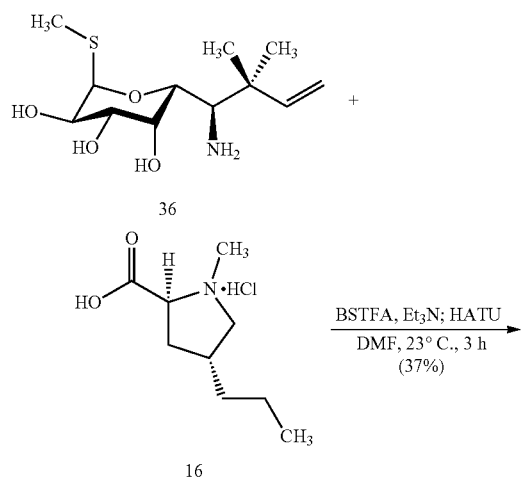

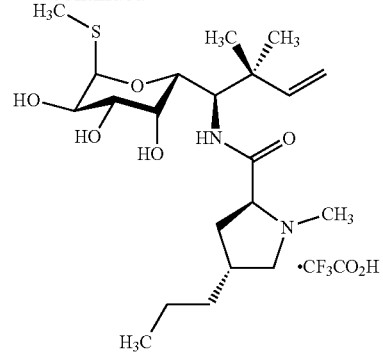

FSA-217009

In a conical 0.5-2 mL microwave vial, aminotriol 36 (27 mg, 97 μmol, 1 equiv) was dried by azeotropic removal of benzene. The dried material was dissolved in N,N-dimethylformamide (490 μL), and to this solution were added triethylamine (61 μL, 440 μmol, 4.5 equiv) and N,O-bis(trimethylsilyl)trifluoroacetamide (39 μL, 150 μmol, 1.5 equiv) at 23° C. The solution was stirred at 23° C. for 1 h to ensure complete O-silylation. Trans-4-n-propyl-L-hygric acid hydrochloride (16, 26 mg, 130 μmol, 1.3 equiv) and HATU (56 mg, 150 μmol, 1.5 equiv) were then added sequentially, and the resulting canary-yellow solution was stirred at 23° C. for 3 h, at which point LCMS analysis demonstrated full consumption of aminotriol starting material and its (oligo)trimethylsilylated congeners. The mixture was diluted with ethyl acetate (25 mL), and the diluted mixture was washed sequentially with saturated aqueous sodium bicarbonate solution (10 mL) and saturated aqueous sodium chloride solution (10 mL). The washed organic solution was dried over sodium sulfate, the dried solution was filtered, and the filtrate was concentrated to give a colorless residue. This residue was re-dissolved in 1:1 methanol-1N aqueous hydrogen chloride solution; this solution was incubated at 23° C. for 1 h to ensure complete desilylation of the coupling product mixture, and was then concentrated to afford a dull yellow oily residue. This crude residue was purified by HPLC-MS on a Waters SunFire Prep C18 column (5 μm, 250×19 mm; eluting with 0.1% trifluoroacetic acid-2.5% acetonitrile-water, grading to 0.1% trifluoroacetic acid-50% acetonitrile-water over 40 min, with a flow rate of 15 mL/min; monitored by UV absorbance at 210 nm and ESI+ selected ion monitoring [m/z=431]; R$_t$=31.7 min) to afford reverse-prenyl analog FSA-217009.CF$_3$CO$_2$H as a white solid (19 mg, 37%). $^1$H NMR (500 MHz, CD$_3$OD) δ 8.27 (d, J=8.9 Hz, 1H), 5.99 (dd, J=17.5, 10.8 Hz, 1H), 5.20 (d, J=5.7 Hz, 1H), 5.02 (d, J=17.6 Hz, 1H), 4.97 (d, J=10.8 Hz, 1H), 4.29-4.23 (m, 2H), 4.13 (app t, J=8.1 Hz, 1H), 4.05 (dd, J=10.3, 5.7 Hz, 1H), 3.86 (d, J=3.2 Hz, 1H), 3.76 (dd, J=11.1, 6.8 Hz, 1H), 3.46 (dd, J=10.3, 3.2 Hz, 1H), 2.93 (s, 3H), 2.86 (app t, J=11.0 Hz, 1H), 2.38-2.28 (m, 1H), 2.22-2.18 (m, 2H), 2.18 (s, 3H), 1.52-1.43 (m, 2H), 1.40-1.31 (m, 2H), 1.13 (s, 3H), 1.12 (s, 3H), 0.95 (t, J=7.3 Hz, 3H). HRMS (ESI+, m/z): [M+H]$^+$ calc'd for C$_{21}$H$_{38}$N$_2$O$_5$S, 431.2574; found 431.2594.

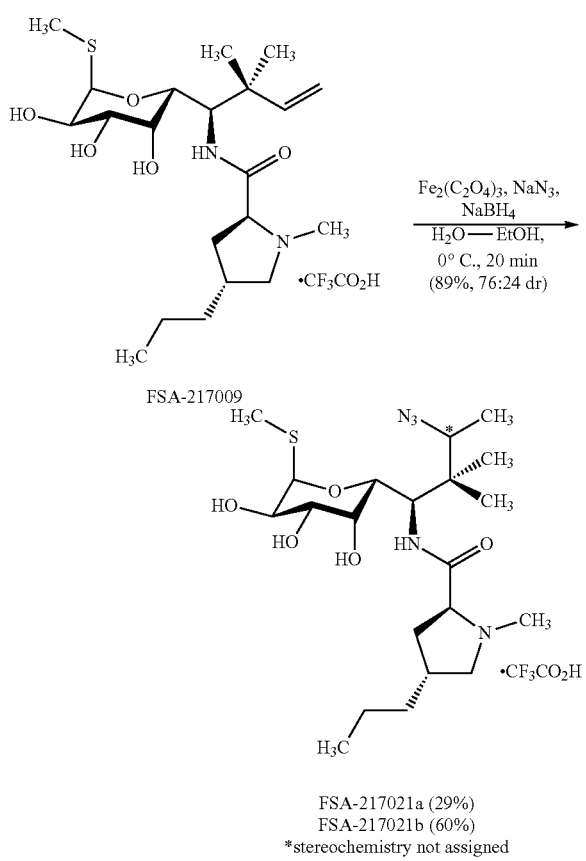

FSA-217021a (29%)
FSA-217021b (60%)
*stereochemistry not assigned

To begin, a 0.050 M stock solution of ferric oxalate was prepared by stirring ferric oxalate hexahydrate (100 mg) in 4.1 mL water until completely dissolved (ca. 24 h). An aliquot of this solution (920 µL, 46 µmol, 5.0 equiv) was then transferred to an 8-mL glass vial fitted with a stir bar and a silicone septum screw-cap, and this solution was chilled to 0° C. before nitrogen gas was bubbled through it for 5 min to remove any residual dioxygen. An aqueous solution of sodium azide (73 µL, 1.0 M, 73 µmol, 8.0 equiv) was then added, causing the lemon-lime solution to turn a deep sunset orange. Ethanol (190 proof, 460 µL) was added next to the ice-cold solution, followed by an ethanolic solution of FSA-217009.CF$_3$CO$_2$H (5.0 mg, 9.2 µmol, 1 equiv). Finally, under a stream of nitrogen gas (to help exclude oxygen) sodium borohydride (2.8 mg, 73 µmol, 8.0 equiv) was added in two portions over 5 min with rapid stirring (CAUTION: Addition of sodium borohydride to water causes rapid hydrogen gas evolution—the vial should be ventilated to avoid overpressurization). After 20 min of stirring at 0° C., LCMS analysis showed complete consumption of starting material. The reaction mixture was quenched with the addition of aqueous ammonia solution (28% w/w, 400 µL), and the mixture was extracted exhaustively with 10% v/v methanol-dichloromethane (5×10 mL). The combined extracts were dried over sodium sulfate, filtered, and concentrated to afford a colorless residue that was subjected to preparative HPLC-MS on a Waters SunFire Prep C18 column (5 µm, 250×19 mm; eluting with 0.1% trifluoroacetic acid-15% acetonitrile-water, grading to 0.1% trifluoroacetic acid-50% acetonitrile-water over 40 min, with a flow rate of 15 mL/min; monitored by UV absorbance at 210 nm and ESI+ selected ion monitoring [m/z=474]; dr=76:24; FSA-217021a R$_t$=26.3 min; FSA-217021b R$_t$=26.7 min) to provide diastereomeric products FSA-217021a.2 CF$_3$CO$_2$H (1.4 mg, 29%) and FSA-217021b.2CF$_3$CO$_2$H (3.0 mg, 60%) as white solids.

FSA-217021a: $^1$H NMR (600 MHz, CD$_3$OD) δ 5.24 (d, J=5.7 Hz, 1H), 4.54 (d, J=8.2 Hz, 1H), 4.31 (d, J=8.2 Hz, 1H), 4.10 (dd, J=9.9, 7.5 Hz, 1H), 4.07 (dd, J=5.6, 4.7 Hz, 1H), 3.92 (q, J=6.7 Hz, 1H), 3.85 (d, J=3.2 Hz, 1H), 3.77 (dd, J=11.2, 7.0 Hz, 1H), 3.49 (dd, J=10.3, 3.3 Hz, 1H), 2.94 (s, 3H), 2.88 (app t, J=10.9 Hz, 1H), 2.40-2.35 (m, 1H), 2.24-2.20 (m, 2H), 2.20 (s, 3H), 1.52-1.48 (m, 2H), 1.43-1.31 (m, 2H), 1.28 (d, J=6.7 Hz, 3H), 1.00 (s, 3H), 0.96 (t, J=7.3 Hz, 3H), 0.88 (s, 3H). HRMS (ESI+, m/z): [M+H]$^+$ calc'd for C$_{21}$H$_{39}$N$_5$O$_5$S, 474.2745; found 474.2763.

FSA-2017021b: $^1$H NMR (600 MHz, CD$_3$OD) δ 5.24 (d, J=5.7 Hz, 1H), 4.44 (d, J=9.4 Hz, 1H), 4.28 (d, J=9.4 Hz, 1H), 4.14 (app t, J=7.9 Hz, 1H), 4.06 (dd, J=10.3, 5.7 Hz, 1H), 3.91 (q, J=6.7 Hz, 1H), 3.80 (d, J=2.7 Hz, 1H), 3.77 (dd, J=11.1, 7.0 Hz, 1H), 3.46 (dd, J=10.4, 3.2 Hz, 1H), 2.94 (s, 3H), 2.88 (app t, J=11.0 Hz, 1H), 2.40-2.32 (m, 1H), 2.25-2.22 (m, 5H), 1.52-1.47 (m, 2H), 1.41-1.33 (m, 2H), 1.31 (d, J=6.6 Hz, 3H), 1.02 (s, 3H), 0.97-0.94 (m, 6H). HRMS (ESI+, m/z): [M+H]$^+$ calc'd for C$_{21}$H$_{39}$N$_5$O$_5$S, 474.2745; found 474.2762.

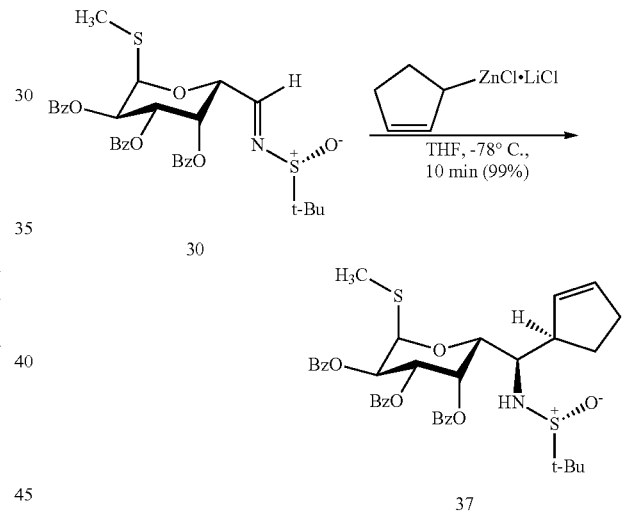

A solution of sulfinimine 30 (150 mg, 240 µmol, 1 equiv) in tetrahydrofuran (1.00 µL) was chilled to −78° C. With constant stirring, a freshly titrated solution of 2-cyclopentenylzinc chloride-lithium chloride complex (0.35 M in tetrahydrofuran, 2.06 mL, 721 µmol, 3.0 equiv) was added dropwise over 3 min. After 10 min of stirring at −78° C., TLC analysis (60% ethyl acetate-hexanes, UV) indicated that the starting material was fully consumed, and the reaction was quenched by the addition of saturated aqueous ammonium chloride solution (7 mL). The mixture was warmed to 23° C., and was extracted with ethyl acetate (3×10 mL). The combined organic extracts were then washed with saturated aqueous sodium chloride solution (10 mL), and the washed organic solution was dried over sodium sulfate. The dried solution was filtered, and the filtrate was concentrated to give a colorless film. This crude residue was purified by flash-column chromatography (12 g silica gel; eluting with 10% ethyl acetate-hexanes initially; grading to 50% ethyl acetate-hexanes) to provide cyclopentenylated product 37 as a brilliant white solid (165 mg, 99%). $^1$H NMR (600 MHz, CDCl₃) δ 8.11 (d, J=8.1 Hz, 2H), 7.97 (d, J=8.2 Hz, 2H), 7.76 (d, J=8.2 Hz, 2H), 7.62 (app t, J=7.4 Hz, 1H), 7.50 (app t, J=7.5 Hz, 3H), 7.40 (app t, J=7.8 Hz, 1H), 7.37 (app t, J=7.6 Hz, 2H), 7.22 (app t, J=7.6 Hz, 2H), 6.25 (d, J=2.6 Hz, 1H), 5.93 (d, J=5.3 Hz, 1H), 5.89-5.87 (m, 1H), 5.83-4.77 (m, 3H), 4.78 (d, J=6.3 Hz, 1H), 3.58 (d, J=8.2 Hz, 1H), 3.53-3.50 (m, 1H), 3.33 (br, 1H), 2.38-2.27 (m, 2H), 2.17 (s, 3H), 2.03 (app dtd, J=13.4, 9.1, 4.4 Hz, 1H), 1.64 (app ddt, J=13.1, 9.7, 6.5 Hz, 1H), 1.14 (s, 9H). HRMS (ESI+, m/z): [M+H]⁺ calc'd for C₃₇H₄₁NO₈S₂, 692.2346; found 692.2371.

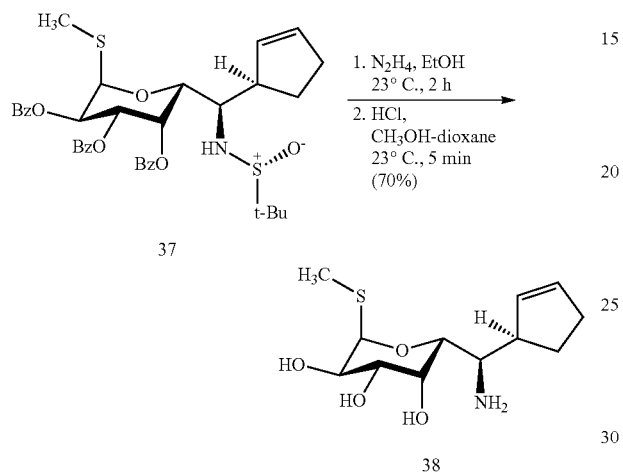

J=16.4, 9.1, 6.9, 2.4 Hz), 2.06 (s, 3H), 2.06-2.02 (m, 1H), 1.72-1.68 (m, 1H). HRMS (ESI+, m/z): [M+H]⁺ calc'd for C₁₂H₂₁NO₄S, 276.1264; found 276.1263.

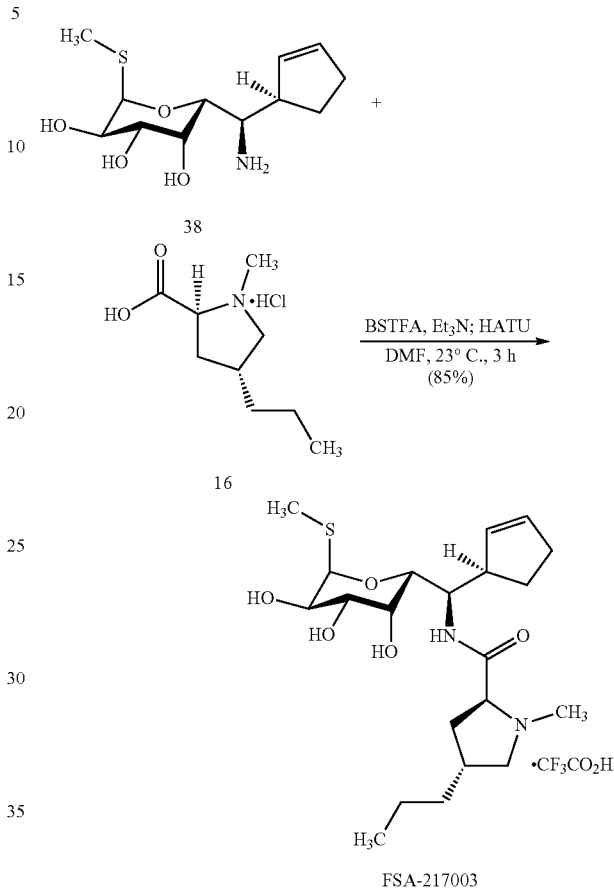

In a 2-5 mL glass microwave vial, sulfinamide 37 (165 mg, 238 μmol, 1 equiv) was dissolved in ethanol (200 proof, 2.17 mL). To this solution was then added anhydrous hydrazine (217 μL) at 23° C.; after 2 h of stirring, FIA-HRMS analysis of the reaction mixture indicated that debenzoylation was complete. The mixture was diluted with toluene (2 mL), and the diluted mixture was concentrated in vacuo. The dried residue was then dissolved in anhydrous methanol (595 μL), and the resulting solution was treated with hydrogen chloride solution (4 M in 1,4-dioxane) at 23° C. Upon acidification, a white precipitate formed immediately. Within 5 min, LCMS analysis of the reaction mixture revealed that removal of the tert-butanesulfinyl group was complete. The mixture was diluted with toluene (2 mL), and the diluted mixture was concentrated in vacuo; in order to remove residual hydrogen chloride, the residue was re-concentrated twice more from 25% v/v methanol-toluene. The dried, off-white powder thus obtained was then treated with Amberlyst A26 resin (hydroxide form, 1.00 g) and methanol (10 mL). After stirring this mixture for 1 h, the ion-exchange beads were filtered off, and the filtrate was concentrated to afford crude product in its free-base form, contaminated with benzoylhydrazine by-product. These components were separated by flash-column chromatography (5.0 g silica gel; eluting with 0.5% ammonium hydroxide-5% methanol-dichloromethane initially, grading to 2% ammonium hydroxide-20% methanol-dichloromethane) to provide pure aminotriol 38 as a white solid (46 mg, 70%). ¹H NMR (500 MHz, CD₃OD) δ 5.90 (app dq, J=4.6, 2.3 Hz, 1H), 5.74 (app dq, J=6.1, 2.2 Hz, 1H), 5.28 (d, J=5.6 Hz, 1H), 4.10 (dd, J=10.2, 5.7 Hz, 1H), 4.09 (dd, J=3.4, 1.1 Hz, 1H), 3.96 (dd, J=8.2, 1.3 Hz, 1H), 3.58 (dd, J=10.1, 3.3 Hz, 1H), 3.17 (app dddq, J=9.2, 7.0, 4.8, 2.4 Hz, 1H), 3.01 (dd, J=8.3, 4.3 Hz, 1H), 2.47-2.39 (m, 1H), 2.36-2.28 (app dddq, In a conical 0.5-2 mL microwave vial, aminotriol 38 (20 mg, 73 μmol, 1 equiv) was dried by azeotropic removal of benzene. The dried material was dissolved in N,N-dimethylformamide (360 μL), and to this solution were added triethylamine (46 μL, 330 μmol, 4.5 equiv) and N,O-bis(trimethylsilyl)trifluoroacetamide (29 μL, 110 μmol, 1.5 equiv) at 23° C. The solution was stirred at 23° C. for 1 h to ensure complete O-silylation. Trans-4-n-propyl-L-hygric acid hydrochloride (16, 18 mg, 87 μmol, 1.2 equiv) and HATU (36 mg, 94 μmol, 1.3 equiv) were then added sequentially, and the resulting canary-yellow solution was stirred at 23° C. for 3 h, at which point LCMS analysis demonstrated full consumption of aminotriol starting material and its (oligo)trimethylsilylated congeners. The mixture was diluted with ethyl acetate (25 mL), and the diluted mixture was washed with saturated aqueous sodium chloride solution-saturated aqueous sodium bicarbonate solution (1:1, 10 mL). The washed organic solution was dried over sodium sulfate, the dried solution was filtered, and the filtrate was concentrated to give a colorless residue. This residue was re-dissolved in 1:1 methanol-1N aqueous hydrogen chloride solution (5 mL); this solution was incubated at 23° C. for 1 h to ensure complete desilylation of the coupling product mixture, and was then concentrated to afford a dull yellow oily residue. This residue was then re-dissolved in methanol (5 mL), and was treated with Amberlyst A26 resin (500 mg, hydroxide form). The heterogeneous mixture was stirred at 23° C. for 30 minutes, at which point the ion-exchange beads were removed by filtration, and the filtrate was concentrated to afford crude product in its free-base form as a colorless oil. This residue was purified by flash-column chromatography (3.0 g silica gel; eluting with 0.1% ammonium hydroxide-1% methanol-dichloromethane initially; grading to 1% ammonium hydroxide-10% methanol-dichloromethane) to obtain FSA-217003 as an off-white foaming solid (27 mg, 85%).

The crude residue obtained after desilylation with methanolic hydrogen chloride could also be purified by HPLC-MS on a Waters SunFire Prep C18 column (5 μm, 250×19 mm; eluting with 0.1% trifluoroacetic acid-2.5% acetonitrile-water, grading to 0.1% trifluoroacetic acid-40% acetonitrile-water over 40 min, with a flow rate of 15 mL/min; monitored by UV absorbance at 210 nm and ESI+ selected ion monitoring [m/z=429]; $R_t$=35.7 min) to afford FSA-217003.CF$_3$CO$_2$H as a white solid. It was in this form that the material was evaluated in in vitro susceptibility assays. H NMR (hydrotrifluoroacetate salt, 500 MHz, CD$_3$OD) δ 5.95 (dd, J=5.7, 2.4 Hz, 1H), 5.71 (dd, J=5.8, 2.2 Hz, 1H), 5.30 (d, J=5.7 Hz, 1H), 4.37 (dd, J=10.0, 3.6 Hz, 1H), 4.17-4.14 (m, 2H), 4.11 (dd, J=10.2, 5.7 Hz, 1H), 3.81 (d, J=3.1 Hz, 1H), 3.77 (dd, J=11.1, 6.9 Hz, 1H), 3.55 (dd, J=10.2, 3.3 Hz, 1H), 3.30-3.27 (m, 1H), 2.93 (s, 3H), 2.87 (app t, J=11.0 Hz, 1H), 2.36-2.28 (m, 3H), 2.21-2.12 (m, 2H), 2.10 (s, 3H), 2.08-2.02 (m, 1H), 1.59-1.32 (m, 5H), 0.95 (t, J=7.2 Hz, 3H). HRMS (ESI+, m/z): [M+H]$^+$ calc'd for C$_{21}$H$_{36}$N$_2$O$_5$S, 429.2422; found 429.2418.

In a 1-mL glass vial fitted with a magnetic stir bar and PTFE-lined screw cap, cyclopentene analog FSA-217003.CF$_3$CO$_2$H (5.0 mg, 9.2 μmol, 1 equiv) was dissolved in 50% v/v tert-butanol-water. To this solution were then added AD-mix-α (15 mg) and AD-mix-β (15 mg) at 23° C., and the vial was sealed. After 20 h of stirring at 23° C., LCMS analysis indicated that the reaction was complete (≥60% conversion of starting material). The reaction mixture was diluted with methanol (2 mL), causing a yellow precipitate to form, and this suspension was passed through a 0.2-μm PTFE filter. The filtrate was concentrated and the crude residue was purified by preparative HPLC on a Waters SunFire Prep C18 column (5 μm, 250×19 mm; eluting with 0.1% trifluoroacetic acid-2.5% acetonitrile-water initially, grading to 0.1% trifluoroacetic acid-40% acetonitrile-water over 40 min; monitored by UV-210 nm and ESI+ selected ion monitoring [m/z=463]; dr=42:58; FSA-217039a $R_t$=18.2 min, FSA-217039b $R_t$=19.9 min) to provide diastereomeric cyclopentanediol analogs FSA-217039a.CF$_3$CO$_2$H (1.6 mg, 30%) and FSA-217039b.CF$_3$CO$_2$H (2.1 mg, 39%) as white solids.

FSA-217039a: $^1$H NMR (600 MHz, CD$_3$OD) δ 5.26 (d, J=5.6 Hz, 1H), 4.27 (app t, J=7.9 Hz, 1H), 4.23 (dd, J=7.5, 1.3 Hz, 1H), 4.15 (dd, J=10.1, 5.5 Hz, 1H), 4.07 (dd, J=10.2, 5.6 Hz, 1H), 3.95 (dd, J=3.4, 1.3 Hz, 1H), 3.90 (app q, J=4.8 Hz, 1H), 3.77 (dd, J=7.6, 5.0 Hz, 1H), 3.78-3.74 (m, 1H), 3.57 (dd, J=10.2, 3.3 Hz, 1H), 2.94 (s, 3H), 2.86 (app t, J=10.8 Hz, 1H), 2.41-2.34 (m, 2H0, 2.22-2.17 (m, 2H), 2.11 (s, 3H), 2.01-1.96 (m, 1H), 1.98 (app dtd, J=14.3, 9.0, 5.4 Hz, 1H), 1.84 (app ddt, J=14.4, 10.4, 5.3 Hz, 1H), 1.64 (dddd, J=13.3, 8.8, 7.0, 4.3 Hz, 1H), 1.49-1.46 (m, 2H), 1.40-1.34 (m, 2H), 0.95 (t, J=7.3 Hz, 3H). HRMS (ESI+, m/z): [M+H]$^+$ calc'd for C$_{21}$H$_{38}$N$_2$O$_7$S, 463.2472; found 463.2490

FSA-217039b: $^1$H NMR (600 MHz, CD$_3$OD) δ 5.27 (d, J=5.7 Hz, 1H), 4.31-4.25 (m, 3H), 4.10 (dd, J=10.2, 5.6 Hz, 1H), 4.06-4.01 (m, 2H), 3.89 (d, J=3.3 Hz, 1H), 3.79 (dd, J=11.2, 6.9 Hz, 1H), 3.55 (dd, J=10.2, 3.3 Hz, 1H), 2.95 (s, 3H), 2.87 (app t, J=10.9 Hz, 1H), 2.38-2.22 (m, 4H), 2.12 (s, 3H), 1.94-1.90 (m, 1H), 1.71-1.62 (m, 3H), 1.51-1.47 (m, 2H), 1.41-1.34 (m, 2H), 0.96 (t, J=7.3 Hz, 3H). HRMS (ESI+, m/z): [M+H]$^+$ calc'd for C$_{21}$H$_{38}$N$_2$O$_7$S, 463.2472; found 463.2486.

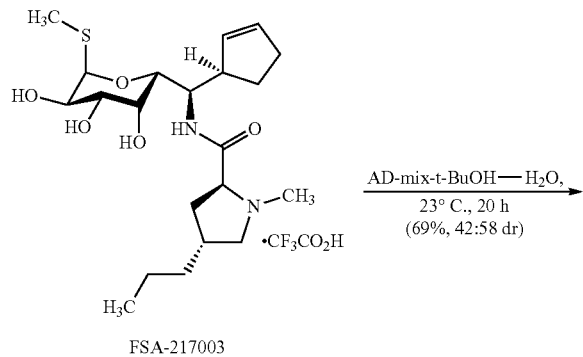

FSA-217003

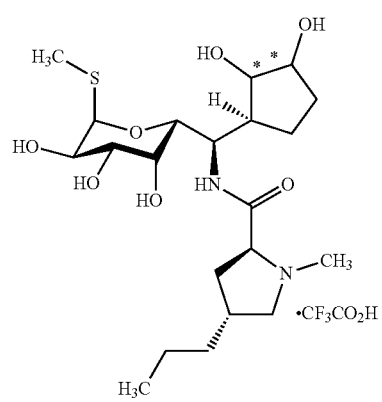

FSA-217039a (30%)
FSA-217039b (39%)
*stereochemistry not assigned

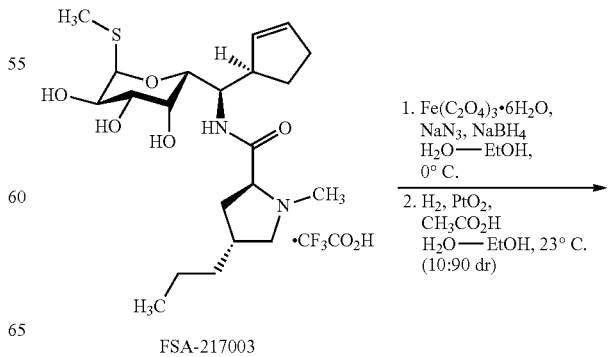

FSA-217003

1. Fe(C$_2$O$_4$)$_3$·6H$_2$O, NaN$_3$, NaBH$_4$
   H$_2$O—EtOH,
   0° C.
2. H$_2$, PtO$_2$,
   CH$_3$CO$_2$H
   H$_2$O—EtOH, 23° C.
   (10:90 dr)

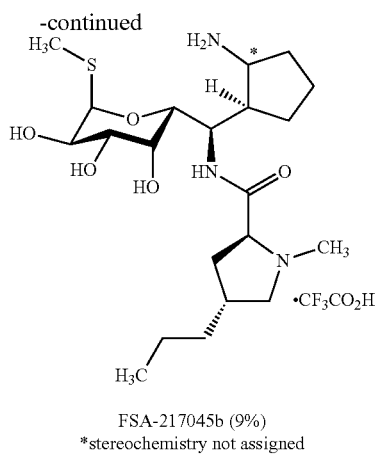

FSA-217045b (9%)
*stereochemistry not assigned

To begin, a 0.050 M stock solution of ferric oxalate was prepared by stirring ferric oxalate hexahydrate (200 mg) in 8.2 mL water until completely dissolved (ca. 24 h). An aliquot of this solution (4.20 mL, 0.210 mmol, 5.00 equiv) was transferred to a 10-20 mL glass microwave vial fitted with a stir bar and a rubber septum, and this solution was chilled to 0° C. before nitrogen gas was bubbled through it for 5 min to remove any residual dioxygen. An aqueous solution of sodium azide (1.00 M, 336 µL, 0.336 mmol, 8.00 equiv) was then added, causing the lemon-lime solution to turn a deep sunset orange. Ethanol (190 proof, 2.10 mL) was added next to the ice-cold solution, followed by an ethanolic solution of FSA-217003.$CF_3CO_2H$ (18.0 mg, 42.0 µmol, 1 equiv). Finally, under a stream of nitrogen gas (to help exclude oxygen), sodium borohydride (12.7 mg, 0.336 mmol, 8.00 equiv) was added in two portions over 5 min with rapid stirring (CAUTION: Addition of sodium borohydride to water causes rapid hydrogen gas evolution—the vial should be ventilated to avoid overpressurization). After 20 min of stirring at 0° C., LCMS analysis of the reaction mixture showed that no starting material remained. The reaction was quenched with the addition of aqueous ammonia solution (28 w/w, 2.0 mL), and the mixture was extracted exhaustively with 10% v/v methanol-dichloromethane (4×10 mL). The organic extracts were dried over sodium sulfate, filtered, and concentrated to provide a colorless residue that was then re-dissolved in 50% v/v ethanol-water (840 µL) and transferred to a 4-mL glass vial fitted with a stir bar and silicone septum screw cap. Acetic acid (60.1 µL, 1.05 mmol, 25.0 equiv) and platinum(IV) oxide (30 mg, 132 µmol, 3.15 equiv) were added to this solution, the vial was sealed, and the mixture was stirred rapidly under 1 atm of hydrogen gas at 23° C. After 2.5 h, LCMS analysis indicated that no azide intermediate remained, and activated charcoal (300 mg) was added in order to adsorb platinum black particles. The mixture was stirred at 23° C. for 5 min to ensure complete adsorption before the black suspension was filtered through a Celite pad. The filter cake was rinsed with methanol (2×2 mL), and the filtrate was concentrated to give a colorless residue that was subjected to preparative HPLC-MS on a Waters SunFire Prep C18 column (5 µm, 250×19 mm; eluting with 0.1% trifluoroacetic acid-2.5% acetonitrile-water initially, grading to 0.1% trifluoroacetic acid-35 acetonitrile-water over 40 min, with a flow rate of 15 mL/min; monitored by UV-210 nm and ESI+ selected ion monitoring [m/z=223.5]; dr=10:90; major diastereomer $R_t$=20.8 min) to provide the major diastereomer FSA-217045b.$2CF_3CO_2H$ as a white solid (2.49 mg, 9%). $^1$H NMR (500 MHz, $CD_3OD$) δ 5.33 (d, J=5.7 Hz, 1H), 4.50 (app t, J=4.8 Hz, 1H), 4.31 (d, J=5.3 Hz, 1H), 4.17 (dd, J=9.9, 7.2 Hz, 1H), 4.13 (dd, J=10.1, 5.7 Hz, 1H), 3.96 (d, J=3.1 Hz, 1H), 3.76 (dd, J=11.2, 7.0 Hz, 1H), 3.73-3.70 (m, 1H), 3.53 (dd, J=10.1, 3.1 Hz, 1H), 2.92 (s, 3H), 2.91 (app t, J=10.9 Hz, 1H), 2.65 (app dq, J=12.9, 4.1 Hz, 1H), 2.39 (app hept, J=7.3 Hz, 1H), 2.29-2.23 (m, 1H), 2.20-2.14 (m, 1H), 2.17 (s, 3H), 2.11-2.07 (m, 1H), 1.99-1.94 (m, 1H), 1.79-1.69 (m, 3H), 1.53-1.45 (m, 3H), 1.37 (tq, J=13.5, 6.1 Hz, 2H), 0.95 (t, J=7.3 Hz, 3H). HRMS (ESI+, m/z): [M+H]$^+$ calc'd for $C_{21}H_{39}N_3O_5S$, 446.2683; found 446.2693.

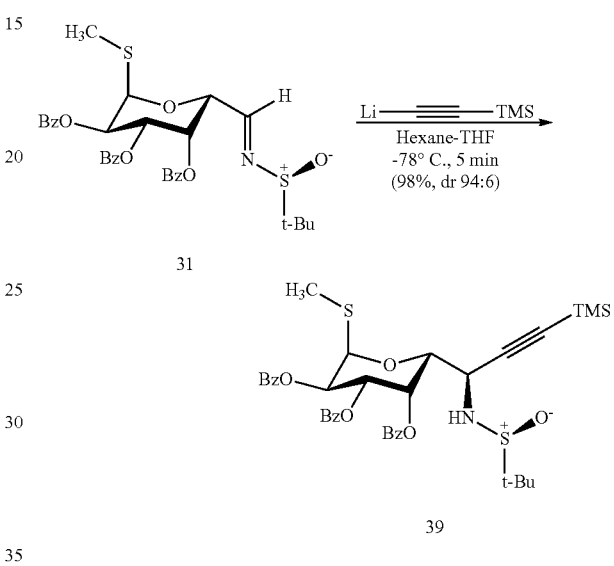

Ina 25-mL round-bottomed flask, ethynyltrimethylsilane (51.7 µL, 369 µmol, 2.30 equiv) was dissolved in hexanes (2.92 mL). This solution was chilled to −78° C. before it was treated with the dropwise addition of freshly titrated n-butyllithium solution (2.30 M in hexane, 160 µL, 369 µmol, 2.30 equiv). The resulting mixture was stirred at −78° C. for 15 min, then warmed to 0° C. for 15 min to ensure complete deprotonation. The lithium acetylide solution was then chilled again to −78° C. before a solution of sulfinimine 31 (100 mg, 160 µmol, 1 equiv) in tetrahydrofuran (1.29 µL) was added dropwise by cannula. After 5 min, FIA-HRMS analysis showed complete consumption of sulfinimine starting material, and excess lithium acetylide was quenched with the addition of saturated aqueous ammonium chloride solution (5 mL). The resulting mixture was extracted with ethyl acetate (3×10 mL), the combined organic extracts were dried over sodium sulfate, the dried solution was filtered, and the filtrate was concentrated to provide an orange-colored oil. $^1$H-NMR analysis indicated that propargyl sulfinamide product (39) was sufficiently pure for use in subsequent deprotection operations without further purification (113 mg, 98%, dr≥94:6). $^1$H NMR (600 MHz, $CDCl_3$) δ 8.08 (dd, J=8.3, 1.3 Hz, 2H), 7.97 (dd, J=8.4, 1.4 Hz, 2H), 7.76 (dd, J=8.4, 1.4 Hz, 2H), 7.65-7.62 (m, 1H), 7.53-7.49 (m, 3H), 7.42 (tt, J=7.4, 1.3 Hz, 1H), 7.40-7.37 (m, 2H), 7.25-7.22 (m, 2H), 6.01 (dd, J=3.1, 1.0 Hz, 1H), 5.94 (d, J=5.6 Hz, 1H), 5.87 (dd, J=10.6, 3.1 Hz, 1H), 5.83 (dd, J=10.6, 5.5 Hz, 1H), 4.70 (d, J=10.0 Hz, 1H), 4.28 (dd, J=9.9, 6.7 Hz, 1H), 4.00 (d, J=6.8 Hz, 1H), 2.21 (s, 3H), 1.23 (s, 9H), 0.15 (s, 9H). HRMS (ESI+, m/z): [M+H]$^+$ calc'd for $C_{37}H_{43}NO_8S_2Si$, 722.2272; found 722.2300.

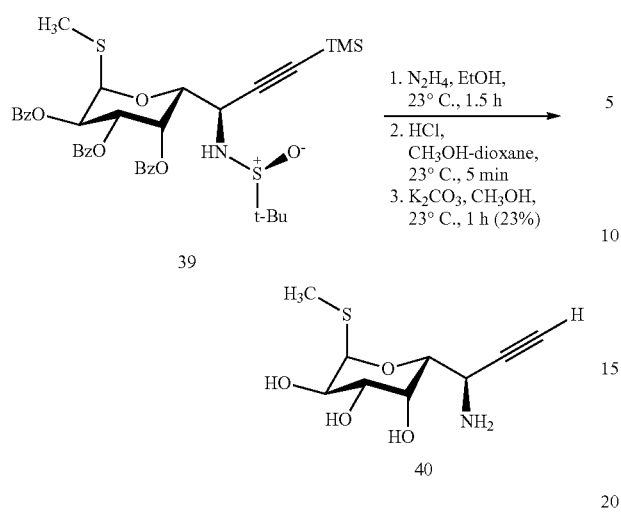

In a conical 0.5-2 mL glass microwave vial, sulfinamide 39 (38 mg, 53 μmol, 1 equiv) was dissolved in ethanol (200 proof, 48 μL). Anhydrous hydrazine (48 μL) was added, and after stirring at 23° C. for 1.5 h, FIA-HRMS showed debenzoylation was complete. The mixture was diluted with toluene (1 mL), and the diluted solution was concentrated in vacuo. The dried residue was then dissolved in anhydrous methanol (130 μL) before hydrogen chloride solution (4 M in 1,4-dioxane, 130 μL) was added. Upon acidification of the reaction mixture, a thick white precipitate formed immediately, and within 5 min, LCMS analysis showed removal of the tert-butanesulfinyl group was complete. The mixture was diluted with toluene (1 mL) and was concentrated in vacuo; in order to remove residual hydrogen chloride, the residue was re-concentrated twice more from 25% methanol-toluene. The dried residue was then dissolved in methanol (1.0 mL), and the solution was treated with Amberlyst A26 resin (hydroxide form, 200 mg) and potassium carbonate (2.0 mg). After 1 h of stirring at 23° C., LCMS analysis showed that removal of the trimethylsilyl group was complete, and the mixture was filtered through a Celite pad in order to remove insoluble salts and the ion-exchange beads. The filtrate was concentrated in vacuo to give a light yellow, oily residue that was purified by flash-column chromatography (4.0 g silica gel; eluting with 0.5% ammonium hydroxide-5% methanol-dichloromethane initially, grading to 2% ammonium hydroxide-2% methanol-dichloromethane) to provide pure aminotriol 40 (2.9 mg, 23%) as a white solid. $^1$H NMR (600 MHz, CD$_3$OD) δ 5.31 (d, J=5.6 Hz, 1H), 4.16 (dd, J=3.3, 1.2 Hz, 1H), 4.11 (dd, J=10.1, 5.6 Hz, 1H), 4.09 (dd, J=7.9, 1.1 Hz, 1H), 3.97 (dd, J=7.9, 2.3 Hz, 1H), 3.63 (dd, J=10.0, 3.4 Hz, 1H), 2.80 (d, J=2.3 Hz, 1H), 2.10 (s, 3H). MS (ESI+, m/z): [M+H]$^+$ calc'd for C$_9$H$_{15}$NO$_4$S, 234.1; found 234.1.

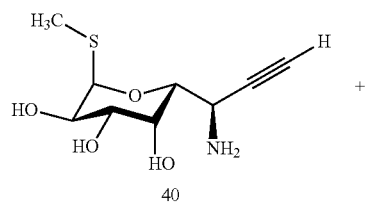

+

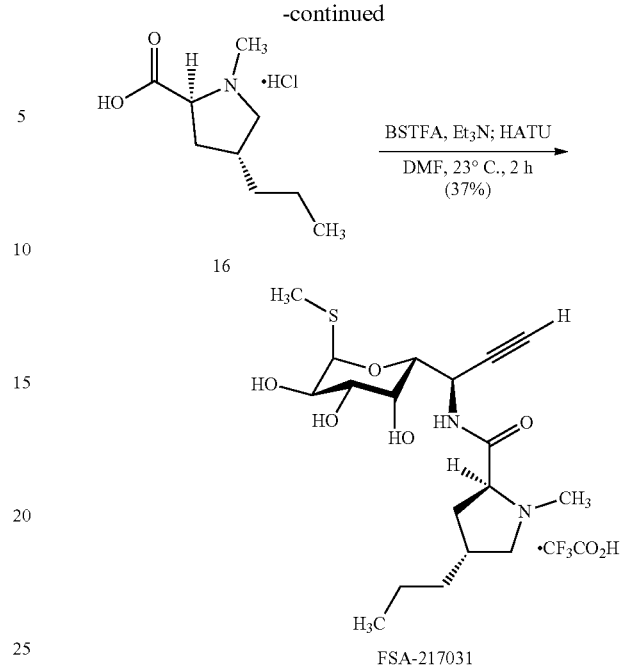

In a 4-mL glass vial fitted with a magnetic stir bar and silicone septum screw-cap, aminotriol 40 (2.9 mg, 12 μmol, 1 equiv) was dissolved in N,N-dimethylformamide (124 μL). To this solution were added triethylamine (7.8 μL, 56 μmol, 4.5 equiv) and N,O-bis(trimethylsilyl)trifluoroacetamide (5.0 μL, 19 μmol, 1.50 equiv); and the resulting solution was stirred at 23° C. for 1 h to ensure complete O-silylation. To this reaction mixture were then added trans-4-n-propyl-L-hygric acid hydrochloride (16, 3.1 mg, 15 μmol, 1.2 equiv) and HATU (6.1 mg, 16 μmol, 1.3 equiv). Upon addition of HATU, the reaction mixture attained a canary yellow color. After stirring this mixture at 23° C. for 2 h, LCMS analysis showed complete consumption of aminotriol starting material and its (oligo)trimethylsilylated congeners. Excess HATU and activated prolyl intermediate were quenched with the addition of 1N aqueous hydrogen chloride solution (400 μL) and methanol (400 μL). The mixture was stirred at 23° C. for 10 min, whereupon LCMS analysis showed complete desilylation of (oligo)trimethylsilylated product derivatives. The mixture was concentrated to dryness under a stream of nitrogen, and the residue was purified by preparative HPLC-MS on a Waters SunFire Prep C18 column (5 μm, 250×19 mm; eluting with 0.1% trifluoroacetic acid-15% acetonitrile-water, grading to 0.1% trifluoroacetic acid-50% acetonitrile-water over 40 min, with a flow rate of 15 mL/min; monitored by UV absorbance at 210 nm and ESI+ selected ion monitoring [m/z=387]; R$_t$=11.7 min) to provide FSA-217031.2CF$_3$CO$_2$H as a white solid (2.3 mg, 37%). $^1$H NMR (500 MHz, CD$_3$OD) δ 5.32 (d, J=5.7 Hz, 1H), 5.01 (app dt, J=9.3, 1.8 Hz, 1H), 4.27 (d, J=9.3 Hz, 1H), 4.16 (dd, J=9.6, 7.1 Hz, 1H), 4.11 (dd, J=10.0, 5.6 Hz, 1H), 3.91 (app dt, J=3.1, 1.4 Hz, 1H), 3.77 (dd, J=10.9, 6.9 Hz, 1H), 3.61 (ddd, J=10.1, 3.3, 1.4 Hz, 1H), 2.93 (s, 3H), 2.89 (app t, J=11.1 Hz, 1H), 2.80 (dd, J=2.5, 1.5 Hz, 1H), 2.41-2.33 (m, 1H), 2.25-2.18 (m, 2H), 2.12 (s, 3H), 1.51-1.45 (m, 2H), 1.42-1.33 (m, 2H), 0.96 (t, J=7.3 Hz, 3H). HRMS (ESI+, m/z): [M+H]$^+$ calc'd for C$_{18}$H$_{30}$N$_2$O$_5$S, 387.1948; found 387.1967.

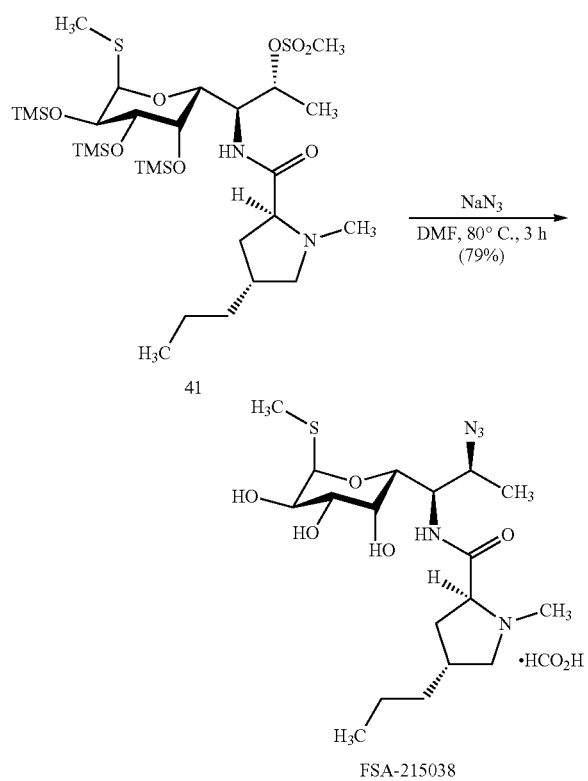

FSA-215038

A 10-20 mL glass microwave vial was charged with a stir bar, 7-O-methanesulfonyl-2,3,4-tris-O-(trimethylsilyl)lincomycin (41, 400 mg, 570 µmol, 1 equiv),[26] sodium azide (371 mg, 5.70 mmol, 10 equiv), and anhydrous N,N-dimethylformamide (5.70 mL). The vial was sealed, stirring was initiated, and the mixture was heated to 80° C. in a preheated oil bath behind a blast shield. After 3 h, LCMS analysis showed complete disappearance of (oligo)desilylated starting material; the mixture was consequently transferred to a separatory funnel containing 50% v/v saturated aqueous sodium bicarbonate solution-saturated aqueous sodium chloride solution (20 mL). The mixture was extracted exhaustively with ethyl acetate (5×20 mL), and the combined organic extracts were then washed with fresh saturated aqueous sodium chloride solution (20 mL). The washed organic solution was then dried over sodium sulfate, the dried solution was filtered, and the filtrate was concentrated. The residue was re-dissolved in methanol (4 mL), and 1N aqueous hydrogen chloride solution (4 mL) was added to effect desilylation of the product mixture. The mixture was stirred at 23° C. for 1 h before it was concentrated in vacuo. Residual N,N-dimethylformamide was removed by re-concentration from 50% v/v methanol-toluene. The dried residue was then re-dissolved in methanol (14 mL), and the solution was treated with Amberlyst A26 resin (hydroxide form, 4.0 g). The resulting suspension was stirred at 23° C. for 1 h before the ion-exchange beads were removed by filtration. The filtrate was concentrated to afford crude 7-(S)-deoxyazidolincomycin (FSA-215038, 195 mg, 79%) in its free-base form as a dull white solid. This material was suitable for use subsequent steps without further purification.

For purposes of characterization and in vitro antimicrobial screening, a small sample was purified by preparative HPLC on a Waters SunFire Prep C18 column (5 µm, 250×19 mm; eluting with 0.1% formic acid-water initially, grading to 0.1% formic acid-40% acetonitrile-water over 30 min, with a flow rate of 15 mL/min; monitored by UV absorbance at 210 nm; $R_f$=20.1 min) to provide the product in hydroformate salt form (FSA-215038.HCO$_2$H) as a white solid with the following spectroscopic properties: $^1$H NMR (600 MHz, CD$_3$OD) δ 8.40 (s, 1H), 5.30 (d, J=5.6 Hz, 1H), 4.29 (dd, J=10.0, 1.8 Hz, 1H), 4.19 (dd, J=1.2 Hz, 1H), 4.11-4.08 (m, 2H), 3.76 (dd, J=3.4, 1.2 Hz, 1H), 3.71 (dd, J=9.8, 6.1 Hz, 1H), 3.59 (dd, J=10.2, 3.3 Hz, 1H), 3.57 (dd, J=10.2, 6.7 Hz, 1H), 2.72 (s, 3H), 2.56 (app t, J=10.4 Hz, 1H), 2.34-2.26 (m, 1H), 2.17-2.13 (m, 1H), 2.13 (s, 3H), 2.12-2.08 (m, 1H), 1.47-1.41 (m, 2H), 1.39-1.32 (m, 2H), 1.30 (d, J=6.7 Hz, 1H), 0.94 (t, J=7.2 Hz, 3H). HRMS (ESI+, m/z): [M+H]$^+$ calc'd for C$_{18}$H$_{33}$N$_5$O$_5$S, 432.2275; found 432.2279.

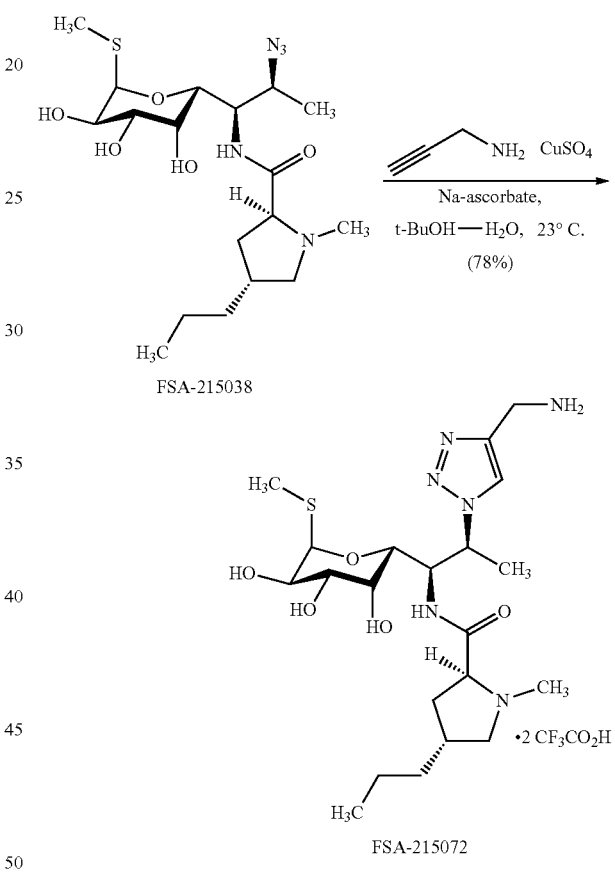

FSA-215072

In a 1-mL glass vial, FSA-215038 (11 mg, 25 µmol, 1 equiv) was dissolved in 50% v/v tert-butanol-water (250 µL). Propargylamine (6.5 µL, 0.10 mmol, 4.0 equiv) was added, followed by aqueous sodium ascorbate solution (0.10 M, 100 µL, 10 µmol, 0.40 equiv). Aqueous cupric sulfate solution (0.10 M, 26 µL, 2.6 µL, 0.10 equiv) was finally added, and within 1 min, a faint yellow color evolved. After 21 h of stirring at 23° C., LCMS analysis indicated full consumption of starting material; the mixture was diluted with water to a total volume of 900 µL, and the mixture was purified by preparative HPLC-MS on a Waters SunFire Prep C18 column (5 µm, 250×19 mm; eluting with 0.1% trifluoroacetic acid-water initially, grading to 0.1% trifluoroacetic acid-30% acetonitrile-water over 40 min, with a flow rate of 15 mL/min; monitored by UV absorbance at 210 nm and ESI+ selected ion monitoring [m/z=487]; $R_t$=21.0 min) to provide the product as a white solid (18 mg, 78%). $^1$H NMR (600 MHz, CD$_3$OD) δ 8.10 (s, 1H), 5.25 (d, J=5.6 Hz, 1H), 5.18 (qd, J=7.0, 3.6 Hz, 1H), 4.76 (dd, J=9.8, 3.5 Hz, 1H), 4.26 (s, 2H), 4.19 (dd, J=9.2, 7.2 Hz, 1H), 4.08 (dd, J=10.3, 5.6 Hz, 1H), 4.02 (dd, J=9.8, 1.5 Hz, 1H), 3.80 (dd, J=3.3, 1.4 Hz, 1H), 3.77 (dd, J=11.1, 6.8 Hz, 1H), 3.44 (dd, J=10.3, 3.2 Hz, 1H), 2.93 (s, 3H), 2.87 (app t, J=11.0 Hz, 1H), 2.38-2.33 (m, 1H), 2.27-2.22 (m, 2H), 2.18 (s, 3H), 1.60 (d, J=7.1 Hz, 3H), 1.49 (app q, J=7.6 Hz, 2H), 1.43-1.34 (m, 2H), 0.96 (t, J=7.3 Hz, 3H). HRMS (ESI+, m/z): [M+2H]$^{2+}$ calc'd for C$_{21}$H$_{38}$N$_6$O$_5$S, 244.1385; found 244.1387.

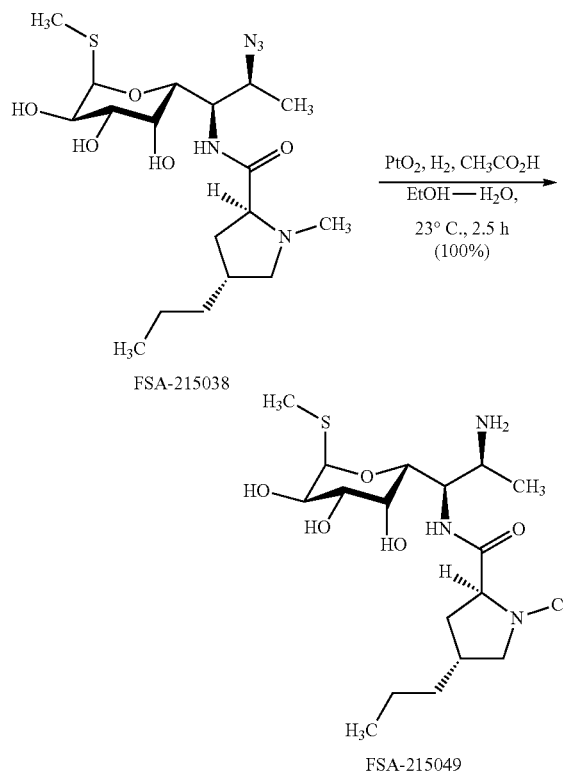

To a 25-mL round-bottomed flask were added a stir bar, 7-(S)-deoxyazidolincomycin (FSA-215038, 136 mg, 315 µmol, 1 equiv), ethanol (190 proof, 1.58 mL), water (1.58 mL), and acetic acid (180 µL, 3.15 mmol, 10.0 equiv). To this solution was added platinum(IV) oxide (71.6 mg, 1.00 equiv). To the neck of the flask was then fitted a 3-way stopcock, to which a hydrogen-filled balloon was attached. By use of the 3-way stopcock, the headspace of the reaction vessel was evacuated, then back-filled with hydrogen gas; this procedure was repeated 5 times. After 2.5 h of stirring at 23° C. under 1 atm of hydrogen, the reaction mixture was judged to be complete by LCMS analysis. The headspace of the reaction was carefully replaced with nitrogen gas, and activated charcoal (250 mg) was added to adsorb platinum particles. After stirring 2 min, the platinum was fully adsorbed, and the black suspension was filtered through a pad of Celite (2×5 mL methanol rinses). The filtrate was concentrated to give a colorless oil. Upon repeated re-concentration of this residue from 50% v/v methanol-toluene, 7-(S)-deoxyaminolincomycin dihydroacetate (FSA-215049.2 CH$_3$CO$_2$H, 168 mg, 100%) was obtained as an off-white solid. This material was suitable for use in subsequent transformations without further purification.

For purposes of characterization and in vitro antimicrobial screening, a small sample was purified by preparative HPLC on a Waters SunFire Prep C18 column (5 µm, 250×19 mm; eluting with 0.1% trifluoroacetic acid-water initially, grading to 0.1% trifluoroacetic acid-30% acetonitrile-water over 35 min, with a flow rate of 15 mL/min; monitored by UV absorbance at 210 nm; R$_f$=18.8 min) to provide the product in bis(hydrotrifluoroacetate) salt form as a white solid with the following spectroscopic properties: $^1$H NMR (600 MHz, CD$_3$OD) δ 5.33 (d, J=5.6 Hz, 1H), 4.61 (dd, J=8.0, 3.1 Hz, 1H), 4.39 (dd, J=8.0, 1.3 Hz, 1H), 4.24 (dd, J=9.6 Hz, 7.4 Hz, 1H), 4.12 (dd, J=10.2, 5.6 Hz, 1H), 3.91 (dd, J=3.1 Hz, 1.2 Hz, 1H), 3.79-3.73 (m, 2H), 3.53 (dd, J=10.2, 3.2 Hz, 1H), 2.94 (s, 3H), 2.91 (app t, J=11.0 Hz, 1H), 2.42-2.34 (m, 1H), 2.28-2.22 (m, 2H), 2.20 (s, 3H), 1.51-1.48 (m, 2H), 1.41-1.36 (m, 2H), 1.35 (d, J=6.9 Hz, 3H), 0.95 (t, J=7.3 Hz, 3H). HRMS (ESI+, m/z): [M+H]$^+$ calc'd for C$_{18}$H$_{35}$N$_3$O$_5$S, 406.2370; found 406.2378.

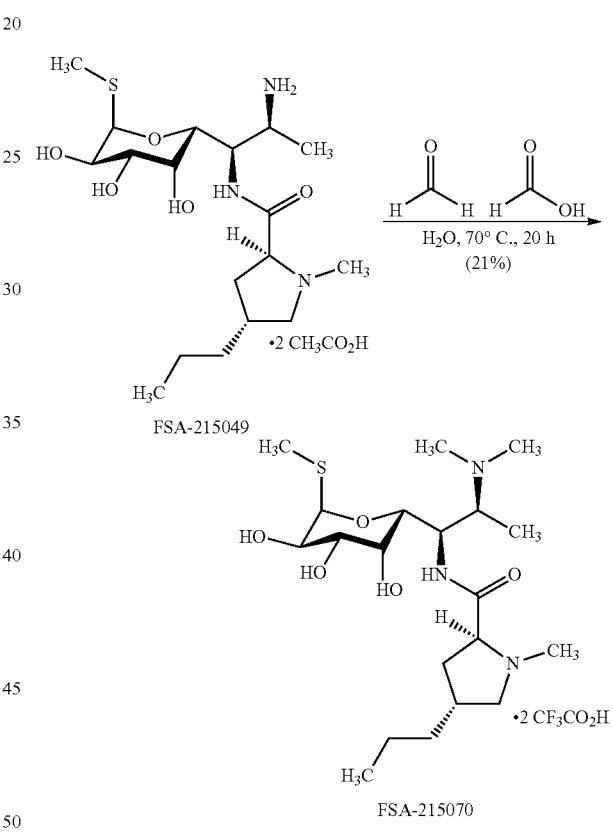

In a 12×100 mm glass test tube fitted with a magnetic stir bar, 7-(S)-deoxyaminolincomycin dihydroacetate (FSA-215049.2 CH$_3$CO$_2$H, 12 mg, 23 µmol, 1 equiv) was dissolved in water (230 µL). To this solution were then added formalin (17 µL, 230 µmol, 10 equiv) and formic acid (8.8 µL, 230 µmol, 10 equiv). The reaction mixture was heated to 70° C. in a pre-heated oil bath, and after 20 h of stirring at that temperature, LCMS analysis demonstrated complete conversion of starting material to dimethylated product. The mixture was directly subjected to purification by preparative HPLC-MS on a Waters SunFire Prep C18 column (5 µm, 250×19 mm; eluting with 0.1% trifluoroacetic acid-water initially, grading to 0.1% trifluoroacetic acid-30% acetonitrile-water over 40 min, with a flow rate of 15 mL/min; monitored by UV absorbance at 210 nm and ESI+ selected ion monitoring [m/z=217.5]; R$_f$=23.7 min) to provide the product as a white solid (3.2 mg, 21%). $^1$H NMR (600 MHz, CD$_3$OD) δ 5.33 (d, J=5.5 Hz, 1H), 5.01 (dd, J=9.7, 3.2 Hz, 1H), 4.38 (dd, J=9.7, 1.3 Hz, 1H), 4.20 (dd, J=9.6, 7.3 Hz, 1H), 4.10 (dd, J=10.3, 5.5 Hz, 1H), 3.86 (dd, J=3.2, 1.3 Hz, 1H), 3.77 (dd, J=11.1, 6.8 Hz, 1H), 3.52 (dd, J=10.4, 3.2 Hz, 1H), 3.39 (qd, J=6.8, 3.2 Hz, 1H), 3.10 (br s, 3H), 2.94 (s, 3H), 2.93-2.89 (br m, 4H), 2.42-2.34 (m, 1H), 2.27 (s, 3H), 2.25-2.21 (m, 2H), 1.51-1.48 (m, 2H), 1.48 (d, J=6.8 Hz, 3H), 1.41-1.33 (m, 2H), 0.96 (t, J=7.3 Hz, 3H). HRMS (ESI+, m/z): [M+2H]$^{2+}$ calc'd for C$_{20}$H$_{39}$N$_3$O$_5$S, 217.6378; found 217.6384.

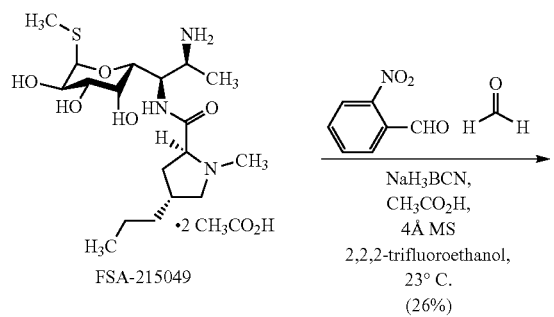

FSA-215049

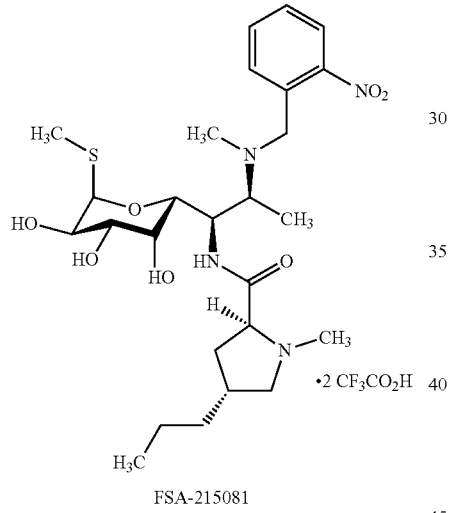

FSA-215081

As ortho-nitrobenzylamines are photosensitive, all operations were conducted with careful exclusion of light, using aluminum foil to shield flasks, test tubes, and sample vials whenever possible. In a 1-dram glass vial fitted with a magnetic stir bar and a PTFE-lined screw cap, 7-(S)-deoxyaminolincomycin dihydroacetate (FSA-215049.2 CH$_3$CO$_2$H, 13 mg, 25 μmol, 1 equiv) was dissolved in 2,2,2-trifluoroethanol (250 μL), and acetic acid (14 μL, 250 μmol, 10 equiv) was added. 2-Nitrobenzaldehyde (4.5 mg, 30 μmol, 1.2 equiv) was added, followed by powdered, activated 4Å molecular sieves (13 mg). The vial was sealed, and the mixture was stirred at 23° C. for 15 min before sodium cyanoborohydride (3.9 mg, 62 μmol, 2.5 equiv) was added. After 20 min of additional stirring, LCMS analysis indicated >90% conversion of starting material to mono-nitrobenzylated intermediate; at this point, formalin (3.7 μL, 49 μmol, 2.0 equiv) was added. After 2 h, LCMS analysis indicated incomplete conversion to tertiary amine product; additional formalin (3.7 μL, 49 μmol, 2.0 equiv) and sodium cyanoborohydride (3.9 mg, 62 μmol, 2.5 equiv) were added sequentially, and the vial was re-sealed. After 22 h of stirring, the reaction was judged to be complete by LCMS analysis, and the mixture was diluted with methanol (2 mL). The diluted mixture was filtered through a 0.2-μm PTFE filter, and the filtrate was concentrated to give a dull white solid. This residue was purified by preparative HPLC-MS on a Waters SunFire Prep C18 column (5 μm, 250×19 mm; eluting with 0.1% trifluoroacetic acid-water initially, grading to 0.1% trifluoroacetic acid-30% acetonitrile-water over 40 min, with a flow rate of 15 mL/min; monitored by UV absorbance at 254 nm and ESI+ selected ion monitoring [m/z=278]; R$_f$=33.2 min) to provide the product as a white solid (5.0 mg, 26%). $^1$H NMR (500 MHz, CD$_3$OD) δ 8.35 (d, J=8.2 Hz, 1H), 7.90 (app t, J=7.3 Hz, 1H), 7.83 (app t, J=7.8 Hz, 1H), 7.80-7.76 (br, 1H), 5.42 (br, 1H), 5.31 (br, 1H), 5.20 (br, 1H), 4.48 (d, J=9.0 Hz, 1H), 4.26 (br, 1H), 4.21 (br, 1H), 4.07 (dd, J=10.3, 5.5 Hz, 1H), 3.88 (d, J=2.4 Hz, 1H), 3.78 (dd, J=11.0, 7.0 Hz, 1H), 3.66 (br, 1H), 3.55 (d, J=10.3 Hz, 1H), 3.00 (br s, 3H), 2.96 (s, 3H), 2.92 (app t, J=11.0 Hz, 1H), 2.42 (br, 3H), 2.28 (br, 3H), 1.74 (br, 2H), 1.61 (br, 1H), 1.53-1.49 (m, 2H), 1.43-1.35 (m, 2H), 0.97 (t, J=7.3 Hz, 3H). Owing to anisotropism arising through the action of the nitrophenyl ring, the resonances of many protons proximal to the C7 substituent were broadened. HRMS (ESI+, m/z): [M+H]$^+$ calc'd for C$_{26}$H$_{42}$N$_4$O$_7$S, 555.2847; found 555.2842.

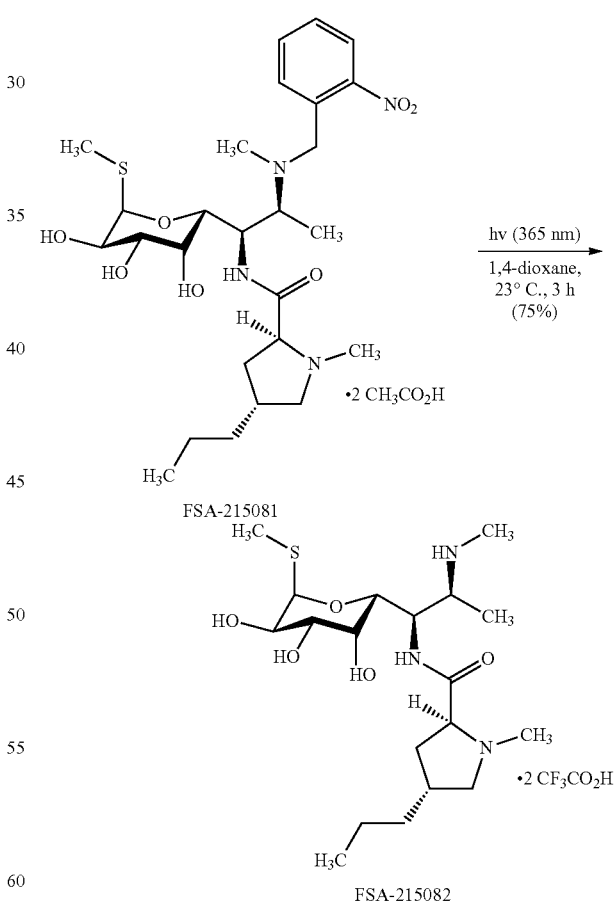

In a 12×100 mm glass test tube, ortho-nitrobenzylamine FSA-215081.2 CF$_3$CO$_2$H (2.0 mg, 2.6 μmol, 1 equiv) was dissolved in 1,4-dioxane (1.2 mL). The tube was capped with a rubber septum, and the solution was sparged of any dioxygen by bubbling nitrogen gas through it for 5 min; the apparatus was maintained under a positive pressure of nitrogen gas throughout the course of the reaction. The test tube was then placed within a mirrored-glass Dewar flask, and a thin-layer chromatography ultraviolet lamp was placed on top. The mixture was irradiated with long-wave ultraviolet irradiation (365 nm) at 23° C. without stirring for 3 h, at which point LCMS analysis showed complete consumption of starting material. The mixture was concentrated to dryness in vacuo to give a light brown residue, and this residue was purified by preparative HPLC-MS on a Waters SunFire Prep C18 column (5 µm, 250×19 mm; eluting with 0.1% trifluoroacetic acid-water initially, grading to 0.1% trifluoroacetic acid-30% acetonitrile-water over 40 min, with a flow rate of 15 mL/min; monitored by UV absorbance at 210 nm and ESI+ selected ion monitoring [m/z=420]; $R_f$=22.9 min) to provide the product as a white solid (1.2 mg, 75%). $^1$H NMR (600 MHz, $CD_3OD$) δ 5.33 (d, J=5.6 Hz, 1H), 4.78 (dd, J=9.0, 2.8 Hz, 1H), 4.39 (dd, J=9.0, 1.4 Hz, 1H), 4.20 (dd, J=9.8, 7.1 Hz, 1H), 4.11 (dd, J=10.3, 5.5 Hz, 1H), 3.88 (dd, J=3.3, 1.3 Hz, 1H), 3.77 (dd, J=11.1, 6.8 Hz, 1H), 3.52 (dd, J=10.3, 3.2 Hz, 1H), 3.47 (qd, J=6.7, 2.5 Hz, 1H), 2.94 (s, 3H), 2.91 (app t, J=10.9 Hz, 1H), 2.78 (s, 3H), 2.41-2.34 (m, 1H), 2.25 (s, 3H), 2.24-2.19 (m, 2H), 1.51-1.47 (m, 2H), 1.40 (d, J=6.9 Hz, 1.39-1.32 (m, 2H), 0.96 (t, J=7.3 Hz, 3H). HRMS (ESI+, m/z): $[M+2H]^{2+}$ calc'd for $C_{19}H_{37}N_3O_5S$, 210.6300; found 210.6296.

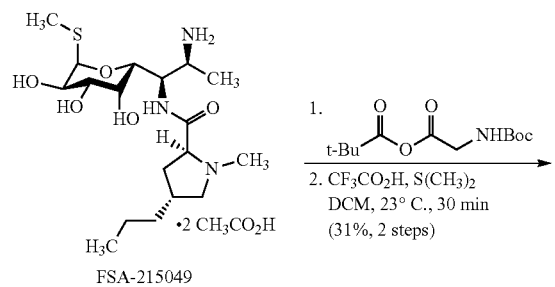

FSA-215049

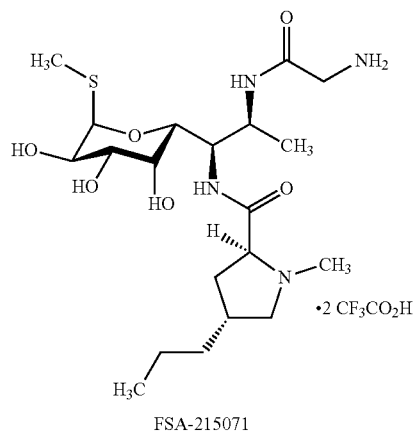

FSA-215071

Preparation of a 0.40 M solution of Boc-Gly-OPiv: In a flame-dried 10-mL round-bottomed flask, N-α-t-butyloxycarbonyl glycine (100 mg, 570 µmol) was dissolved in dichloromethane (1.4 mL). Triethylamine (80 µL, 570 µmol) was added at 23° C., and the mixture was chilled to 0° C. before pivaloyl chloride (70 µL, 570 µmol) was added dropwise, causing a white precipitate to form. This white suspension was stirred at 0° C. for 30 min, then allowed to settle prior to use.

In a 12×100 mm test tube, aminolincomycin FSA-215049.$2CH_3CO_2H$ (20 mg, 49 µmol, 1 equiv) was dissolved in dichloromethane (990 µL). The solution was chilled to 0° C., and triethylamine (69 µL, 0.49 mmol, 10 equiv) was added. An aliquot was removed via syringe from the supernatant of the Boc-Gly-OPiv solution prepared above (0.40 M, 190 µL, 74 µmol, 1.5 equiv), and was added dropwise to the chilled reaction mixture. After 5 min of stirring at 0° C., LCMS analysis indicated complete consumption of starting material. Methanol (500 µL) was added, and the mixture was warmed to 23° C.; after 1 h, the mixture was then concentrated to dryness in vacuo. The dried residue was then dissolved in 33% v/v trifluoroacetic acid-dichloromethane (300 µL) to which a drop of dimethyl sulfide had been added as a t-butyl cation scavenger. The mixture was stirred at 23° C. and Boc removal was monitored by LCMS; after 30 min, the reaction was judged to be complete, and the reaction mixture was diluted with 1.0 mL of toluene. The diluted reaction mixture was concentrated to dryness, and the residue was purified by preparative HPLC-MS on a Waters SunFire Prep C18 column (5 µm, 250×19 mm; eluting with 0.1% trifluoroacetic acid-water initially, grading to 0.1% trifluoroacetic acid-25% acetonitrile-water over 40 min, with a flow rate of 15 mL/min; monitored by UV absorbance at 210 nm and ESI+ selected ion monitoring [m/z=691]; $R_f$=22.9 min) to provide the product as a white solid (10 mg, 31%). $^1$H NMR (600 MHz, $CD_3OD$) δ 5.23 (d, J=5.6 Hz, 1H), 4.42-4.38 (m, 2H), 4.23 (app t, J=8.4 Hz, 1H), 4.18 (dd, J=9.6, 1.3 Hz, 1H), 4.07 (dd, J=10.3, 5.6 Hz, 1H), 3.83 (dd, J=3.3, 1.3 Hz, 1H), 3.78 (dd, J=11.1, 7.0 Hz, 1H), 3.74 (d, J=16.0 Hz, 1H), 3.68 (d, J=16.0 Hz, 1H), 3.50 (dd, J=10.3, 3.3 Hz, 1H), 2.94 (s, 3H), 2.89 (app t, J=10.9 Hz, 1H), 2.41-2.34 (m, 1H), 2.29-2.24 (m, 2H), 2.14 (s, 3H), 1.51-1.46 (m, 2H), 1.41-1.33 (m, 2H), 1.16 (d, J=6.7 Hz, 3H), 0.95 (t, J=7.3 Hz, 3H). HRMS (ESI+, m/z): $[M+2H]^{2+}$ calc'd for $C_{20}H_{38}N_4O_6S$, 232.1329; found 232.1331.

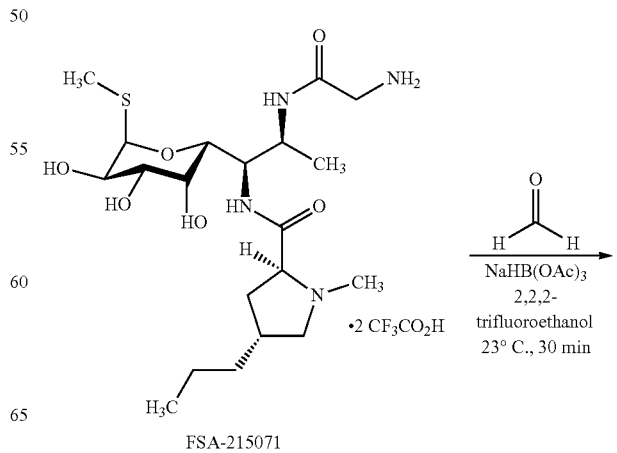

FSA-215071

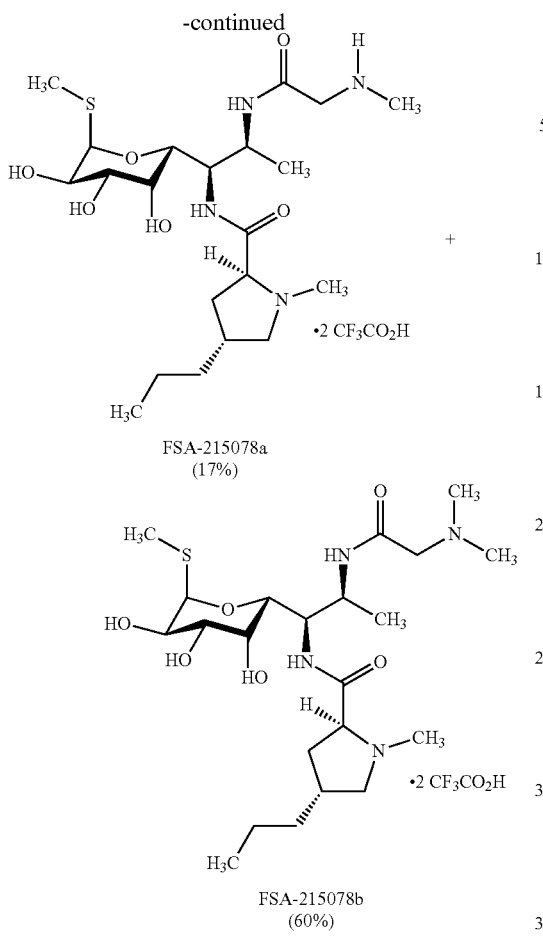

FSA-215078a
(17%)

FSA-215078b
(60%)

In a 1-mL glass vial, glycinamide FSA-215071·2CF$_3$CO$_2$H (3.0 mg, 4.3 μmol, 1 equiv) was dissolved in 2,2,2-trifluoroethanol (150 μL). Formalin (0.97 μL, 13 μmol, 3.0 equiv) was then added, the vial was sealed with a PTFE-lined screw cap, and the mixture was stirred at 23° C. After 10 min, sodium triacetoxyborohydride (2.3 mg, 11 μmol, 2.5 equiv) was then added; N-methylation was monitored by LCMS, and after 30 min, a roughly 1:1:2 mixture of starting material, mono-, and di-methylated species was observed. This mixture was diluted with 750 μL of 0.1% formic acid-water, and the resulting mixture was purified by preparative HPLC-MS on a Waters SunFire Prep C18 column (5 μm, 250×19 mm; eluting with 0.1% trifluoroacetic acid-water initially, grading to 0.1% trifluoroacetic acid-30% acetonitrile-water over 40 min, with a flow rate of 15 mL/min; monitored by UV absorbance at 210 nm and ESI+ total ion current; FSA-215078a R$_t$=22.6 min; FSA-215078b R$_t$=23.4 min) to provide FSA-215078a·2CF$_3$CO$_2$H (0.51 mg, 17%) and FSA-215078b·2CF$_3$CO$_2$H (1.9 mg, 60%) as white solids.

FSA-215078a: $^1$H NMR (500 MHz, CD$_3$OD) δ 5.25 (d, J=5.6 Hz, 1H), 4.42-4.37 (m, 2H), 4.23-4.17 (m, 2H), 4.08 (dd, J=10.3, 5.6 Hz, 1H), 3.83-3.81 (m, 3H), 3.78 (dd, J=11.0, 6.6 Hz, 1H), 3.50 (dd, J=10.3, 3.3 Hz, 1H), 2.94 (s, 3H), 2.89 (app t, J=11.0 Hz, 1H), 2.73 (s, 3H), 2.42-2.35 (m, 1H), 2.30-2.24 (m, 2H), 2.16 (s, 3H), 1.52-1.47 (m, 2H), 1.42-1.34 (m, 2H), 1.18 (d, J=6.8 Hz, 3H), 0.96 (t, J=7.3 Hz, 3H). HRMS (ESI+, m/z): [M+H]$^+$ calc'd for C$_{21}$H$_{40}$N$_4$O$_6$S, 477.2741; found 477.2743.

FSA-215078b: $^1$H NMR (500 MHz, CD$_3$OD) δ 5.23 (d, J=5.6 Hz, 1H), 4.45-4.40 (m, 2H), 4.22 (app t, J=8.2, 1H), 4.15 (d, J=9.8 Hz, 1H), 4.07 (dd, J=10.3, 5.6 Hz, 1H), 3.98 (ABq, Δδ$_{AB}$=0.04, J$_{AB}$=15.5 Hz, 2H), 3.83 (d, J=2.9 Hz, 1H), 3.77 (dd, J=11.2, 7.0 Hz, 1H), 3.49 (dd, J=10.3, 3.2 Hz, 1H), 2.94 (s, 9H), 2.88 (app t, J=10.9 Hz, 1H), 2.42-2.35 (m, 2H), 2.27 (app t, J=8.5 Hz, 2H), 2.17 (s, 3H), 1.52-1.46 (m, 2H), 1.41-1.33 (m, 2H), 1.17 (d, J=6.7 Hz, 3H), 0.95 (t, J=7.3 Hz, 3H). HRMS (ESI+, m/z): [M+H]$^+$ calc'd for C$_{22}$H$_{42}$N$_4$O$_6$S, 491.2898; found 491.2916.

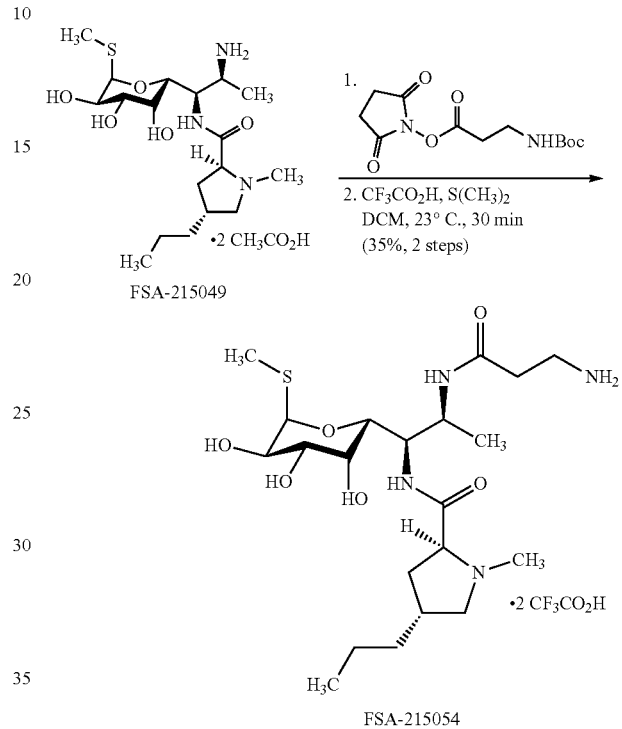

FSA-215049

FSA-215054

In a 4-mL glass vial, FSA-215049·2 CH$_3$CO$_2$H (19 mg, 46 μmol, 1 equiv) was dissolved in acetonitrile (380 μL). A dilute aqueous solution of thymol blue (77 μL) was added, and the mixture was basified by the addition of 1N aqueous sodium hydroxide solution until pH 8-9 was achieved (evidenced by a chartreuse-green color). N-Boc-p-Alanine N-hydroxysuccinimide ester (26 mg, 92 μmol, 2.0 equiv) was added, and the mixture was stirred at 23° C. After 19 h, LCMS analysis indicated complete consumption of starting material, and the reaction mixture was concentrated to dryness in vacuo. The dried residue was then re-dissolved in 33% v/v trifluoroacetic acid-dichloromethane (300 μL) to which a drop of dimethyl sulfide had been added as a t-butyl cation scavenger. The vibrant yellow solution was stirred at 23° C., and after 30 min, LCMS analysis showed complete removal of the N-Boc protecting group. The mixture was diluted with toluene (1.0 mL), and the mixture was concentrated to dryness in vacuo. The crude residue thus obtained was then purified by preparative HPLC-MS on a Waters SunFire Prep C18 column (5 μm, 250×19 mm; eluting with 0.1% trifluoroacetic acid-water initially, grading to 0.1% trifluoroacetic acid-30% acetonitrile-water over 40 min, with a flow rate of 15 mL/min; monitored by UV absorbance at 210 nm and ESI+ selected ion monitoring [m/z=239]; R$_t$=21.5 min) to provide the product as a white solid (11 mg, 35%). $^1$H NMR (600 MHz, CD$_3$OD) δ 5.22 (d, J=5.6 Hz, 1H), 4.38 (dd, J=9.8, 3.1 Hz, 1H), 4.35 (dd, J=6.8, 3.1 Hz, 1H), 4.24 (app t, J=8.4 Hz, 1H), 4.17 (d, J=9.7, 1.3 Hz, 1H), 4.07 (dd, J=10.3, 5.6 Hz, 1H), 3.83 (dd, J=3.3, 1.3 Hz, 1H), 3.78 (dd, J=11.1, 7.0 Hz, 1H), 3.50 (dd, J=10.3, 3.2 Hz, 1H), 3.21-3.13 (m, 2H), 2.94 (s, 3H), 2.89 (app t, J=10.9 Hz, 1H), 2.64 (td, J=6.7, 2.3 Hz, 2H), 2.41-2.35 (m, 1H), 2.28-2.25 (m, 2H), 2.12 (s, 3H), 1.51-1.47 (m, 2H), 1.41-1.33 (m, 2H), 1.14 (d, J=6.7 Hz, 3H), 0.95 (t, J=7.3 Hz, 3H). HRMS (ESI+, m/z): [M+2H]$^{2+}$ calc'd for $C_{21}H_{40}N_4O_6S$, 239.1407; found 239.1405.

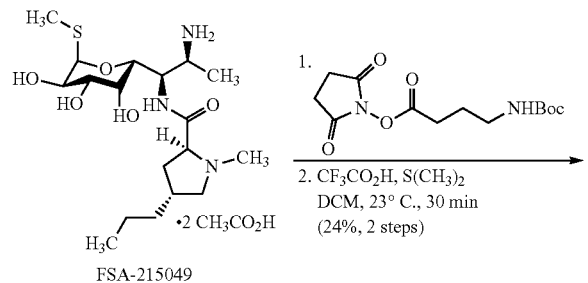

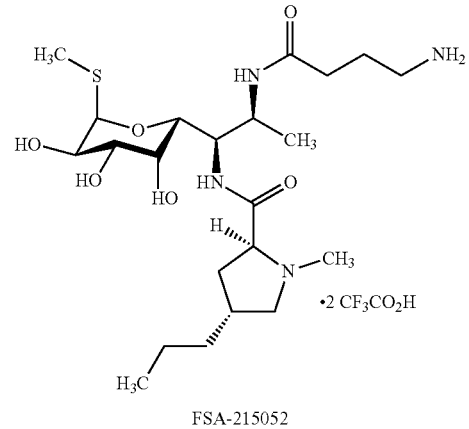

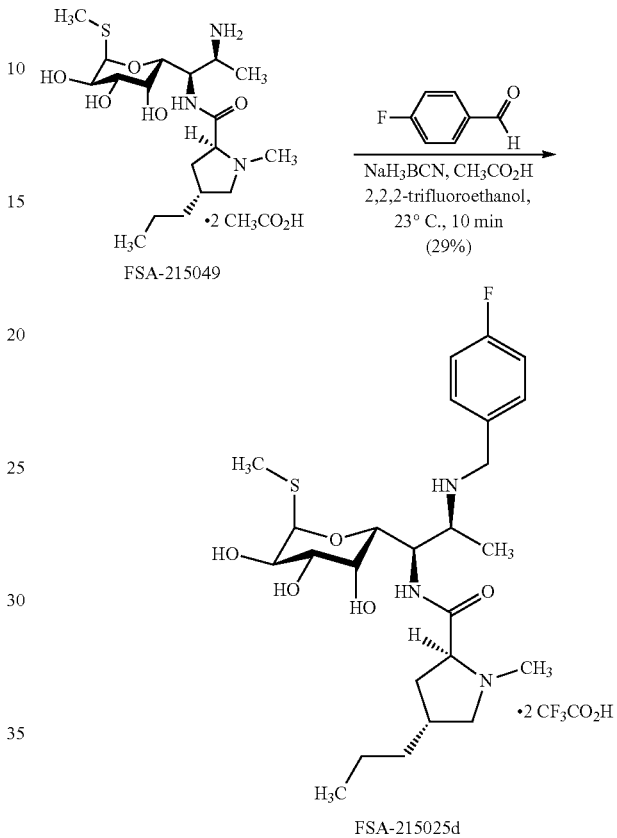

In a 12×100 mm glass test tube, FSA-215049.2 CH$_3$CO$_2$H (19 mg, 46 μmol, 1 equiv) was dissolved in acetonitrile (380 μL). A dilute aqueous solution of thymol blue (77 μL) was added, and the 1N aqueous sodium hydroxide solution was added until pH 8-9 was achieved (evidenced by a chartreuse-green color). 4-(tert-Butoxycarbonylamino)butyric acid N-hydroxysuccinimide ester (17 mg, 55 μmol, 1.2 equiv) was then added at 23° C., and stirring was maintained for 23 h, at which point LCMS analysis indicated complete consumption of starting material. The mixture was concentrated in vacuo, and the dried residue was re-dissolved in 33% v/v trifluoroacetic acid-dichloromethane (300 μL) to which a drop of dimethyl sulfide had been added as t-butyl cation scavenger. Boc removal was monitored by LCMS, and after 30 min, was judged to be complete. The mixture was diluted with toluene (1.0 mL), and the resulting mixture was concentrated in vacuo. The crude residue thus obtained was then purified by preparative HPLC-MS on a Waters SunFire Prep C18 column (5 μm, 250×19 mm; eluting with 0.1% trifluoroacetic acid-water initially, grading to 0.1% trifluoroacetic acid-30% acetonitrile-water over 40 min, with a flow rate of 15 mL/min; monitored by UV absorbance at 210 nm and ESI+ selected ion monitoring [m/z=246]; R$_f$=22.3 min) to provide the product as a white solid (7.8 mg, 24%). $^1$H NMR (600 MHz, CD$_3$OD) δ 5.22 (d, J=5.6 Hz, 1H), 4.38 (dd, J=9.7, 3.0 Hz, 1H), 4.35 (dd, J=6.8, 3.1 Hz, 1H), 4.24 (dd, J=9.2, 7.5 Hz, 1H), 4.17 (dd, J=9.7, 1.4 Hz, 1H), 4.08 (dd, J=10.3, 5.6 Hz, 1H), 3.83 (dd, J=3.4, 1.3 Hz, 1H), 3.78 (dd, J=11.2, 7.0, 1H), 3.50 (dd, J=10.3, 3.3 Hz, 1H), 3.00-2.96 (m, 2H), 2.94 (s, 3H), 2.89 (app t, J=10.9 Hz, 1H), 2.40-2.36 (m, 3H), 2.28-2.24 (m, 2H), 2.11 (s, 3H), 1.96-1.90 (m, 2H), 1.52-1.45 (m, 2H), 1.41-1.33 (m, 2H), 1.12 (d, J=6.7 Hz, 3H), 0.95 (t, J=7.3 Hz, 3H). HRMS (ESI+, m/z): [M+2H]$^{2+}$ calc'd for $C_{22}H_{42}N_4O_6S$, 246.1485; found 246.1489.

A 4-mL glass vial fitted with a stir bar and a PTFE-lined screw cap was charged sequentially with 7-(S)-deoxyaminolincomycin dihydroacetate (FSA-215049.2CH$_3$CO$_2$H, 17 mg, 32 μmol, 1 equiv), 2,2,2-trifluoroethanol (320 μL), acetic acid (19 μL, 320 μmol, 10 equiv), 4-fluorobenzaldehyde (4.2 μL, 39 μmol, 1.2 equiv), and powdered, activated 4A molecular sieves (17 mg). The vial was sealed and the mixture was stirred at 23° C. for 15 min. Sodium cyanoborohydride (3.1 mg, 49 μmol, 1.5 equiv) was then added, and the vial was re-sealed. After 10 min, LCMS analysis indicated the reaction was complete, and the mixture was diluted with methanol (3 mL). The resulting mixture was filtered by passage through a 0.2-μm PTFE filter, the filtrate was concentrated, and the residue was purified by preparative HPLC on a Waters SunFire Prep C18 column (5 μm, 250×19 mm; eluting with 0.1% trifluoroacetic acid-water initially, grading to 0.1% trifluoroacetic acid-35% acetonitrile-water over 40 min, with a flow rate of 15 mL/min; monitored by UV absorbance at 254 nm; R$_f$=31.0 min) to provide the product as a white solid (7.0 mg, 29%). $^1$H NMR (600 MHz, CD$_3$OD) δ 7.61-7.57 (m, 2H), 7.22-7.18 (m, 2H), 5.30 (d, J=5.5 Hz, 1H), 4.81 (dd, J=7.6, 3.1 Hz, 1H), 4.42 (dd, J=7.6, 1.2 Hz, 1H), 4.39 (d, J=13.3 Hz, 1H), 4.28 (d, J=13.3 Hz, 1H), 4.21 (dd, J=9.9, 7.0 Hz, 1H), 4.08 (dd, J=10.1, 5.6 Hz, 1H), 3.94 (dd, J=3.1. 1.2 Hz, 1H), 3.76 (dd, J=11.1, 7.0 Hz, 1H), 3.72 (qd, J=6.9, 3.1 Hz, 1H), 2.93 (s, 3H), 2.90 (app t, J=11.0 Hz, 1H), 2.39-2.31 (m, 1H), 2.26-2.22 (m, 1H), 2.20 (s, 3H), 2.19-2.14 (m, 1H), 1.51-1.46 (m, 2H), 1.41 (d, J=6.9 Hz, 3H), 1.39-1.31 (m, 2H), 0.95 (t, J=7.3 Hz, 3H). $^{19}$F NMR (471 MHz, CD$_3$OD) δ −77.22 (s, 6F), −113.51 (s, 1F). HRMS (ESI+, m/z): [M+2H]$^{2+}$ calc'd for C$_{25}$H$_{40}$FN$_3$O$_5$S, 257.6409; found 257.6408.

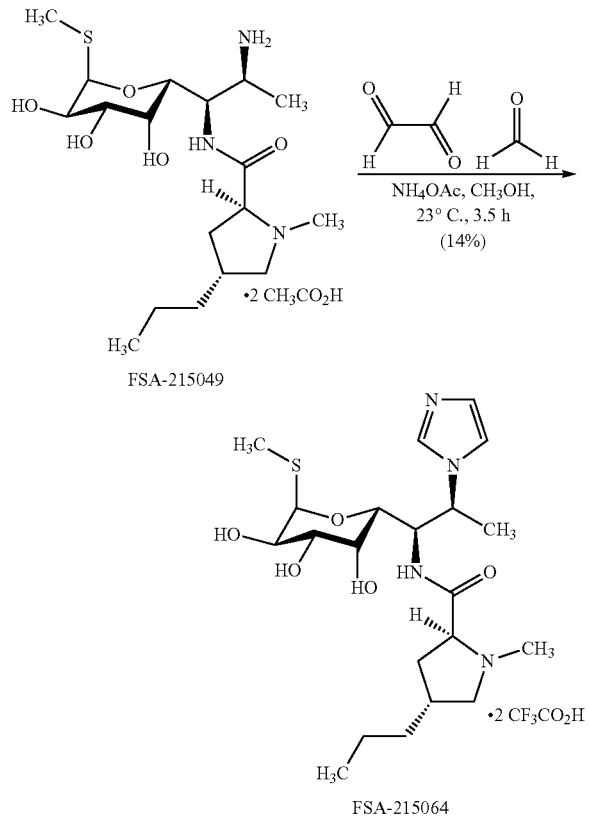

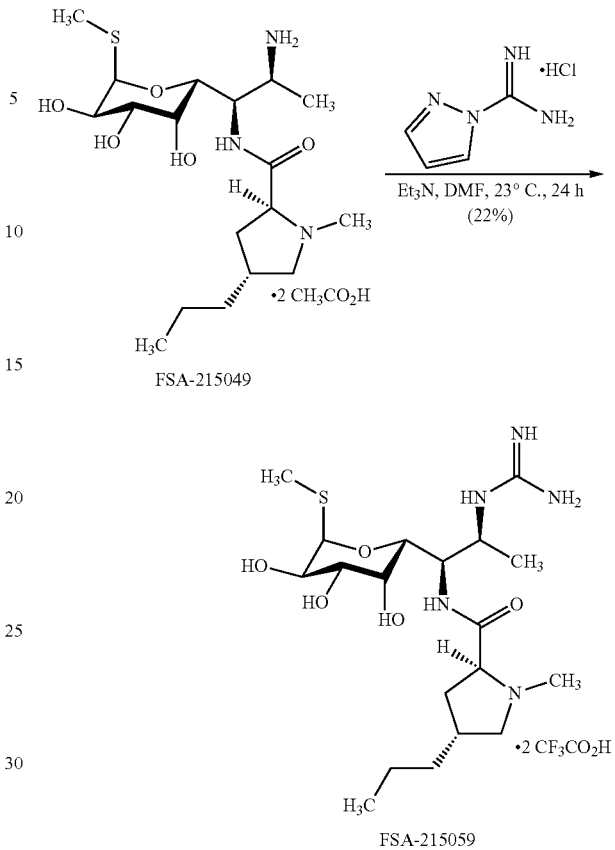

In a glass 1-mL vial fitted with a stir bar and a PTFE-lined screw cap, 7-(S)-deoxyaminolincomycin dihydroacetate (FSA-215049.2 CH$_3$CO$_2$H, 20 mg, 38 μmol, 1 equiv) was dissolved in methanol (380 μL). To this solution, ammonium acetate (8.8 mg, 110 μmol, 3.0 equiv), aqueous glyoxal solution (40 wt %, 8.5 μL, 110 μmol, 3.0 equiv), and formalin (17 μL, 110 μmol, 3.0 equiv) were added sequentially. The vial was sealed, and the mixture was stirred at 23° C. for 3.5 h, whereupon LCMS analysis showed complete consumption of starting material. The reaction mixture was purified directly by preparative HPLC on a Waters SunFire Prep C18 column (5 μm, 250×19 mm; eluting with 0.1% trifluoroacetic acid-water initially, grading to 0.1% trifluoroacetic acid-30% acetonitrile-water over 30 min, with a flow rate of 15 mL/min; monitored by UV absorbance at 254 nm; R$_t$=19.9 min) to provide the product as a white solid (3.7 mg, 14%).
$^1$H NMR (600 MHz, CD$_3$OD) δ 9.01 (app t, J=1.5 Hz, 1H), 7.69 (app t, J=1.8 Hz, 1H), 7.62 (app t, J=1.7 Hz, 1H), 5.24 (d, J=5.5 Hz, 1H), 4.95 (qd, J=7.0, 4.8 Hz, 1H), 4.74 (dd, J=9.1, 4.8 Hz, 1H), 4.16 (dd, J=9.9, 7.1 Hz, 1H), 4.07 (dd, J=10.3, 5.5 Hz, 1H), 4.00 (dd, J=9.2, 1.5 Hz, 1H), 3.82 (dd, J=3.3, 1.4 Hz, 1H), 3.75 (dd, J=11.2, 7.0 Hz, 1H), 3.50 (dd, J=10.3, 3.2 Hz, 1H), 2.91 (s, 3H), 2.88 (app t, J=11.0 Hz, 1H), 2.38-2.32 (m, 1H), 2.28 (s, 3H), 2.25-2.20 (m, 1H), 2.12-2.08 (m, 1H), 1.67 (d, J=7.0 Hz, 3H), 1.51-1.47 (m, 2H), 1.41-1.35 (m, 2H), 0.96 (t, J=7.2 Hz, 3H). HRMS (ESI+, m/z): [M+2H]$^{2+}$ calc'd for C$_{21}$H$_{36}$N$_4$O$_6$S, 229.1276; found 229.1287.

In a 1-dram vial, 7-(S)-deoxyaminolincomycin dihydroacetate (FSA-215049.2 CH$_3$CO$_2$H, 20 mg, 38 μmol, 1 equiv) was dissolved in N,N-dimethylformamide (380 μL). Triethylamine (27 μL, 0.19 mmol, 5.0 equiv) and 1H-pyrazole-1-carboxamidine hydrochloride (6.7 mg, 46 μmol, 1.2 equiv) were added sequentially, and the resulting mixture was stirred at 23° C. After 19 h, guanylation was incomplete, and additional triethylamine (27 μL, 0.19 mmol, 5.0 equiv) and 1H-pyrazole-1-carboxamidine hydrochloride (6.7 mg, 46 μmol, 1.2 equiv) were added. After 5.5 h of further stirring at 23° C., LCMS analysis indicated complete consumption of starting material. The reaction mixture was diluted with 3 mL of 50% v/v toluene-methanol, and the diluted mixture was concentrated in vacuo. The residue was repeatedly concentrated from 50% v/v methanol-toluene (3×3 mL) in order to remove residual N,N-dimethylformamide, and the dried residue was then purified by preparative HPLC-MS on a Waters SunFire Prep C18 column (5 μm, 250×19 mm; eluting with 0.1% trifluoroacetic acid-water initially, grading to 0.1% trifluoroacetic acid-30% acetonitrile-water over 40 min, with a flow rate of 15 mL/min; monitored by UV absorbance at 210 nm and ESI+ selected ion monitoring [m/z=448]; R$_t$=36.0 min) to provide the product as a white solid (5.6 mg, 22%). $^1$H NMR (600 MHz, CD$_3$OD) δ 5.25 (d, J=5.5 Hz, 1H), 4.48 (dd, J=10.0, 2.7 Hz, 1H), 4.26 (dd, J=10.1, 1.3 Hz, 1H), 4.25-4.21 (m, 1H), 4.08 (dd, J=10.2, 5.6 Hz, 1H), 3.98 (qd, J=6.7, 2.7 Hz, 1H), 3.85 (dd, J=3.3, 1.3 Hz, 1H), 3.78 (dd, J=11.2, 6.9 Hz, 1H), 3.52 (dd, J=10.3, 3.3 Hz, 1H), 2.95 (s, 3H), 2.91 (app t, J=10.9 Hz, 1H), 2.41-2.35 (m, 1H), 2.28-2.25 (m, 2H), 2.17 (s, 3H), 1.51-1.47 (m, 2H), 1.41-1.33 (m, 2H), 1.23 (d, J=6.7 Hz, 3H), 0.95 (t, J=7.3 Hz, 3H). HRMS (ESI+, m/z): [M+2H]$^{2+}$ calc'd for $C_{19}H_{37}N_5O_5S$, 224.6330; found 224.6332.

FSA-215028c was made in a manner analogous to the examples described above using appropriate starting materials and intermediates.

Biological Assays

Minimum inhibitory concentrations (MICs) for compounds described herein have been determined for strains of several Gram positive and Gram negative strains. Data for exemplary compounds described herein is shown in Tables 3-8.

TABLE 3

MIC (μg/mL) of compounds against Gram positive and Gram negative strains

| Species | Genotype | Clinda-mycin | FSA-215025d | FSA-215028c | FSA-215038 | FSA-215049 | FSA-215052 |
|---|---|---|---|---|---|---|---|
| S. aureus | ATCC 29213 | 0.25 | 4 | 64 | 0.25 | 64 | >64 |
| S. aureus | BAA 977 iErmA | 0.25 | 4 | 32 | 0.5 | 64 | >64 |
| S. aureus | MP-549 msr(a) USA 300 | 0.125 | — | — | — | 32 | — |
| S. aureus | MMX 3035 cErmA | >64 | — | — | — | — | — |
| S. pneumoniae | ATCC 49619 | 0.12 | 2 | 16 | 0.25 | 8 | >64 |
| S. pneumoniae | MMX 3028 cErmB | >64 | — | — | — | — | — |
| S. pneumoniae | MMX 3031 cMefA | 0.06 | — | — | — | — | — |
| S. pyogenes | ATCC 19615 | 0.06 | 1 | 8 | 0.125 | 16 | 32 |
| S. pyogenes | MMX 946 Macrolide-Resistant | >64 | — | — | — | — | — |
| E. faecalis | ATCC 29212 | 16 | >64 | >64 | 32 | >64 | >64 |
| E. faecalis | UNT-047 VRE | >32 | — | — | — | — | — |
| C. difficile | BAA 1805 | 8 | — | — | — | >64 | — |
| B. fragilis | ATCC 25285 | 0.5 | — | — | — | — | — |
| K. pneumoniae | ATCC 10031 | 8 | >64 | >64 | >64 | >64 | >64 |
| E. coli | ATCC 25922 | >64 | >64 | >64 | >64 | >64 | >64 |
| E. coli | MP-9 ΔTolC | 8 | >64 | >64 | >64 | >64 | >64 |
| E. coli | MP-74 LptD mutant | 2 | — | — | — | >64 | — |
| H. influenzae | ATCC 49247 | 16 | — | — | — | >64 | — |

TABLE 4

MIC (μg/mL) of compounds against Gram positive and Gram negative strains

| Species | Genotype | FSA-215054 | FSA-215059 | FSA-215064 | FSA-215070 | FSA-215071 | FSA-215072 |
|---|---|---|---|---|---|---|---|
| S. aureus | ATCC 29213 | >64 | 32 | 64 | 64 | >64 | >64 |
| S. aureus | BAA 977 iErmA | >64 | 32 | >64 | 64 | >64 | >64 |
| S. aureus | MP-549 msr(a) USA 300 | — | — | — | 64 | >64 | — |
| S. pneumoniae | ATCC 49619 | >64 | 8 | 16 | 16 | 8 | 8 |
| S. pyogenes | ATCC 19615 | 64 | 4 | 8 | 32 | 16 | 8 |
| E. faecalis | ATCC 29212 | >64 | >64 | >64 | >64 | >64 | >64 |
| C. difficile | BAA 1805 | — | — | — | >64 | >64 | — |
| K. pneumoniae | ATCC 10031 | >64 | >64 | >64 | >64 | >64 | >64 |
| E. coli | ATCC 25922 | >64 | >64 | >64 | >64 | >64 | >64 |
| E. coli | MP-9 ΔTolC | >64 | >64 | >64 | >64 | >64 | >64 |
| E. coli | MP-74 LptD mutant | — | >64 | >64 | >64 | >64 | >64 |
| H. influenzae | ATCC 49247 | — | — | — | >64 | >64 | — |

TABLE 5

MIC (μg/mL) of compounds against Gram positive and Gram negative strains

| Species | Genotype | FSA-215078a | FSA-215078b | FSA-215081 | FSA-215082 | FSA-214080 | FSA-214084 |
|---|---|---|---|---|---|---|---|
| S. aureus | ATCC 29213 | >64 | >64 | 4 | 64 | >64 | >64 |
| S. aureus | BAA 977 iErmA | >64 | >64 | 4 | 64 | — | — |
| S. aureus | MP-549 msr(a) USA 300 | >64 | >64 | 4 | >64 | — | — |
| S. pneumoniae | ATCC 49619 | 16 | 8 | 2 | 16 | >64 | >64 |
| S. pyogenes | ATCC 19615 | 8 | 8 | 1 | 32 | >64 | >64 |
| E. faecalis | ATCC 29212 | >64 | >64 | >64 | >64 | >64 | >64 |
| C. difficile | BAA 1805 | >64 | >64 | — | >64 | — | — |
| B. fragilis | ATCC 25285 | >64 | — | — | >64 | — | — |
| K. pneumoniae | ATCC 10031 | >64 | >64 | >64 | >64 | — | — |
| E. coli | ATCC 25922 | >64 | >64 | >64 | >64 | >64 | >64 |
| E. coli | MP-9 ΔTolC | >64 | >64 | >64 | >64 | — | — |
| E. coli | MP-74 LptD mutant | >64 | >64 | >64 | >64 | — | — |
| H. influenzae | ATCC 49247 | >64 | >64 | >64 | >64 | — | — |

TABLE 6

MIC (μg/mL) of compounds against Gram positive and Gram negative strains

| Species | Genotype | FSA-214082b | FSA-214043 | FSA-214087 | FSA-214088 | FSA-214099 | FSA-215003 |
|---|---|---|---|---|---|---|---|
| S. aureus | ATCC 29213 | >64 | 32 | 32 | >64 | 64 | 8 |
| S. aureus | MP-549 msr(a) USA 300 | — | — | 32 | — | — | 0.125 |
| S. aureus | MMX 3035 cErmA | — | — | >64 | — | — | >64 |
| S. pneumoniae | ATCC 49619 | >64 | 4 | 8 | >64 | 16 | 4 |
| S. pneumoniae | MMX 3028 cErmB | — | — | >64 | — | — | >64 |
| S. pneumoniae | MMX 3031 cMefA | — | — | 32 | — | — | 0.125 |
| S. pyogenes | ATCC 19615 | >64 | 8 | 8 | >64 | 32 | 2 |
| S. pyogenes | MMX 946 MacRes | — | — | >64 | — | — | >64 |
| E. faecalis | ATCC 29212 | >64 | 64 | >64 | >64 | >64 | 32 |
| E. faecalis | MMX 847 MacRes | — | — | >64 | — | — | >64 |
| E. coli | ATCC 25922 | >64 | >64 | >64 | >64 | >64 | >64 |
| E. coli | MP-9 ΔTolC | — | — | >64 | — | — | 4 |

TABLE 7

MIC (μg/mL) of compounds against Gram positive and Gram negative strains

| Species | Genotype | FSA-215009 | FSA-215011 | FSA-2140836 | FSA-215031 | FSA-215036 | FSA-216092 |
|---|---|---|---|---|---|---|---|
| S. aureus | ATCC 29213 | 64 | >64 | >64 | 8 | >64 | >64 |
| S. aureus | BAA 977 iErmA | — | — | — | 8 | >64 | — |
| S. aureus | MP-549 msr(a) USA 300 | — | — | — | — | — | >64 |
| S. pneumoniae | ATCC 49619 | 64 | 2 | >64 | 2 | 16 | >64 |
| S. pyogenes | ATCC 19615 | 32 | >64 | >64 | 2 | 64 | >64 |
| E. faecalis | ATCC 29212 | >64 | >64 | >64 | 32 | >64 | >64 |
| K. pneumoniae | ATCC 10031 | — | — | — | >64 | >64 | >64 |
| E. coli | ATCC 25922 | >64 | >64 | >64 | >64 | >64 | >64 |
| E. coli | MP-9 ΔTolC | — | — | — | >64 | >64 | >64 |
| E. coli | MP-74 LptD mutant | — | — | — | — | — | >64 |
| H. influenzae | ATCC 49247 | — | — | — | — | — | >64 |

TABLE 8

MIC (μg/mL) of compounds against Gram positive and Gram negative strains

| Species | Genotype | FSA-215077 | FSA-217003 | FSA-217009 | FSA-217021a | FSA-217021b | FSA-217031 |
|---|---|---|---|---|---|---|---|
| S. aureus | ATCC 29213 | >64 | 1 | 0.25 | 4 | 0.25 | 64 |
| S. aureus | BAA 977 iErmA | >64 | — | — | — | — | — |
| S. aureus | MP-549 msr(a) USA 300 | >64 | 1 | 0.25 | 4 | 0.25 | 32 |
| S. pneumoniae | ATCC 49619 | >64 | 0.5 | 0.5 | 2 | 0.12 | 4 |
| S. pyogenes | ATCC 19615 | >64 | 0.5 | 0.12 | 2 | 0.12 | 8 |
| E. faecalis | ATCC 29212 | >64 | 64 | 64 | >64 | 64 | 64 |
| K. pneumoniae | ATCC 10031 | >64 | >64 | >64 | >64 | >64 | >64 |
| E. coli | ATCC 25922 | >64 | >64 | >64 | >64 | >64 | >64 |
| E. coli | MP-9 ΔTolC | >64 | >64 | >64 | >64 | 32 | >64 |
| E. coli | MP-74 LptD mutant | >64 | >64 | 32 | >64 | 8 | >64 |
| H. influenzae | ATCC 49247 | >64 | >64 | 64 | >64 | 32 | >64 |

TABLE 9

MIC (μg/mL) of compounds against Gram positive and Gram negative strains

| Species | Genotype | FSA-217039a | FSA-217039b | FSA-217045a | FSA-217045b |
|---|---|---|---|---|---|
| S. aureus | ATCC 29213 | >64 | 4 | >64 | >64 |
| S. aureus | BAA 977 iErmA | — | — | — | — |
| S. aureus | MP-549 msr(a) USA 300 | >64 | 8 | >64 | >64 |
| S. pneumoniae | ATCC 49619 | 8 | 1 | 64 | 32 |
| S. pyogenes | ATCC 19615 | 8 | 0.5 | >64 | >64 |
| E. faecalis | ATCC 29212 | >64 | >64 | >64 | >64 |
| K. pneumoniae | ATCC 10031 | >64 | >64 | >64 | >64 |
| E. coli | ATCC 25922 | >64 | >64 | >64 | >64 |
| E. coli | MP-9 ΔTolC | >64 | >64 | >64 | >64 |

TABLE 9-continued

MIC (μg/mL) of compounds against Gram positive and Gram negative strains

| Species | Genotype | FSA-217039a | FSA-217039b | FSA-217045a | FSA-217045b |
|---|---|---|---|---|---|
| E. coli | MP-74 LptD mutant | >64 | >64 | >64 | >64 |
| H. influenzae | ATCC 49247 | >64 | >64 | >64 | >64 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

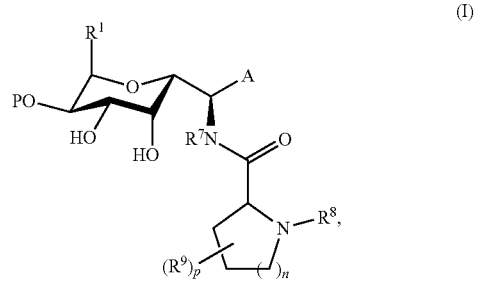

or a pharmaceutically acceptable salt thereof, wherein:
each occurrence of P is independently hydrogen or a protecting group;
A is substituted or unsubstituted carbocyclyl, substituted or unsubstituted heterocyclyl,

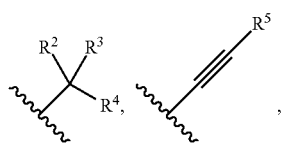

or —$CHF_2$; or A and $R^7$ are joined to form a substituted or unsubstituted heterocyclic ring;
$R^1$ is substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted aralkyl, substituted or unsubstituted heteroaryl, substituted or unsubstituted heteroaralkyl, —$OR^A$, —$N(R^A)_2$, or —$SR^A$, wherein $R^A$ of —$SR^A$ is unsubstituted alkyl, substituted or unsubstituted carbocyclyl, substituted or unsubstituted heterocyclyl, substituted or unsubstituted heteroaryl, or a sulfur protecting group;
$R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —$OR^A$, —$N_3$, —$N(R^A)_2$, —$SR^A$, —CN, —SCN, —$C(=NR^A)R^A$, —$C(=NR^A)OR^A$, —$C(=NR^A)N(R^A)_2$, —$C(=O)R^A$, —$C(=O)OR^A$, —$C(=O)N(R^A)_2$, —$NO_2$, —$NR^AC(=O)R^A$, —$NR^AC(=O)OR^A$, —$NR^AC(=O)N(R^A)_2$, —$NR^AC(=NR^A)N(R^A)_2$, —$OC(=O)R^A$, —$OC(=O)OR^A$, —$OC(=O)N(R^A)_2$, —$NR^AS(O)_2R^A$, —$OS(O)_2R^A$, or —$S(O)_2R^A$;

R³ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

R⁴ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

R⁵ is hydrogen, halogen, substituted or unsubstituted alkyl, substituted or unsubstituted carbocyclyl, substituted or unsubstituted heterocyclyl, substituted or unsubstituted aryl, substituted or unsubstituted heteroaryl, or substituted or unsubstituted heteroaliphatic;

R⁷ is hydrogen or unsubstituted alkyl; or A and R⁷ are joined to form a substituted or unsubstituted heterocyclic ring;

R⁸ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaliphatic, —C(=NR^A)R^A, —C(=NR^A)OR^A, —C(=NR^A)N(R^A)₂, —C(=O)R^A, —C(=O)OR^A, —C(=O)N(R^A)₂, —S(O)₂R^A, or a nitrogen protecting group;

each occurrence of R⁹ is independently, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroaliphatic, —OR^A, —N(R^A)₂, —SR^A, —CN, —SCN, —C(=NR^A)R^A, —C(=NR^A)OR^A, —C(=NR^A)N(R^A)₂, —C(=O)R^A, —C(=O)OR^A, —C(=O)N(R^A)₂, —NO₂, —NR^AC(=O)R^A, —NR^AC(=O)OR^A, —NR^AC(=O)N(R^A)₂, —NR^AC(=NR^A)N(R^A)₂, —OC(=O)R^A, —OC(=O)OR^A, —OC(=O)N(R^A)₂, —NR^AS(O)₂R^A, —OS(O)₂R^A, or —S(O)₂R^A;

n is 1 or 2;

p is 1-3;

each occurrence of R^A is, independently, hydrogen, substituted or unsubstituted acyl, substituted or unsubstituted alkyl, substituted or unsubstituted alkenyl, substituted or unsubstituted alkynyl, substituted or unsubstituted heteroaliphatic, substituted or unsubstituted carbocyclyl, substituted or unsubstituted carbocyclylalkyl, substituted or unsubstituted heterocyclyl, substituted or unsubstituted aryl, substituted or unsubstituted aralkyl, substituted or unsubstituted heteroaryl, substituted or unsubstituted hetaralkyl, a nitrogen protecting group when attached to a nitrogen atom, an oxygen protecting group when attached to an oxygen atom, or a sulfur protecting group when attached to a sulfur atom, or two R^A groups are joined to form a substituted or unsubstituted heterocyclic ring, or a substituted or unsubstituted heteroaryl ring;

provided that when R¹ is —SR^A and R^A is C₁₋₆ unsubstituted alkyl, A is not unsubstituted C₃₋₆ cycloalkyl,

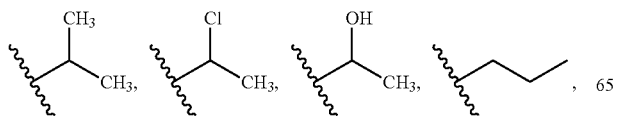

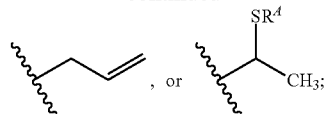

and provided that when A is

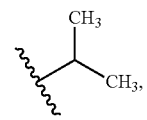

R¹ is not —OR^A, wherein R^A is substituted or unsubstituted alkyl.

2. The compound of claim 1, or a pharmaceutically acceptable salt thereof, wherein:

A is

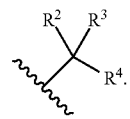

3. The compound of claim 2, or a pharmaceutically acceptable salt thereof, wherein:

R² is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, substituted or unsubstituted heteroalkyl, —OR^A, —N₃, —N(R^A)₂, —SR^A, —NR^AC(=O)R^A, or —OC(=O)N(R^A)₂.

4. The compound of claim 2, or a pharmaceutically acceptable salt thereof, wherein:

R³ is hydrogen, substituted or unsubstituted alkyl, or substituted or unsubstituted alkenyl.

5. The compound of claim 2, or a pharmaceutically acceptable salt thereof, wherein:

R⁴ is hydrogen, substituted or unsubstituted alkyl, or substituted or unsubstituted alkenyl.

6. The compound of claim 1, or a pharmaceutically acceptable salt thereof, wherein:

A is

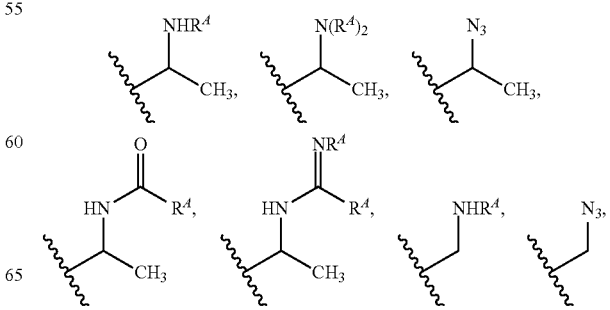

-continued

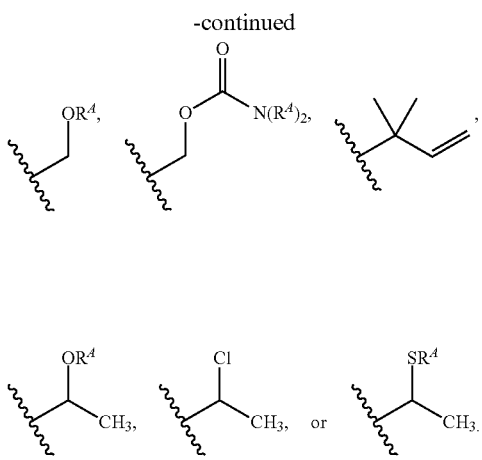

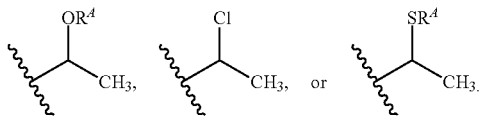

7. The compound of claim 1, or a pharmaceutically acceptable salt thereof, wherein:

A is

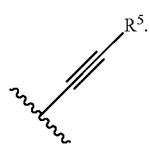

8. The compound of claim 1, or a pharmaceutically acceptable salt thereof, wherein:

$R^1$ is substituted or unsubstituted alkenyl, substituted or unsubstituted carbocyclyl, substituted or unsubstituted heterocyclyl, substituted or unsubstituted heteroaryl, substituted or unsubstituted heteroaralkyl, —OR$^A$, —N(R$^A$)$_2$, or —SR$^A$.

9. The compound of claim 1, or a pharmaceutically acceptable salt thereof, wherein:

$R^1$ is —SR$^A$ or

10. The compound of claim 1, or a pharmaceutically acceptable salt thereof, wherein:

$R^8$ is hydrogen, substituted or unsubstituted alkyl, or —C(=O)R$^A$.

11. The compound of claim 1, or a pharmaceutically acceptable salt thereof, wherein:

$R^9$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or substituted or unsubstituted heteroalkyl.

12. The compound of claim 1, wherein the compound is of Formula (I-a), (I-b), (I-c), or (I-d):

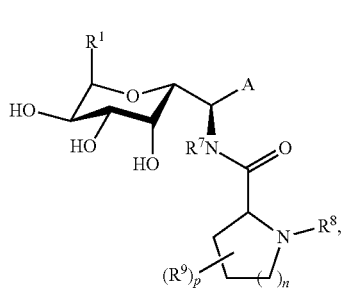
(I-a)

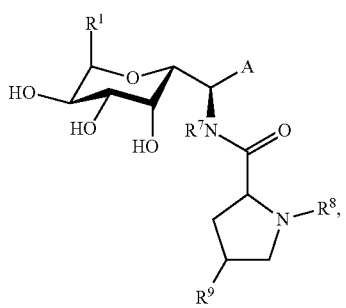
(I-b)

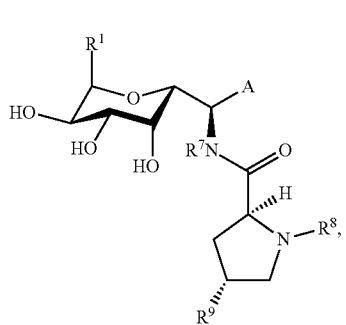
(I-c)

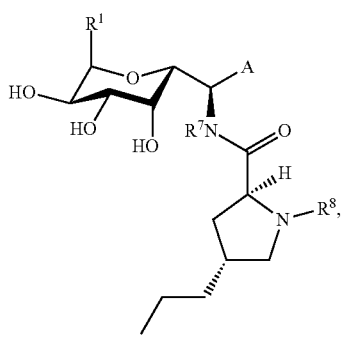
(I-d)

or a pharmaceutically acceptable salt thereof.

13. The compound of claim 1, wherein the compound is of Formula (II), (II-a), (II-b), (II-c), or (II-d):
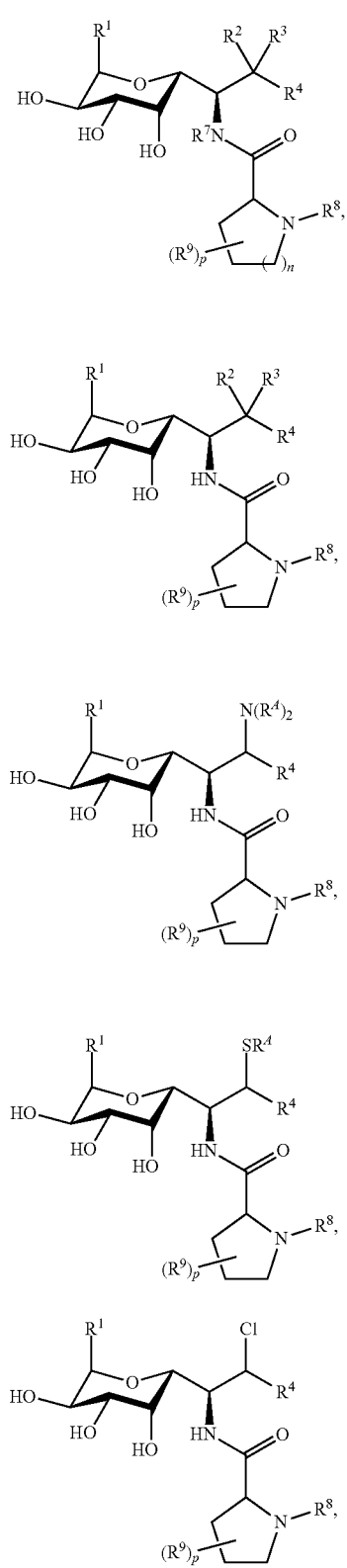
or a pharmaceutically acceptable salt thereof.
14. The compound of claim 1, wherein the compound is of Formula (III) or (III-a):
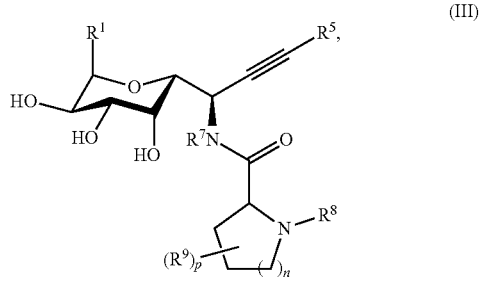
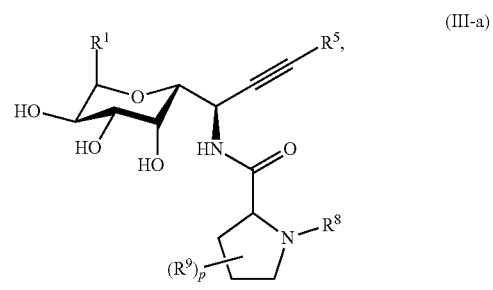
or a pharmaceutically acceptable salt thereof.
15. The compound of claim 1, or a pharmaceutically acceptable salt thereof, wherein the compound is:
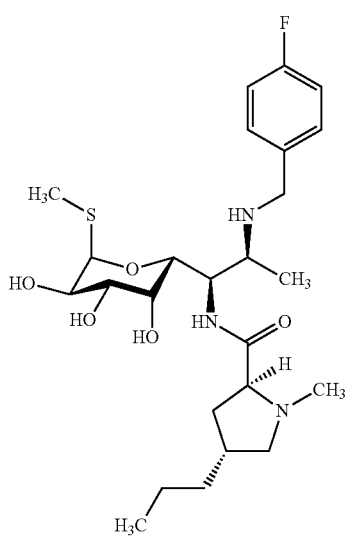

-continued
FSA-215028c
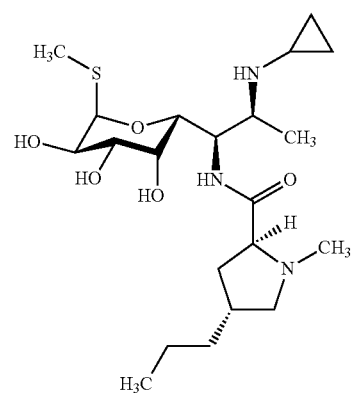
FSA-215038
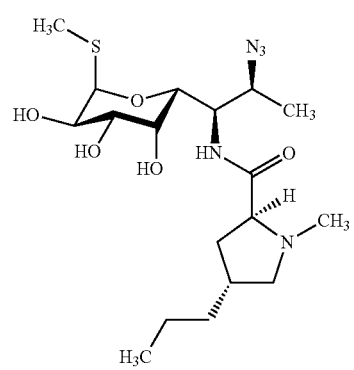
FSA-215049
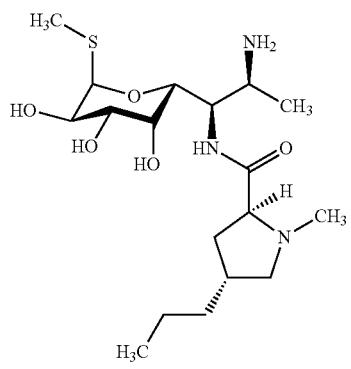
FSA-215052
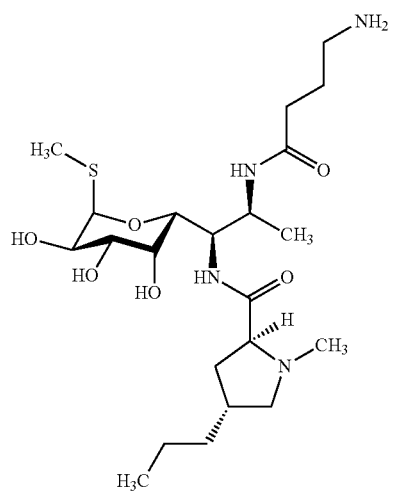
-continued
FSA-215054
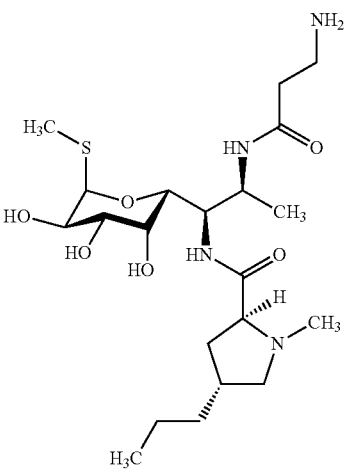
FSA-215059
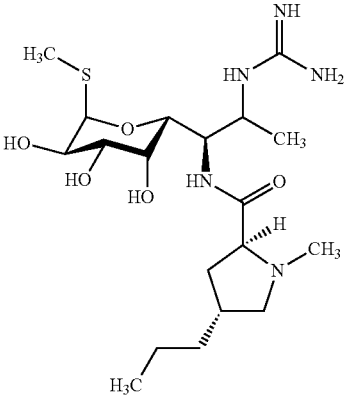
FSA-215064
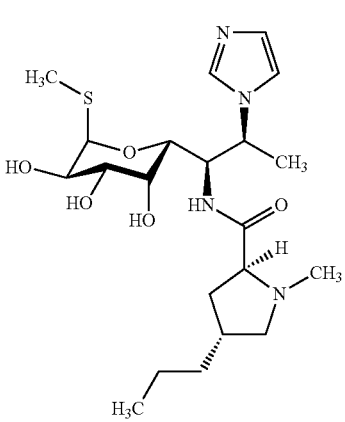
FSA-215070
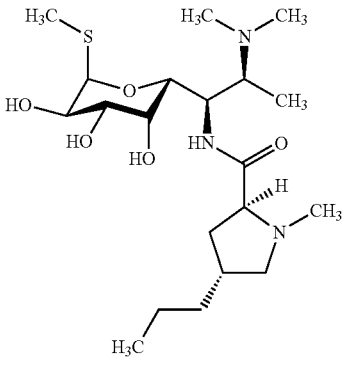

FSA-215071
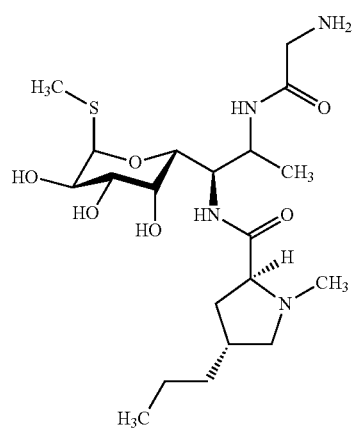
FSA-215078b
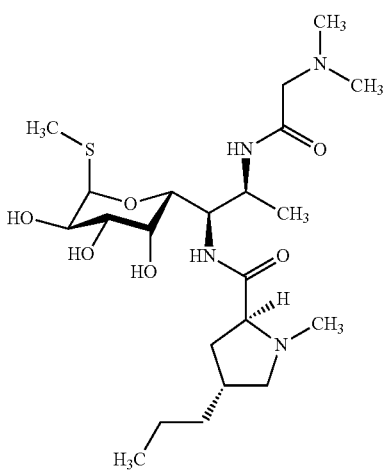
FSA-215072
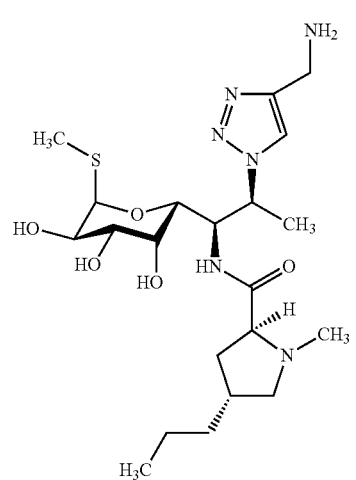
FSA-215081
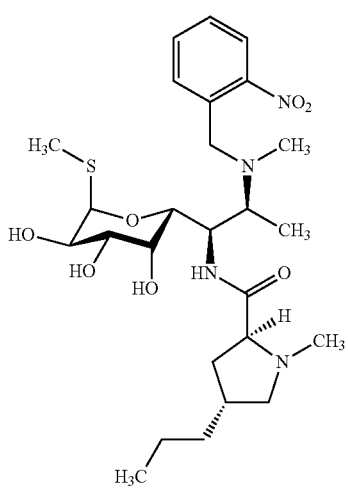
FSA-215078a
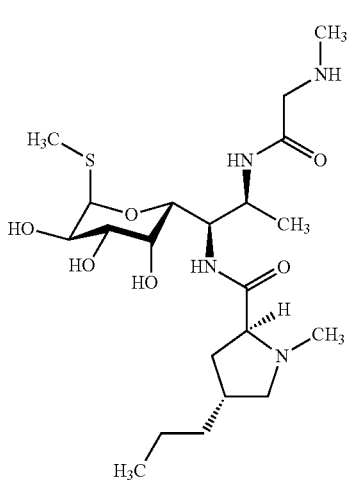
FSA-215082
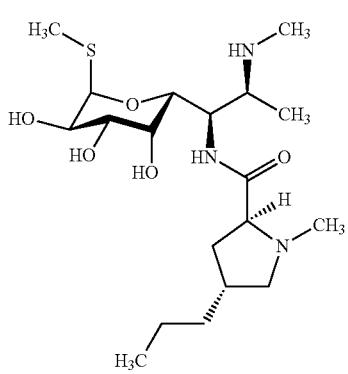

171
-continued
172
-continued
FSA-214080
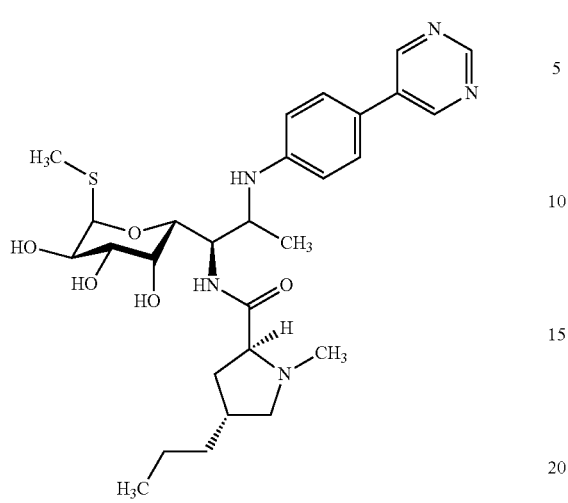
FSA-214043
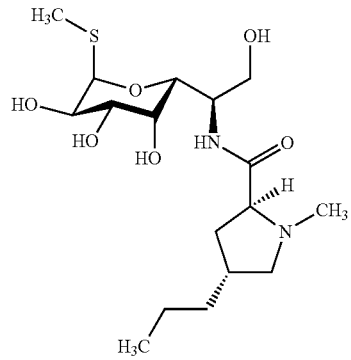
FSA-214084
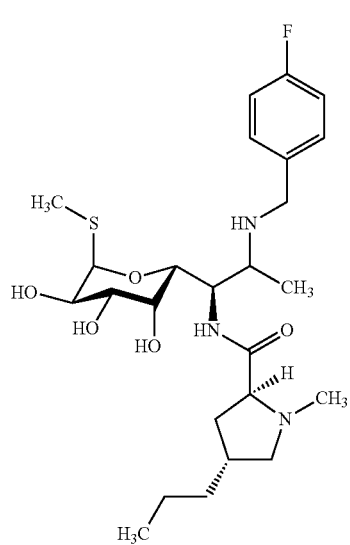
FSA-214087
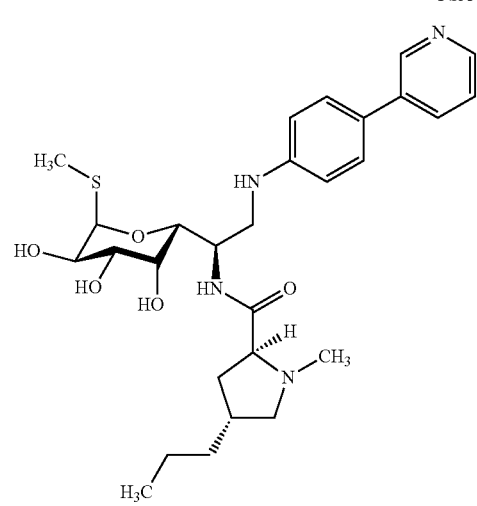
FSA-214082b
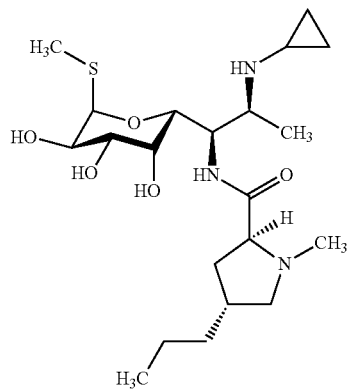
FSA-214088
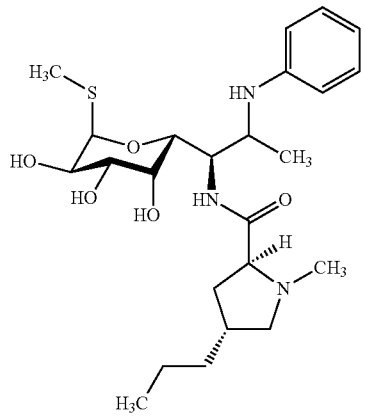

-continued
FSA-214099
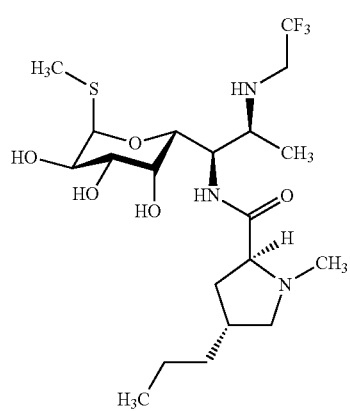
FSA-215003
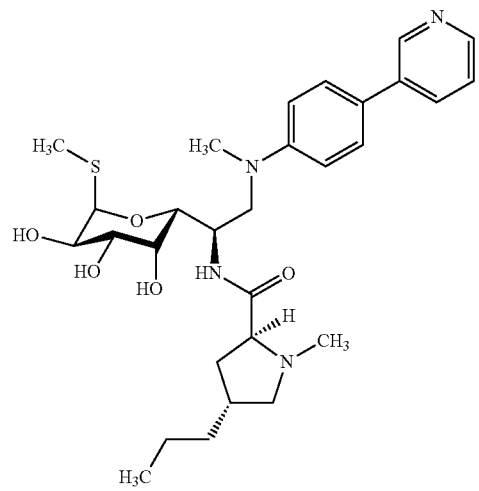
FSA-215009
-continued
FSA-215011
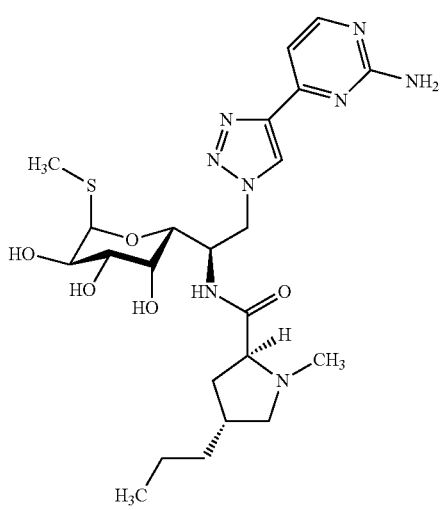
FSA-214083b
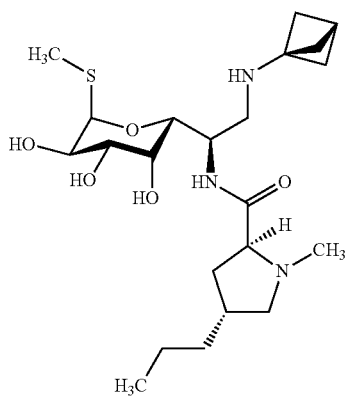
FSA-215036
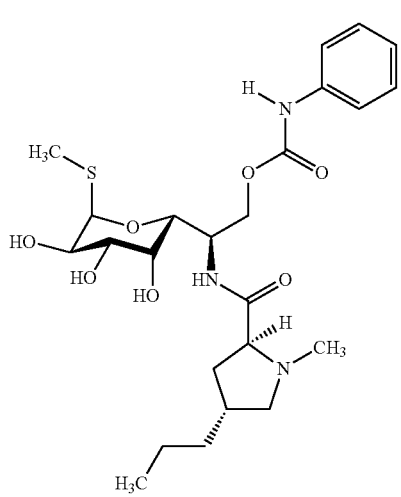

175
-continued
FSA-216092
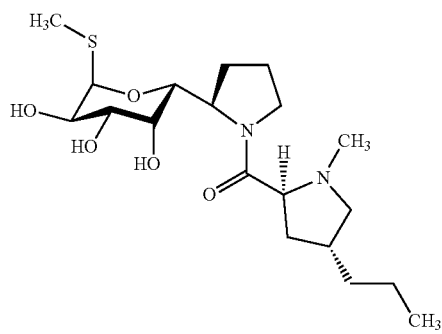
FSA-217009
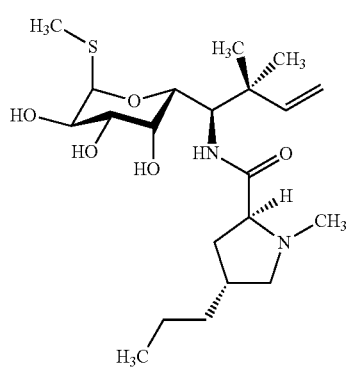
FSA-215077
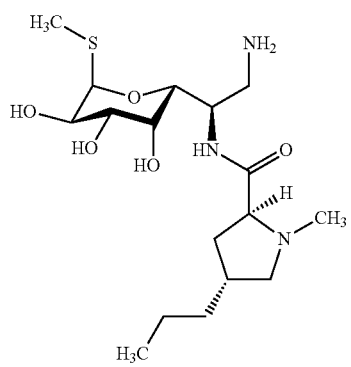
FSA-217021
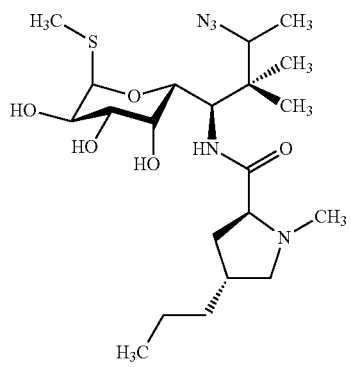
176
-continued
FSA-217039
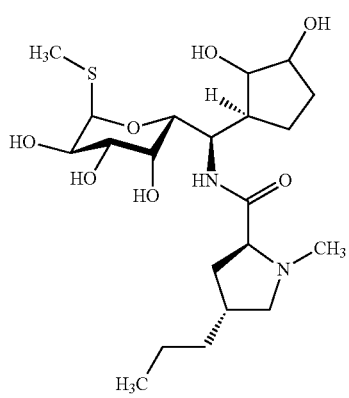
FSA-217045
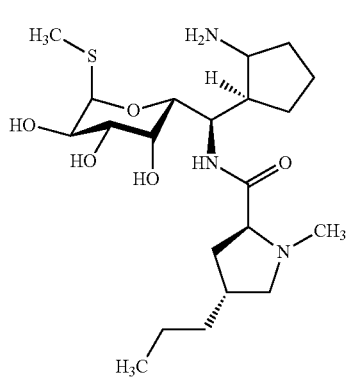
FSA-217003
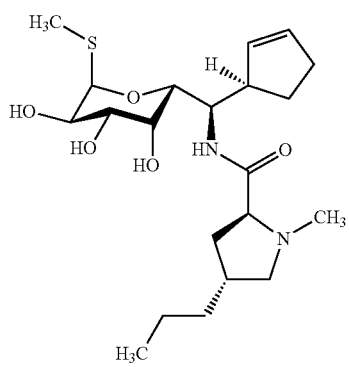
FSA-217031
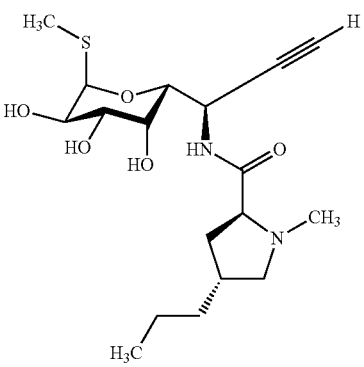

177
-continued

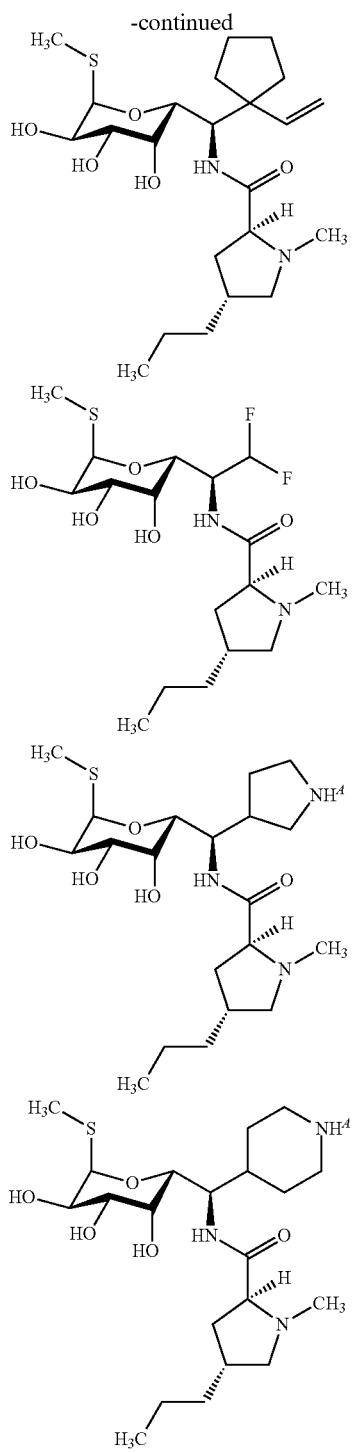

178
-continued

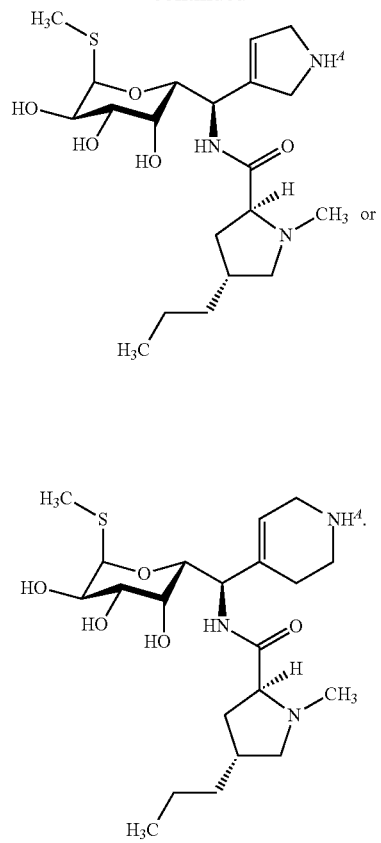

16. The compound of claim 1, or a pharmaceutically acceptable salt thereof, wherein $R^1$ is —SCH$_3$.

17. The compound of claim 1, or a pharmaceutically acceptable salt thereof, wherein n is 1.

18. A pharmaceutical composition comprising a compound of claim 1, or a pharmaceutically acceptable salt thereof, and a pharmaceutically acceptable excipient.

19. A method of treating an infectious disease comprising administering an effective amount of a compound of claim 1, or pharmaceutically acceptable salt thereof.

20. A method of killing or inhibiting the growth of a microorganism comprising contacting the microorganism with an effective amount of a compound of claim 1, or pharmaceutically acceptable salt thereof.

* * * * *

UNITED STATES PATENT AND TRADEMARK OFFICE
CERTIFICATE OF CORRECTION

PATENT NO. : 11,566,039 B2  
APPLICATION NO. : 16/637477  
DATED : January 31, 2023  
INVENTOR(S) : Andrew G. Myers et al.

Page 1 of 7

It is certified that error appears in the above-identified patent and that said Letters Patent is hereby corrected as shown below:

In the Claims

In Claim 1, at Column 160, Lines 17-27, formula: 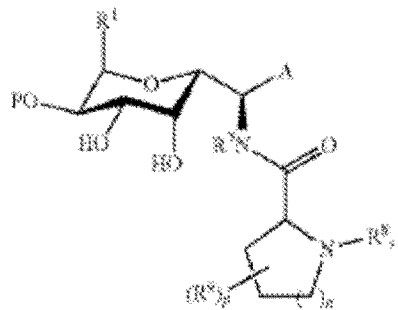 should be replaced with the formula: 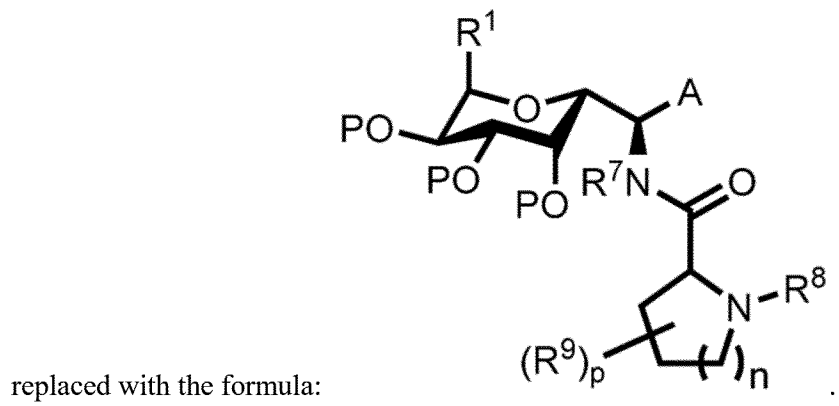 .

Signed and Sealed this  
Seventeenth Day of October, 2023

Katherine Kelly Vidal  
*Director of the United States Patent and Trademark Office*

CERTIFICATE OF CORRECTION (continued)
U.S. Pat. No. 11,566,039 B2

In Claim 15, at Column 171, Lines 1-22, formula: 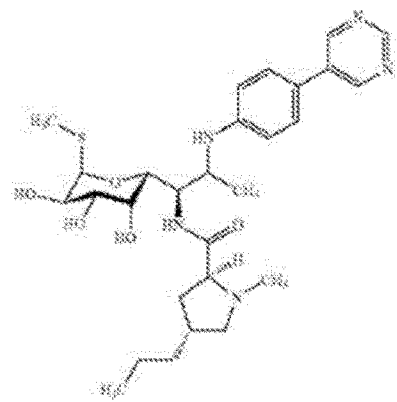 should be replaced with the formula: 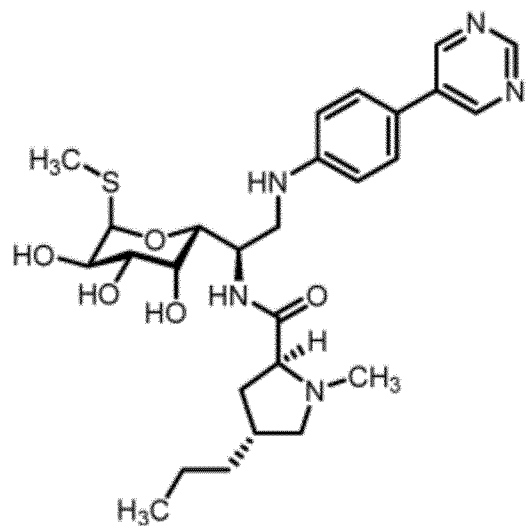 .

In Claim 15, at Column 171, Lines 26-46, formula: 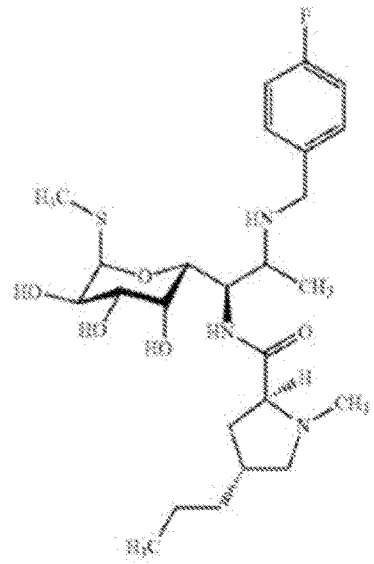 should be replaced with the formula: 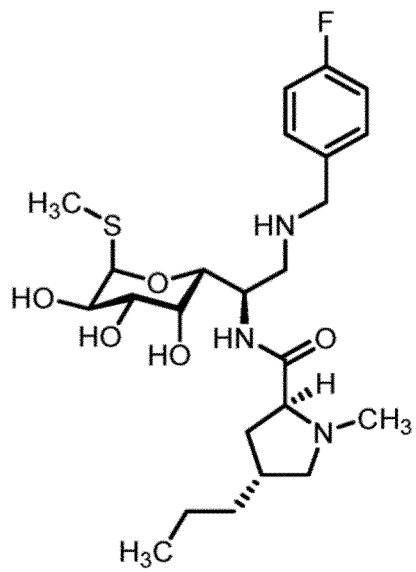 .
In Claim 15, at Column 171, Lines 51-66, formula: 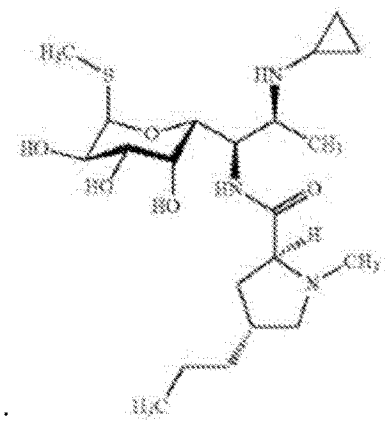 should be replaced with the formula: 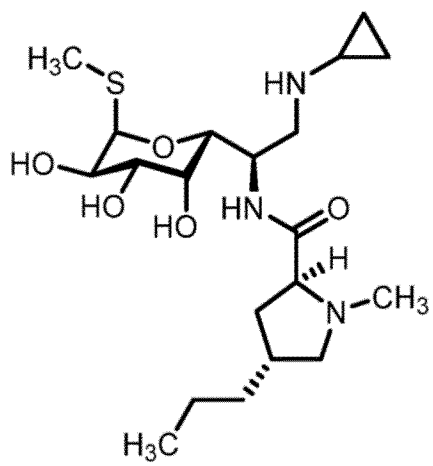 .

CERTIFICATE OF CORRECTION (continued)
U.S. Pat. No. 11,566,039 B2

In Claim 15, at Column 172, Lines 51-66, formula: 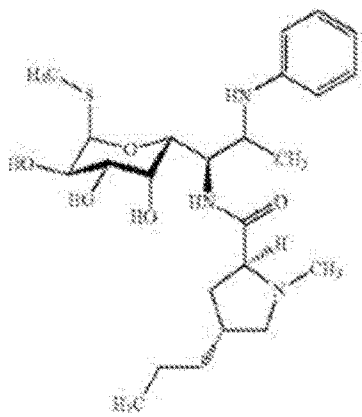 should be replaced with the formula: 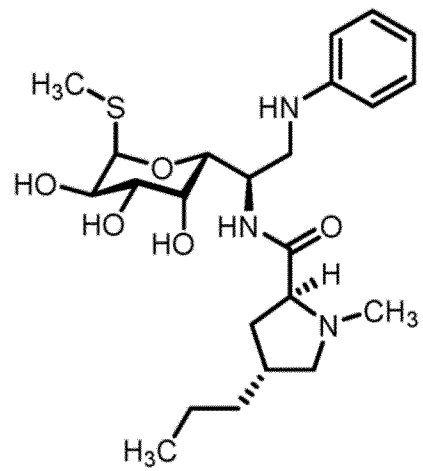 .

In Claim 15, at Column 173, Lines 1-18, formula: 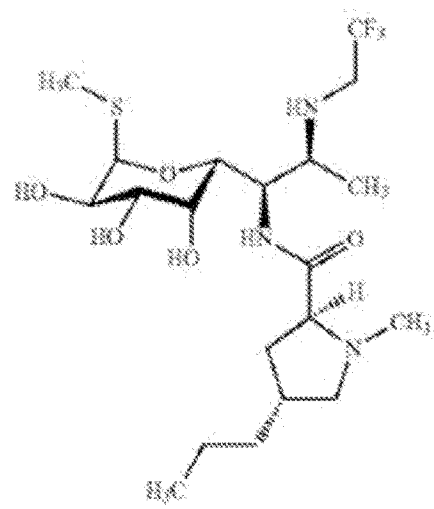 should be replaced with the formula: 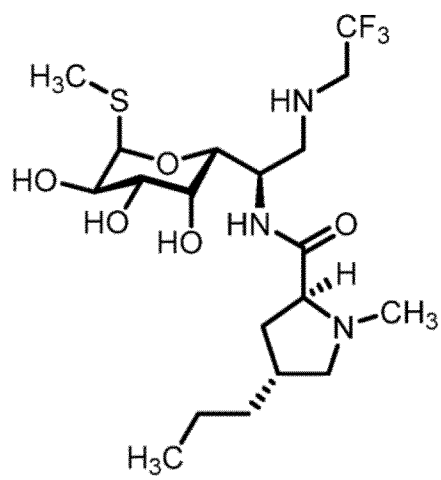 .
In Claim 15, at Column 177, Lines 28-41, formula: 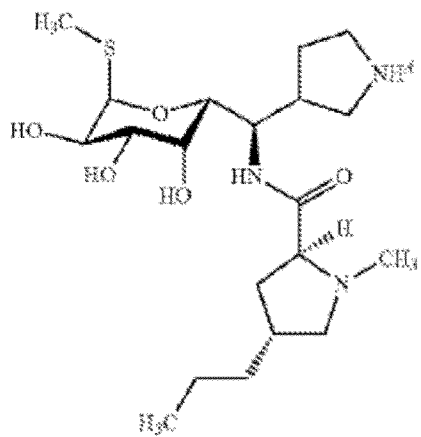 should be replaced with the formula: 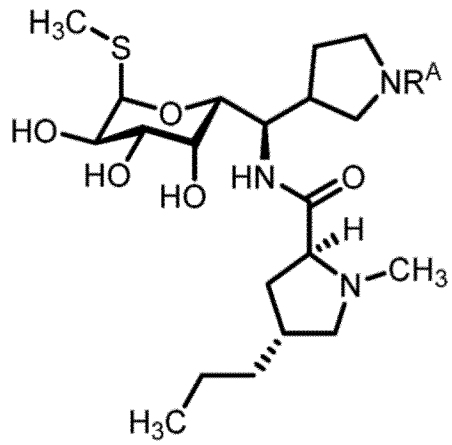 .

CERTIFICATE OF CORRECTION (continued)
U.S. Pat. No. 11,566,039 B2

Page 6 of 7

In Claim 15, at Column 177, Lines 42-55, formula: 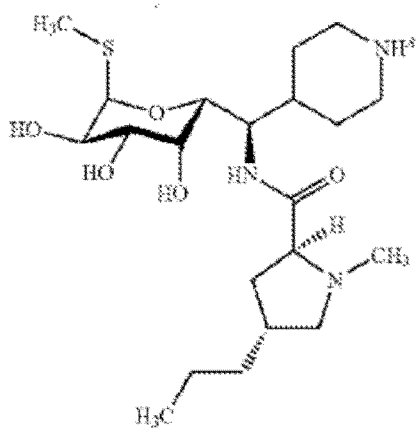 should be replaced with the formula: 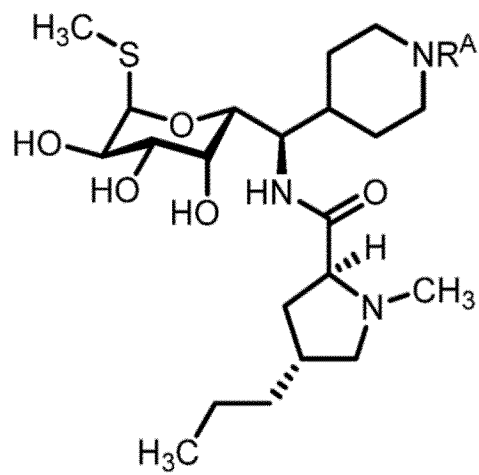.

In Claim 15, at Column 178, Lines 1-15, formula: 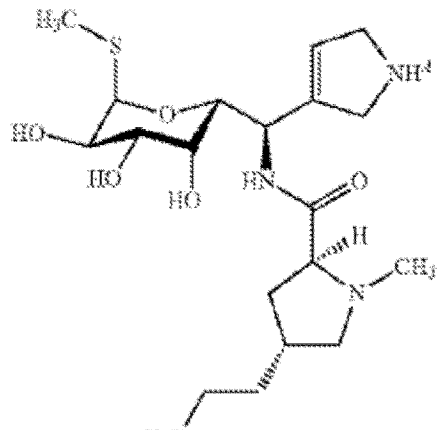 should be replaced with the formula: 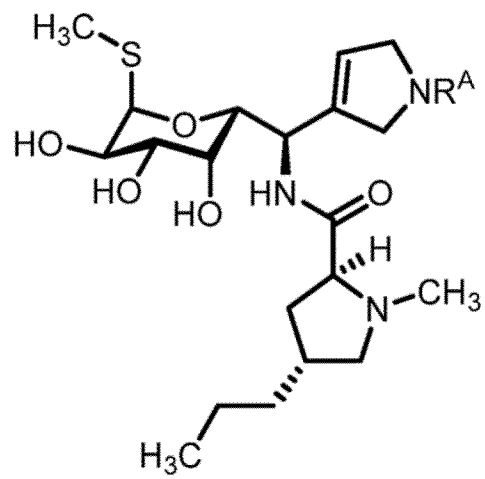 .
In Claim 15, at Column 178, Lines 20-33, formula: 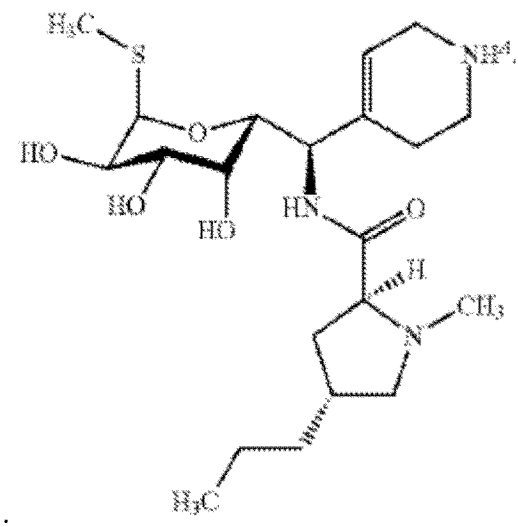 should
be replaced with the formula: 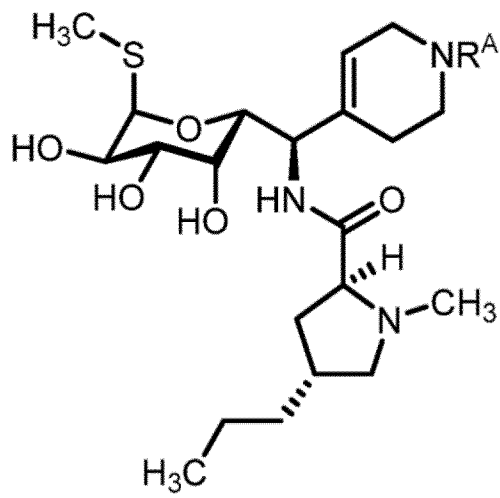 .